(12) United States Patent
Crouse et al.

(10) Patent No.: US 8,178,658 B2
(45) Date of Patent: May 15, 2012

(54) PESTICIDAL COMPOSITIONS

(75) Inventors: Gary D. Crouse, Noblesville, IN (US); Thomas C. Sparks, Greenfield, IN (US); CaSandra L. McLeod, Indianapolis, IN (US); David A. Demeter, Fishers, IN (US); Kristy Bryan, Carmel, IN (US); Annette V. Brown, Indianapolis, IN (US); William H. Dent, III, Indianapolis, IN (US); Denise P. Cudworth, Indianapolis, IN (US); Jaime S. Nugent, Brownsburg, IN (US); Ricky Hunter, Westfield, IN (US); Jack G. Samaritoni, Avon, IN (US)

(73) Assignee: Dow AgroSciences, LLC, Indianapolis, IN (US)

( * ) Notice: Subject to any disclaimer, the term of this patent is extended or adjusted under 35 U.S.C. 154(b) by 411 days.

(21) Appl. No.: 12/369,056

(22) Filed: Feb. 11, 2009

(65) Prior Publication Data
US 2009/0209476 A1 Aug. 20, 2009

Related U.S. Application Data

(60) Provisional application No. 61/065,475, filed on Feb. 12, 2008.

(51) Int. Cl.
*A61K 31/7034* (2006.01)
*A61K 31/7048* (2006.01)
*A61K 31/706* (2006.01)
*A61K 31/7056* (2006.01)
*A61K 31/35* (2006.01)
*C07H 17/04* (2006.01)
*C07D 309/10* (2006.01)
*C07D 309/12* (2006.01)

(52) U.S. Cl. ......... 536/17.4; 514/32; 514/459; 549/416; 549/417; 549/419

(58) Field of Classification Search .................. None
See application file for complete search history.

(56) References Cited

FOREIGN PATENT DOCUMENTS
WO PCT/US2009/033711 7/2009

OTHER PUBLICATIONS

Melucci et al., "Shaping Thiophene Oligomers into Fluorescent Nanobeads Forming Two-Dimensionally Patterned Assemblies by the Capillary Effect" Macromolecules (2005) vol. 38 pp. 10050-10054.*
Braga et al., "Making Crystals from Crystals: a Green Route to Crystal Engineering and Polymorphism" Chemical Communications (2005) pp. 3635-3645.*
Jain et al., "Polymorphism in Pharmacy" Indian Drugs (1986) vol. 23 No. 6, pp. 315-329.*
Lieberman et al., "Pharmaceutical Dosage Forms" vol. 2, published 1990 by Marcel Dekker, INC, pp. 462-472.*
Vippagunta et al., "Crystalline Solids" Advanced Drug Delivery Reviews (2001) vol. 48 pp. 3-26.*
Zhou et al., "Metabolites of an orally active antimicrobial prodrug 2,5-bis(4-amidinophenyl)furan-bis-O-methylamidoxime, identified by liquid chromatography/tandem mass spectrometry" Journal of Mass Spectrometry (2004) vol. 39 pp. 351-360.*
J.S. Brimacombe, F. Hunedy, and A. Husan; "Syntheses of 6-Deoxy-2,4- and 3,4-Di-O-Methyl-D-Allose;" Carbohydrate Research, 10 (1969) pp. 141-151, Elsevier Publishing Company, Amsterdam, Belgium.
Kenji Oshima, Ei-Ichi Kitazono, and Yasuhiro Aoyama; "Complexation-Induced Activation of Sugar OH Groups. Regioselective Alkylation of MEthyl Fucopyranoside via Cyclic Phenylboronate in the Presence of Amine;" Tetrahedron Letters, vol. 38, No. 28, pp. 5001-5004, 1997; Elseiver Science Ltd., Great Britain.
Ken-Ichi Sato, Hiroshi Seki, Akira Yoshitomo, Hiroshi Nanaumi, Yoshimitsu Takai and Yoshiharu Ishido; "Novel Synthetic Approaches to Man B1-4GLCNAc and LEX Units from N-Acetyl-lactosamine;" J. Carbohydrate Chemistry, 17(4&5), pp. 703-727, 1998, Marcel Dekker, Inc.

* cited by examiner

*Primary Examiner* — Eric S Olson
(74) *Attorney, Agent, or Firm* — Carl D. Corvin

(57) ABSTRACT

The invention disclosed in this document is related to the field of pesticides and their use in controlling pests. A compound having the following structure is disclosed.

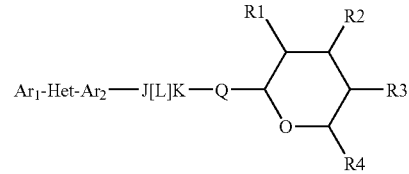

8 Claims, No Drawings

PESTICIDAL COMPOSITIONS

CROSS-REFERENCE TO RELATED APPLICATION

This application claims the benefit of U.S. Provisional Application Ser. No. 61/065,475 filed on Feb. 12, 2008 the entire contents of such is hereby incorporated by reference.

FIELD OF THE INVENTION

The invention disclosed in this document is related to the field of pesticides and their use in controlling pests.

BACKGROUND OF THE INVENTION

Pests cause millions of human deaths around the world each year. Furthermore, there are more than ten thousand species of pests that cause losses in agriculture. These agricultural losses amount to billions of U.S. dollars each year. Termites cause damage to various structures such as homes. These termite damage losses amount to billions of U.S. dollars each year. As a final note, many stored food pests eat and adulterate stored food. These stored food losses amount to billions of U.S. dollars each year, but more importantly, deprive people of needed food.

There is an acute need for new pesticides. Insects are developing resistance to pesticides in current use. Hundreds of insect species are resistant to one or more pesticides. The development of resistance to some of the older pesticides, such as DDT, the carbamates, and the organophosphates, is well known. But, resistance has even developed to some of the newer pesticides. Therefore, a need exists for new pesticides and particularly for pesticides that have new modes of action.

Substituents (Non-Exhaustive List)

The examples given for the substituents are (except for halo) non-exhaustive and must not be construed as limiting the invention disclosed in this document.

"alkenyl" means an acyclic, unsaturated (at least one carbon-carbon double bond), branched or unbranched, substituent consisting of carbon and hydrogen, for example, vinyl, allyl, butenyl, pentenyl, hexenyl, heptenyl, octenyl, nonenyl, and decenyl.

"alkenyloxy" means an alkenyl further consisting of a carbon-oxygen single bond, for example, allyloxy, butenyloxy, pentenyloxy, hexenyloxy, heptenyloxy, octenyloxy, nonenyloxy, and decenyloxy.

"alkoxy" means an alkyl further consisting of a carbon-oxygen single bond, for example, methoxy, ethoxy, propoxy, isopropoxy, 1-butoxy, 2-butoxy, isobutoxy, tert-butoxy, pentoxy, 2-methylbutoxy, 1,1-dimethylpropoxy, hexoxy, heptoxy, octoxy, nonoxy, and decoxy.

"alkyl" means an acyclic, saturated, branched or unbranched, substituent consisting of carbon and hydrogen, for example, methyl, ethyl, propyl, isopropyl, 1-butyl, 2-butyl, isobutyl, tert-butyl, pentyl, 2-methylbutyl, 1,1-dimethylpropyl, hexyl, heptyl, octyl, nonyl, and decyl.

"alkynyl" means an acyclic, unsaturated (at least one carbon-carbon triple bond, and any double bonds), branched or unbranched, substituent consisting of carbon and hydrogen, for example, ethynyl, propargyl, butynyl, pentynyl, hexynyl, heptynyl, octynyl, nonynyl, and decynyl.

"halo" means fluoro, chloro, bromo, and iodo.

"haloalkoxy" means a haloalkyl further consisting of a carbon-oxygen single bond, for example, fluoromethoxy, difluoromethoxy, and trifluoromethoxy, 2-fluoroethoxy, 1,1,2,2,2-pentafluoroethoxy, 1,1,2,2-tetrafluoro-2-bromoethoxy and 1,1,2,2-tetrafluoroethoxy.

"haloalkyl" means an alkyl further consisting of, from one to the maximum possible number of, identical or different, halos, for example, fluoromethyl, difluoromethyl, trifluoromethyl, 2-fluoroethyl, 2,2,2-trifluoroethyl, chloromethyl, trichloromethyl, and 1,1,2,2-tetrafluoroethyl.

"halophenyloxy" means a phenyloxy having one or more, identical or different, halos.

"hydroxyalkyl" means an alkyl having one or more hydroxy groups.

DETAILED DESCRIPTION OF THE INVENTION

The compounds of this invention have the following formula:

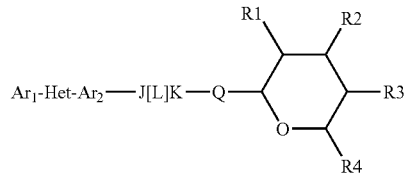

wherein:
(a) $Ar_1$ is
(1) furanyl, phenyl, pyridazinyl, pyridyl, pyrimidinyl, thienyl, or
(2) substituted furanyl, substituted phenyl, substituted pyridazinyl, substituted pyridyl, substituted pyrimidinyl, or substituted thienyl,
wherein said substituted furanyl, substituted phenyl, substituted pyridazinyl, substituted pyridyl, substituted pyrimidinyl, and substituted thienyl, have one or more substituents independently selected from H, OH, F, Cl, Br, I, CN, $NO_2$, $C_1$-$C_6$ alkyl, $C_1$-$C_6$ haloalkyl, $C_1$-$C_6$ hydroxyalkyl, $C_3$-$C_6$ cycloalkyl, $C_3$-$C_6$ halocycloalkyl, $C_3$-$C_6$ hydroxycycloalkyl, $C_3$-$C_6$ cycloalkoxy, $C_3$-$C_6$ halocycloalkoxy, $C_3$-$C_6$ hydroxycycloalkoxy, $C_1$-$C_6$ alkoxy, $C_1$-$C_6$ haloalkoxy, $C_2$-$C_6$ alkenyl, $C_2$-$C_6$ alkynyl, $S(=O)_n$($C_1$-$C_6$ alkyl), $S(=O)_n$($C_1$-$C_6$ haloalkyl), $OSO_2$($C_1$-$C_6$ alkyl), $OSO_2$($C_1$-$C_6$ haloalkyl), $C(=O)H$, $C(=O)OH$, $C(=O)NR_xR_y$, ($C_1$-$C_6$ alkyl)$NR_xR_y$, $C(=O)$($C_1$-$C_6$ alkyl), $C(=O)O$($C_1$-$C_6$ alkyl), $C(=O)$($C_1$-$C_6$ haloalkyl), $C(=O)O$($C_1$-$C_6$ haloalkyl), $C(=O)$($C_3$-$C_6$ cycloalkyl), $C(=O)O$($C_3$-$C_6$ cycloalkyl), $C(=O)$($C_2$-$C_6$ alkenyl), $C(=O)O$($C_2$-$C_6$ alkenyl), ($C_1$-$C_6$ alkyl)$O$($C_1$-$C_6$ alkyl), ($C_1$-$C_6$ alkyl)$S$($C_1$-$C_6$ alkyl), $C(=O)$($C_1$-$C_6$ alkyl)$C(=O)O$($C_1$-$C_6$ alkyl), phenyl, phenoxy, substituted phenyl and substituted phenoxy (wherein such substituted phenyl and substituted phenoxy have one or more substituents independently selected from H, OH, F, Cl, Br, I, CN, $NO_2$, $C_1$-$C_6$ alkyl, $C_1$-$C_6$ haloalkyl, $C_1$-$C_6$ hydroxyalkyl, $C_3$-$C_6$ cycloalkyl, $C_3$-$C_6$ halocycloalkyl, $C_3$-$C_6$ hydroxycycloalkyl, $C_3$-$C_6$ cycloalkoxy, $C_3$-$C_6$ halocycloalkoxy, $C_3$-$C_6$ hydroxycycloalkoxy, $C_1$-$C_6$ alkoxy, $C_1$-$C_6$ haloalkoxy, $C_2$-$C_6$ alkenyl, $C_2$-$C_6$ alkynyl, $S(=O)_n$($C_1$-$C_6$ alkyl), $S(=O)_n$($C_1$-$C_6$ haloalkyl), $OSO_2$($C_1$-$C_6$ alkyl), $OSO_2$($C_1$-$C_6$ haloalkyl), $C(=O)H$, $C(=O)OH$, $C(=O)NR_xR_y$, ($C_1$-$C_6$ alkyl)$NR_xR_y$, $C(=O)$($C_1$-$C_6$ alkyl), $C(=O)O$($C_1$-$C_6$ alkyl), $C(=O)$($C_1$-$C_6$ haloalkyl), $C(=O)O$($C_1$-$C_6$ haloalkyl), $C(=O)$($C_3$-

$C_6$ cycloalkyl), $C(=O)O(C_3\text{-}C_6$ cycloalkyl), $C(=O)(C_2\text{-}C_6$ alkenyl), $C(=O)O(C_2\text{-}C_6$ alkenyl), $(C_1\text{-}C_6$ alkyl)$O(C_1\text{-}C_6$ alkyl), $(C_1\text{-}C_6$ alkyl)$S(C_1\text{-}C_6$ alkyl), $C(=O)(C_1\text{-}C_6$ alkyl)$C(=O)O(C_1\text{-}C_6$ alkyl)phenyl, and phenoxy);

(b) Het is a 5 or 6 membered, saturated or unsaturated, heterocyclic ring, containing one or more heteroatoms independently selected from nitrogen, sulfur, or oxygen, and where $Ar_1$ and $Ar_2$ are not ortho to each other (but may be meta or para, such as, for a five membered ring they are 1,3 and for a 6 membered ring they are either 1,3 or 1,4), and where said heterocyclic ring may also be substituted with one or more substituents independently selected from H, OH, F, Cl, Br, I, CN, $NO_2$, oxo, $C_1\text{-}C_6$ alkyl, $C_1\text{-}C_6$ haloalkyl, $C_1\text{-}C_6$ hydroxyalkyl, $C_3\text{-}C_6$ cycloalkyl, $C_3\text{-}C_6$ halocycloalkyl, $C_3\text{-}C_6$ hydroxycycloalkyl, $C_3\text{-}C_6$ cycloalkoxy, $C_3\text{-}C_6$ halocycloalkoxy, $C_3\text{-}C_6$ hydroxycycloalkoxy, $C_1\text{-}C_6$ alkoxy, $C_1\text{-}C_6$ haloalkoxy, $C_2\text{-}C_6$ alkenyl, $C_2\text{-}C_6$ alkynyl, $S(=O)_n(C_1\text{-}C_6$ alkyl), $S(=O)_n(C_1\text{-}C_6$ haloalkyl), $OSO_2(C_1\text{-}C_6$ alkyl), $OSO_2(C_1\text{-}C_6$ haloalkyl), $C(=O)H$, $C(=O)OH$, $C(=O)NR_xR_y$, $(C_1\text{-}C_6$ alkyl)$NR_xR_y$, $C(=O)(C_1\text{-}C_6$ alkyl), $C(=O)O(C_1\text{-}C_6$ alkyl), $C(=O)(C_1\text{-}C_6$ haloalkyl), $C(=O)O(C_1\text{-}C_6$ haloalkyl), $C(=O)(C_3\text{-}C_6$ cycloalkyl), $C(=O)O(C_3\text{-}C_6$ cycloalkyl), $C(=O)(C_2\text{-}C_6$ alkenyl), $C(=O)O(C_2\text{-}C_6$ alkenyl), $(C_1\text{-}C_6$ alkyl)$O(C_1\text{-}C_6$ alkyl), $(C_1\text{-}C_6$ alkyl)$S(C_1\text{-}C_6$ alkyl), $C(=O)(C_1\text{-}C_6$ alkyl)$C(=O)O(C_1\text{-}C_6$ alkyl), phenyl, phenoxy, substituted phenyl and substituted phenoxy (wherein such substituted phenyl and substituted phenoxy have one or more substituents independently selected from H, OH, F, Cl, Br, I, CN, $NO_2$, $C_1\text{-}C_6$ alkyl, $C_1\text{-}C_6$ haloalkyl, $C_1\text{-}C_6$ hydroxyalkyl, $C_3\text{-}C_6$ cycloalkyl, $C_3\text{-}C_6$ halocycloalkyl, $C_3\text{-}C_6$ hydroxycycloalkyl, $C_3\text{-}C_6$ cycloalkoxy, $C_3\text{-}C_6$ halocycloalkoxy, $C_3\text{-}C_6$ hydroxycycloalkoxy, $C_1\text{-}C_6$ alkoxy, $C_1\text{-}C_6$ haloalkoxy, $C_2\text{-}C_6$ alkenyl, $C_2\text{-}C_6$ alkynyl, $S(=O)_n(C_1\text{-}C_6$ alkyl), $S(=O)_n(C_1\text{-}C_6$ haloalkyl), $OSO_2(C_1\text{-}C_6$ alkyl), $OSO_2(C_1\text{-}C_6$ haloalkyl), $C(=O)H$, $C(=O)OH$, $C(=O)NR_xR_y$, $(C_1\text{-}C_6$ alkyl)$NR_xR_y$, $C(=O)(C_1\text{-}C_6$ alkyl), $C(=O)O(C_1\text{-}C_6$ alkyl), $C(=O)(C_1\text{-}C_6$ haloalkyl), $C(=O)O(C_1\text{-}C_6$ haloalkyl), $C(=O)(C_3\text{-}C_6$ cycloalkyl), $C(=O)O(C_3\text{-}C_6$ cycloalkyl), $C(=O)(C_2\text{-}C_6$ alkenyl), $C(=O)O(C_2\text{-}C_6$ alkenyl), $(C_1\text{-}C_6$ alkyl)$O(C_1\text{-}C_6$ alkyl), $(C_1\text{-}C_6$ alkyl)$S(C_1\text{-}C_6$ alkyl), $C(=O)(C_1\text{-}C_6$ alkyl)$C(=O)O(C_1\text{-}C_6$ alkyl), phenyl, and phenoxy);

(c) $Ar_2$ is
(1) furanyl, phenyl, pyridazinyl, pyridyl, pyrimidinyl, thienyl, or
(2) substituted furanyl, substituted phenyl, substituted pyridazinyl, substituted pyridyl, substituted pyrimidinyl, or substituted thienyl,
wherein said substituted furanyl, substituted phenyl, substituted pyridazinyl, substituted pyridyl, substituted pyrimidinyl, and substituted thienyl, have one or more substituents independently selected from H, OH, F, Cl, Br, I, CN, $NO_2$, $C_1\text{-}C_6$ alkyl, $C_1\text{-}C_6$ haloalkyl, $C_1\text{-}C_6$ hydroxyalkyl, $C_3\text{-}C_6$ cycloalkyl, $C_3\text{-}C_6$ halocycloalkyl, $C_3\text{-}C_6$ hydroxycycloalkyl, $C_3\text{-}C_6$ cycloalkoxy, $C_3\text{-}C_6$ halocycloalkoxy, $C_3\text{-}C_6$ hydroxycycloalkoxy, $C_1\text{-}C_6$ alkoxy, $C_1\text{-}C_6$ haloalkoxy, $C_2\text{-}C_6$ alkenyl, $C_2\text{-}C_6$ alkynyl, $S(=O)_n(C_1\text{-}C_6$ alkyl), $S(=O)_n(C_1\text{-}C_6$ haloalkyl), $OSO_2(C_1\text{-}C_6$ alkyl), $OSO_2(C_1\text{-}C_6$ haloalkyl), $C(=O)H$, $C(=O)OH$, $C(=O)NR_xR_y$, $(C_1\text{-}C_6$ alkyl)$NR_xR_y$, $C(=O)(C_1\text{-}C_6$ alkyl), $C(=O)O(C_1\text{-}C_6$ alkyl), $C(=O)(C_1\text{-}C_6$ haloalkyl), $C(=O)O(C_1\text{-}C_6$ haloalkyl), $C(=O)(C_3\text{-}C_6$ cycloalkyl), $C(=O)O(C_3\text{-}C_6$ cycloalkyl), $C(=O)(C_2\text{-}C_6$ alkenyl), $C(=O)O(C_2\text{-}C_6$ alkenyl), $(C_1\text{-}C_6$ alkyl)$O(C_1\text{-}C_6$ alkyl), $(C_1\text{-}C_6$ alkyl)$S(C_1\text{-}C_6$ alkyl), $C(=O)(C_1\text{-}C_6$ alkyl)$C(=O)O(C_1\text{-}C_6$ alkyl), phenyl, phenoxy, substituted phenyl and substituted phenoxy (wherein such substituted phenyl and substituted phenoxy have one or more substituents independently selected from H, OH, F, Cl, Br, I, CN, $NO_2$, $C_1\text{-}C_6$ alkyl, $C_1\text{-}C_6$ haloalkyl, $C_1\text{-}C_6$ hydroxyalkyl, $C_3\text{-}C_6$ cycloalkyl, $C_3\text{-}C_6$ halocycloalkyl, $C_3\text{-}C_6$ hydroxycycloalkyl, $C_3\text{-}C_6$ cycloalkoxy, $C_3\text{-}C_6$ halocycloalkoxy, $C_3\text{-}C_6$ hydroxycycloalkoxy, $C_1\text{-}C_6$ alkoxy, $C_1\text{-}C_6$ haloalkoxy, $C_2\text{-}C_6$ alkenyl, $C_2\text{-}C_6$ alkynyl, $S(=O)_n(C_1\text{-}C_6$ alkyl), $S(=O)_n(C_1\text{-}C_6$ haloalkyl), $OSO_2(C_1\text{-}C_6$ alkyl), $OSO_2(C_1\text{-}C_6$ haloalkyl), $C(=O)H$, $C(=O)OH$, $C(=O)NR_xR_y$, $(C_1\text{-}C_6$ alkyl)$NR_xR_y$, $C(=O)(C_1\text{-}C_6$ alkyl), $C(=O)O(C_1\text{-}C_6$ alkyl), $C(=O)(C_1\text{-}C_6$ haloalkyl), $C(=O)O(C_1\text{-}C_6$ haloalkyl), $C(=O)(C_3\text{-}C_6$ cycloalkyl), $C(=O)O(C_3\text{-}C_6$ cycloalkyl), $C(=O)(C_1\text{-}C_6$ haloalkyl), $C(=O)(C_2\text{-}C_6$ alkenyl), $C(=O)O(C_2\text{-}C_6$ alkenyl), $(C_1\text{-}C_6$ alkyl)$O(C_1\text{-}C_6$ alkyl), $(C_1\text{-}C_6$ alkyl)$S(C_1\text{-}C_6$ alkyl), $C(=O)(C_1\text{-}C_6$ alkyl)$C(=O)O(C_1\text{-}C_6$ alkyl), phenyl, and phenoxy);

(d) J is O, N, NR5, CR5, C=O, or J and $Ar_2$ form a 3, 4, 5, or 6 membered ring, such as an indane or an indole, as, for example, in the following structures:

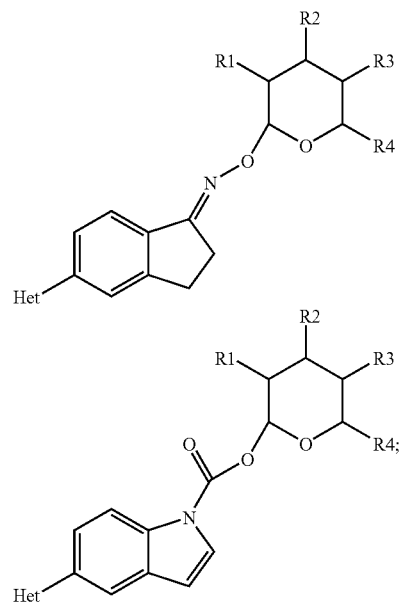

(e) L is a single or double bond;
(f) K is CR5, C=O, N, NR5, or C=S;
(g) Q is O or S;
(h) R1 is H, OH, F, Cl, Br, I, oxo, $C_1\text{-}C_6$ alkyl, $C_1\text{-}C_6$ haloalkyl, $C_1\text{-}C_6$ alkoxy, $C_3\text{-}C_6$ cycloalkoxy, $C_1\text{-}C_6$ haloalkoxy, $C_2\text{-}C_6$ alkenyloxy, $(C_1\text{-}C_6$ alkyl)$O(C_1\text{-}C_6$ alkyl), $(C_1\text{-}C_6$ alkyl)$O(C_1\text{-}C_6$ alkoxy), $OC(=O)(C_1\text{-}C_6$ alkyl), $OC(=O)(C_3\text{-}C_6$ cycloalkyl), $OC(=O)(C_1\text{-}C_6$ haloalkyl), $OC(=O)(C_2\text{-}C_6$ alkenyl), or $NR_xR_y$;

(i) R2 is H, OH, F, Cl, Br, I, oxo, $C_1\text{-}C_6$ alkyl, $C_1\text{-}C_6$ haloalkyl, $C_1\text{-}C_6$ alkoxy, $C_3\text{-}C_6$ cycloalkoxy, $C_1\text{-}C_6$ haloalkoxy, $C_2\text{-}C_6$ alkenyloxy, $(C_1\text{-}C_6$ alkyl)$O(C_1\text{-}C_6$ alkyl), $(C_1\text{-}C_6$ alkyl)$O(C_1\text{-}C_6$ alkoxy), $OC(=O)(C_1\text{-}C_6$ alkyl), $OC(=O)(C_3\text{-}C_6$ cycloalkyl), $OC(=O)(C_1\text{-}C_6$ haloalkyl), $OC(=O)(C_2\text{-}C_6$ alkenyl), or $NR_xR_y$;

(j) R3 is H, OH, F, Cl, Br, I, oxo, $C_1\text{-}C_6$ alkyl, $C_1\text{-}C_6$ haloalkyl, $C_1\text{-}C_6$ alkoxy, $C_3\text{-}C_6$ cycloalkoxy, $C_1\text{-}C_6$ haloalkoxy, $C_2\text{-}C_6$ alkenyloxy, $(C_1\text{-}C_6$ alkyl)$O(C_1\text{-}C_6$ alkyl), ($C_1$-$C_6$ alkyl)O($C_1$-$C_6$ alkoxy), OC(=O)($C_1$-$C_6$ alkyl), OC(=O)($C_3$-$C_6$ cycloalkyl), OC(=O)($C_1$-$C_6$ haloalkyl), OC(=O)($C_2$-$C_6$ alkenyl), or $NR_xR_y$;

(k) R4 is H, $C_1$-$C_6$ alkyl, $C_1$-$C_6$ haloalkyl, $C_1$-$C_6$ alkoxy, $C_1$-$C_6$ haloalkoxy, $C_2$-$C_6$ alkenyloxy, ($C_1$-$C_6$ alkyl)O($C_1$-$C_6$ alkyl); and (l) R5 is H, OH, F, Cl, Br, I, CN, $NO_2$, $C_1$-$C_6$ alkyl, $C_1$-$C_6$ haloalkyl, $C_1$-$C_6$ hydroxyalkyl, $C_3$-$C_6$ cycloalkyl, $C_3$-$C_6$ halocycloalkyl, $C_3$-$C_6$ hydroxycycloalkyl, $C_3$-$C_6$ cycloalkoxy, $C_3$-$C_6$ halocycloalkoxy, $C_3$-$C_6$ hydroxycycloalkoxy, $C_1$-$C_6$ alkoxy, $C_1$-$C_6$ haloalkoxy, $C_2$-$C_6$ alkenyl, $C_2$-$C_6$ alkynyl, S(=O)$_n$($C_1$-$C_6$ alkyl), S(=O)$_n$($C_1$-$C_6$ haloalkyl), $OSO_2$($C_1$-$C_6$ alkyl), $OSO_2$($C_1$-$C_6$ haloalkyl), C(=O)H, C(=O)OH, C(=O)$NR_xR_y$, ($C_1$-$C_6$ alkyl)$NR_xR_y$, C(=O)($C_1$-$C_6$ alkyl), C(=O)O($C_1$-$C_6$ alkyl), C(=O)($C_1$-$C_6$ haloalkyl), C(=O)O($C_1$-$C_6$ haloalkyl), C(=O)($C_3$-$C_6$ cycloalkyl), C(=O)O($C_3$-$C_6$ cycloalkyl), C(=O)($C_2$-$C_6$ alkenyl), C(=O)O($C_2$-$C_6$ alkenyl), ($C_1$-$C_6$ alkyl)O($C_1$-$C_6$ alkyl), ($C_1$-$C_6$ alkyl)S($C_1$-$C_6$ alkyl), C(=O)($C_1$-$C_6$ alkyl)C(=O)O($C_1$-$C_6$ alkyl), phenyl, phenoxy, wherein each alkyl, haloalkyl, hydroxyalkyl, cycloalkyl, halocycloalkyl, hydroxycycloalkyl, cycloalkoxy, halocycloalkoxy, hydroxycycloalkoxy, alkoxy, haloalkoxy, alkenyl, alkynyl, phenyl, and phenoxy are optionally substituted with one or more substituents independently selected from OH, F, Cl, Br, I, CN, $NO_2$, oxo, $C_1$-$C_6$ alkyl, $C_1$-$C_6$ haloalkyl, $C_1$-$C_6$ hydroxyalkyl, $C_3$-$C_6$ cycloalkyl, $C_3$-$C_6$ halocycloalkyl, $C_3$-$C_6$ hydroxycycloalkyl, $C_3$-$C_6$ cycloalkoxy, $C_3$-$C_6$ halocycloalkoxy, $C_3$-$C_6$ hydroxycycloalkoxy, $C_1$-$C_6$ alkoxy, $C_1$-$C_6$ haloalkoxy, $C_2$-$C_6$ alkenyl, $C_2$-$C_6$ alkynyl, S(=O)$_n$($C_1$-$C_6$ alkyl), S(=O)$_n$($C_1$-$C_6$ haloalkyl), $OSO_2$($C_1$-$C_6$ alkyl), $OSO_2$($C_1$-$C_6$ haloalkyl), C(=O)H, C(=O)OH, C(=O)$NR_xR_y$, ($C_1$-$C_6$ alkyl)$NR_xR_y$, C(=O)($C_1$-$C_6$ alkyl), C(=O)O($C_1$-$C_6$ alkyl), C(=O)($C_1$-$C_6$ haloalkyl), C(=O)O($C_1$-$C_6$ haloalkyl), C(=O)($C_3$-$C_6$ cycloalkyl), C(=O)O($C_3$-$C_6$ cycloalkyl), C(=O)($C_2$-$C_6$ alkenyl), C(=O)O($C_2$-$C_6$ alkenyl), ($C_1$-$C_6$ alkyl)O($C_1$-$C_6$ alkyl), ($C_1$-$C_6$ alkyl)S($C_1$-$C_6$ alkyl), C(=O)($C_1$-$C_6$ alkyl)C(=O)O($C_1$-$C_6$ alkyl), phenyl, and phenoxy;

(m) n=0, 1, or 2;

(n) $R_x$ and $R_y$ are independently selected from H, $C_1$-$C_6$ alkyl, $C_1$-$C_6$ haloalkyl, $C_1$-$C_6$ hydroxyalkyl, $C_3$-$C_6$ cycloalkyl, $C_3$-$C_6$ halocycloalkyl, $C_3$-$C_6$ hydroxycycloalkyl, $C_3$-$C_6$ cycloalkoxy, $C_3$-$C_6$ halocycloalkoxy, $C_3$-$C_6$ hydroxycycloalkoxy, $C_1$-$C_6$ alkoxy, $C_1$-$C_6$ haloalkoxy, $C_2$-$C_6$ alkenyl, $C_2$-$C_6$ alkynyl, S(=O)$_n$($C_1$-$C_6$ alkyl), S(=O)$_n$($C_1$-$C_6$ haloalkyl), $OSO_2$($C_1$-$C_6$ alkyl), $OSO_2$($C_1$-$C_6$ haloalkyl), C(=O)H, C(=O)OH, C(=O)($C_1$-$C_6$ alkyl), C(=O)O($C_1$-$C_6$ alkyl), C(=O)($C_1$-$C_6$ haloalkyl), C(=O)O($C_1$-$C_6$ haloalkyl), C(=O)($C_3$-$C_6$ cycloalkyl), C(=O)O($C_3$-$C_6$ cycloalkyl), C(=O)($C_2$-$C_6$ alkenyl), C(=O)O($C_2$-$C_6$ alkenyl), ($C_1$-$C_6$ alkyl)O($C_1$-$C_6$ alkyl), ($C_1$-$C_6$ alkyl)S($C_1$-$C_6$ alkyl), C(=O)($C_1$-$C_6$ alkyl)C(=O)O($C_1$-$C_6$ alkyl), phenyl, and phenoxy.

In another embodiment of this invention:

(a) $Ar_1$ is phenyl, pyridazinyl, pyridyl, thienyl, substituted phenyl, substituted pyridazinyl, substituted pyridyl, or substituted thienyl, wherein said substituted phenyl, substituted pyridazinyl, substituted pyridyl, and substituted thienyl, have one or more substituents independently selected from F, Cl, Br, I, CN, $NO_2$, $C_1$-$C_6$ alkyl, $C_1$-$C_6$ haloalkyl, $C_1$-$C_6$ hydroxyalkyl, $C_1$-$C_6$ haloalkoxy, $C_2$-$C_6$ alkenyl, S(=O)$_n$($C_1$-$C_6$ alkyl), S(=O)$_n$($C_1$-$C_6$ haloalkyl), $OSO_2$($C_1$-$C_6$ haloalkyl), C(=O)($C_1$-$C_6$ alkyl), ($C_1$-$C_6$ alkyl)S($C_1$-$C_6$ alkyl), and phenoxy (wherein such substituted phenoxy has one or more substituents independently selected from F, Cl, Br, or I).

In another embodiment of the invention:

(a) $Ar_1$ is substituted phenyl or substituted pyridyl wherein said substituted phenyl and substituted pyridyl, have one or more substituents independently selected from F, Cl, Br, I, CN, $NO_2$, $C_1$-$C_6$ alkyl, $C_1$-$C_6$ haloalkyl, $C_1$-$C_6$ hydroxyalkyl, $C_1$-$C_6$ haloalkoxy, $C_2$-$C_6$ alkenyl, S(=O)$_n$($C_1$-$C_6$ alkyl), S(=O)$_n$($C_1$-$C_6$ haloalkyl), $OSO_2$($C_1$-$C_6$ haloalkyl), C(=O)($C_1$-$C_6$ alkyl), ($C_1$-$C_6$ alkyl)S($C_1$-$C_6$ alkyl), and phenoxy (wherein such substituted phenoxy has one or more substituents independently selected from F, Cl, Br, or I).

In another embodiment of the invention:

(a) $Ar_1$ is substituted phenyl wherein said substituted phenyl has one or more substituents independently selected from F, Cl, Br, I, $C_1$-$C_6$ alkyl, $C_1$-$C_6$ haloalkyl, and $C_1$-$C_6$ haloalkoxy.

In another embodiment of the invention:

(b) Het is imidazolyl, isothiazolyl, isoxazolyl, 1,2,4-oxadiazolyl, 1,3,4-oxadiazolyl, oxazolinyl, oxazolyl, piperazinyl, piperidinyl, pyrazinyl, pyrazolinyl, pyrazolyl, pyridazinyl, pyridyl, pyrimidinyl, pyrrolyl, 1,2,3,4-tetrazolyl, thiadiazolyl, thiazolinyl, thiazolyl, 1,2,3-triazinyl, 1,2,4-triazinyl, 1,3,5-triazinyl, 1,2,3-triazolyl, 1,2,4-triazolyl, substituted imidazolyl, substituted isothiazolyl, substituted isoxazolyl, substituted 1,2,4-oxadiazolyl, substituted 1,3,4 oxadiazolyl, substituted oxazolinyl, substituted oxazolyl, substituted piperazinyl, substituted piperidinyl, substituted pyrazinyl, substituted pyrazolinyl, substituted pyrazolyl, substituted pyridazinyl, substituted pyridyl, substituted pyrimidinyl, substituted pyrrolyl, substituted tetrazolyl, substituted thiadiazolyl, substituted thiazolinyl, substituted thiazolyl, substituted 1,2,3-triazinyl, substituted 1,2,4-triazinyl, substituted 1,3,5-triazinyl, substituted 1,2,3-triazolyl, and substituted 1,2,4-triazolyl, where said substituted groups have one or more substituents independently selected from H, OH, F, Cl, Br, I, CN, $NO_2$, oxo, $C_1$-$C_6$ alkyl, $C_1$-$C_6$ haloalkyl, $C_1$-$C_6$ hydroxyalkyl, $C_3$-$C_6$ cycloalkyl, $C_3$-$C_6$ halocycloalkyl, $C_3$-$C_6$ hydroxycycloalkyl, $C_3$-$C_6$ cycloalkoxy, $C_3$-$C_6$ halocycloalkoxy, $C_3$-$C_6$ hydroxycycloalkoxy, $C_1$-$C_6$ alkoxy, $C_1$-$C_6$ haloalkoxy, $C_2$-$C_6$ alkenyl, $C_2$-$C_6$ alkynyl, S(=O)$_n$($C_1$-$C_6$ alkyl), S(=O)$_n$($C_1$-$C_6$ haloalkyl), $OSO_2$($C_1$-$C_6$ alkyl), $OSO_2$($C_1$-$C_6$ haloalkyl), C(=O)H, C(=O)OH, C(=O)$NR_xR_y$, ($C_1$-$C_6$ alkyl)$NR_xR_y$, C(=O)($C_1$-$C_6$ alkyl), C(=O)O($C_1$-$C_6$ alkyl), C(=O)($C_1$-$C_6$ haloalkyl), C(=O)($C_3$-$C_6$ cycloalkyl), C(=O)O($C_3$-$C_6$ cycloalkyl), C(=O)($C_1$-$C_6$ haloalkyl), C(=O)($C_2$-$C_6$ alkenyl), C(=O)O($C_2$-$C_6$ alkenyl), ($C_1$-$C_6$ alkyl)O($C_1$-$C_6$ alkyl), ($C_1$-$C_6$ alkyl)S($C_2$-$C_6$ alkyl), C(=O)($C_1$-$C_6$ alkyl)C(=O)O($C_1$-$C_6$ alkyl)phenyl, phenoxy, substituted phenyl and substituted phenoxy (wherein such substituted phenyl and substituted phenoxy have one or more substituents independently selected from H, OH, F, Cl, Br, I, CN, $NO_2$, oxo, $C_1$-$C_6$ alkyl, $C_1$-$C_6$ haloalkyl, $C_1$-$C_6$ hydroxyalkyl, $C_3$-$C_6$ cycloalkyl, $C_3$-$C_6$ halocycloalkyl, $C_3$-$C_6$ hydroxycycloalkyl, $C_3$-$C_6$ cycloalkoxy, $C_3$-$C_6$ halocycloalkoxy, $C_3$-$C_6$ hydroxycycloalkoxy, $C_1$-$C_6$ alkoxy, $C_1$-$C_6$ haloalkoxy, $C_2$-$C_6$ alkenyl, $C_2$-$C_6$ alkynyl, S(=O)$_n$($C_1$-$C_6$ alkyl), S(=O)$_n$($C_1$-$C_6$ haloalkyl), $OSO_2$($C_1$-$C_6$ alkyl), $OSO_2$($C_1$-$C_6$ haloalkyl), C(=O)H, C(=O)OH, C(=O)$NR_xR_y$, ($C_1$-$C_6$ alkyl)$NR_xR_y$, C(=O)($C_1$-$C_6$ alkyl), C(=O)O($C_1$-$C_6$ alkyl), C(=O)($C_1$-$C_6$ haloalkyl), C(=O)($C_3$-$C_6$ cycloalkyl), C(=O)O($C_3$-$C_6$ cycloalkyl), C(=O)($C_1$-$C_6$ haloalkyl), C(=O)($C_2$-$C_6$ alkenyl), C(=O)O($C_2$-$C_6$ alkenyl), ($C_1$-$C_6$ alkyl)O($C_1$-$C_6$ alkyl), ($C_1$-$C_6$ alkyl)S($C_1$-$C_6$ alkyl), C(=O)($C_1$-$C_6$ alkyl)C(=O)O($C_1$-$C_6$ alkyl)phenyl, and phenoxy).

In another embodiment of this invention:

(b) Het is imidazolyl, isoxazolyl, 1,2,4-oxadiazolyl, 1,3,4-oxadiazolyl, oxazolyl, piperazinyl, pyrazinyl, pyrazolyl, pyridazinyl, pyridyl, pyrimidinyl, pyrrolyl, 1,2,3,4-tetrazolyl, thiadiazolyl, thiazolyl, 1,2,4-triazinyl, 1,3,5-triazinyl, 1,2,3-triazolyl, 1,2,4-triazolyl, substituted imidazolyl, substituted 1,3,4-oxadiazolyl, substituted piperazinyl, substituted pyrazolyl, substituted pyrimidinyl, and substituted 1,2,4-triazolyl, where said substituted groups have one or more substituents independently selected from F, Cl, Br, I, CN, $NO_2$, oxo, $C_1$-$C_6$ alkyl, $C_1$-$C_6$ haloalkyl, $C_1$-$C_6$ hydroxyalkyl, $C_1$-$C_6$ alkoxy, $C_1$-$C_6$ haloalkoxy, $C_2$-$C_6$ alkenyl, $S(=O)_n(C_1$-$C_6$ alkyl), $S(=O)_n(C_1$-$C_6$ haloalkyl), $OSO_2(C_1$-$C_6$ haloalkyl), $C(=O)O(C_1$-$C_6$ alkyl), and $(C_1$-$C_6$ alkyl$)S(C_1$-$C_6$ alkyl), In another embodiment of this invention:

(b) Het is imidazolyl, isoxazolyl, 1,2,4-oxadiazolyl, pyrazinyl, pyrimidinyl, thiazolyl, 1,3,5-triazinyl, 1,2,4-triazolyl, substituted imidazolyl, substituted pyrazolyl, and substituted 1,2,4-triazolyl, where said substituted groups have one or more substituents independently selected from oxo, $C_1$-$C_6$ alkyl, $C_1$-$C_6$ haloalkyl, $C_2$-$C_6$ alkenyl, and $C(=O)O$ ($C_1$-$C_6$ alkyl), In another embodiment of this invention:

(c) $Ar_2$ is phenyl, pyridazinyl, pyridyl, thienyl, substituted phenyl, substituted pyridazinyl, substituted pyridyl, or substituted thienyl, wherein said substituted phenyl, substituted pyridazinyl, substituted pyridyl, and substituted thienyl, have one or more substituents independently selected from F, Cl, Br, I, CN, $NO_2$, $C_1$-$C_6$ alkyl, $C_1$-$C_6$ haloalkyl, $C_1$-$C_6$ hydroxyalkyl, $C_1$-$C_6$ haloalkoxy, $C_2$-$C_6$ alkenyl, $S(=O)_n(C_1$-$C_6$ alkyl), $S(=O)_n(C_1$-$C_6$ haloalkyl), $OSO_2(C_1$-$C_6$ haloalkyl), $C(=O)(C_1$-$C_6$ alkyl), $(C_1$-$C_6$ alkyl$)S(C_1$-$C_6$ alkyl), and phenoxy (wherein such substituted phenoxy has one or more substituents independently selected from F, Cl, Br, or I).

In another embodiment of the invention:

(c) $Ar_2$ is substituted phenyl or substituted pyridyl wherein said substituted phenyl and substituted pyridyl, have one or more substituents independently selected from F, Cl, Br, I, CN, $NO_2$, $C_1$-$C_6$ alkyl, $C_1$-$C_6$ haloalkyl, $C_1$-$C_6$ hydroxyalkyl, $C_1$-$C_6$ haloalkoxy, $C_2$-$C_6$ alkenyl, $S(=O)_n(C_1$-$C_6$ alkyl), $S(=O)_n(C_1$-$C_6$ haloalkyl), $OSO_2(C_1$-$C_6$ haloalkyl), $C(=O)$ ($C_1$-$C_6$ alkyl), $(C_1$-$C_6$ alkyl$)S(C_1$-$C_6$ alkyl), and phenoxy (wherein such substituted phenoxy has one or more substituents independently selected from F, Cl, Br, or I).

In another embodiment of the invention:

(c) $Ar_2$ is substituted phenyl wherein said substituted phenyl has one or more substituents independently selected from F, Cl, Br, I, $C_1$-$C_6$ alkyl, $C_1$-$C_6$ haloalkyl, and $C_1$-$C_6$ alkoxy.

In another embodiment of this invention:

(d) J is NR5, CR5, or C=O.

In another embodiment of this invention:

(f) K is C=O, N, NR5, or C=S.

In another embodiment of this invention:

(h) R1 is H or $C_1$-$C_6$ alkoxy.

In another embodiment of this invention:

(i) R2 is H, $C_1$-$C_6$ alkoxy or $C_2$-$C_6$ alkenyloxy.

In another embodiment of this invention:

(j) R3 is $C_1$-$C_6$ alkoxy.

In another embodiment of this invention:

(k) R4 is H, $C_1$-$C_6$ alkyl, $C_1$-$C_6$ alkoxy, or $(C_1$-$C_6$ alkyl)O ($C_1$-$C_6$ alkyl).

In another embodiment of this invention:

(l) R5 is H, $C_1$-$C_6$ alkyl, $C_1$-$C_6$ haloalkyl, $C_1$-$C_6$ hydroxyalkyl, $C_2$-$C_6$ alkenyl, $C(=O)(C_1$-$C_6$ alkyl), $(C_1$-$C_6$ alkyl)O ($C_1$-$C_6$ alkyl), and $C(=O)(C_1$-$C_6$ alkyl)$C(=O)O(C_1$-$C_6$ alkyl).

In another embodiment of this invention:

(1) R5 is H, $C_1$-$C_6$ alkyl, $C_1$-$C_6$ alkoxy, or $C_1$-$C_6$ haloalkyl. In another embodiment of the invention:

(a) $Ar_1$ is phenyl, pyridyl, thienyl, substituted phenyl, substituted pyridazinyl, or substituted pyridyl, wherein said substituted phenyl has one or more substituents independently selected from F, Cl, Br, I, CN, $CH_3$, $C_3H_7$, $C_4H_9$, $OCH_3$, $OC_4H_9$, $CF_3$, $C_2F_5$, $C_3F_7$, $OCF_3$, $OC_2F_5$, $OCH_2CF_3$, $OCF_2CHF_2$, $SCF_3$, $SCH_3$, $S(=O)CF_3$, $S(=O)_2CF_3$, OPhCl, and $C(OH)C_2H_5$;

wherein said substituted pyridazinyl has one or more Cl, wherein said substituted pyridyl has one or more substituents independently selected from F, Cl, I, $CF_3$, $OCF_3$, $OCF_2CHFCF_3$, and $OCH_2CF_3$.

In another embodiment of this invention:

(b) Het is imidazolyl, isoxazolyl, 1,3,4-oxadiazolyl, pyrazinyl, pyrazolinyl, pyrazolyl, pyridyl, pyrimidinyl, pyrrolyl, 1,2,3,4-tetrazolyl, thiazolyl, 1,3,5-triazinyl, 1,2,3-triazolyl, 1,2,4-triazolyl, substituted pyrazolinyl, substituted pyrimidinyl, or substituted 1,2,4-triazolyl, wherein said substituted pyrazolyl has one or more substituents independently selected from H, $CH_3$, $C_3H_7$, $C(=O)OCH_3$, $C(=O)OC_2H_5$, and $C(=O)OC_4H_9$, wherein said substituted pyrimidinyl has one or more substituents independently selected from $CF_3$ and $C_3F_7$, wherein said substituted 1,2,4-triazolyl has one or more substituents selected from $CH_3$ and oxo.

In another embodiment of this invention:

(c) $Ar_2$ is phenyl, thienyl, or substituted phenyl, wherein said substituted phenyl has one or more substituents independently selected from F, Cl, $OCH_3$, and $CF_3$.

In another embodiment of this invention:

(d) J is NH, CH, $CCH_3$, or C=O.

In another embodiment of this invention:

(h) R1 is $OCH_3$ or $OC_2H_5$.

In another embodiment of this invention:

(i) R2 is $OCH_2CH=CH_2$, $OCH_3$, $OC_2H_5$, $OC_3H_7$, or $OC_4H_9$.

In another embodiment of this invention:

k) R3 is OH, $OCH_3$, $OC_2H_5$, or $OC_3H_7$;

In another embodiment of this invention:

(k) R4 is $CH_3$ or $CH_2OCH_3$.

In another embodiment of this invention:

(a) $Ar_1$ is furanyl, phenyl, pyridazinyl, pyridyl, pyrimidinyl, thienyl, substituted furanyl, substituted phenyl, substituted pyridazinyl, substituted pyridyl, substituted pyrimidinyl, or substituted thienyl, wherein said substituted furanyl, substituted phenyl, substituted pyridazinyl, substituted pyridyl, substituted pyrimidinyl, and substituted thienyl, have one or more substituents independently selected from H, F, Cl, Br, I, CN, $NO_2$, oxo, $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, $C_1$-$C_6$ haloalkoxy, $S(=O)_nC_1$-$C_6$ alkyl, $S(=O)_nC_1$-$C_6$ haloalkyl, $OSO_2C_1$-$C_6$ haloalkyl, $C(=O)OC_1$-$C_6$ alkyl, $C(=O)C_1$-$C_6$ alkyl, $C(=O)C_1$-$C_6$ haloalkyl, phenyl, phenoxy, halophenoxy, and $C_1$-$C_6$ hydroxyalkyl;

(b) Het is a 5 or 6 membered, saturated or unsaturated, heterocyclic ring, containing one or more heteroatoms independently selected from nitrogen, sulfur, or oxygen, and where $Ar_1$ and $Ar_2$ are not ortho to each other (but may be meta or para, such as, for a five membered ring they are 1,3, and for a 6 membered ring they are either 1,3 or 1,4 respectively), and where said heterocyclic ring may also be substituted with one or more substituents independently selected from H, F, Cl, Br, I, CN, $NO_2$, oxo, $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, $C_1$-$C_6$ haloalkoxy, $S(=O)_nC_1$-$C_6$ alkyl, $S(=O)_nC_1$-$C_6$ haloalkyl, $OSO_2C_1$-$C_6$ haloalkyl, $C(=O)OC_1$-$C_6$ alkyl, $C(=O)C_1$-$C_6$ alkyl, $C(=O)C_1$-$C_6$ haloalkyl, phenyl, phenoxy, halophenoxy, and $C_1$-$C_6$ hydroxyalkyl;

(c) Ar2 is furanyl, phenyl, pyridazinyl, pyridyl, pyrimidinyl, thienyl, substituted furanyl, substituted phenyl, substituted pyridazinyl, substituted pyridyl, substituted pyrimidinyl, or substituted thienyl, wherein said substituted furanyl, substituted phenyl, substituted pyridazinyl, substituted pyridyl, substituted pyrimidinyl, and substituted thienyl, have one or more substituents independently selected from H, F, Cl, Br, I, CN, $NO_2$, oxo, $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, $C_1$-$C_6$ haloalkoxy, $S(=O)_n C_1$-$C_6$ alkyl, $S(=O)_n C_1$-$C_6$ haloalkyl, $OSO_2 C_1$-$C_6$ haloalkyl, $C(=O)OC_1$-$C_6$ alkyl, $C(=O)C_1$-$C_6$ alkyl, $C(=O)C_1$-$C_6$ haloalkyl, phenyl, phenoxy, halophenoxy, and $C_1$-$C_6$ hydroxyalkyl;

(d) J is O, N, NR5, CR5, or C=O;

(e) L is a single or double bond;

(f) K is CR5, C=O, N, NR5, or C=S;

(g) Q is O or S;

(h) R1 is $C_1$-$C_6$ alkyl, $C_1$-$C_6$ alkyl-O—$C_1$-$C_6$ alkyl, $C_1$-$C_6$ haloalkyl, halo, oxo, $C_1$-$C_6$ haloalkoxy, $C_1$-$C_6$ alkyl-O—$C_1$-$C_6$ alkoxy, H, OH, $C_1$-$C_6$ alkoxy, $C_2$-$C_6$ alkenyloxy;

(i) R2 is $C_1$-$C_6$ alkyl, $C_1$-$C_6$ alkyl-O—$C_1$-$C_6$ alkyl, $C_1$-$C_6$ haloalkyl, halo, oxo, $C_1$-$C_6$ haloalkoxy, $C_1$-$C_6$ alkyl-O—$C_1$-$C_6$ alkoxy, H, OH, $C_1$-$C_6$ alkoxy, $C_2$-$C_6$ alkenyloxy;

(j) R3 is $C_1$-$C_6$ alkyl, $C_1$-$C_6$ alkyl-O—$C_1$-$C_6$ alkyl, $C_1$-$C_6$ haloalkyl, halo, oxo, $C_1$-$C_6$ haloalkoxy, $C_1$-$C_6$ alkyl-O—$C_1$-$C_6$ alkoxy, H, OH, $C_1$-$C_6$ alkoxy, $C_2$-$C_6$ alkenyloxy;

(k) R4 is $C_1$-$C_6$ alkyl, $C_1$-$C_6$ alkyl-O—$C_1$-$C_6$ alkyl, $C_1$-$C_6$ haloalkyl, H, $C_1$-$C_6$ alkoxy, $C_1$-$C_6$ haloalkoxy, $C_2$-$C_6$ alkenyloxy (l) R5 is H or $C_1$-$C_6$ alkyl; and (m) n=0, 1, or 2.

While these embodiments have been expressed, other embodiments and combinations of these expressed embodiments and other embodiments, are possible.

Preparation of Pyranose-Intermediates

A wide variety of pyranoses (in different structural forms, for example, D and L) can be used to make the compounds of this invention. For example, the following non-exhaustive list of pyranoses may be used: ribose, arabinose, xylose, lyxose, ribulose, xylulose, allose, altrose, glucose, mannose, gulose, idose, galactose, talose, psicose, fructose, sorbose, tagatose, fucose, mycarose, quinovose, oleandrose, rhamnose, and paratose. In most of the examples below, L-rhamnose was used to make pyranose-intermediates.

In general, pyranose-intermediates can be made as follows (using L-rhamnose as an example). O-alkylated rhamnose derivatives can be prepared from commercially available L-rhamnose or L-rhamnose hydrate by using an alkyl iodide and powdered potassium hydroxide in dry dimethyl sulfoxide (DMSO) at from 5° C. to 15° C. The fully alkylated product is then isolated by extraction of the dimethyl sulfoxide solution with hexanes, followed by concentration of the hexane layer under vacuum. This intermediate alkyl pyranoside is then treated directly with aqueous HCl or other aqueous acid, which forms the free hydroxy sugar, usually as a mixture of α- and β-anomers.

Alternatively, the per-alkylated L-rhamnose can be isolated by hydrolysis of spinosad or other tri-(O-alkyl)rhamnosylated natural product, using conditions similar to those described for the isolation of methyl oleandroside from avermectin $B_2$ (Loewe et al. *J. Org. Chem.* 1994, 59, 7870). Thus, treatment of technical spinosad with excess concentrated sulfuric acid in dry methanol (MeOH) results in hydrolysis of the rhamnose sugar and conversion into the methyl pyranoside. The pure methylpyranoside can then be removed from the reaction medium by exhaustive extraction with hexanes or other hydrocarbon solvent. The pure rhamnopyranoside can then be isolated in ca. 65-75% overall yield by distillation of the crude liquor under vacuum.

The 3-O-ethyl-2,4-di-O-methyl rhamnose can be prepared in a similar manner, starting from spinetoram. Other alkylated derivatives can be likewise produced by starting with the appropriately functionalized spinosoid derivatives, which are made from any spinosyn factor which has one or more free hydroxyl groups attached to rhamnose (for example, spinosyn J) using conditions described in DeAmicis et al. U.S. Pat. No. 6,001,981, 1999.

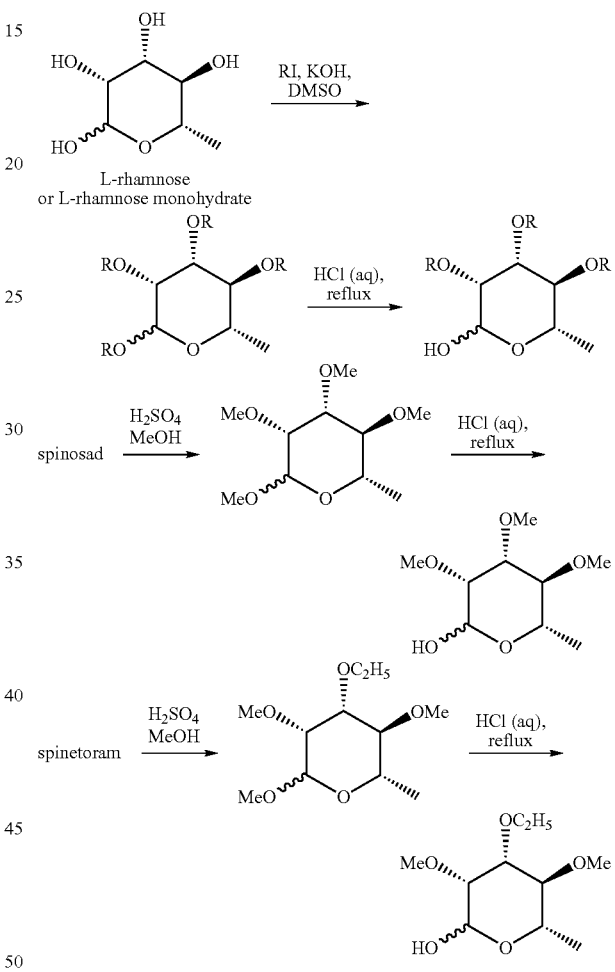

A rhamnose precursor that is selectively alkylated with a larger substituent at C3 has been described (see, for example, Pozsgay et al. *Can. J. Chem.* 1987, 65, 2764). An alternate route, which avoids the use of tin reagents, is described below. Reaction of the methylpyranoside of L-rhamnose with one equivalent of phenylboronic acid, or triphenylboroxole, under conditions that allow for removal of water, results in formation of a boron acetal. Treatment of this acetal with an alkyl halide and silver oxide, in a polar aprotic solvent such as dimethyl formamide, at from 0° C. to 110° C. results in a selective alkylation at C3-OH, giving the 3-O-alkyl methylpyranoside. This material can then be further methylated at positions 2-OH and 4-OH with methyl iodide, using conditions described previously. The fully alkylated rhamnose can then be hydrolyzed as described above to give 2,4-di-O-methyl-3-O-alkyl-L-rhamnose.

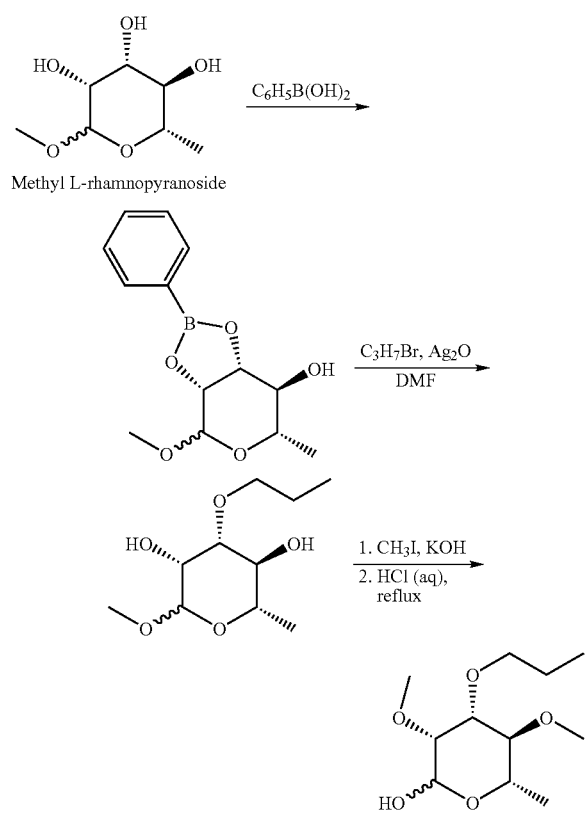

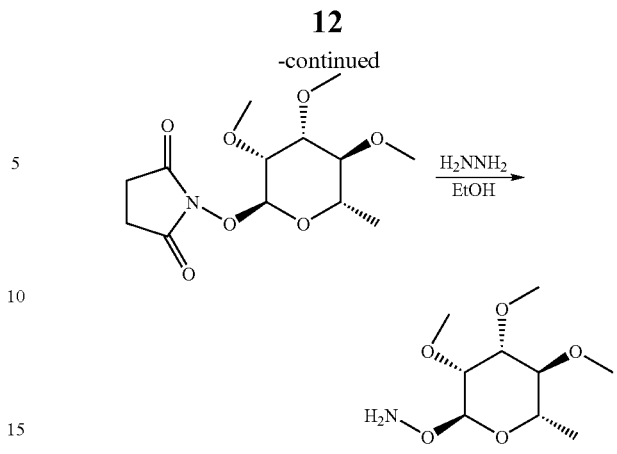

Preparation of Triaryl-Intermediates

Compounds of this invention are prepared by linking the above-described pyranoses to a triaryl intermediate, $Ar_1$-Het-$Ar_2$, by means of a covalent linker J[L]KQ (defined above). A wide variety of triaryl precursors can be used to prepare compounds of this invention, provided that they contain a suitable functional group on $Ar_2$ to which the pyranose intermediate can be attached in order to form the covalent linker. Suitable functional groups include an amino, oxoalkyl, formyl, or carboxylic acid group. These triaryl-intermediates can be prepared by methods previously described in the chemical literature. Several of these methods are described below.

Intermediates wherein 'Het' is a disubstituted pyridine, pyrimidine, pyrazine or pyridizine can be made by coupling of a halo- or alkylthio-substituted pyridine, pyrimidine or pyrazine with an aryl boronic acid or borate ester, under Suzuki arylation conditions. See, for example, the following.

For pyridines: Couve-Bonnaire et al. *Tetrahedron* 2003, 59, 2793 and Puglisi et al. *Eur. J. Org. Chem.* 2003, 1552.

For pyrazines: Schultheiss and Bosch *Heterocycles* 2003, 60, 1891.

For pyrimidines: Qing et al. *J. Fluorine Chem.* 2003, 120, 21 and Ceide and Montalban *Tetrahedron Lett.* 2006, 47, 4415.

For 2,4-diaryl pyrimidines: Schomake rand Delia, *J. Org. Chem.* 2001, 66, 7125.

Illustrations of making such pyranose-intermediates are given in the examples.

Hydroxylamino pyranose-intermediates can also be made. For example, they can be prepared from the corresponding rhamnose derivative and N-hydroxy succinimide (NHS) under conditions in which the water formed is removed azeotropically, to form an N-succinimidoyl hydroxylamine adduct. In one embodiment, these conditions involve combining rhamnose and NHS in toluene or benzene, adding a catalytic amount of an acid such as p-toluenesulfonic acid (TsOH), and heating to reflux in an apparatus equipped with a Dean-Stark trap. Conversion to the free hydroxylamine intermediate is accomplished by treatment of the succinimidoyl adduct with excess hydrazine hydrate or anhydrous hydrazine in an alcoholic solvent such as methanol (MeOH) or ethanol (EtOH). Reaction of the O-rhamnosyl hydroxylamine with an aldehyde or ketone using EtOH or other lower alcohol solvent at from ambient temperature to reflux then produces an O-rhamnosyl oxime.

Thus, successive palladium-catalyzed arylations, using 4-formylphenyl boronic acid and 4-trifluoromethoxyphenyl boronic acid, can generate virtually any particular substitution pattern, as shown in the scheme below:

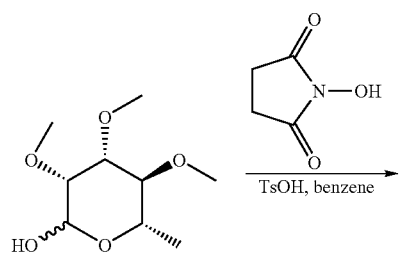

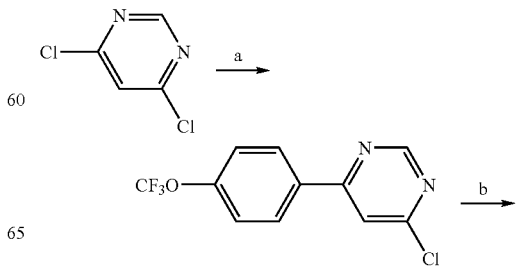

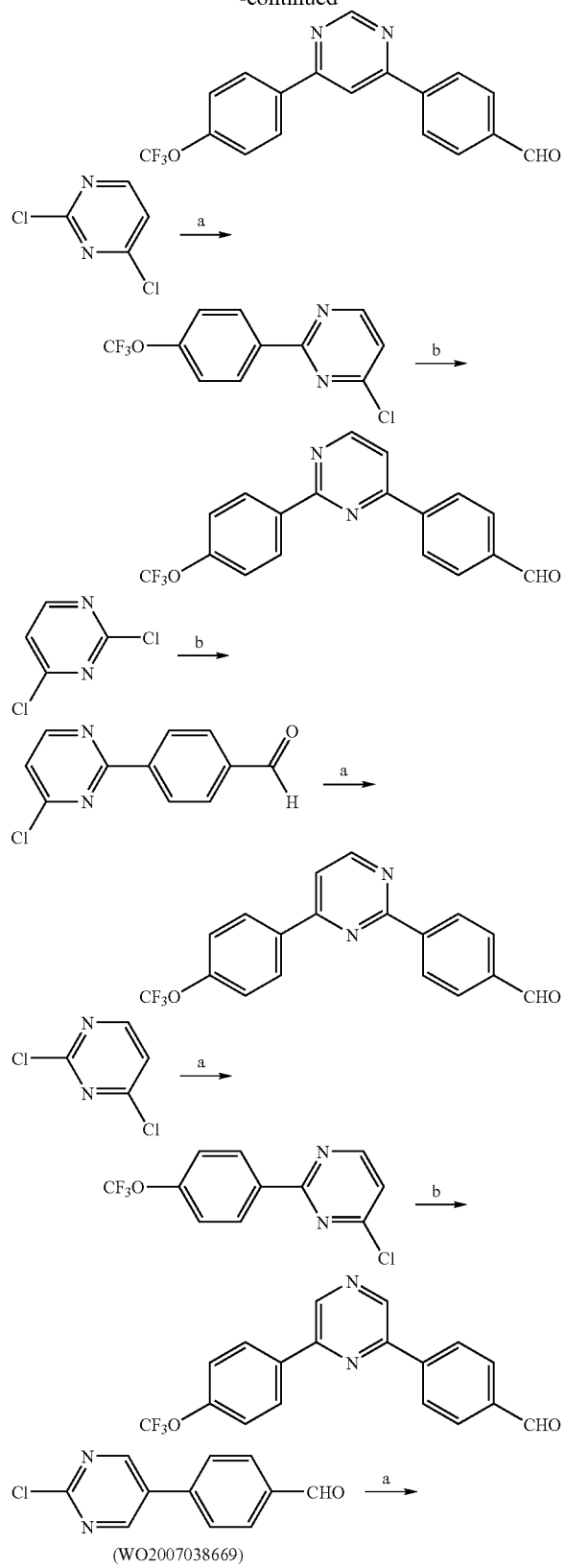
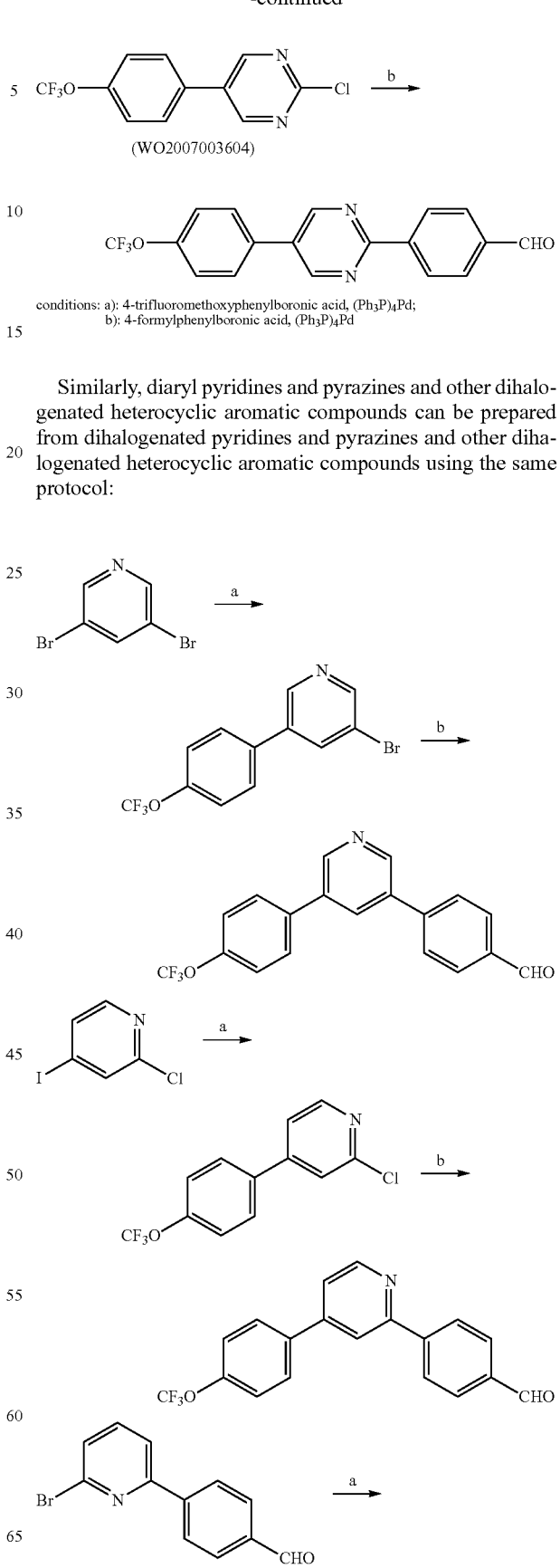
conditions: a): 4-trifluoromethoxyphenylboronic acid, (Ph₃P)₄Pd;
b): 4-formylphenylboronic acid, (Ph₃P)₄Pd
Similarly, diaryl pyridines and pyrazines and other dihalogenated heterocyclic aromatic compounds can be prepared from dihalogenated pyridines and pyrazines and other dihalogenated heterocyclic aromatic compounds using the same protocol:

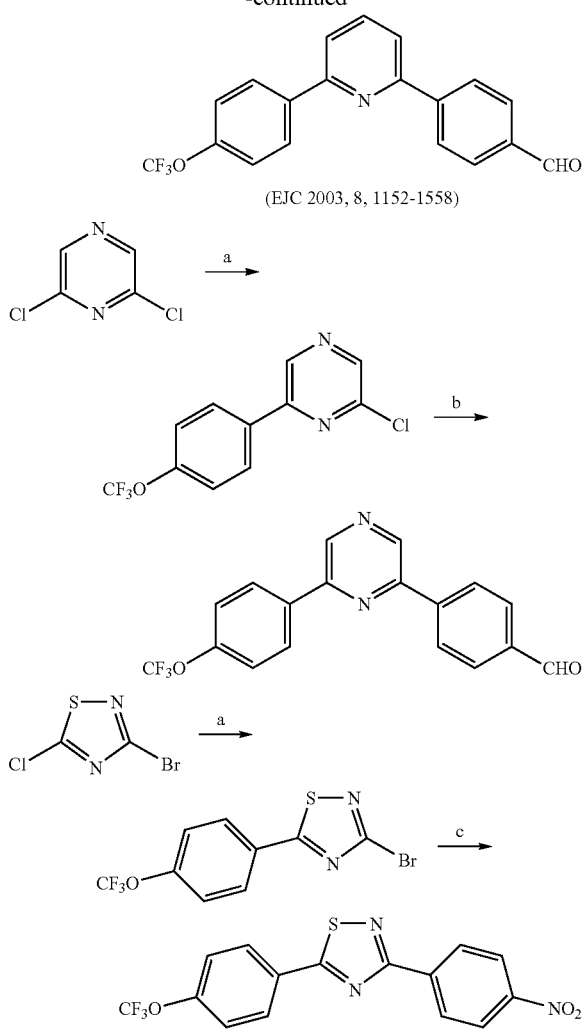

(EJC 2003, 8, 1152-1558)

conditions: a): 4-trifluoromethoxyphenylboronic acid, (Ph₃P)₄Pd;
b): 4-formylphenylboronic acid, (Ph₃P)₄Pd; c) 4-nitrophenylboronic acid, (Ph₃P)₄Pd The halo- or alkylthio-pyrimidine and pyridine precursors are either commercially available, or may be synthesized by routes described in the literature (Rorig and Wagner U.S. Pat. No. 3,149,109, 1964; Kreutzberger and Tesch *Arzneim.-Forsch.* 1978, 28, 235).

Compounds where 'Het' is a 1,3-diaryl-6-perfluoroalkyl pyrimidine can be prepared according to the following scheme. The 2-methylthio substituted pyrimidine was arylated under modified Suzuki conditions (Liebeskind and Srogl *Org. Lett.* 2002, 4, 979) to give 2-phenyl pyrimidines, which then were reduced to the corresponding anilines using, for example, a Pd/C catalyst in EtOH under hydrogen atmosphere.

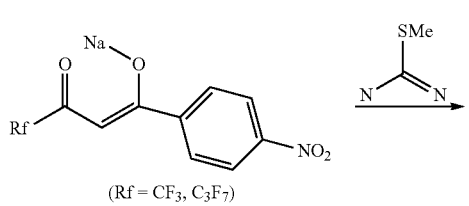

(Rf = CF₃, C₃F₇)

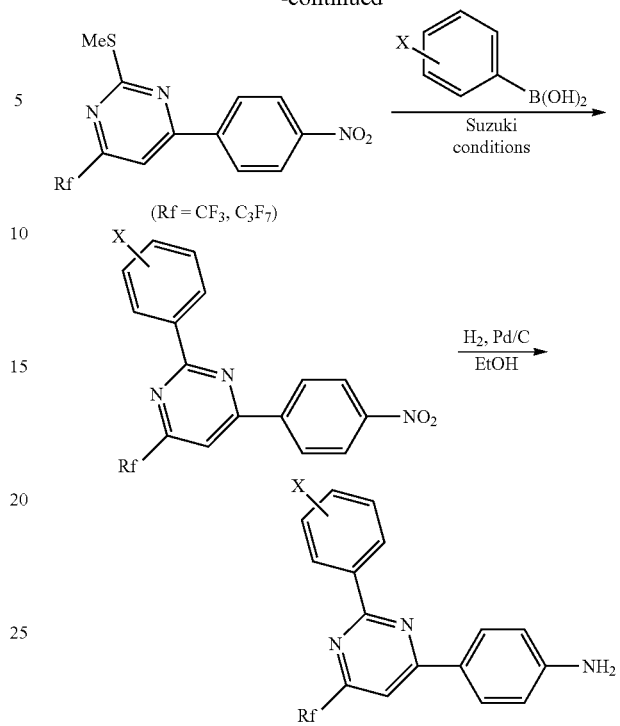

Intermediate compounds wherein 'Het' is a 1,3-disusbstituted 1,2,4-triazole can be prepared according to one of the following schemes.

Route A: 1,3-diaryl 1,2,4-triazoles were prepared from the corresponding —NH 3-aryl 1,2,4-triazoles by following a published route for N-arylation of imidazoles (Lin et al. *J. Org. Chem.* 1979, 44, 4160). Coupling of 1,2,4-triazoles to aryl halides was done under thermal or, preferably, microwave conditions (Antilla et al. *J. Org. Chem.* 2004, 69, 5578). (DIBAL is diisobutylaluminum hydride.)

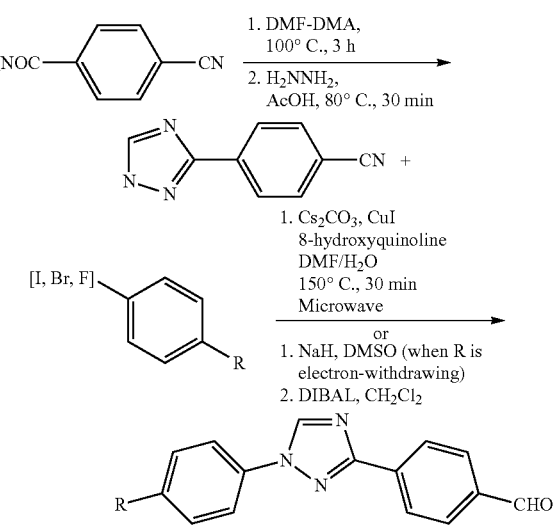

Route B: Bromination of hydrazones followed by treatment of the bromohydrazone with tetrazole results in formation of the 1,3-diaryl 1,2,4-triazole (Butler and Fitzgerald *J. Chem. Soc., Perkin Trans.* 11988, 1587).

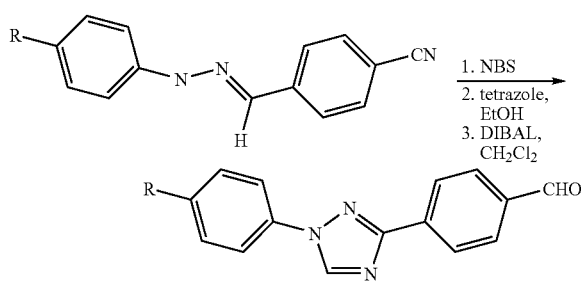

Route C. 1,2,4-Triazole compounds in which the 5-position is further substituted with an alkyl or substituted alkyl group can be prepared according to the following scheme (Paulvannan and Hale *Tetrahedron* 2000, 56, 8071):

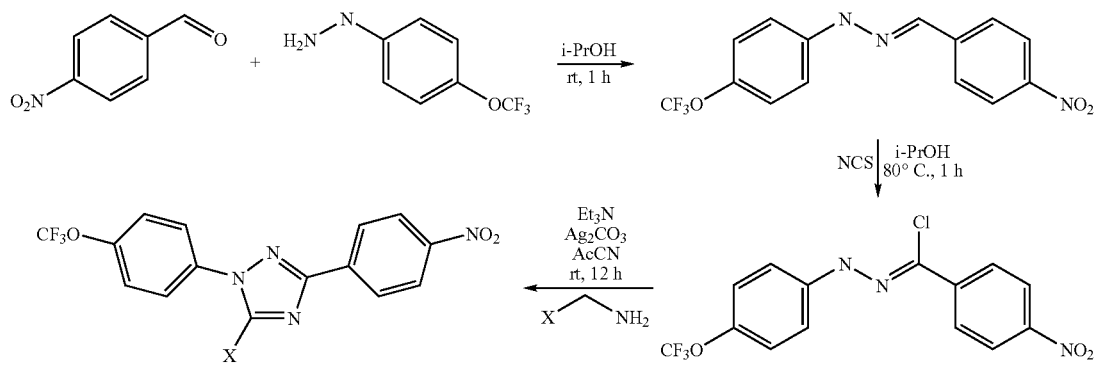

Compounds where 'Het' is an imidazole can be prepared according to one of the following schemes:

Route A (Step 1: Lynch et al. *J. Am. Chem. Soc.* 1994, 116, 11030. Step 2: Liu et al. *J. Org. Chem.* 2005, 70, 10135):

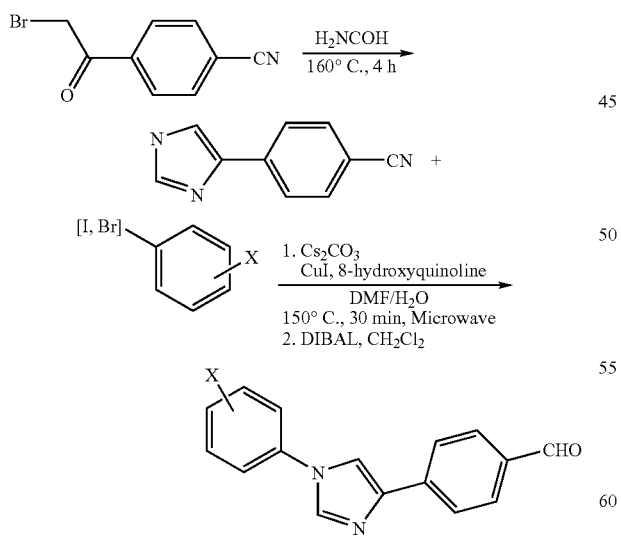

Route B. For halo-aryl groups that also contain an activating group such as nitro or cyano, displacement of an aryl halide with an imidazole, using a base such as potassium carbonate in a polar aprotic solvent such as N,N-dimethylformamide (DMF) or dimethyl sulfoxide (DMSO) can be accomplished in the following manner (Bouchet et al., *Tetrahedron* 1979, 35, 1331):

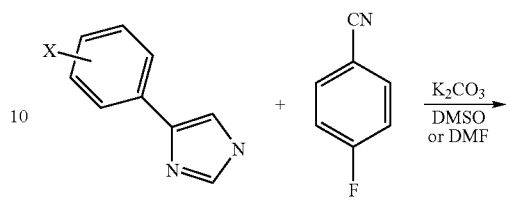

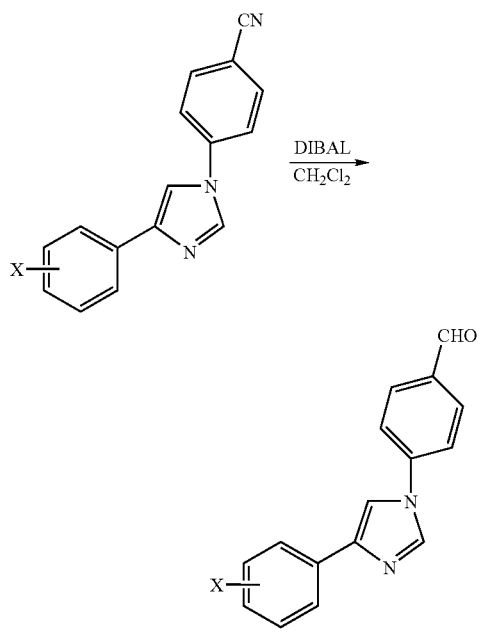

Route C: Following a procedure first described by Porretta et al. (*Farmaco, Edizione Scientifica* 1985, 40, 404), an N-phenacyl aniline is treated with potassium thiocyanate in acidic medium (HCl), and the resulting 2-mercapto imidazole is then converted into the desulfurized diaryl imidazole by treatment with nitric acid in acetic acid.

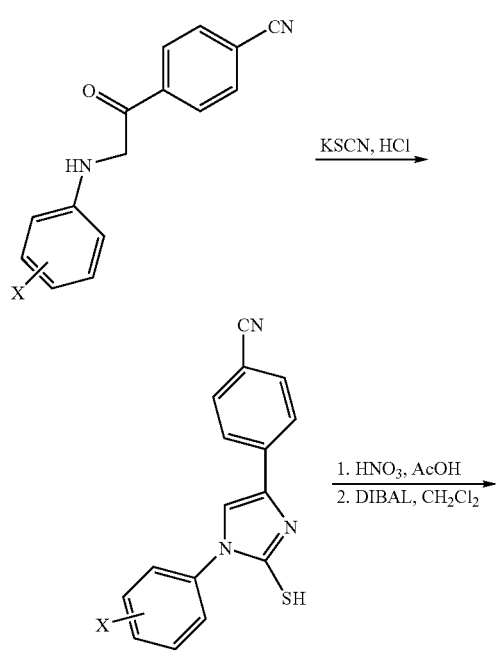

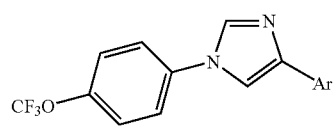

Compounds where 'Het' is a 1,4-disubstituted 1,2,3-triazole can be prepared according to the following scheme (Feldman et al. *Org. Lett.* 2004, 6, 3897):

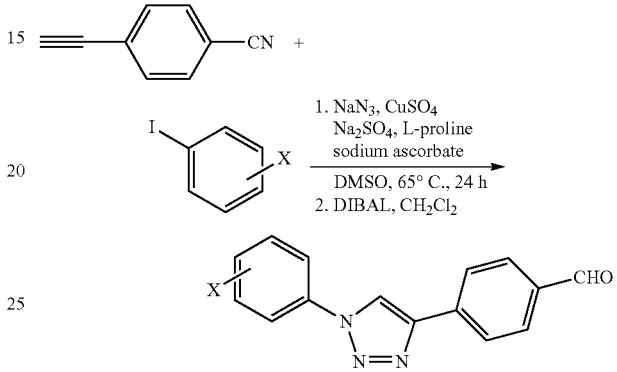

Compounds where 'Het' is a 3,5-disubstituted 1,2,4-triazole can be prepared according to the following scheme (Yeung et al. *Tetrahedron Lett.* 2005, 46, 3429):

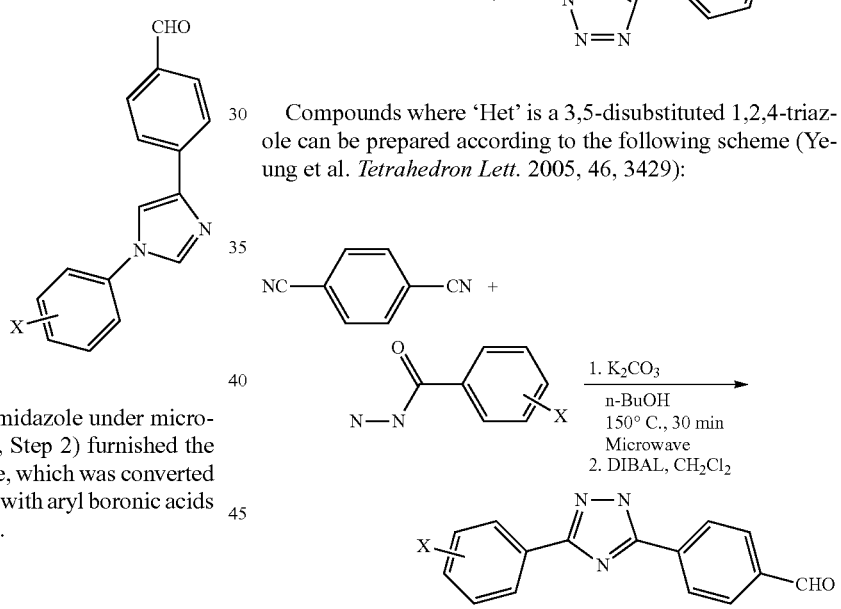

Route D. N-Arylation of 4-bromoimidazole under microwave irradiation conditions (Route A, Step 2) furnished the intermediate 1-aryl-4-bromoimidazole, which was converted into triaryl-intermediates by treatment with aryl boronic acids under palladium-catalyzed conditions.

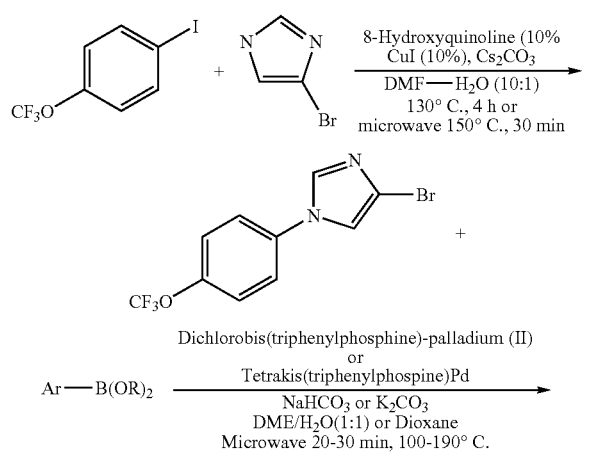

Compounds where 'Het' is a 1,3-disubstituted 1,2,4-triazolin-5-one can be prepared according to the following scheme (Pirrung and Tepper *J. Org. Chem.* 1995, 60, 2461 and Lyga *Synth. Commun.* 1986, 16, 163). (DPPA is diphenyl phosphoryl azide.):

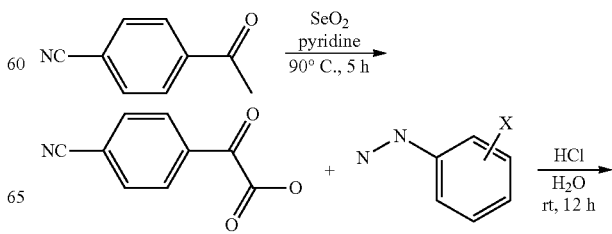

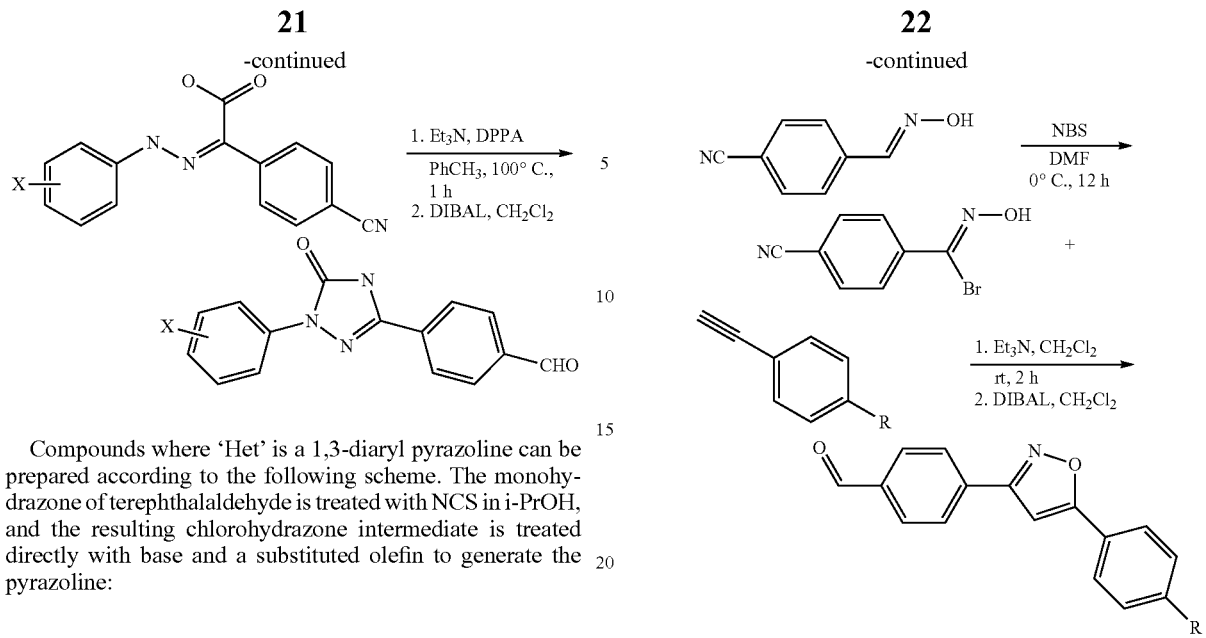

Compounds where 'Het' is a 1,3-diaryl pyrazoline can be prepared according to the following scheme. The monohydrazone of terephthalaldehyde is treated with NCS in i-PrOH, and the resulting chlorohydrazone intermediate is treated directly with base and a substituted olefin to generate the pyrazoline:

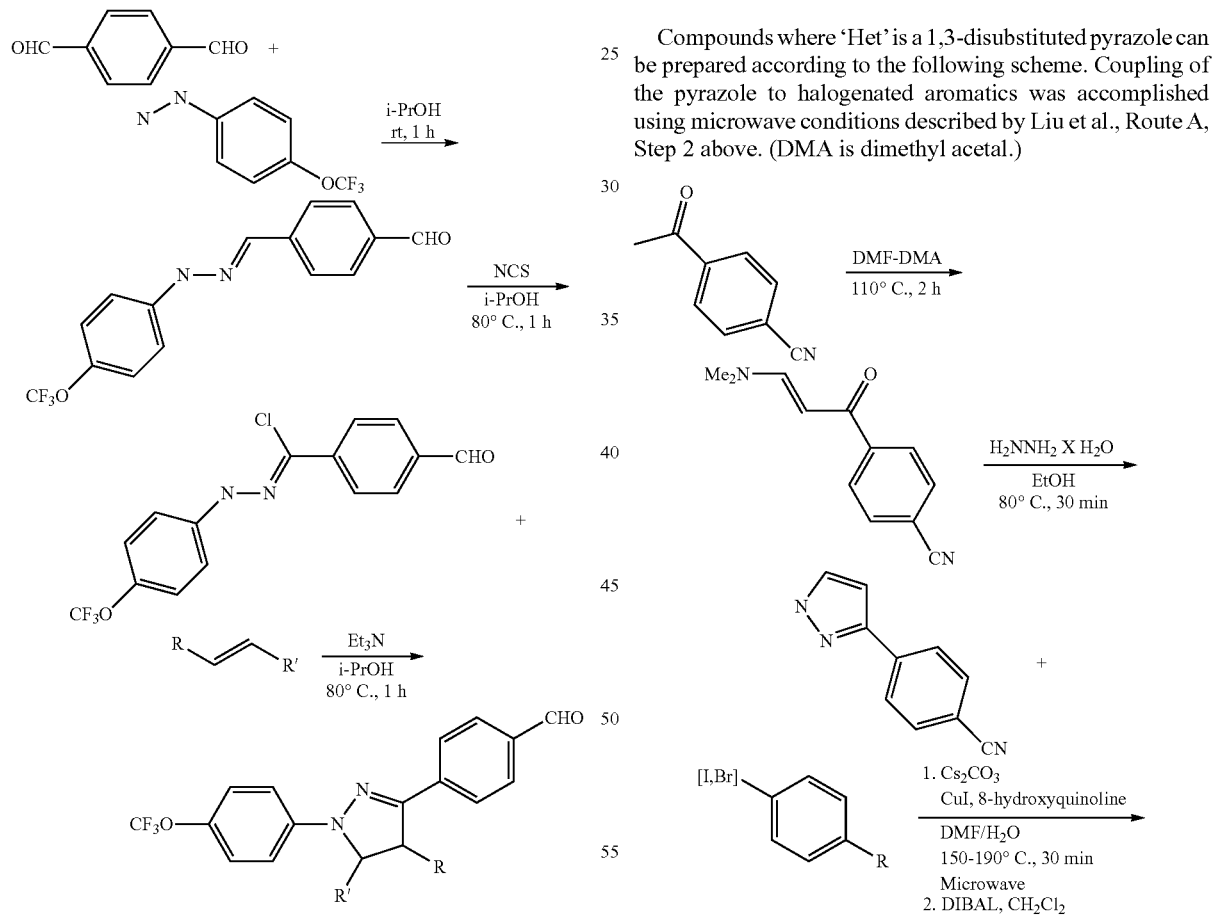

Compounds where 'Het' is a 3,5-disubstituted isoxazole can be prepared according to the following scheme:

Compounds where 'Het' is a 1,3-disubstituted pyrazole can be prepared according to the following scheme. Coupling of the pyrazole to halogenated aromatics was accomplished using microwave conditions described by Liu et al., Route A, Step 2 above. (DMA is dimethyl acetal.)

Compounds where 'Het' is a 2,4-disubstituted thiazole are prepared by condensation of a thioamide to an α-halo acetophenone in a protic solvent such as ethanol (for example, Potts and Marshall *J. Org. Chem.* 1976, 41, 129).

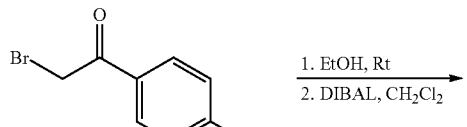

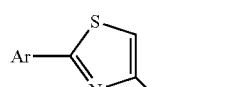

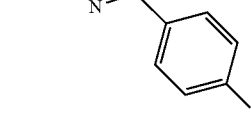

Compounds where 'Het' is a 1,4-disubstituted 1,2,4-triazolin-5-one are prepared according to the following scheme (Henbach DE 2724819 A1, 1978 with slight modification to two steps):

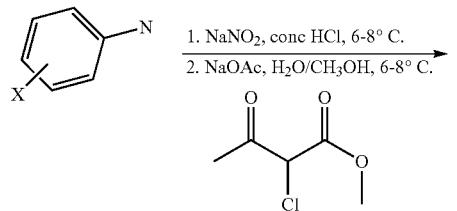

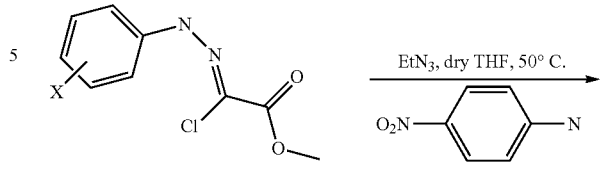

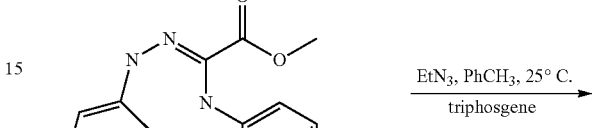

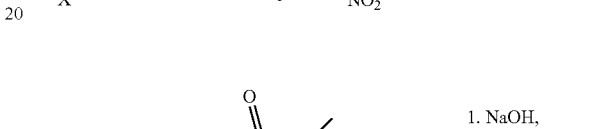

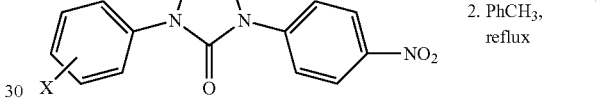

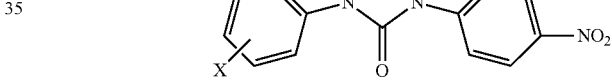

Compounds where 'Het' is a 2,4-disubstituted oxazoline are prepared starting from the α-bromoacetophenone according to the following scheme (Periasamy et al. *Synthesis* 2003, 1965 and Liu et al. *J. Am. Chem. Soc.* 2007, 129, 5834).

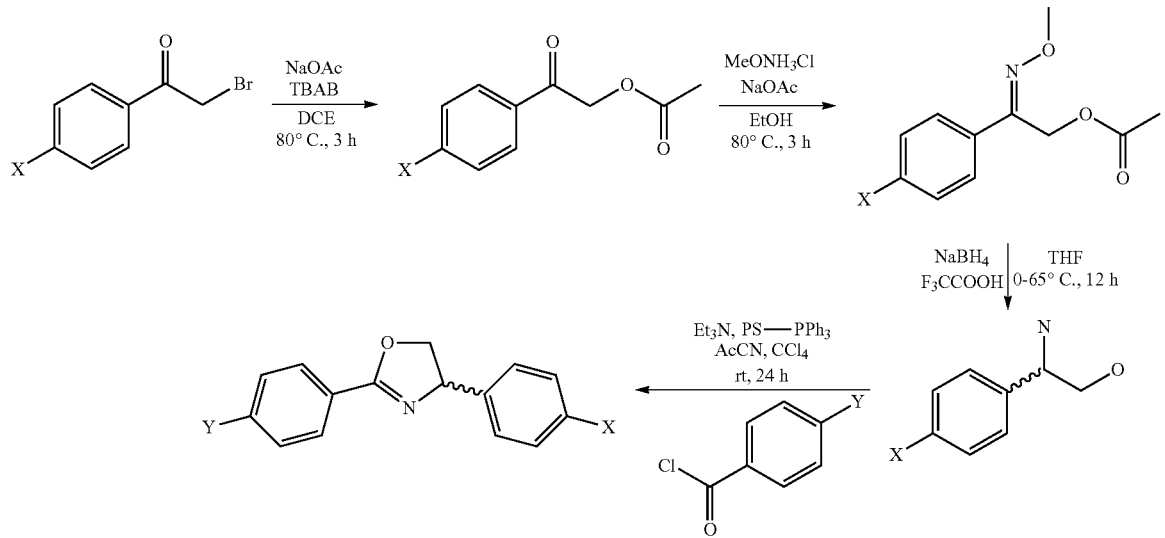

Compounds where 'Het' is a 2,5-disubstituted oxazoline are prepared according to the following scheme (Favretto et al. *Tetrahedron Lett.* 2002, 43, 2581 and Liu et al. *J. Am. Chem. Soc.* 2007, 129, 5834):

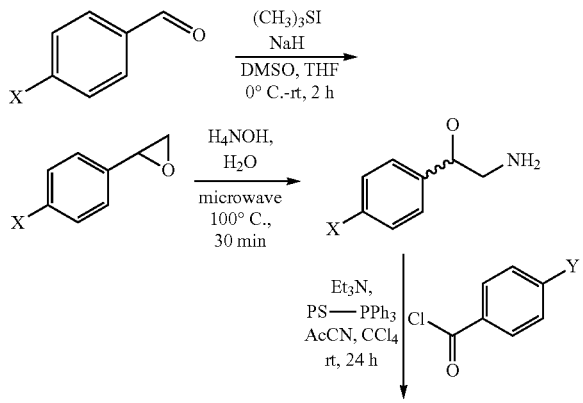

Compounds where 'Het' is a 1,4-disubstituted piperazine are prepared according to the following scheme (Evans et al. *Tetrahedron Lett.* 1998, 39, 2937):

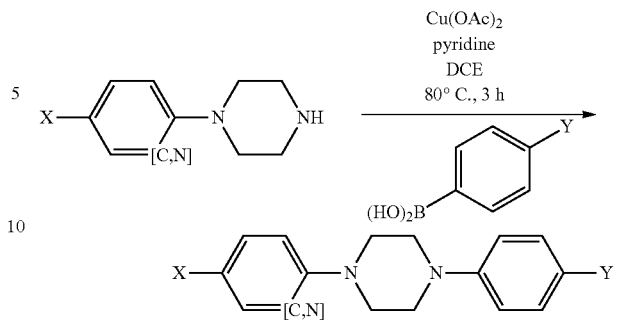

Compounds where 'Het' is a 1,3-disubstituted pyrazoline are prepared by addition of an aryl hydrazine to a β-dimethylamino propiophenone as shown in the following scheme, which is described in Linton et al. *Tetrahedron Lett.* 2007, 48, 1993, and Wheatley et al. *J. Am. Chem. Soc.* 1954, 76, 4490. In addition to the pyrazoline, a minor amount of bis-addition leads to the corresponding dimethylaminomethyl pyrazoline. These materials can be separated chromatographically.

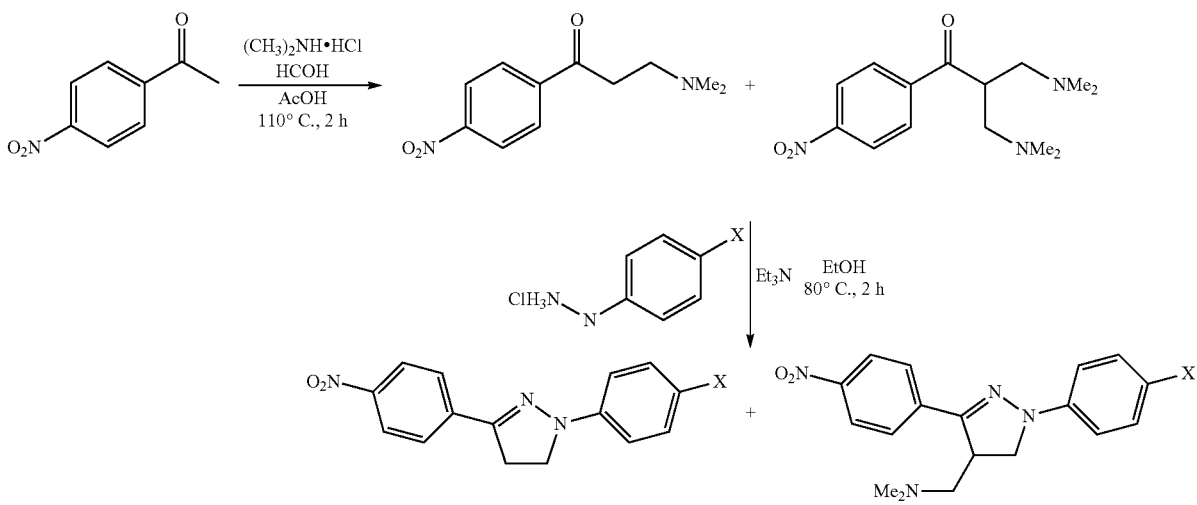

Compounds where 'Het' is a 3,5-disubstituted 1,2,4-triazine are prepared according to the following scheme (Reid et al. *Bioorg. Med. Chem. Lett.* 2008, 18, 2455 and Saraswathi and Srinivasan *Tetrahedron Lett.* 1971, 2315):

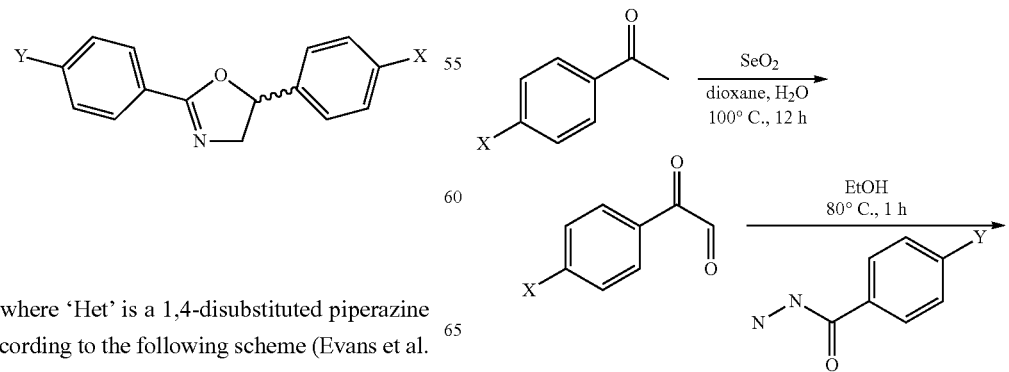

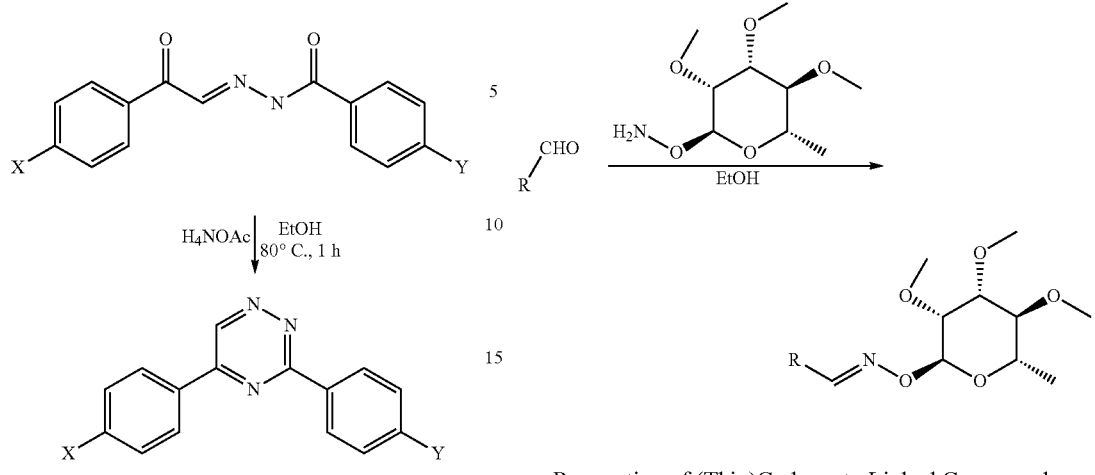

Compounds where 'Het' is a 2-ketopiperazine or 2,5-diketopiperazine are prepared as in the following scheme. The nitrophenyl glycine ester can be acylated using chloroacetyl chloride, and the intermediate N-chloroacetylated glycine ester, upon treatment with an aniline, undergoes displacement and ring closure at from 120 to 180° C. to form a diketopiperazine. Alternatively, monoketo saturated or unsaturated piperazines can be formed from the acetal intermediate below, by hydrolysis and ring closure.

Preparation of (Thio)Carbamate-Linked Compounds

Carbamate- or thio-carbamate linked compounds can be prepared from the corresponding aryl amines by conversion into either an isocyanate, isothiocyanate or p-nitrophenyl carbamate, followed by treatment with the appropriate alcohol (ROH) and an organic or inorganic base in a suitable solvent such as tetrahydrofuran (THF), at temperatures between 0 and 100° C.

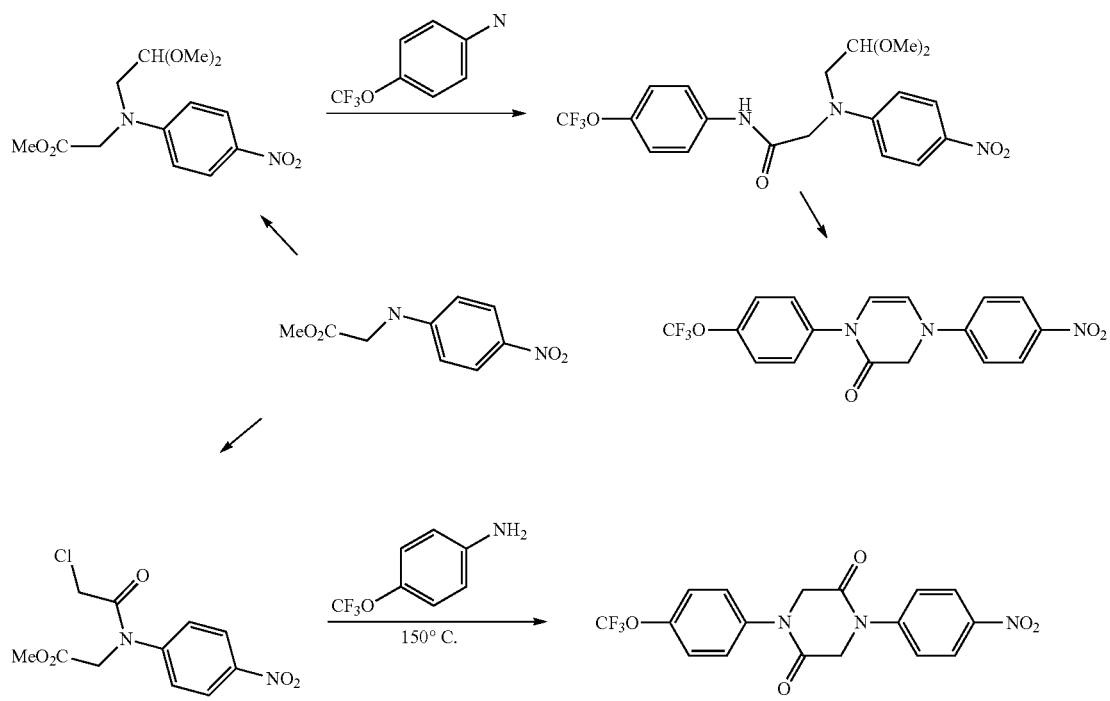

Preparation of Oxime-Linked Compounds

Oxime-linked compounds can be prepared from the corresponding aryl aldehydes or ketones by reaction with the corresponding 2-hydroxylamino sugar, in an organic solvent such as MeOH or EtOH, at temperatures between 0 and 100° C.

Alternatively, an isocyanate intermediate can be generated from the carboxylic acid by treating with a source of azide such as diphenylphosphoryl azide (DPPA). The acyl azide then can be made to undergo a Curtius rearrangement by heating to 110° C. in toluene, and the resulting isocyanate treated with an appropriate sugar and a base as described above to generate the carbamate.

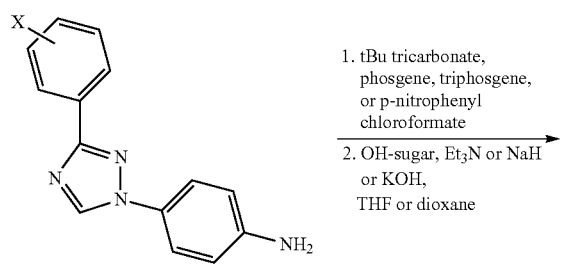

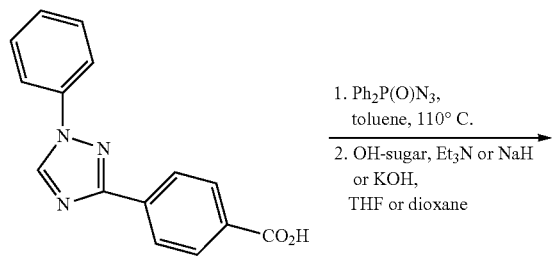

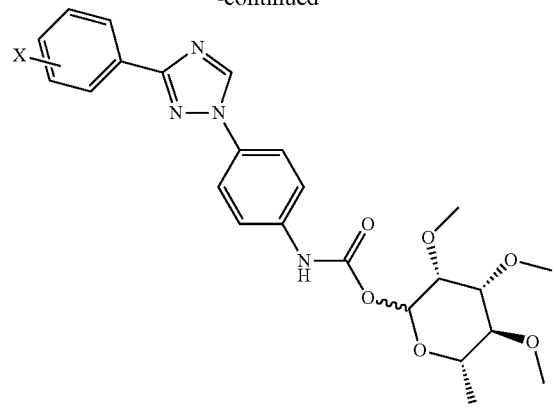

In these reactions, the α-configuration at C1 of the rhamnose moiety is usually the major product, although a minor amount of the β-anomer is also formed. These two isomers may be separated by chromatography, or they may be used as a mixture.

Carbamates can also be prepared via nitrophenyl carbonates as shown later. It is advantageous to treat the pyrimidinylaniline first with a strong base such as lithium or potassium hexamethlydisilazide (HMDS) followed by the nitrophenyl carbonate. The p-nitrophenyl carbonate can be prepared by reaction of the tri-O-methylrhamnose hemi-acetal with p-nitrophenyl chloroformate in pyridine/dioxane.

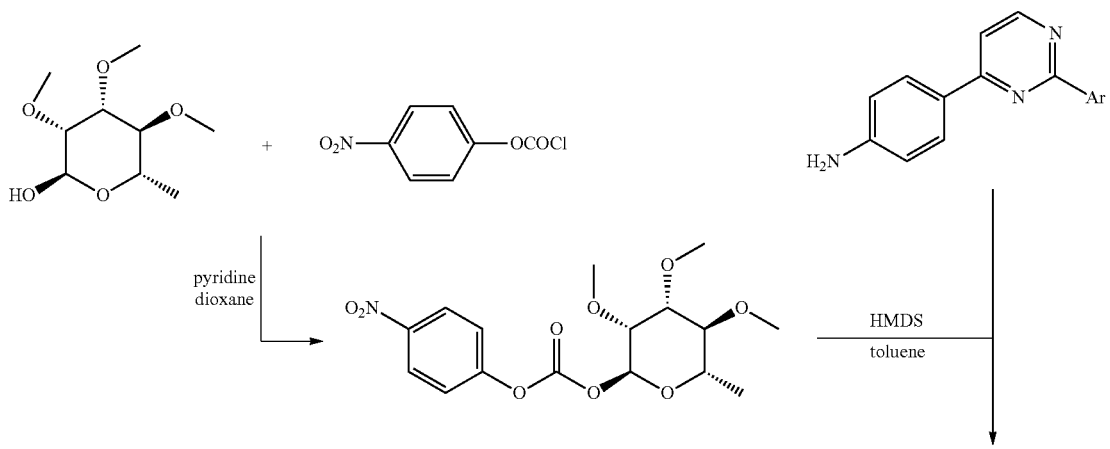

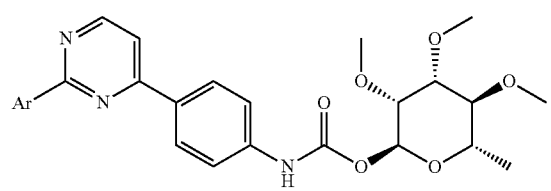

Thio-carbamate derivatives can be prepared from the S-alkyl rhamnose, which is generated from the rhamnosyl pyranoside by treatment with Lawesson's reagent (Bernardes et al. *Angew. Chem. Int. Ed.* 2006, 45, 4007). Treatment of the glycosyl thiol with an isocyanate or p-nitrophenyl carbamate and an organic base such as triethylamine furnishes the thio-carbamate.

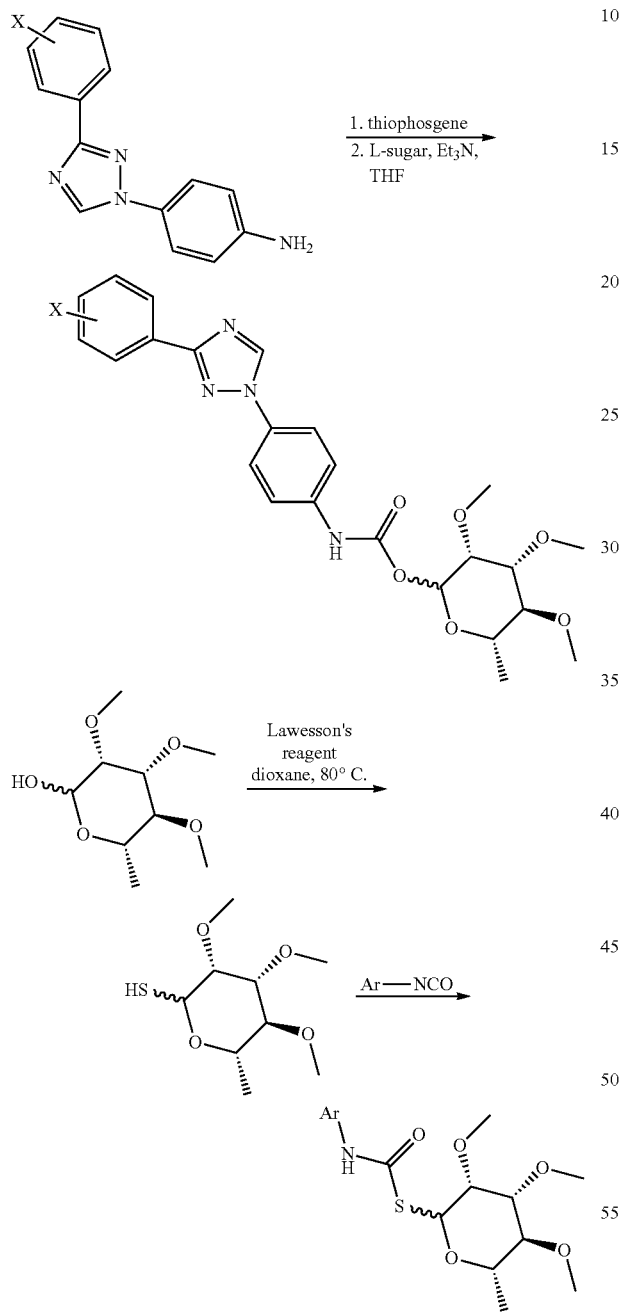

Preparation of Hydroxamate-Linked Compounds

Hydroxamic ester-linked compounds can be prepared by treatment of an acid chloride with the hydroxylamine and an organic base such as triethylamine:

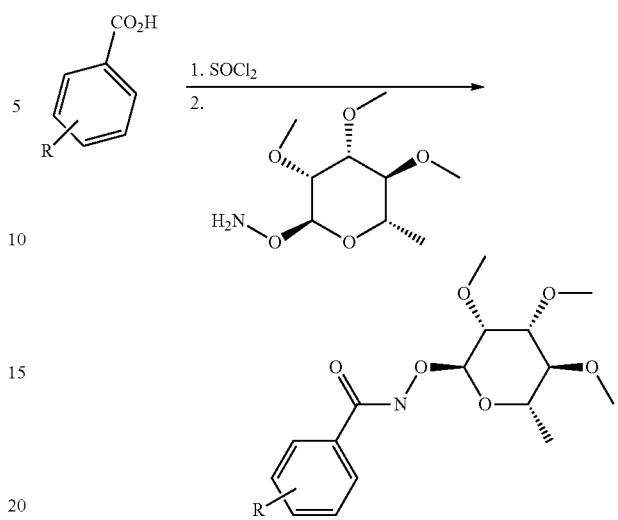

Preparation of compounds within the scope of this invention can be done by the synthesis of an appropriate triaryl intermediate containing an acid, aldehyde, ketone, or amino functional group for attachment to the pyranose-intermediate.

EXAMPLES

These examples are for illustration purposes and are not to be construed as limiting the invention disclosed in this document to only the embodiments disclosed.

Example 1

Preparation of (3R,4R,5S,6S)-2,3,4,5-tetramethoxy-6-methyl-tetrahydropyran (Compound E-1)

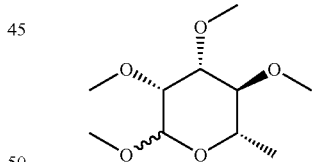

A solution of L-rhamnose hydrate (40 g, 0.22 mol) in 450 mL of dry dimethyl sulfoxide was placed in a 2 L 3-neck round bottom flask and stirred mechanically while powdered KOH (75 g, 1.34 mol) was added in one portion. Iodomethane (187 g, 1.32 mol) was added to this solution at a rate such that the temperature of the solution was maintained below 30° C. A dry ice-acetone bath was used intermittently to maintain this temperature. After the addition was complete (about 2 h), the solution was stirred an additional 3 h, then it was allowed to stand at ambient temperature overnight. This clear solution was then extracted with 4×500 mL of hexanes, and the combined hexane solution was washed with brine before drying and evaporation of solvent. There was obtained 44 g (92%) of a light orange solution. Distillation gave 40 g of a colorless oil, bp 150° C. (0.5 mm Hg).

Example 2

Preparation of (3R,4R,5S,6S)-3,4,5-trimethoxy-6-methyl-tetrahydropyran-2-ol (Compound E-2)

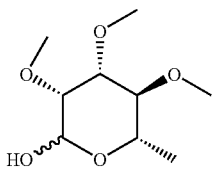

A solution of 35.7 g (0.162 mol) of E-1 in 300 mL of 2 N hydrochloric acid was heated at 98° C. for 5 h, was then cooled to room temperature, and was extracted with four 170-mL portions of dichloromethane (DCM). The combined extracts were dried over magnesium sulfate and decolorized with charcoal. Concentration gave 24.7 g (74%) of the titled compound as a viscous oil. A portion of the crude product (960 mg) was vacuum distilled using a Kuhgelrohr apparatus collecting 890 mg at 145-155° C. (1-2 mm).

Example 3

Preparation of (3R,4R,5S,6S)-4-ethoxy-2,3,5-trimethoxy-6-methyl-tetrahydropyran (Compound E-3)

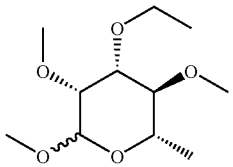

Sulfuric acid (300 mL, 98%, 5.6 mol) was added slowly to a stirred solution of 2.5 L of methanol in a 4 L Erlenmeyer flask. When the solution had cooled to ambient temperature, 3'-OEt spinosyn J/L (350 g, 0.47 mol, prepared as in DeAmicis et al., U.S. Pat. No. 6,001,981, 1999) was added and the resulting solution was heated at reflux for 6 h. The cooled solution was transferred to a 4 L separatory funnel and extracted with 3×1 L of hexanes. The combined organic solution was dried and concentrated in vacuo, then distilled using a Kugelrohr apparatus. There was obtained 65 g (60%) of colorless oil, bp 165° C. (10 mTorr).

Example 4

Preparation of (2R,3R,4R,5S,6S)-2,3,5-trimethoxy-6-methyl-4-propoxy-tetrahydropyran (Compound E-5)

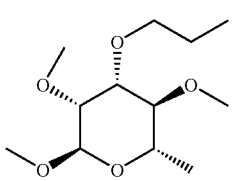

Step 1. (2R,3R,4R,5R,6S)-2-Methoxy-6-methyl-4-propoxy-tetrahydropyran-3,5-diol. Following the procedure described by Aoyama et al. (*Tetrahedron Lett.* 1997, 38, 5001) for preparation of the 3,4-boronate ester of methyl α-L-fucopyranoside, methyl α-L-rhamnopyranoside was converted into the 2,3-boronate ester. The crude ester (10.0 g, 37.7 mmol) was dissolved in 150 mL of toluene and treated with iodopropane (8.0 g, 47 mmol), silver oxide (21.8 g, 94.3 mmol) and triethylamine (4.77 g, 47.1 mmol). The solution was heated to 100° C. and allowed to stir overnight (16 h). After cooling and filtering, the solution was concentrated to a gummy oil and was purified by silica gel chromatography eluting with an EtOAc-hexane gradient to obtain 5.9 g of pure product.

Step 2. The material from Step 1 was methylated using MeI and KOH, under conditions described in Example 1 to furnish compound E-4.

The pyranose-intermediates listed in Table 1 (Compounds E-1 through E-E-22) were prepared by the routes described earlier and illustrated in Examples 1-4.

An example of the preparation of 2-O-succinimidoyl pyranose-intermediates is described below.

Example 5

Preparation of 1-((2S,3R,4R,5S,6S)-3,4,5-trimethoxy-6-methyl-tetrahydropyran-2-yloxy)-pyrrolidine-2,5-dione (Compound E-23)

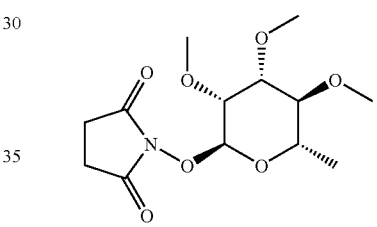

To a stirred solution of 2,3,4-tri-O-methyl-L-rhamnose (6.5 g, 31.5 mmol) and N-hydroxysuccinimide (5.4 g, 47 mmol) in 50 mL of benzene was added 50 mg (cat) of p-toluenesulfonic acid. The solution was heated to reflux and water was collected using a Dean-Stark trap. After 4 h, the solution was cooled and the supernatant toluene layer was separated from a small amount of insoluble gum. The organic layer was washed with 20 mL of saturated NaHCO$_3$ solution, then dried over MgSO$_4$ and concentrated to a solid. Recrystallization from ether-hexanes gave 4.95 g (52%) of the title compound as an off-white solid.

Example 6

Preparation of 1-((2S,3R,4R,5S,6S)-5-hydroxy-3,4-dimethoxy-6-methyl-tetrahydropyran-2-yloxy)-pyrrolidine-2,5-dione (Compound E-24)

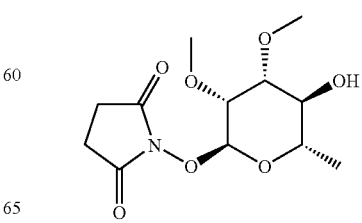

A solution of (2R,3R,4R,5S,6S)-5-benzyloxy-3,4-dimethoxy-6-methyl-tetrahydropyran-2-ol (10.5 g, 26.6 mmol, prepared according to Wu et al. *Carbohydr. Res.* 1998, 306, 493), N-hydroxysuccinimide (5.0 g, 50 mmol) and TsOH (250 mg, cat.) in 100 mL of benzene was heated at reflux for 24 h with removal of water using a Dean-Stark trap. The brown solution was cooled, filtered, washed with saturated sodium bicarbonate solution and concentrated. The gummy oil was purified by chromatography on silica gel, eluting with 70:30 hexanes:acetone. The pure O-succinimide (7.5 g, 14.5 mmol) was then transferred to a 500 mL Parr hydrogenation apparatus and debenzylated using 0.95 g of Pd(OH)$_2$/C in 75 mL of EtOH. The solution, which took up 19 psi of hydrogen over 24 h, was then filtered and concentrated, leaving a solid residue which was recrystallized from EtOH to give 3.25 g of a white solid.

The O-succinimidyl pyranose-intermediates listed in Table 2 (Compounds E-23 through E-29) were prepared by the routes described earlier and illustrated in Examples 5 and 6.

An example of the preparation of 2-hydroxylamino pyranose-intermediates from the corresponding O-succinimidoyl pyranose-intermediates is described next.

Example 7

Preparation of O-((2S,3R,4R,5S,6S)-3,4,5-trimethoxy-6-methyl-tetrahydropyran-2-yl)-hydroxylamine (Compound E-30)

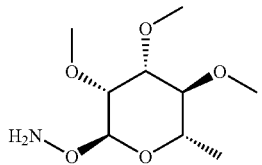

The 2,3,4-tri-O-methyl-N-succinimidyl rhamnose derivative E-23 (0.50 g, 1.6 mmol), prepared according to Example 5 was dissolved in 5 mL of absolute EtOH and treated with an excess of hydrazine hydrate (0.4 g, 8 mmol). The solution was allowed to stir at ambient temperature for 60 min, whereupon a voluminous white precipitate formed. An additional 5 mL of EtOH was added, and the solution was stirred at ambient temperature overnight. The solution was filtered and concentrated, then purified by chromatography (100% EtOAc) to furnish E-30 as a crystalline solid.

The pyranose-intermediates in Table 3 (Compounds E-30 through E-38) were prepared by the routes described earlier and as illustrated in Example 7.

Examples 8-63 illustrate the preparation of additional molecules useful in making various embodiments of this invention.

Example 8

Preparation of 4-[1-(4-trifluoromethoxyphenyl)-1H-pyrrol-3-yl]-benzaldehyde

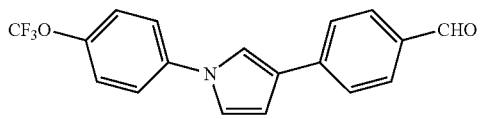

Step 1. 1-(4-Trifluoromethoxyphenyl)-1H-pyrrole. The compound was prepared according to Colotta et al. *J. Med. Chem.* 2006, 49, 6015. A solution of 4-trifluoromethoxyphenyl amine (500 mg, 2.82 mmol, 1.00 eq) and 2,5-diethoxy tetrahydrofuran (452 mg, 2.82 mmol, 1.00 eq) in glacial acetic acid (20 mL) was heated at 90° C. for 1 h before being dried onto silica gel. The residue was then slurried in refluxing hexane, filtered hot, and concentrated to dryness affording the desired intermediate (519 mg, 81%).

Step 2. 3-Bromo-1-(4-trifluoromethoxyphenyl)-1H-pyrrole. The compound was prepared according to Bray et al. *J. Org. Chem.* 1990, 55, 6317. To a solution of 1-(4-trifluoromethoxyphenyl)-1H-pyrrole (519 mg, 2.29 mmol, 1.00 eq) in THF (250 mL) at −78° C. was added a 0.05 M solution of N-bromosuccinimide (408 mg, 2.29 mmol, 1.00 eq) in THF over 45 min. The vessel was slowly warmed to room temperature before concentration to afford the crude bromopyrrole, which was shown to consist of 55% desired intermediate by GC/MS. The material was used in the subsequent reaction without further purification.

Step 3. 4-[1-(4-Trifluoromethoxyphenyl)-1H-pyrrol-3-yl]-benzaldehyde. A suspension of crude 3-bromo-1-(4-trifluoromethoxyphenyl)-1H-pyrrole (356 mg, 1.26 mmol, 1.00 eq), 4-formylphenylboronic acid (283 mg, 1.89 mmol, 1.50 eq), bis(triphenylphosphine)palladium(II) dichloride (27 mg, 0.04 mmol, 0.03 eq), 2 M Na$_2$CO$_3$ (aq) (1.26 mL, 2.52 mmol, 2.0 eq), and 1,4-dioxane (5 mL) were heated at 150° C. in a microwave reaction vessel for 45 min. The cooled solution was then diluted with EtOAc (20 mL), filtered over Celite®, concentrated to dryness, and purified via chromatography (2:2:1, hexane:EtOAc:acetone) to afford the desired intermediate (79 mg, 21%).

Example 9

Preparation of 4-[1-(4-trifluoromethoxyphenyl)-4,5-dihydro-1H-pyrazol-3-yl]-benzaldehyde

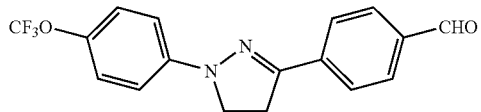

Step 1. 1-(4-Trifluoromethoxyphenyl)-pyrazolidin-3-one: The compound was prepared according to Rees and Tsoi *Chem. Commun.* 2000, 415. A suspension of (4-trifluoromethoxyphenyl)-hydrazine hydrochloride (300 mg, 1.32 mmol, 1.00 eq), 3-chloropropionyl chloride (167 mg, 1.32 mmol, 1.00 eq), and PS-DIEA (1.30 g, 5.28 mmol, 4.00 eq) in THF (20 mL) was stirred at ambient temperature for 12 h. The solution was then filtered, concentrated to dryness, and purified via chromatography (2:2:1, hexane:EtOAc:acetone) to afford the desired intermediate (120 mg, 37%).

Step 2. 3-Chloro-1-(4-trifluoromethoxyphenyl)-4,5-dihydro-1H-pyrazole: The general procedure was taken from Wang et al. *Tetrahedron Lett.* 2005, 46, 2631. To a solution of 1-(4-trifluoromethoxyphenyl)-pyrazolidin-3-one (120 mg, 0.49 mmol, 1.00 eq) in toluene (20 mL) was slowly added phosphoryl chloride (22.5 mg, 1.47 mmol, 3.00 eq). The mixture was then heated at 80° C. for 1 h before cooling to room temperature and quenching with H$_2$O (10 mL). The vessel was stirred under an atmosphere of N$_2$ for 8 h before the product was extracted into EtOAc (200 mL), dried (MgSO$_4$), and concentrated under reduced pressure. GC/MS proved 88% formation of the desired intermediate, which was used in subsequent reactions without further purification.

Step 3. 4-[1-(4-Trifluoromethoxyphenyl)-4,5-dihydro-1H-pyrazol-3-yl]-benzaldehye: A suspension of 3-chloro-1-(4-trifluoromethoxyphenyl)-4,5-dihydro-1H-pyrazole (114 mg, 0.43 mmol, 1.00 eq), 4-formylphenylboronic acid (97 mg, 0.65 mmol, 1.50 eq), bis(triphenylphosphine)palladium (II) dichloride (10 mg, 0.01 mmol, 0.03 eq), 2 M Na$_2$CO$_3$ (aq) (0.43 mL, 0.86 mmol, 2.0 eq), and 1,4-dioxane (5 mL) were heated at 150° C. in a microwave reaction vessel for 45 min. The cooled solution was then diluted with EtOAc (20 mL), filtered over Celite®, concentrated to dryness, and purified via chromatography (2:2:1, hexane:EtOAc:acetone) to afford the desired intermediate (50 mg, 0.15 mmol, 31%).

Example 10

Preparation of 4-[1-(5-bromo-2-chlorophenyl)-1H-imidazol-4-yl]-benzaldehyde

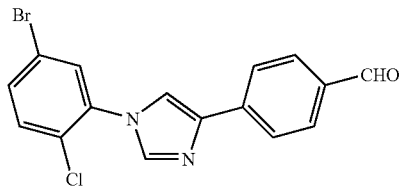

Step 1. 4-[1-(5-Bromo-2-chlorophenyl)-1H-imidazol-4-yl]-benzonitrile.

The compound was prepared according to Liu et al. *J. Org. Chem.* 2005, 70, 10135. 4-(1H-Imidazol-4-yl)-benzonitrile, (75 mg, 0.44 mmol, prepared from 4-(2-bromo-acetyl)-benzonitrile using the method of Lynch et al. *J. Am. Chem. Soc.* 1994, 116, 11030), 4-bromo-1-chloro-2-iodobenzene (169 mg, 0.532 mmol), Cs$_2$CO$_3$ (577 mg, 1.77 mmol), CuI (3 mg, 0.013 mmol), 8-hydroxyquinoline (2 mg, 0.013 mmol), and DMF/H$_2$O (2 mL 10:1 solution) were combined in a 10 mL CEM Microwave reaction vessel fitted with magnetic stir bar and subjected to microwave irradiation at 150° C. for 30 min. The contents were then filtered and concentrated to dryness affording intermediate 5-bromo-2-chlorophenyl)-1H-imidazol-4-yl]-benzonitrile (68 mg, 43%).

Step 2. 4-[1-(5-Bromo-2-chlorophenyl)-1H-imidazol-4-yl]-benzaldehyde. To a suspension of the nitrile (68 mg, 0.19 mmol) in DCM (3 mL) at −78° C. was slowly added diisobutylaluminum hydride (DIBAL) in toluene (0.48 mL, 0.475 mmol). The ice bath was then removed and the temperature allowed to warm to between 0 and 10° C. where it was held for 2 h. The contents were again cooled to −78° C. and slowly made acidic (pH=6) with 1 N HCl (aq). The flask was warmed to ambient temperature overnight before removal of the remaining aluminum salts by filtration. The filtrate was then washed with H$_2$O (5 mL), brine (5 mL), dried (Mg$_2$SO$_4$), and concentrated to dryness affording the intermediate 1-(5-bromo-2-chlorophenyl)-1H-imidazol-4-yl]-benzaldehyde (33 mg, 48%).

Example 11

Preparation of 4-[5-(4-Propylphenyl)-isoxazol-3-yl]-benzaldehyde

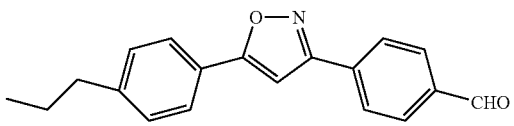

Step 1. 4-(Hydroxyiminomethyl)-benzonitrile. The compound was prepared according to Biasotti et al. *Bioorg. Med. Chem.* 2003, 11, 2247. A suspension of 4-formylbenzonitrile (500 mg, 3.81 mmol, 1.00 eq), hydroxylamine hydrochloride (290 mg, 4.19 mmol, 1.10 eq), and sodium acetate (1.56 g, 19.05 mmol, 5.00 eq) in MeOH (50 mL) was heated at 70° C. for 4 h before concentration to dryness. The residue was then slurried in Et$_2$O, filtered, and concentrated to afford the desired intermediate (496 mg, 3.39 mmol, 89%).

Step 2. 4-(Hydroxyimino-bromomethyl)-benzonitrile. The compound was prepared according to Tanaka et al. *Bull. Chem. Soc. Jpn.* 1984, 57, 2184. A 0.05 M solution of N-bromosuccinimide (724 mg, 4.07 mmol, 1.20 eq) in DCM was added dropwise to a 0° C. solution of 4-(hydroxyiminomethyl)-benzonitrile (496 mg, 3.39 mmol, 1.00 eq) in DCM (50 mL). The solution was warmed to room temperature before being volumetrically partitioned between two different reaction vials. Each vial was then concentrated and the crude residues were used without further purification.

Step 3. 4-[5-(4-Propylphenyl)-isoxazol-3-yl]-benzonitrile. A solution of 4-(hydroxyimino-bromomethyl)-benzonitrile (381 mg, 1.70 mmol), triethylamine (0.71 mL, 5.10 mmol, 3.0 eq), and 1-ethynyl-4-propylbenzene (1.23 g, 8.50 mmol, 5.0 eq) in toluene (20 mL) was heated at 100° C. for 1 h before concentration to dryness and purification via normal phase chromatography to afford the desired intermediate (108 mg, 22%). Reduction of the nitrile to the corresponding aldehyde was accomplished following the DIBAL procedure described earlier.

Example 12

Preparation of 4-{1-[4-(1-hydroxypropyl)-phenyl]-1H-pyrazol-3-yl}-benzaldehyde

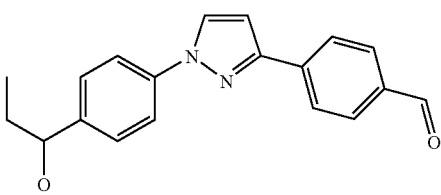

Step 1. 3-(4-Cyanophenyl)pyrazole. To a round bottom flask equipped with mechanical stir bar and reflux condenser were added p-cyanoacetophenone (5 g, 34.44 mmol) and dimethylformamide dimethylacetal (40 mL). The mixture was stirred at reflux for 5 h before concentration under reduced pressure afforded the crude dimethylamino-acryloylbenzonitrile intermediate. The residue was then suspended in a minimal volume of EtOH (~20 mL), charged with hydrazine monohydrate (1.67 mL, 34.4 mmol), and heated at 80° C. for 30 min before concentration to yield the crude 3-(4-cyanophenyl)pyrazole material (5.59 g, 33 mmol, 96%), of sufficient purity for use in the subsequent reaction.

Step 2. 4-[1-(4-Propionyl-phenyl)-1H-pyrazol-3-yl]-benzonitrile. 4-(1H-Pyrazol-3-yl)-benzonitrile (100 mg, 0.591 mmol), 1-(4-bromophenyl)-propan-1-one (126 mg, 0.591 mmol), $Cs_2CO_3$ (770 mg, 2.364 mmol), CuI (4 mg, 0.018 mmol), 8-hydroxyquinoline (3 mg, 0.018 mmol), and DMF/$H_2O$ (2 mL 10:1 solution) were combined in a 10 mL CEM Microwave reaction vessel fitted with magnetic stir bar and subjected to microwave irradiation at 150° C. for 30 min. The contents were then filtered and concentrated to dryness affording the nitrile (158 mg, 0.508 mmol, 86%). Reduction of the nitrile to the corresponding aldehyde was accomplished following the DIBAL procedure described earlier.

Example 13

Preparation of 5-(4-formylphenyl)-2-(4-trifluoromethoxy-phenyl)-3,4-dihydro-2H-pyrazole-3,4-dicarboxylic acid diethyl ester

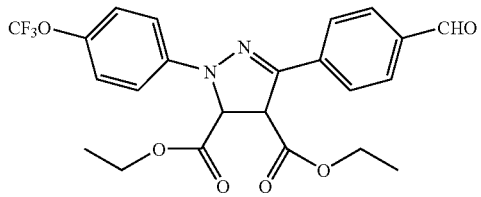

Step 1. Preparation of 4-[(4-trifluoromethoxyphenyl)-hydrazonomethyl]-benzaldehyde. The compound was prepared according to Paulvannan et al. *Tetrahedron*. 2000, 56, 8071. To a stirred solution of benzene-1,4-dicarbaldehyde (1.50 g, 11.2 mmol, 1.0 eq) in i-PrOH (250 mL) was added 4-trifluoromethoxy)phenylhydrazine hydrochloride (2.55 g, 11.2 mmol, 1.0 eq) portionwise over 5 min. The solution was stirred at ambient temperature for 1 h before concentration to dryness and purification via chromatography (2:2:1, hexane:EtOAc:acetone) to afford the intermediate (2.48 g, 72%).

Step 2. Chloro-hydrazone synthesis. The intermediate was prepared according to Lokanatha Rai and Hassner *Synth. Commun.* 1989, 19, 2799. A solution of 4-[(4-trifluoromethoxyphenyl)-hydrazonomethyl]-benzaldehyde (2.48 g, 8.05 mmol, 1.00 eq) and N-chlorosuccinimide (1.61 g, 12.08 mmol, 1.5 eq) in i-PrOH (100 mL) was heated at 80° C. for 1 h. The solution was then cooled and volumetrically partitioned evenly between six different reaction vessels to each contain 1.34 mmol of the intermediate.

Step 3. Pyrazoline synthesis. The compounds were prepared according to Paulvannan et al. *Tetrahedron* 2000, 56, 8071. To each reaction vessel were added triethylamine (0.56 mL, 4.02 mmol, 3.00 eq) and the respective acrylates (6.70 mmol, 5.00 eq). The vessels were then heated at 70° C. for 90 min before concentration to dryness and purification via chromatography (2:2:1, hexane:EtOAc:acetone). Reduction of the nitriles to the corresponding aldehydes was accomplished following the DIBAL procedure described earlier.

Example 14

Preparation of 4-{1-[4-(2,2,2-trifluoroethoxy)-phenyl]-1H-imidazol-4-yl}-benzaldehyde

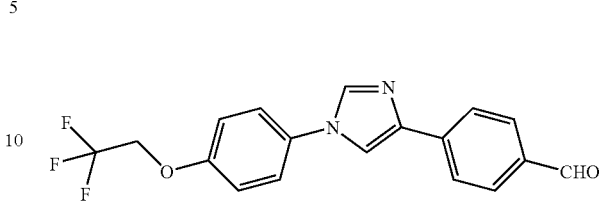

4-(2-Bromoacetyl)-benzonitrile (58 mg, 0.21 mmol) and 4-(2,2,2-trifluoroethoxy)-phenylamine (50 mg, 0.21 mmol) were combined in a 100 mL Erlenmeyer flask fitted with magnetic stir bar. The contents were dissolved in 1 mL of EtOH and stirred at ambient temperature for 2 h. The crude intermediate was then transferred to a 100 mL round bottom flask containing KSCN (21 mg, 0.21 mmol) and conc. HCl (18 uL, 0.21 mmol). The vessel was heated at 80° C. for 1 h before its contents were poured into 5 mL of a 1:1 $H_2O$/$NH_4OH$ solution. The solution was allowed to stand for 24 h, and then the solid was filtered and washed with ether to afford the intermediate imidazolethiol (32 mg, 0.086 mmol, 33%). An aqueous solution of $HNO_3$ (1.35 mL, 0.387 mmol) and $KNO_3$ (1 mg, 0.003 mmol) was then added dropwise over 10 min to a suspension of the imidazolethiol in 2 mL of acetic acid. After stirring for 2 h at ambient temperature the solution was poured into crushed ice and neutralized (pH=7) with 0.1 N NaOH (aq). The intermediate nitrile was isolated by vacuum filtration and dried in a 45° C. vacuum oven for 12 h (23 mg, 78%), mp 179° C. Reduction to the corresponding aldehyde was accomplished using DIBAL under conditions described previously.

Example 15

Preparation of 4-[1-(4-propylphenyl)-1H-imidazol-4-yl]-benzaldehyde

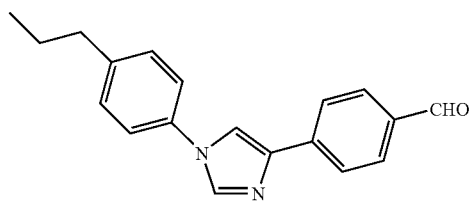

4-Propylaniline (2.70 g, 20 mmol) was added dropwise to a solution of 4-cyanophenacyl bromide (2.20 g, 10 mmol) in 5 mL of DMF. This solution was then added to 20 mL of a hot (180° C.) formamide solution over 5 min, and this solution was allowed to stir at 180° C. for 2 h. The cooled solution was then poured onto 100 mL of ice, and extracted with 2×75 mL of ether. After drying and concentrating, the resulting dark oil was purified by chromatography (3:1:2 hexanes:EtOAc:DCM). The first product (510 mg) was identified as 4-(5-propyl-1H-indol-3-yl)-benzonitrile, mp 140° C. The second fraction (275 mg) was identified as the desired imidazole. $^1$H NMR (400 MHz, $CDCl_3$) δ 7.95 (d, J=6 Hz, 2H), 7.90 (s, 1H), 7.70 (d, J=6 Hz, 2H), 7.68 (s, 1H), 7.38 (d, J=4 Hz, 2H), 7.31 (d, J=4 Hz, 2H), 2.69 (t, J=8.9 Hz, 2H), 1.68 (m, 2H), 0.98 (t, J=7.5 Hz, 3H); mp 133° C.; ESIMS 288.1 (M+H).

Reduction to the corresponding aldehyde was accomplished using DIBAL under conditions described previously. $^1$H NMR (300 MHz, CDCl$_3$) δ 10.02 (s, 1H), 8.03 (d, J=6 Hz, 2H), 7.92 (d, J=6 Hz, 2H), 7.90 (s, 1H), 7.72 (s, 1H), 7.38 (d, J=4 Hz, 2H), 7.31 (d, J=4 Hz, 2H), 2.69 (t, J=8.9 Hz, 2H), 1.68 (m, 2H), 0.98 (t, J=7.5 Hz, 3H); ESIMS 291.1 (M+H); mp 97° C.

Example 16

Preparation of 4-[1-(4-trifluoromethoxyphenyl)-1H-imidazol-4-yl]-benzaldehyde

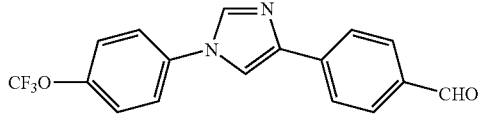

4-Trifluoromethoxyaniline (2.20 g, 12.4 mmol) was added dropwise to a solution of 4-cyanophenacyl bromide (1.50 g, 6.7 mmol) in 5 mL of DMF. This solution was then added to 20 mL of a hot (180° C.) formamide solution over 5 min, and this solution was allowed to stir at 180° C. for 2 h. The cooled solution was then poured onto 100 mL of ice, and extracted with 2×75 mL of ether. After drying and concentrating, the resulting semi-solid was crystallized from MeOH/H$_2$O. A second recrystallization from MeOH/H$_2$O removed traces of the formanilide impurity and furnished 200 mg of pure product, mp 155° C. Anal. Calcd. for C$_{17}$H$_{10}$F$_3$N$_3$O: C, 62.01; H, 3.06; N, 12.76. Found: C, 61.53; H, 3.13; N, 12.55. Reduction to the corresponding aldehyde was accomplished using DIBAL under conditions described previously. $^1$H NMR (300 MHz, CDCl$_3$) δ 10.0 (s, 1H), 8.05-7.90 (m, 5H), 7.70 (s, 1H), 7.50 (d, J=6 Hz, 2H), 7.42 (d, J=6 Hz, 2H); MS 333.0 (M+H); mp 112° C.

Example 17

Preparation of 4-[1-(4-trifluoromethoxyphenyl)-1H-imidazol-4-yl]-benzoic acid

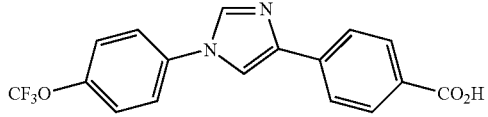

A solution of the nitrile (1.1 g, 3.3 mmol) in EtOH (5 mL) and water (2 mL) was treated with 1 g of NaOH (20 mmol), and the solution was heated to reflux for 6 h. It was then cooled and made acidic with 1 N HCl, and the resulting white solid was filtered and air-dried to give 1.1 g of the acid as a light grey solid.

$^1$H NMR (400 MHz, CDCl$_3$) δ 11.4 (s, 1H), 7.90 (d, J=6.4 Hz, 2H), 7.89 (s, 1H), 7.80 (d, J=8.6 Hz, 2H), 7.63 (d, J=1.3 Hz, 1H), 7.49 (d, J=9.3 Hz, 2H), 7.38 (d, J=8.9 Hz, 2H); mp 230° C.

Example 18

Preparation of 4-[4-(4-trifluoromethylphenyl)-1H-imidazol-1-yl]-benzaldehyde

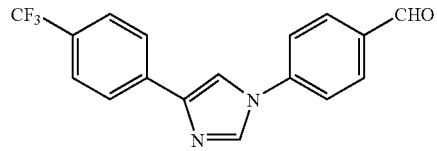

4-Trifluoromethylphenyl imidazole (4.0 g, 19 mmol), 4-fluorobenzonitrile (1.2 g, 8.5 mmol) and potassium carbonate (1.5 g, 10.9 mmol) were combined in 15 mL of DMSO and heated at 100° C. for 6 h. The cooled solution was then poured onto 100 mL of water and the resulting solid was filtered and air-dried to give 4.65 g of the imidazole nitrile as a white solid: mp 252° C.; $^1$H NMR (300 MHz, CDCl$_3$) δ 8.05 (s, 1H), 7.95 (d, J=8 Hz, 2H), 7.85 (d, 2H), 7.72 (s, 1H), 7.72 (d, J=8 Hz, 2H), 7.62 (d, J=8 Hz, 2H); MS 314.1 (M+H). Anal. Calcd. for C$_{16}$H$_{10}$F$_3$N$_3$O$_2$: C, 65.18; H, 3.22; N, 13.41. Found: C, 64.49; H, 3.23; N, 13.08. A portion of the nitrile (3.8 g) was reduced in the presence of DIBAL under conditions described previously to give 2.41 g of the corresponding aldehyde. $^1$H NMR (300 MHz, CDCl$_3$) δ 10.1 (s, 1H), 8.10 (d, J=8 Hz, 2H), 8.05 (s, 1H), 7.95 (d, J=8 Hz, 2H), 7.75 (s, 1H), 7.7 (m, 4H); MS 317.1 (M+H); mp 141° C.

Example 19

Preparation of 4-bromo-1-(4-trifluoromethoxyphenyl)-1H-imidazole

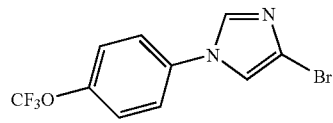

A round bottom flask was charged with 4-bromoimidazole (1.15 g, 7.81 mmol), CuI (0.07 g, 0.36 mmol), 8-hydroxyquinoline (0.05 g, 0.36 mmol), cesium carbonate (3.39 g, 10.4 mmol) and 4-trifluoromethoxyiodobenzene (1.50 g, 5.21 mmol). A 10:1 mixture of DMF (15 mL) and H$_2$O (1.5 mL) were added to the reaction mixture, and the solution was heated to 130° C. for 4 h. The reaction mixture was then diluted with EtOAc and washed sequentially with water, ammonium chloride (saturated), water and sodium bicarbonate. The organics were dried over MgSO$_4$, filtered and purified on a reverse phase column to give 820 mg of imidazole as a white solid. MS 308.0 (M+H); mp 139-141° C.

Example 20

Preparation of 4-methoxy-2-[1-(4-trifluoromethoxyphenyl)-1H-imidazol-4-yl]-benzaldehyde

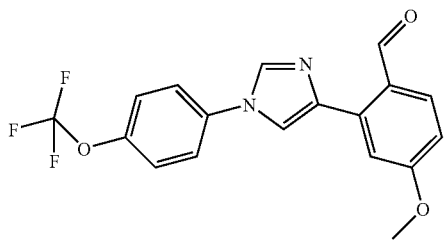

4-Bromo-1-(4-trifluoromethoxyphenyl)-1H-imidazole (100 mg, 0.326 mmol), 2-formyl-5-methoxyphenylboronic acid (73 mg, 0.41 mmol), bis(triphenylphosphine)palladium dichloride (2 mg, 0.003 mmol), sodium bicarbonate (49 mg, 0.59 mmol) and 1:1 DME/H$_2$O (8:8 mL) were combined and added to a microwave vessel. The reaction mixture was heated in the microwave with stirring at 100° C. for 12 min. The microwave took 5 min to reach 100° C., then maintained at 100° C. for 12 min, and then cooled. TLC (1:1 EtOAc:cyclohexane) showed the presence of starting materials, thus the sample was heated to 100° C. for another 8 min. Upon cooling a precipitate formed; this was filtered and washed with water to give 86 mg of a grey solid. ESIMS 363.0 (M+H).

The following intermediate was also prepared using this procedure:

Example 21

Preparation of 2-fluoro-4-[1-(4-trifluoromethoxyphenyl)-1H-imidazol-4-yl]-benzaldehyde

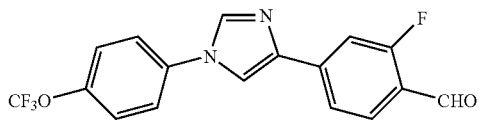

ESIMS 351.0 (M+H).

Example 22

Preparation of 1-{4-fluoro-3-[1-(4-trifluoromethoxyphenyl)-1H-imidazol-4-yl]-phenyl}-ethanone

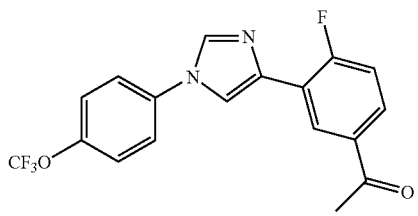

4-Bromo-1-(4-trifluoromethoxyphenyl)-1H-imidazole (200 mg, 0.651 mmol), 5-acetyl-2-fluorophenylboronic acid (178 mg, 0.977 mmol), tetrakis(triphenylphosphine)palladium(0) (7 mg, 0.007 mmol), a 2 N aqueous solution of potassium carbonate (0.651 mL) and dioxane (8 mL) were combined and added to a microwave vessel. The reaction mixture was heated in the microwave with stirring to 150° C. for 20 min. LC-MS indicated 88% anticipated product; TLC (1:1 hexanes:EtOAc) indicated the presence of starting material plus 3 other materials. EtOAc and water were added to the reaction mixture. The aqueous layer was extracted with EtOAc and the organic extracts were washed with brine, dried over MgSO$_4$, and concentrated in vacuo. The crude product was purified by chromatography with gradient elution (100% hexanes to 100% EtOAc) resulting in 90 mg of an off-white solid. ESIMS 265.0 (M+H); mp 129° C.

Example 23

Preparation of 4-[1-(4-trifluoromethoxyphenyl)-1H-[1,2,4]triazol-3-yl]-benzaldehyde

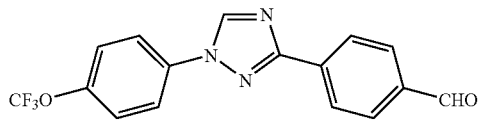

Step 1. 4-(1H-[1,2,4]Triazol-3-yl)-benzonitrile. The general procedure outlined by Lin et. al. (*J. Org. Chem.* 1979, 44, 4163) for preparation of 3-(4-nitrophenyl)-1H-[1,2,4]triazole was used. 4-Cyanobenzamide (21.63 g, 0.148 mol) was dissolved in DMF-DMA (100 mL) and was stirred at reflux under N$_2$ for 8 h. The mixture was concentrated to dryness and suspended in 50 mL of AcOH. The vessel was then charged with hydrazine monohydrate (7.18 mL, 0.148 mmol) and stirred at reflux for 1 h before concentration. The desired 4-(1H-[1,2,4]triazol-3-yl)-benzonitrile was obtained in 98% purity by trituration with Et$_2$O followed by filtration (12.17 g, 0.072 mol, 48%).

Step 2. 4-[1-(4-Trifluoromethoxyphenyl)-1H-[1,2,4]triazol-3-yl]-benzonitrile. The triazole (70 mg, 0.41 mmol), 1-iodo-4-trifluoromethoxybenzene (142 mg, 0.493 mmol), Cs$_2$CO$_3$ (535 mg, 1.644 mmol), CuI (3 mg, 0.012 mmol), 8-hydroxyquinoline (2 mg, 0.012 mmol), and DMF/H$_2$O (2 mL 10:1 solution) were combined in a 10 mL CEM Microwave reaction vessel fitted with magnetic stir bar and subjected to microwave irradiation at 150° C. for 30 min. The contents were then filtered and concentrated to dryness affording the 1,3-diphenyl triazole intermediate (18 mg, 13%).

Step 3. 4-[1-(4-Trifluoromethoxy-phenyl)-1H-[1,2,4]triazol-3-yl]-benzaldehyde. The nitrile was reduced with DIBAL under conditions previously described. $^1$H NMR (300 MHz, CDCl$_3$) δ 10.1 (s, 1H), 8.61 (s, 1H), 8.37 (d, J=9 Hz, 2H), 8.0 (d, J=8.4 Hz, 2H), 7.8 (d, J=9 Hz, 2H), 7.4 (d, J=8.4 Hz, 2H); ESIMS 334.2 (M+H); mp 137-140° C.

Example 24

Preparation of 4-[1-(4-pentafluoroethylsulfanylphenyl)-1H-[1,2,4]triazol-3-yl]-benzaldehyde

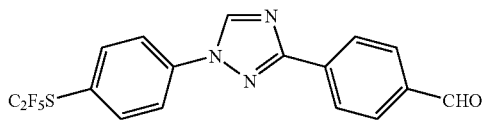

Step 1. 1-Bromo-4-pentafluoroethylsulfanylbenzene. The title compound was prepared using perfluoroalkylation conditions originally described by Popov et. al. *J. Fluorine Chem.* 1982, 21, 365. To a solution of 4-bromobenzenethiol (500 mg, 2.64 mmol, 1.00 eq) and triethylbenzyl ammonium chloride (60 mg, 0.26 mmol, 0.10 eq) in 10 mL of 1:1 $Et_2O$/NaOH (25% aq) at 0° C. was bubbled 1,1,1,2,2-pentafluoro-2-iodoethane gas for 30 min (>5 eq). During this time a UV lamp was directed at the reaction vessel while the temperature was maintained below 10° C. by intermittent use of an ice bath. The contents were then warmed to room temperature, extracted into $Et_2O$ (300 mL), dried ($MgSO_4$), and concentrated under reduced pressure. A portion of this crude material was used in subsequent reactions without further purification (200 mg residue: 120 mg product, 0.39 mmol, 1.2 eq).

Step 2. 4-[1-(4-Pentafluoroethylsulfanylphenyl)-1H-[1,2,4]triazol-3-yl]-benzonitrile. Coupling with 4-(1H-[1,2,4]triazol-3-yl)-benzonitrile as described above gave 4-[1-(4-pentafluoroethylsulfanylphenyl)-1H-[1,2,4]triazol-3-yl]-benzonitrile: 70 mg, 46%. Reduction with DIBAL, as described previously, gave the corresponding aldehyde.

Example 25

Preparation of 4-[1-(4-pentafluoroethyloxy-phenyl)-1H-[1,2,4]triazol-3-yl]-benzaldehyde

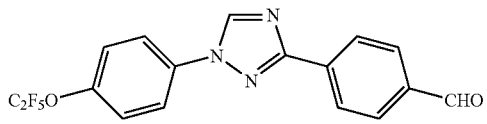

Step 1. A solution of 3-p-tolyl-1H-[1,2,4]triazole (4.85 g, 30.5 mmol), 4-bromophenyl pentafluoroethyl ether (10.0 g, 34.4 mmol), $Cs_2CO_3$ (25 g, 77 mmol), CuI (1.25 g, 6.5 mmol) and 8-hydroxyquinoline (0.35 g, 2.4 mmol) in 50 mL of 9:1 DMF/$H_2O$ was stirred vigorously and heated to 130° C. (internal temperature) for 20 h. The solution was then cooled, poured into water, and acidified with 2 N HCl to pH 2. Ether (250 mL) was then added and the solution was shaken and filtered before separating layers. The organic layer was dried and concentrated, and the resulting gummy solid was heated with 100 mL of hexanes. The hot hexane layer was decanted from insoluble residue, the resulting solution cooled to 0° C. and the precipitated solid was filtered and air-dried to furnish 7.0 g (61% based on starting triazole) of 1-(4-pentafluoroethyloxy-phenyl)-3-p-tolyl-1H-[1,2,4]triazole as an off-white solid, mp 130-132° C.; ESIMS 370.8 (M+H).

Step 2. The product from Step 1 (7.0 g, 18.7 mmol) was dissolved in 200 mL of acetonitrile and stirred at ambient temperature while ceric ammonium nitrate (32 g, 58 mmol) in 60 mL of water was added in portions over 10 min. The solution was then heated to reflux for 4 h, cooled, and diluted with 200 mL of water. The solution was extracted with 2×200 mL of ether, and the combined organic layer was dried and concentrated to give an orange oil. This material was dissolved in 40 mL of dioxane and treated with a solution of KOH (5 g, 90 mmol) in 20 mL of water. The solution was heated to reflux for 2 h, then cooled and diluted with 100 mL of water. The aldehyde precipitated and was collected by filtration. Recrystallization from MeOH/$H_2O$ gave the pure aldehyde as a white solid. $^1$H NMR (300 MHz, $CDCl_3$) δ 10.1 (s, 1H), 8.65 (s, 1H), 8.40 (d, J=8.4 Hz, 2H), 8.0 (d, J=8.4 Hz, 2H), 7.85 (d, J=9 Hz, 2H), 7.45 (d, J=9 Hz, 2H); ESIMS 384.2 (M+H); mp 137-144° C.

Example 26

Preparation of 4-[1-(4-pentafluoroethyloxy-phenyl)-1H-[1,2,4]triazol-3-yl]-benzoic acid

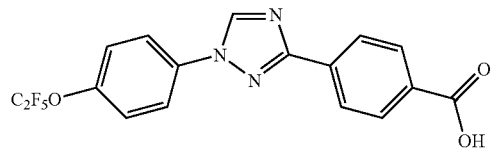

A solution of 4-[1-(4-pentafluoroethyloxy-phenyl)-1H-[1,2,4]triazol-3-yl]-benzaldehyde (1.7 g, 4.4 mmol), sodium bromate (2.1 g, 13.9 mmol) and sodium bisulfate (0.53 g, 4.5 mmol) in 50 mL of acetonitrile was heated to reflux for 5 h, during which time a voluminous precipitate formed. The solution was then cooled and poured into 100 mL of water, filtered, and dried to furnish 1.67 g of the acid as a white solid. $^1$H NMR (300 MHz, $CDCl_3$) δ 10.1 (s, 1H), 8.65 (s, 1H), 8.40 (d, J=8.4 Hz, 2H), 8.0 (d, J=8.4 Hz, 2H), 7.85 (d, J=9 Hz, 2H), 7.45 (d, J=9 Hz, 2H); ESIMS 399.2 (M+H⁺); mp 225° C.

Example 27

Preparation of 4-[1-(4-pentafluoroethyloxy-phenyl)-1H-[1,2,4]triazol-3-yl]-benzoyl azide

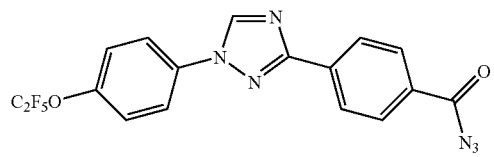

A solution of 4-[1-(4-pentafluoroethyloxy-phenyl)-1H-[1,2,4]triazol-3-yl]-benzoic acid (1.67 g, 4.2 mmol), diphenylphosphoryl azide (1.26 g, 4.58 mmol) and triethylamine (0.5 g, 5 mmol) in 10 mL of dry t-BuOH was heated to 75° C. for 90 min, resulting in dissolution of the starting acid and subsequent precipitation of the azide. The cooled solution was then poured onto 10 g of ice, and the resulting mixture was filtered and dried to furnish 0.80 g of the azide as a white solid. $^1$H NMR (300 MHz, $CDCl_3$) δ 10.1 (s, 1H), 8.65 (s, 1H), 8.40 (d, J=8.4 Hz, 2H), 8.0 (d, J=8.4 Hz, 2H), 7.85 (d, J=9 Hz, 2H), 7.45 (d, J=9 Hz, 2H); ESIMS 399.2 (M+H); mp 175° C. dec.

Example 28

Preparation of 4-[1-(4-butyl-phenyl)-1H-[1,2,4]triazol-3-yl]-benzaldehyde

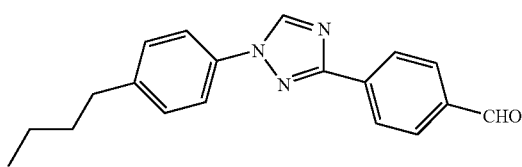

Step 1. 4-[1-(4-Butyl-phenyl)-1H-[1,2,4]triazol-3-yl]-benzonitrile. A solution of 4-n-butyl phenyl hydrazine (1.0 g, 5 mmol) and 4-cyanobenzaldehyde (0.8 g, 6.0 mmol) in 15 mL of i-PrOH was heated on a steam bath for 2 h and then was cooled and diluted with 5 mL of water. The resulting orange solid was filtered and air-dried to give 1.30 g of the hydrazone as a yellow solid, mp 107° C. A solution of this hydrazone (1.1 g, 4.0 mmol) and NCS (0.67 g, 5 mmol) in 20 mL of i-PrOH was stirred under nitrogen at ambient temperature for 2 h, during which time the original solid dissolved and a new solid formed. The resulting orange solution was then treated with tetrazole (0.45 g, 6.4 mmol) and triethylamine (960 µL, 7.0 mmol). The orange-brown solution was heated at reflux for 2 h. The solution was then cooled, diluted with 25 mL of water, extracted with EtOAc, dried, concentrated, and purified by chromatography (Biotage, 4:1 Hex:EtOAc) to give 0.42 g (35%) of the triazole as an off-white solid. $^1$H NMR (300 MHz, CDCl$_3$) δ 8.58 (s, 1H), 8.33 (d, J=8 Hz, 2H), 7.78 (d, J=8 Hz, 2H), 7.64 (d, J=8.2 Hz, 2H), 7.33 (d, J=8.2 Hz, 2H), 2.70 (t, J=7.8 Hz, 2H), 1.63 (m, 2H), 1.38 (m, 2H), 0.95 (t, J=7.5 Hz, 3H); ESIMS 303.1; mp 124° C.

Step 2. 4-[1-(4-Butyl-phenyl)-1H-[1,2,4]triazol-3-yl]-benzaldehyde. Reduction with DIBAL, as described previously, gave the corresponding aldehyde. $^1$H NMR (300 MHz, CDCl$_3$) δ 10.08 (s, 1H), 8.58 (s, 1H), 8.37 (d, J=8 Hz, 2H), 7.98 (d, J=8 Hz, 2H), 7.62 (d, J=8.2 Hz, 2H), 7.33 (d, J=8.2 Hz, 2H), 2.70 (t, J=7.8 Hz, 2H), 1.63 (m, 2H), 1.38 (m, 2H), 0.95 (t, J=7.5 Hz, 3H); ESIMS 306.1; mp 124° C.

Example 29

Preparation of 4-[1-(4-pentafluoroethyl-phenyl)-1H-[1,2,4]triazol-3-yl]-benzaldehyde

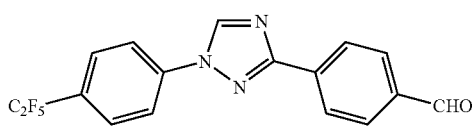

Step 1. 1-(4-Pentafluoroethyl-phenyl)-3-p-tolyl-1H-[1,2,4]triazole. Pentafluoroethyl iodide (521 mg, 2.12 mmol) was condensed into a vial containing 1-bromo-4-iodobenzene (300 mg, 1.06 mmol), copper(0) powder (135 mg, 2.12 mmol), and DMSO (5 mL). The vial was then sealed and subjected to microwave irradiation at 150° C. for 60 min. GC/MS proved consumption of the starting material yielding both 1-bromo-4-pentafluoroethylbenzene and 1-iodo-4-pentafluoroethyl-benzene intermediates. The mixture (1.06 mmol), was transferred to a 250 mL round bottom flask and 3-p-tolyl-1H-[1,2,4]triazole (169 mg, 1.06 mmol), Cs$_2$CO$_3$ (1.38 g, 4.24 mmol), CuI (202 mg, 1.06 mmol), 8-hydroxyquinoline (2 mg, 0.011 mmol), and DMF/H$_2$O (12 mL 10:1 solution) were added and the solution was refluxed at 160° C. for 6 h. Upon completion, the cooled contents were poured into H$_2$O and precipitation was allowed for 1 h. The precipitate was collected by vacuum filtration and dried overnight in a 45° C. vacuum oven. The crude 1-(4-pentafluoroethylphenyl)-3-p-tolyl-1H-[1,2,4]triazole intermediate was used in step 2 without further purification.

Step 2. Oxidation to the aldehyde. Ammonium cerium(IV) nitrate (3.32 g, 4.24 mmol) and the intermediate from Step 1 were combined in a round bottom flask with acetonitrile and water (20 mL, 1:1). The solution was stirred at reflux at 110° C. for 4 h, affording a mixture of the 3-(4-nitrooxymethyl-phenyl)-1-(4-pentafluoroethyl-phenyl)-1H-[1,2,4]triazole and 4-[1-(4-pentafluoroethyl-phenyl)-1H-[1,2,4]triazol-3-yl]-benzaldehyde intermediates. The acetonitrile was removed under vacuum and the crude intermediate precipitates were collected by filtration. The material was then combined with powdered KOH (178 mg, 3.18 mmol) in dioxane and water (10 mL, 1:1) and was stirred at reflux at 105° C. for 90 min before the dioxane was removed under vacuum allowing precipitation of the intermediate from water. The 4-[1-(4-pentafluoroethylphenyl)-1H-[1,2,4]triazol-3-yl]-benzaldehyde intermediate was collected by filtration (35 mg, 0.095 mmol, 9% overall from 4-tolyl triazole).

Example 30

Preparation of trifluoromethanesulfonic acid 4-[3-(4-formyl-phenyl)-[1,2,4]triazol-1-yl]-phenyl ester

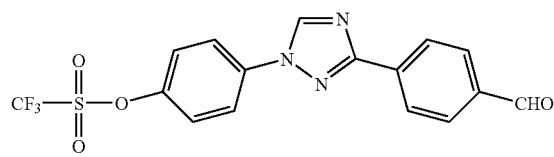

Step 1. 1-(4-Methoxyphenyl)-3-p-tolyl-1H-[1,2,4]triazole was prepared by coupling 3-p-tolyl-1H-[1,2,4]triazole with 4-iodoanisole under conditions described in Step 1 of the previous example. This material was then demethylated using conditions described in Hitchcock et al. *Synlett* 2006, 2625. Boron tribromide (1 M solution in hexanes; 1.67 mL, 1.67 mmol) was added dropwise to a solution of 1-(4-methoxyphenyl)-3-p-tolyl-1H-[1,2,4]triazole (300 mg, 1.28 mmol) in DCM (10 mL) at 0° C. under N$_2$. After addition was complete, the vessel was warmed to ambient temperature before refluxing at 40° C. for 6 h. The cooled contents were then quenched with H$_2$O before removal of the DCM and partitioning between EtOAc and water. The organic layer was collected, washed with brine, dried (MgSO$_4$), concentrated, and purified via chromatography (3:1:1, hexanes:EtOAc:acetone) to afford the 4-(3-p-tolyl-[1,2,4]triazol-1-yl)-phenol intermediate (219 mg, 0.872 mmol, 68%). Trifluoromethanesulfonic anhydride (0.16 mL, 0.96 mmol) was added dropwise to a solution of the phenol and 4-tert-butyl-2,6-dimethylpyridine (142 mg, 0.872 mmol) in DCM (10 mL) at 0° C.

under $N_2$. The vessel was warmed to ambient temperature before the solvent was removed under reduced pressure and the residue purified via chromatography (2:2:1, hexanes:EtOAc:acetone) affording the trifluoromethanesulfonic acid 4-(3-p-tolyl-[1,2,4]triazol-1-yl)-phenyl ester intermediate (304 mg, 0.794 mmol, 91%).

Step 2. Oxidation of the 4-methyl intermediate above to the corresponding aldehyde was carried out using ammonium cerium(IV) nitrate under conditions described in Step 2 of the previous example.

Example 31

Preparation of 4-[5-(4-trifluoromethyl-phenyl)-1H-[1,2,4]triazol-3-yl]-benzaldehyde

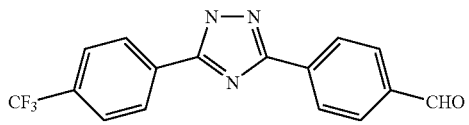

Terephthalonitrile (115 mg, 0.90 mmol), 4-trifluoromethylbenzoic acid hydrazide (92 mg, 0.450 mmol), $K_2CO_3$ (31 mg, 0.225 mmol), and n-butyl alcohol (~2 mL) were combined in a 10 mL CEM Microwave reaction vial fitted with magnetic stir bar and subjected to microwave irradiation at 150° C. for 30 min. The contents were then filtered and concentrated to dryness. Chromatography (3:1 hexanes/EtOAc) afforded the 1,2,4-triazole nitrile (72 mg, 0.230 mmol, 51%). Reduction with DIBAL then generated the corresponding aldehyde.

Example 32

Preparation of 4-[1-(3,4-dichloro-phenyl)-5-oxo-4,5-dihydro-1H-[1,2,4]triazol-3-yl]-benzaldehyde

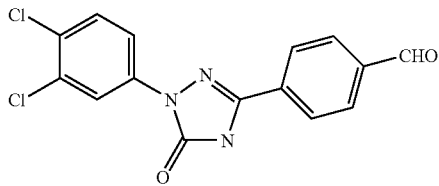

Step 1. 4-Cyanophenyl-oxo-acetic acid. A round bottom flask equipped with mechanical stirrer and reflux condenser was charged with p-cyanoacetophenone (5 g, 34.44 mol), $SeO_2$ (9.55 g, 86.1 mmol), and pyridine (~100 mL). The mixture was stirred at reflux for 6 h before precipitates were removed by filtration and the filtrate was charged with 10% HCl (aq) (20 mL). The filtrate was extracted into EtOAc (3×50 mL) and the combined organic layers were further extracted into nearly saturated $NaHCO_3$. The aqueous layer was then carefully made acidic (pH=1) with conc. HCl affording a small crop of the desired product. The remainder of the oxo acetic acid was obtained by extracting into EtOAc, drying ($MgSO_4$), and concentration (1.69 g, 28%).

Step 2. 4-[1-(3,4-Dichloro-phenyl)-5-oxo-4,5-dihydro-1H-[1,2,4]triazol-3-yl]-benzonitrile. A suspension of 4-cyanophenyl-oxo-acetic acid (100 mg, 0.571 mmol), (3,4-dichlorophenyl)hydrazine hydrochloride (122 mg, 0.571 mmol), 12.1 N HCl (5 uL, 0.057 mmol), and $H_2O$ (~10 mL) in a 25 mL reaction vial was stirred vigorously at ambient temperature for 24 h. The hydrazone was obtained by vacuum filtration and placed into a 100 mL round bottom flask with a magnetic stir bar. The flask was then supplemented with triethylamine (0.08 mL, 0.571 mmol), diphenylphosphoryl azide (157 mg, 0.571 mmol), and toluene (20 mL) before heating at 110° C. for 1 h. Upon cooling the contents were quenched with 10% NaOH (aq) and made acidic (pH 1) with conc. HCl. Precipitation was allowed for 15 min before the intermediate was obtained by vacuum filtration and dried overnight in a 45° C. vacuum oven (16 mg, 8%). The nitrile was reduced to the aldehyde using DIBAL under conditions previously described.

Example 33

Preparation of 4-[1-(4-Chloro-phenyl)-1H-[1,2,3]triazol-4-yl]-benzaldehyde

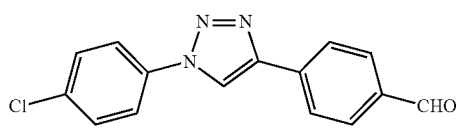

Following the procedure published by Feldman et al. (*Org. Lett.* 2004, 6, 3897), a suspension of 4-ethynylbenzonitrile (50 mg, 0.393 mmol), 1-chloro-4-iodobenzene (94 mg, 0.393 mmol), L-proline (9 mg, 0.079 mmol), ascorbic acid (7 mg, 0.039 mmol), $NaN_3$ (31 mg, 0.472 mmol), $CuSO_4$ (3 mg, 0.020 mmol), and $Na_2SO_4$ (11 mg, 0.079 mmol) in DMSO (1.5 mL) was heated at 65° C. for 24 h. Upon cooling the mixture was diluted with $H_2O$ and stirred for 30 min at ambient temperature. The intermediate 4-[1-(4-chloro-phenyl)-1H[1,2,3]triazol-4-yl]-benzonitrile (54 mg, 48%) was then obtained by vacuum filtration after washing with copious volumes of $H_2O$ and 20% $NH_4OH$ (~20 mL). Reduction to the aldehyde was then conducted under conditions previously described.

Example 34

Preparation of 4-[5-(4-trifluoromethyl-phenyl)-tetrazol-2-yl]-benzaldehyde

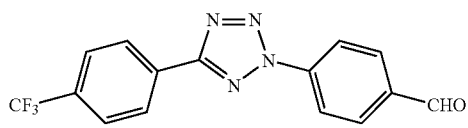

This aldehyde was prepared from 4-trifluoromethylbenzaldehyde by following the route described in Roppe et al. *J. Med. Chem.* 2004, 47, 4645.

Example 35

Preparation of 4-[5-(4-trifluoromethoxy-phenyl)-pyridin-3-yl]-benzaldehyde

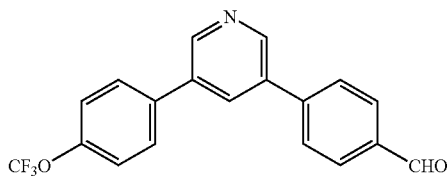

Step 1. 3,5-Dibromopyridine (4.4 mmol), 4-trifluoromethoxyphenyl boronic acid (5.1 mmol), tetrakis(triphenylphosphine)palladium(0) (0.04 mmol), 2 M potassium carbonate (8.44 mmol) and dioxane (21 mL) were combined in a vial and heated by microwave for 10 min at 150° C. The reaction mixture was taken up in ether and washed with brine. The ether layer was dried over magnesium sulfate, was filtered and the solvent removed in vacuo. The crude mixture was purified by silica gel chromatography to yield 130 mg of 3-bromo-5-(4-trifluoromethoxy-phenyl)-pyridine as a yellow solid. $^1$H NMR (400 MHz, CDCl$_3$) δ 8.71 (m, 2H), 8.00 (t, J=2.1 Hz, 1H), 7.58 (d, J=8.8 Hz, 2H), 7.34 (d, J=8.0 Hz, 2H); EIMS 317 m/z (M$^+$).

Step 2. The compound was prepared by palladium-catalyzed arylation of the product of step 1 with 4-formylphenyl boronic acid.

Example 36

Preparation of 4-[4-(4-trifluoromethoxyphenyl)-pyridin-2-yl]-benzaldehyde

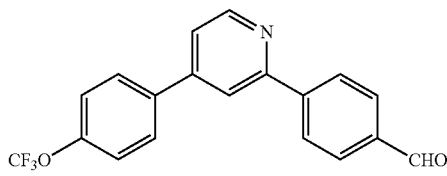

Step 1. The compound was prepared by palladium-catalyzed arylation of 2-chloro-4-iodopyridine with 4-trifluoromethoxyphenyl boronic acid.

Step 2. 2-Chloro-4-(4-trifluoromethoxyphenyl)-pyridine (0.55 mmol) starting from 2-chloro-4-iodopyridine, 4-formylphenyl boronic acid (0.82 mmol), tetrakis(triphenylphosphine)palladium(0) (0.005 mmol), 2 M potassium carbonate (0.55 mL) and dioxane (3 mL) were combined in a vial and irradiated by microwave for 15 min at 150° C. The reaction mixture was taken up in EtOAc and washed with brine. The organic layer was dried over magnesium sulfate, was filtered and the solvent removed in vacuo. Purification by silica gel chromatography (EtOAc/hexanes) yielded 120 mg of an off-white solid. $^1$H NMR (400 MHz, CDCl$_3$) δ 10.11 (s, 1H), 8.81 (d, J=4.8 Hz, 1H), 8.24 (d, J=8.7 Hz, 2H), 8.03 (d, J=8.4 Hz, 2H), 7.96 (m, 1H), 7.73 (d, J=9.0 Hz, 2H), 7.49 (dd, J=5.3, 1.8 Hz, 1H), 7.37 (d, J=8.1 Hz, 2H); EIMS 343 m/z (M$^+$).

Example 37

Preparation of 4-[6-(4-trifluoromethoxy-phenyl)-pyridin-2-yl]-benzaldehyde

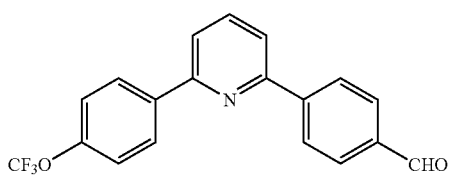

Step 1. 4-(6-Bromopyridin-2-yl)-benzaldehyde (0.31 mmol) was prepared as in Puglisi et al. *Eur. J. Org. Chem.* 2003, 8, 1552-1558.

Step 2. 4-[6-(4-Trifluoromethoxyphenyl)-pyridin-2-yl]-benzaldehyde. 4-(6-Bromo-pyridin-2-yl)-benzaldehyde (0.31 mmol), 4-trifluoromethoxy boronic acid (0.46 mmol), tetrakis(triphenylphosphine)palladium(0) (0.003 mmol), 2 M potassium carbonate (0.31 mL) and dioxane (2 mL) were combined in a vial and irradiated by microwave for 10 min at 150° C. The reaction mixture was taken up in ether and washed with brine. The organic layer was dried over magnesium sulfate, was filtered and the solvent removed in vacuo. Purification by silica gel chromatography (EtOAc/hexanes) yielded 80 mg of the product as an off-white solid. $^1$H NMR (400 MHz, CDCl$_3$) δ 10.11 (s, 1H), 8.32 (d, J=8.5 Hz, 2H), 8.19 (d, J=8.1 Hz, 2H), 8.03 (d, J=8.4 Hz, 2H), 7.89 (t, J=7.9 Hz, 1H), 7.79 (d, J=7.7 Hz, 1H), 7.74 (d, J=8.0 Hz, 1H), 7.35 (d, J=8.3 Hz, 2H); EIMS 343 m/z (M$^+$); mp 109-112° C.

Example 38

Preparation of 4-[6-(4-trifluoromethoxyphenyl)-pyrimidin-4-yl]-benzaldehyde

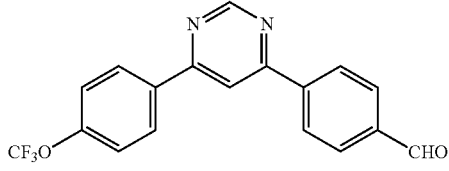

Step 1. 4-Chloro-6-(4-trifluoromethoxy-phenyl)-pyrimidine was prepared by palladium-catalyzed arylation of 4,6-dichloropyrimidine and 4-trifluoromethoxyphenyl boronic acid. $^1$H NMR (400 MHz, CDCl$_3$) δ 9.05 (s, 1H), 8.14 (d, J=9.8 Hz, 2H), 7.74 (m, 1H), 7.36 (d, J=8.4 Hz, 2H); EIMS 274 m/z (M$^+$).

Step 2. The compound was prepared by palladium-catalyzed arylation of the product of step 1 with 4-formylphenyl boronic acid. $^1$H NMR (400 MHz, CDCl$_3$) δ 10.15 (s, 1H), 9.38 (d, J=0.9 Hz, 1H), 8.33 (d, J=8.4 Hz, 2H), 8.23 (d, J=8.5

Hz, 2H), 8.16 (d, J=0.8 Hz, 1H), 8.08 (d, J=8.8 Hz, 2H), 7.40 (d, J=8.1 Hz, 2H); EIMS 344 m/z (M+).

Example 39

Preparation of 4-[2-(4-trifluoromethoxyphenyl)-pyrimidin-4-yl]-benzaldehyde

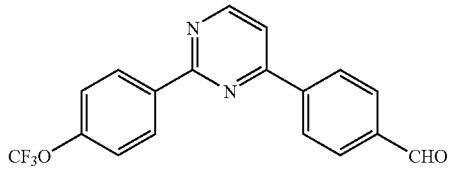

Step 1. 4-Chloro-2-(4-trifluoromethoxyphenyl)-pyrimidine. The title compound was prepared by palladium-catalyzed arylation of 2,4-dichloropyrimidine and 4-trifluoromethoxyphenyl boronic acid. $^1$H NMR (400 MHz, CDCl$_3$) δ 8.68 (d, J=5.6 Hz, 1H), 8.16 (d, J=9.1 Hz, 2H), 7.65 (d, J=5.3 Hz, 1H), 7.36 (dd, J=9.2, 0.9 Hz, 2H); EIMS 274 m/z (M+); mp 70-73° C.

Step 2. The compound was prepared by palladium-catalyzed arylation of the product of step 1 with 4-formylphenyl boronic acid. $^1$H NMR (400 MHz, CDCl$_3$) δ 10.13 (s, 1H), 8.91 (d, J=4.8 Hz, 1H), 8.74 (d, J=8.5 Hz, 2H), 8.28 (d, J=8.4 Hz, 2H), 8.03 (d, J=8.4 Hz, 2H), 7.65 (d, J=5.3 Hz, 1H), 7.39 (d, J=8.6 Hz, 2H); EIMS 344 m/z (M+).

Example 40

Preparation of 4-[4-(4-trifluoromethoxyphenyl)-pyrimidin-2-yl]-benzaldehyde

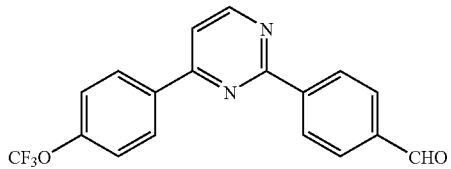

Step 1. 4-(4-Chloropyrimidin-2-yl)-benzaldehyde. The compound was prepared by palladium-catalyzed arylation of 2,4-dichloropyrimidine and 4-formylphenyl boronic acid. $^1$H NMR (400 MHz, CDCl$_3$) δ 10.13 (s, 1H), 8.74 (d, J=5.0 Hz, 1H), 8.27 (d, J=7.8 Hz, 2H), 8.04 (d, J=7.9 Hz, 2H), 7.74 (m, 1H); EIMS 218 m/z (M+).

Step 2. The compound was prepared by palladium-catalyzed arylation of the product of Step 1 with 4-trifluoromethoxyphenyl boronic acid. $^1$H NMR (400 MHz, CDCl$_3$) δ 10.14 (s, 1H), 8.91 (d, J=4.2 Hz, 1H), 8.63 (d, J=8.5 Hz, 2H), 8.37 (d, J=8.4 Hz, 2H), 8.06 (d, J=8.8 Hz, 2H), 7.67 (d, J=5.4 Hz, 1H), 7.35 (d, J=8.7 Hz, 2H); EIMS 344 m/z (M+).

Example 41

Preparation of 4-[6-(4-trifluoromethoxyphenyl)-pyrazin-2-yl]-benzaldehyde

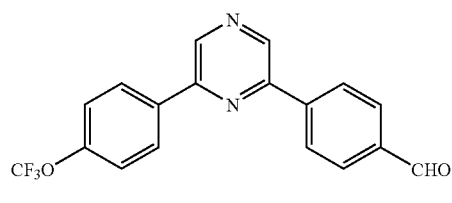

Step 1. 2-Chloro-6-(4-trifluoromethoxyphenyl)-pyrazine. The compound was prepared by palladium-catalyzed arylation of 2,6-dichloropyrazine and 4-trifluoromethoxyphenyl boronic acid. $^1$H NMR (400 MHz, CDCl$_3$) δ 8.94 (s, 1H), 8.57 (s, 1H), 8.10 (d, J=9.0 Hz, 2H), 7.37 (d, J=8.4 Hz, 2H); EIMS 274 m/z (M+); mp 58-60° C.

Step 2. The compound was prepared by palladium-catalyzed arylation of the product of step 1 with 4-formylphenyl boronic acid. $^1$H NMR (400 MHz, CDCl$_3$) δ 10.13 (s, 1H), 9.07 (s, 1H), 9.03 (s, 1H), 8.33 (d, J=8.1 Hz, 2H), 8.21 (d, J=8.7 Hz, 2H), 8.07 (d, J=7.6 Hz, 2H), 7.40 (d, J=8.3 Hz, 2H); EIMS 344 m/z (M+).

Example 42

Preparation of 4-[2-(4-trifluoromethoxyphenyl)-pyrimidin-5-yl]-benzaldehyde

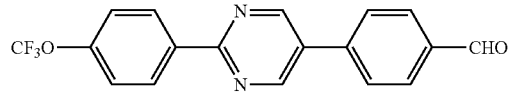

Step 1. 4-(2-Chloropyrimidin-5-yl)-benzaldehyde. The compound was prepared by palladium-catalyzed arylation of 2,5-dichloropyrimidine and 4-formylphenyl boronic acid.

Step 2. 4-(2-Chloropyrimidin-5-yl)-benzaldehyde (0.92 mmol), 4-trifluoromethoxyphenyl boronic acid (1.10 mmol), dichlorobis(triphenylphosphine)palladium(II) (0.01 mmol), 2 M potassium carbonate (0.92 mL) and dioxane (5 mL) were combined in a vial and irradiated by microwave for 10 min at 150° C. The organic layer from the reaction mixture was loaded directly onto silica and dried in vacuo. Purification by silica gel chromatography (EtOAc/hexanes) yielded 140 mg of a white solid. $^1$H NMR (400 MHz, CDCl$_3$) δ 10.11 (s, 1H), 9.07 (s, 2H), 8.57 (d, J=9.0 Hz, 2H), 8.07 (d, J=8.5 Hz, 2H), 7.82 (d, J=8.3 Hz, 2H), 7.35 (d, J=8.3 Hz, 2H); EIMS 344 m/z (M+).

Example 43

Preparation of 4-[5-(4-trifluoromethoxyphenyl)-pyrimidin-2-yl]-benzaldehyde

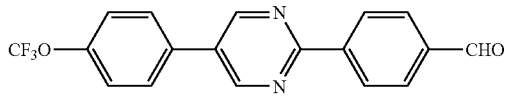

Step 1. 2-Chloro-5-(4-trifluoromethoxyphenyl)-pyrimidine. The compound was prepared by palladium-catalyzed arylation of 2,5-dichloropyrimidine with 4-trifluoromethoxyphenyl boronic acid.

Step 2. 2-Chloro-5-(4-trifluoromethoxyphenyl)-pyrimidine (4.22 mmol), 4-formylphenyl boronic acid (5.1 mmol), dichlorobis(triphenylphosphine)palladium(II) (0.05 mmol), 2 M potassium carbonate (4.2 mL) and dioxane (21 mL) were combined in a vial and irradiated by microwave for 20 min at 150° C. The organic layer from the reaction mixture was loaded directly onto silica and dried in vacuo. Purification by silica gel chromatography (EtOAc/hexanes) yielded 75 mg of a white solid. $^1$H NMR (400 MHz, CDCl$_3$) δ 10.13 (s, 1H), 9.06 (s, 2H), 8.68 (d, J=8.8 Hz, 2H), 8.03 (d, J=8.3 Hz, 2H), 7.68 (d, J=8.8 Hz, 2H), 7.40 (d, J=8.7 Hz, 2H); EIMS 344 m/z (M$^+$).

Example 44

Preparation of 4-heptafluoropropyl-6-(4-nitro-phenyl)-2-(4-trifluoromethyl-phenyl)-pyrimidine

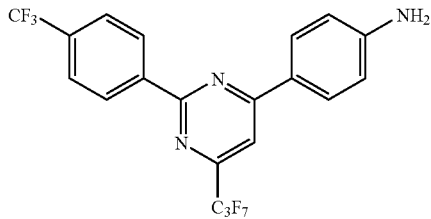

Step 1. 4-Heptafluoropropyl-6-(4-nitrophenyl)-2-(4-trifluoromethyl-phenyl)-pyrimidine. A solution of 4-heptafluoropropyl-2-methylsulfanyl-6-(4-nitrophenyl)-pyrimidine (1.20 g, 2.90 mmol, prepared from 1-(4-nitrophenyl-4,4,5,5,6,6,6-heptafluorohexane-1,3-dione according to Green et al. WO 200138311 A2), 4-trifluoromethylphenylboronic acid (0.608 g, 3.2 mmol), trifurylphosphine (114 mg, 0.49 mmol), and copper (II) 2-thiophenecarboxylate (750 mg, 3.9 mmol) were combined in 15 mL of dry THF and heated to 50° C. The catalyst tris(dibenzylideneacetone)dipalladium(0)-chloroform adduct (60 mg, cat) was then added in three portions over 3 h, and the solution was then allowed to stir at 50° C. overnight. Concentration and chromatography (Biotage, 5:1 hexane/DCM) furnished 0.60 g (40%) of the title compound as a light yellow solid. EIMS 514.0 (M+H); mp 191° C.

Step 2. 4-Heptafluoropropyl-6-(4-aminophenyl)-2-(4-trifluoromethyl-phenyl)-pyrimidine. A solution of 4-heptafluoropropyl-2-(4-trifluoromethylphenyl)-6-(4-nitrophenyl)-pyrimidine (0.18 g, 0.35 mmol), iron powder (0.20 g, 3.5 mmol), ferric ammonium sulfate (0.15 g, 0.3 mmol) in 3:1 EtOH/water was heated on a steam bath for 3 h. Then it was cooled, diluted with 50 mL of Et$_2$O, filtered through Celite®, and concentrated to give the aniline as a yellow solid. $^1$H NMR (300 MHz, CDCl$_3$) δ 8.75 (d, J=8 Hz, 2H), 8.18 (d, J=8 Hz, 2H), 7.90 (s, 1H), 7.80 (d, J=8 Hz, 2H), 6.82 (d, J=8 Hz, 2H), 4.20 (s, 2H).

Example 45

Preparation of 4-trifluoromethyl-6-(4-aminophenyl)-2-(4-trifluoromethyl-phenyl)-pyrimidine

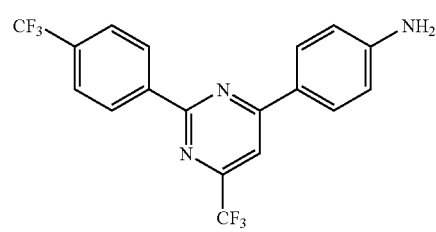

Step 1. 4-Trifluoromethyl-6-(4-nitrophenyl)-2-(4-trifluoromethyl-phenyl)-pyrimidine. A solution of 4-trifluoromethyl-2-methylsulfanyl-6-(4-nitrophenyl)-pyrimidine (1.25 g, 4.0 mmol, prepared from 1-(4-nitrophenyl-4,4,4-trifluorobutane-1,3-dione according to Green et al. WO 200138311 A2), 4-trifluoromethylphenylboronic acid (0.95 g, 5.0 mmol), trifurylphosphine (140 mg, 0.60 mmol), and copper (II) 2-thiophenecarboxylate (1.05 g, 5.0 mmol) were combined in 25 mL of dry THF and heated to 52° C. The catalyst tris(dibenzyl-ideneacetone)dipalladium(0)-chloroform adduct (100 mg) was then added in three portions over 3 h, and the solution was then allowed to stir at 50° C. for 12 h. Concentration and chromatography (Biotage, 4:1 hexane/DCM) furnished 0.67 g (41%) of the title compound as a light yellow solid. $^1$H NMR (300 MHz, CDCl$_3$) δ 8.75 (d, J=8 Hz, 2H), 8.41 (s, 4H), 8.03 (s, 1H), 7.80 (d, J=8 Hz, 2H); EIMS 414.1 (M+H); mp 162° C.

Step 2. 4-Trifluoromethyl-6-(4-aminophenyl)-2-(4-trifluoromethyl-phenyl)-pyrimidine. A solution of 4-trifluoromethyl-2-(4-trifluoromethylphenyl)-6-(4-nitrophenyl)-pyrimidine (0.50 g, 1.2 mmol), iron powder (0.50 g, 9 mmol), ferric ammonium sulfate (0.5 g, 1.0 mmol) in 30 mL of 3:1 EtOH-water was heated on a steam bath for 3 h. Then it was cooled, diluted with 50 mL of diethyl ether, filtered through Celite®, and concentrated. The crude amine was purified by Biotage column (4:1:1 Hexanes/EtOAc/DCM) to give 0.22 g of pure aniline. This material was used directly in the formation of the corresponding carbamate. $^1$H NMR (300 MHz, CDCl$_3$) δ 8.75 (d, J=8 Hz, 2H), 8.16 (d, J=8 Hz, 2H), 7.81 (s, 1H), 7.77 (d, J=8 Hz, 2H), 6.82 (d, J=8 Hz, 2H), 4.15 (s, 2H).

Example 46

Preparation of 4-[2-(4-trifluoromethyl-phenyl)-pyrimidin-4-yl]-phenylamine

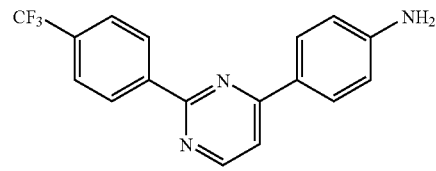

Step 1. 4-(4-Nitrophenyl)-2-(4-trifluoromethyl-phenyl)-pyrimidine. To 82.7 mg (3.60 mmol) of sodium metal dissolved in 3 mL of absolute EtOH was added 938 mg (3.60 mmol) of 4-trifluoromethylbenzamidine hydrochloride dihydrate followed by 4 mL of EtOH. After 30 min, 498 mg (2.26 mmol) of 3-dimethylamino-1-(4-nitrophenyl)-propenone was added and the mixture was heated at reflux approximately 66 h and was allowed to cool. The mixture was concentrated to a tan solid which was triturated under saturated sodium bicarbonate. The solid was collected and air dried to give 937 mg. It was then dissolved in chloroform/EtOAc and was passed over silica gel eluting with 7:3 chloroform/EtOAc to afford 710 mg (91%) of the title compound. $^1$H NMR ε 9.01 (d, J=5.3 Hz, 1H), 8.73 (d, J=8.2 Hz, 2H), 8.43 (s, 4H), 7.82 (d, J=8.1 Hz, 2H), 7.76 (d, J=5.2 Hz, 1H); EIMS 345 (M$^+$, 100), 299 (57); mp 175-176.5° C. Anal. Calcd. for $C_{17}H_{10}F_3N_3O_2$: C, 59.13; H, 2.92; N, 12.17. Found: C, 58.82; H, 2.63; N, 11.98.

Step 2. 4-[2-(4-Trifluoromethyl-phenyl)-pyrimidin-4-yl]-phenylamine. A mixture of 670 mg (1.94 mmol) of the nitrobenzene 4-(4-nitrophenyl)-2-(4-trifluoromethyl-phenyl)-pyrimidine and 75 mg of 10% Pd/C in 30 mL of EtOH was placed on a Parr shaker at 40 psi hydrogen gas at room temperature. After 7 h the mixture was filtered through Celite® and the EtOH was removed in vacuo. The residue was partitioned between EtOAc and saturated sodium bicarbonate, and the organic phase was dried (MgSO$_4$). Concentration gave a solid which was dissolved in EtOAc and was filtered through a plug of silica gel. Concentration gave 500 mg (82%) of the titled compound. $^1$H NMR δ 8.75 (d, J=5.30 Hz, 1H), 8.67 (d, J=8.3 Hz, 2H), 8.10 (d, J=8.9 Hz, 2H), 7.75 (d, J=7.9 Hz, 2H), 7.54 (d, J=5.3 Hz, 1H), 6.80 (d, J=8.6 Hz, 2H), 4.03 (br s, 2H); MS (API-ES+) 316 ([M+H]$^+$, 100); mp 166-167° C. Anal. Calcd. for $C_{17}H_{12}F_3N_3$: C, 64.76; H, 3.84; N, 13.33. Found: C, 64.37; H, 3.71; N, 13.08.

Example 47

Preparation of 2-chloro-4-[3-(4-trifluoromethyl-phenyl)-[1,2,4]triazol-1-yl]-phenylamine

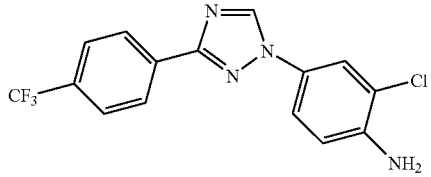

Step 1. 1-(3-Chloro-4-nitrophenyl)-3-(4-trifluoromethyl-phenyl)-1H-[1,2,4]triazole. A solution of NBS (180 mg, 1 mmol) in 4 mL of CH$_2$Cl$_2$ was stirred under nitrogen at 0° C. while dimethyl sulfide (110 mg, 1.8 mmol) was added via syringe. The solution, which forms a white solid, was then cooled to −20° C., and (N-(3-chloro-4-nitrophenyl)-N'-(4-trifluoromethyl-benzylidene)-hydrazine (200 mg, 0.58 mmol) in 4 mL of DCM was added. The solution was allowed to warm to ambient temperature and stirred for an additional 2 h. The resulting orange solution was then diluted with 25 mL of DCM and washed with water and brine before drying and concentrating. The resulting orange solid hydrazonyl bromide (150 mg) was then treated directly with tetrazole (25 mg, 0.35 mmol) and triethylamine (50 μL, 0.35 mmol) in 5 mL of absolute EtOH. The resulting orange-brown solution was heated at reflux for 2 h. TLC shows that the initial bromide was first converted into two yellow intermediates, which then disappeared and were replaced by a single, colorless, spot. The orange solution was then diluted with 10 mL of water, yielding a tan-yellow solid which was filtered, air-dried, and recrystallized from toluene to give 60 mg of a yellow-tan solid. $^1$H NMR (300 MHz, CDCl$_3$) δ 8.60 (s, 1H), 8.41 (d, J=8.7 Hz, 1H), 8.33 (d, J=7.5 Hz, 2H), 7.90 (d, J=2 Hz, 1H), 7.70 (d, J=7.5 Hz, 2H), 7.65 (dd, J=8.7, 2 Hz, 1H); EIMS 368.9; mp 185° C. Anal. Calcd. for $C_{15}H_8ClF_3N_4O_2$: C, 48.86; H, 2.19; N, 15.20. Found: C, 48.39; H, 2.61; N, 14.91.

Step 2. 2-Chloro-4-[3-(4-trifluoromethyl-phenyl)-[1,2,4]triazol-1-yl]-phenylamine. A solution of the nitrophenyl derivative (0.75 g, 2.0 mmol) in 7 mL of MeOH and 3 mL of water was treated with iron powder (0.7 g, 12.5 mmol) and ferrous ammonium sulfate (hexahydrate; 0.7 g, 1.8 mmol). The solution was heated on a steam bath for 3 h, whereupon TLC showed complete conversion to a more polar, fluorescent product. The solution was cooled and filtered, and the filtrate was concentrated in vacuo and purified by chromatography through a short plug of silica gel (7:2:1 hexane/EtOAc/DCM) to give 0.55 g of the amine as a light tan solid. $^1$H NMR (300 MHz, CDCl$_3$) δ 8.40 (s, 1H), 8.31 (d, J=8.4 Hz, 1H), 7.72 (d, J=8.4 Hz, 2H), 7.69 (d, J=2 Hz, 1H), 7.42 (dd, J=8.5, 2 Hz, 1H), 6.9 (d, J=8.4 Hz, 1H); EIMS 340.4, 342.3 (M+H); mp 148° C. Anal. Calcd. for $C_{15}H_{10}ClF_3N_4$: C, 53.19; H, 2.98; N, 16.83. Found: C, 52.90H, 3.10; N, 16.83.

Example 48

Preparation of 4-[1-(4-Trifluoromethoxyphenyl)-1H-[1,2,4]triazol-3-yl]-phenylamine

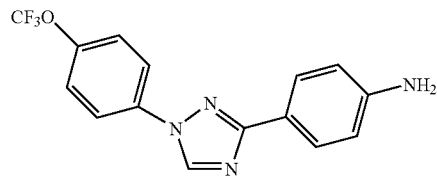

Step 1. 1-(4-Trifluoromethoxyphenyl)-3-(4-nitrophenyl)-1H-[1,2,4]triazole. A solution of NBS (0.70 g, 3.9 mmol) in 25 mL of CH$_2$Cl$_2$ was stirred under nitrogen at 0° C. while dimethyl sulfide (0.40 g, 6.5 mmol) was added via syringe. The solution, which forms a white solid, was then cooled to −20° C., and N-(4-nitrobenzylidene)-N'-(4-trifluoromethoxyphenyl)-hydrazine (0.70 g, 2.15 mmol) in 10 mL of DCM was added. The solution was allowed to warm to ambient temperature and stirred an additional 2 h. The resulting orange solution was then diluted with 25 mL of DCM and washed with water and brine before drying and concentrating. The resulting orange solid hydrazonyl bromide (0.9 g) was then treated directly with tetrazole (154 mg, 2.2 mmol) and triethylamine (280 μL, 0.23 mmol) in 5 mL of absolute EtOH. The resulting orange-brown solution was heated at reflux for 2 h. TLC showed that the initial bromide was first converted into two yellow intermediates, which were replaced by a single, colorless, spot. The orange solution was then concentrated and purified by chromatography (2:1:2 Hexane/EtOAc/DCM), yielding 0.30 g of the title compound as a light yellow solid. $^1$H NMR (300 MHz, CDCl$_3$) δ 8.68 (s, 1H), 8.40 (d, J=5 Hz, 2H), 8.35 (d, J=5 Hz, 2H), 7.85 (d, J=8 Hz, 2H), 7.42 (d, J=8 Hz, 2H); EIMS 350 (M$^+$, 100), 299 (57); mp 147° C.

Step 2. 4-[1-(4-Trifluoromethoxyphenyl)-1H-[1,2,4]triazol-3-yl]-phenylamine. Catalytic reduction using a Pd/C catalyst in EtOH under hydrogen atmosphere gave the corresponding aniline as a light grey solid. $^1$H NMR (300 MHz, CDCl$_3$) δ 8.50 (s, 1H), 8.00 (d, J=8.4 Hz, 2H), 7.78 (d, J=8.7 Hz, 2H), 7.35 (d, J=8 Hz, 2H), 6.76 (d, J=8.7 Hz, 2H), 3.9 (br s, 2H); EIMS 321; mp 160° C.

Example 49

Preparation of 4-[1-(4-Pentafluoroethyloxyphenyl)-1H-[1,2,4]triazol-3-yl]-phenylamine

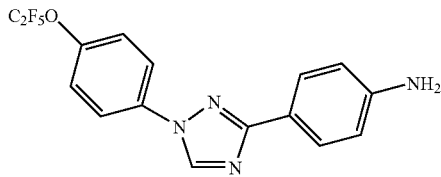

Step 1. 1-(4-Pentafluoroethyloxyphenyl)-3-(4-nitrophenyl)-1H-[1,2,4]triazole. A slurry of 3-(4-nitrophenyl) triazole (11.4 g, 60 mmol), 1-iodo-4-pentafluoroethoxybenzene (20 g, 60 mmol), cesium carbonate (39.0 g, 120 mmol), CuI (3.5 g, 18 mmol), 8-hydroxyquinoline (2.0 g, 13.8 mmol) and 155 mL of 9:1 DMF-H$_2$O were heated at 150° C. for 5 h, then cooled and the contents poured onto 150 mL of water and extracted with 2×100 mL of Et$_2$O. The organic layer was dried and concentrated, and the solid residue recrystallized from MeOH and water to give 11.8 g (49%) of the nitrotriazole as a tan solid. $^1$H NMR (300 MHz, CDCl$_3$) δ 8.68 (s, 1H), 8.40 (d, J=5 Hz, 2H), 8.35 (d, J=5 Hz, 2H), 7.85 (d, J=8 Hz, 2H), 7.42 (d, J=5.2 Hz, 8 Hz, 2H); EIMS 400 (M$^+$); mp 170-175° C.

Step 2. 4-[1-(4-Pentafluoroethyloxyphenyl)-1H-[1,2,4]triazol-3-yl]-phenylamine. Catalytic reduction using a Pd/C catalyst in EtOH under hydrogen atmosphere gave the corresponding aniline as a light tan solid. $^1$H NMR (300 MHz, CDCl$_3$) δ 8.55 (s, 1H), 8.00 (d, J=7 Hz, 2H), 7.78 (d, J=8 Hz, 2H), 7.35 (d, J=8 Hz, 2H), 6.78 (d, J=8 Hz, 2H), 3.9 (br s, 2H); EIMS 371; mp 160° C.

Example 50

Preparation of 4-[1-(4-heptafluoropropyloxyphenyl)-1H-[1,2,4]triazol-3-yl]-phenylamine

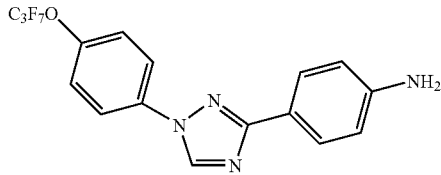

Step 1. 1-(4-Heptafluoropropyloxyphenyl)-3-(4-nitrophenyl)-1H-[1,2,4]triazole. A slurry of 3-(4-nitrophenyl) triazole (1.0 g, 5.2 mmol), 1-iodo-4-heptafluoropropyloxybenzene (6.1 g, 15.8 mmol), cesium carbonate (10.0 g, 30.7 mmol), CuI (900 mg, 4.7 mmol), and 8-hydroxyquinoline (500 mg, 3.4 mmol) in 40 mL of 9:1 DMF-H$_2$O was heated at 150° C. for 12 h, then cooled and the contents poured onto 50 mL of water and 50 mL of concentrated NH$_4$OH. The blue solution was extracted with 100 mL of ether and the organic layer was separated and filtered to remove some insoluble material, then dried and concentrated. The solid residue was recrystallized from MeOH/water to furnish 4.69 g of the nitrophenyl triazole as a light tan solid. $^1$H NMR (300 MHz, CDCl$_3$) δ 8.66 (s, 1H), 8.40 (m, 4H), 7.85 (d, J=8 Hz, 2H), 7.42 (d, J=8 Hz, 2H); EIMS 450.1 (M$^+$); mp 114-116° C.

Step 2. 4-[1-(4-Heptafluoropropyloxyphenyl)-1H-[1,2,4]triazol-3-yl]-phenylamine. Catalytic reduction under the conditions described above gave the corresponding aniline as a light tan solid. $^1$H NMR (300 MHz, CDCl$_3$) δ 8.54 (s, 1H), 8.00 (d, J=8 Hz, 2H), 7.80 (d, J=8 Hz, 2H), 7.40 (d, J=8 Hz, 2H), 6.78 (d, J=8 Hz, 2H), 3.9 (br s, 2H); EIMS 421.3 (M+1); mp 181-183° C.

Example 51

Preparation of 4-[4-(4-trifluoromethylphenyl)-imidazol-1-yl]-phenylamine

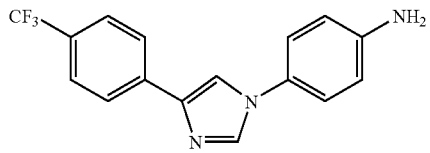

Step 1. 4-[4-(4-Trifluoromethylphenyl)-1H-imidazol-1-yl]-nitrobenzene. 4-Trifluoromethylphenyl imidazole (1.43 g, 6.7 mmol), 4-fluoro nitrobenzene (1.2 g, 8.5 mmol) and potassium carbonate (1.5 g, 10.9 mmol) were combined in 15 mL of DMF and heated at 100° C. for 6 h. The cooled solution was then poured onto 100 mL of water and the resulting solid was filtered and air-dried to give 1.0 g of the title imidazole as a light yellow solid, mp 197° C. Anal. Calcd. for C$_{16}$H$_{10}$F$_3$N$_3$O$_2$: C, 57.66; H, 3.02; N, 12.61. Found: C, 57.69; H, 3.01; N, 12.48.

Step 2. 4-[4-(4-Trifluoromethylphenyl)-imidazol-1-yl]-phenylamine. Catalytic reduction using a Pd/C catalyst in EtOH under hydrogen atmosphere gave the corresponding aniline as a light grey solid. $^1$H NMR (400 MHz, CDCl$_3$) δ 7.90 (d, J=7 Hz, 2H), 7.75 (s, 1H), 7.65 (d, J=7 Hz, 2H), 7.52 (s, 1H), 7.19 (d, J=8 Hz, 2H), 6.75 (d, J=8 Hz, 2H), 3.8 (br s, 2H); EIMS 302.0; mp 142-143° C.

Example 52

Preparation of 4-[1-(4-trifluoromethylphenyl)-1H-imidazol-4-yl]-phenylamine

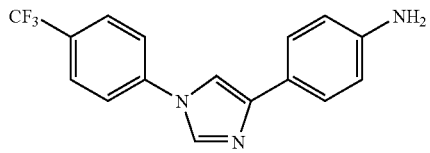

Step 1. 4-[4-(4-Trifluoromethylphenyl)-1H-imidazol-1-yl]-nitrobenzene. Prepared as in step 1 of the preceding example.

Step 2. 4-[1-(4-Trifluoromethylphenyl)-1H-imidazol-4-yl]-phenylamine. Catalytic reduction using a Pd/C catalyst in EtOH under hydrogen atmosphere gave the corresponding aniline as a light grey solid. $^1$H NMR (400 MHz, CDCl$_3$) δ 7.92 (s, 1H), 7.76 (d, J=8 Hz, 2H), 7.66 (d, J=4.5 Hz, 2H), 7.55 (s, 1H), 6.75 (d, J=4.5 Hz, 2H), 3.8 (br s, 2H); EIMS 304.0;

Example 53

Preparation of 4-[1-(4-trifluoromethoxyphenyl)-1H-imidazol-4-yl]-phenylamine

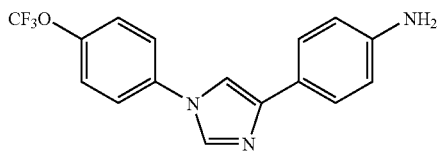

Step 1. 4-(4-Nitrophenyl)-1-(4-trifluoromethoxy-phenyl)-1H-imidazole. The conditions described by Porretta et al. *Farmaco, Edizione Scientifica* 1985, 40, 404 were used to convert 4-trifluoromethoxyaniline (5.3 g, 30 mmol) and α-bromo-4-nitroacetophenone (3.7 g, 15 mmol) into 2.1 g (41% overall yield) of the imidazole.

Step 2. 4-[1-(4-Trifluoromethoxyphenyl)-1H-imidazol-4-yl]-phenylamine. Catalytic reduction using a Pd/C catalyst in EtOH under hydrogen atmosphere gave the corresponding aniline as a light grey solid. $^1$H NMR (300 MHz, CDCl$_3$) δ 7.83 (s, 1H), 7.64 (d, J=4.8 Hz, 2H), 7.47 (d, J=4.4 Hz, 2H), 7.40 (s, 1H), 7.36 (d, J=4.8 Hz, 2H), 6.75 (d, J=4.4 Hz, 2H), 3.5 (br s, 2H); EIMS 320; mp 167° C. Anal. Calcd. for C$_{16}$H$_{12}$F$_3$N$_3$O: C, 60.19; H, 3.79; N, 13.16. Found: C, 59.91; H, 3.67; N, 13.03.

Example 54

Preparation of 4-(4-aminophenyl)-2-(4-trifluoromethoxy-phenyl)-2,4-dihydro-[1,2,4]triazol-3-one

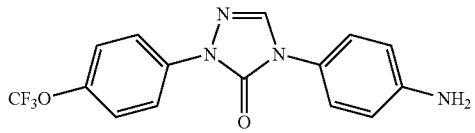

Step 1. 4-(4-Nitrophenyl)-2-(4-trifluoromethoxyphenyl)-2,4-dihydro-[1,2,4]triazol-3-one. The title compound was prepared according to the procedure in Henbach, DE 2724891 A1, 1978, with modifications to three steps: In the addition of the aniline, 4-nitroaniline was used instead of 3,5-dichloroaniline and dry THF was used as solvent instead of toluene. In the formation of the triazolinone ring, triphosgene (0.65 equiv) was used instead of phosgene. $^1$H NMR (300 MHz, CDCl$_3$) δ 8.40 (d, J=8.8 Hz, 2H), 8.05 (d, J=8.8 Hz, 2H), 7.99 (s, 1H), 7.89 (d, J=9.3 Hz, 2H), 7.32 (d, J=9.3 Hz, 2H); ESIMS 367 (M+H); mp 136-140° C.

Step 2. 4-(4-Aminophenyl)-2-(4-trifluoromethoxyphenyl)-2,4-dihydro-[1,2,4]triazol-3-one. The nitrophenyl triazolinone (0.037 g, 0.10 mmol) was dissolved in absolute EtOH (1 mL) under N$_2$. To this was added tin(II) chloride dihydrate (0.114 g, 0.51 mmol), and the mixture was stirred at reflux for 2 h. The mixture was cooled to 25° C., was poured onto ice-H$_2$O (25 mL), and the aqueous mixture was brought to pH 9-10 with 1 N NaOH. The mixture was extracted with Et$_2$O (3×25 mL), and the combined organic extracts were dried (MgSO$_4$), filtered and concentrated to give a dark brown solid (0.0297 g, 87%) that was used without further purification. $^1$H NMR (300 MHz, CDCl$_3$) δ 8.07 (d, J=9.7 Hz, 2H), 7.73 (s, 1H), 7.32-7.23 (m, 4H), 6.77 (d, J=8.5 Hz, 2H), 3.85 (br, 2H); ESIMS 336 (M$^+$); mp 115-120° C.

Example 55

Preparation of 4-[5-(4-trifluoromethylphenyl)-4,5-dihydro-isoxazol-3-yl]-phenylamine

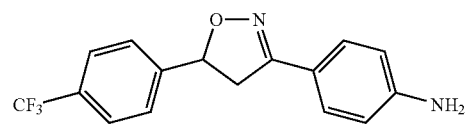

Step 1. {4-[5-(4-Trifluoromethylphenyl)-4,5-dihydro-isoxazol-3-yl]-phenyl}-carbamic acid tert-butyl ester. To a stirred solution of N-chlorosuccinimide (57 mg, 0.424 mmol) and pyridine (3 μL) in 1.7 mL of chloroform was added 4-N-t-BOC-aminobenzaldehyde oxime (100 mg, 0.424 mmol). The reaction was stirred at room temperature for 10 min. 4-Trifluoromethylstyrene (78 μL, 0.53 mmol) was then added and the temperature was increased to 45° C. To this solution was added triethylamine (62 μL, 0.445 mmol) dissolved in 0.5 mL of CHCl$_3$ dropwise. The reaction was stirred at 45° C. for 5 h. The cooled solution was diluted with chloroform (10 mL) and washed with water (2×5 mL). The organic phase was then dried over MgSO$_4$, filtered and concentrated to give the isoxazoline (100 mg, 58%). $^1$H NMR (400 MHz, CDCl$_3$) δ 7.40-7.83 (m, 8H), 6.60 (bs, 1H), 5.76 (dd, J=11.0, 7.7 Hz, 1H), 3.81 (dd, J=16.5, 11.0 Hz, 1H), 3.29 (dd, J=16.5, 7.7 Hz, 1H); EIMS 406 (M$^+$).

Step 2. 4-[5-(4-Trifluoromethylphenyl)-4,5-dihydro-isoxazol-3-yl]-phenylamine. To a stirred solution of the N-BOC isoxazoline (prepared in step 1) in CH$_2$Cl$_2$ (2.5 mL) was added trifluoroacetic acid (6.16 mmol, 0.46 mL) and the reaction was stirred at room temperature for 3 h. The solution was concentrated and the residue was taken up in 5 mL of saturated KHCO$_3$ solution and stirred for 30 min. The mixture was then extracted with CH$_2$Cl$_2$ (3×10 mL). The organic phase was then dried over MgSO$_4$, filtered and concentrated to afford the expected aniline (68 mg, 90%). $^1$H NMR (400 MHz, CDCl$_3$) δ 7.45-7.63 (m, 6H), 6.67 (d, J=8.6 Hz, 2H), 5.72 (dd, J=10.9, 7.6 Hz, 1H), 3.92 (bs, 2H), 3.78 (dd, J=16.7, 10.9 Hz, 1H), 3.25 (dd, J=16.7, 7.6 Hz, 1H); EIMS 306 (M$^+$).

Example 56

Preparation of 4-[3-(4-Trifluoromethoxyphenyl)-4,5-dihydro-isoxazol-5-yl]-phenylamine

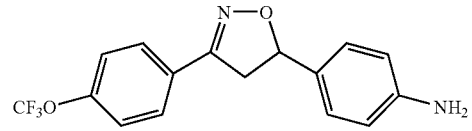

To a stirred solution of N-chlorosuccinimde (0.634 mmol, 85 μL) and pyridine (4 μL) in 2.5 mL of chloroform was added p-trifluoromethoxybenzaldehyde oxime (130 mg, 0.634 mmol). The reaction was heated at 50° C. for 3 h. 4-Aminostyrene (0.793 mmol, 93 μL) was then added followed by a solution of triethylamine (0.666 mmol, 93 μL) dissolved in 0.5 mL of CHCl₃ dropwise. The reaction was stirred at 50° C. for 3 h. The cooled solution was diluted with chloroform (15 mL) and washed with water (2×10 mL). The organic phase was then dried over MgSO₄, filtered and concentrated. The residue was purified via radial chromatography using a 2:1 hexane/EtOAc solution as the eluent (R$_f$=0.18) to afford 4-[3-(4-trifluoromethoxyphenyl)-4,5-dihydro-isoxazol-5-yl]-phenylamine (125 mg; 61%). ¹H NMR (400 MHz, CDCl₃) δ 7.73 (d, J=8.2 Hz, 2H), 7.25 (d, J=8.2 Hz, 2H), 7.17 (d, J=8.2 Hz, 2H), 6.68 (d, J=8.2 Hz, 2H), 5.65 (dd, J=10.9, 8.9 Hz, 1H), 3.55-3.75 (bs, 2H), 3.67 (dd, J=16.8, 10.9 Hz, 1H), 3.30 (dd, J=16.8, 8.9 Hz, 1H); EIMS 322 (M⁺).

Example 57

Preparation of 1-(4-aminophenyl)-3-(4-trifluoromethoxy-phenyl)-1,3-dihydro-imidazol-2-one These compounds were prepared according to the procedure described in Bromidge et al. WO 2003057220 A1 with slight modifications.

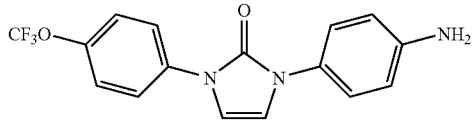

Step 1. (2,2-Dimethoxyethyl)-(4-trifluoromethoxyphenyl) amine. To a stirred solution of 4-trifluoromethoxyaniline (1 mL, 7.46 mmol) and glyoxaldehyde diemethyl acetal (60% v/v in water, 8.95 mmol, 1.6 mL) in 37 mL of EtOH was added 300 mg of 10% palladium on carbon. The mixture was evacuated and flushed with nitrogen three times. Hydrogen was then added in a balloon apparatus and the mixture was stirred under 1 atm of hydrogen for 31 h. The mixture was then filtered through a pad of Celite® and the pad was washed with EtOH (25 mL). The ethanol was removed under reduced pressure and the residue was diluted with 30 mL of CH₂Cl₂. The layers were separated and the organic phase was dried over MgSO₄, filtered and concentrated to give (2,2-dimethoxyethyl)-(4-trifluoromethoxyphenyl) amine (1.7 g, 86%). ¹H NMR (400 MHz, CDCl₃) δ 7.04 (d, J=8.9 Hz, 2H), 6.59 (d, J=8.9 Hz, 2H), 4.56 (t, J=5.4 Hz, 1H), 3.92 (bs, 1H), 3.51 (d, J=5.4 Hz, 2H), 3.42 (s, 6H); EIMS 265 (M⁺).

Step 2. 1-(2,2-Dimethoxyethyl)-3-(4-nitrophenyl)-1-(4-trifluoromethoxyphenyl)-urea. To a stirred solution of (2,2-dimethoxyethyl)-(4-trifluoromethoxyphenyl) amine (3.2 mmol, 0.85 g) dissolved in 32 mL of CH₂Cl₂ was added p-nitrophenyl isocyanate (3.53 mmol, 0.58 g) and the reaction was stirred at room temperature overnight. The mixture was diluted with CH₂Cl₂ (50 mL) and was washed successively with NaHCO₃ (30 mL) and brine (30 mL). The organic phase was then dried over MgSO₄, filtered and concentrated. The residue was purified via radial chromatography using a 2:1 hexane/EtOAc solution as the eluent (R$_f$=0.32) to afford 1-(2,2-dimethoxyethyl)-3-(4-nitrophenyl)-1-(4-trifluoromethoxyphenyl)-urea (0.87 g, 63%). ¹H NMR (400 MHz, CDCl₃) δ 8.15 (d, J=9.2 Hz, 2H), 7.30-7.50 (m, 6H), 7.02 (bs, 1H), 4.65 (t, J=5.4 Hz, 1H), 3.82 (d, J=5.4 Hz, 2H), 3.41 (s, 6H); EIMS 429 (M⁺).

Step 3. 1-(4-Nitrophenyl)-3-(4-trifluoromethoxyphenyl)-1,3-dihydroimidazol-2-one. To a stirred solution of 1-(2,2-dimethoxyethyl)-3-(4-nitrophenyl)-1-(4-trifluoromethoxyphenyl)-urea (0.23 g, 0.53 mmol) dissolved in 28 mL of toluene was added 2 drops of concentrated HCl. The reaction mixture was stirred at reflux for 3 h. The cooled solution was diluted with EtOAc (75 mL) and washed with saturated NaHCO₃ (25 mL) and brine (25 mL). The organic phase was then dried over MgSO₄, filtered and concentrated. The residue was purified via radial chromatography using a 2:1 hexane/EtOAc solution as the eluent (R$_f$=0.28) to afford 1-(4-nitrophenyl)-3-(4-trifluoromethoxyphenyl)-1,3-dihydroimidazol-2-one (134 mg, 71%). ¹H NMR (400 MHz, CDCl₃) δ 8.35 (d, J=9.2 Hz, 2H), 7.93 (d, J=9.2 Hz, 2H), 7.67 (d, J=9.2 Hz, 2H), 7.34 (d, J=9.2 Hz, 2H), 6.87 (d, J=3.3 Hz, 1H), 6.81 (d, J=3.3 Hz, 1H); EIMS 365 (M⁺).

Step 4. 1-(4-Aminophenyl)-3-(4-trifluoromethoxyphenyl)-1,3-dihydro-imidazol-2-one. To a stirred solution of 1-(4-nitrophenyl)-3-(4-trifluoro-methoxyphenyl)-1,3-dihydroimidazol-2-one (120 mg, 0.33 mmol) in 3.5 mL of EtOAc was added tin dichloride (371 mg, 1.64 mmol) and the reaction mixture was stirred at reflux for 3 h. The cooled solution was poured onto ice (15 mL) and the pH was adjusted to pH 7-8 by the addition of 10% NaHCO₃. The mixture was extracted with EtOAc (3×10 mL) and washed with brine (10 mL). The organic phase was then dried over MgSO₄, filtered and concentrated to obtain 1-(4-amino-phenyl)-3-(4-trifluoromethoxyphenyl)-1,3-dihydro-imidazol-2-one. (102 mg, 92%). ¹H NMR (400 MHz, CDCl₃) δ 7.72 (d, J=8.8 Hz, 2H), 7.37 (d, J=8.8 Hz, 2H), 7.32 (d, J=8.8 Hz, 2H), 6.76 (d, J=8.8 Hz, 2H), 6.69 (d, J=3.3 Hz, 1H), 6.65 (d, J=3.3 Hz, 1H); EIMS 335 (M⁺).

Example 58

Preparation of 1-(4-aminophenyl)-3-(4-trifluoromethoxyphenyl)-imidazolidin-2-one

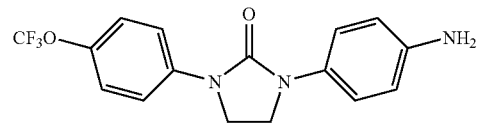

To a solution of 1-(4-nitrophenyl)-3-(4-trifluoromethoxyphenyl)-1,3-dihydroimidazol-2-one (144 mg, 0.395 mmol) in 40 mL of EtOH was added 100 mg of 10% palladium on carbon. The mixture was evacuated and flushed with nitrogen three times. The Parr vessel was pressurized to 45 psi of hydrogen and shaken for 5 h. The depressurized solution was filtered through a pad of Celite® and the pad was washed with EtOH (25 mL). The ethanol was removed under reduced pressure to afford the title product (114 mg, 95%). ¹H NMR (400 MHz, CDCl₃) δ 7.61 (d, J=9.2 Hz, 2H), 7.33 (d, J=9.2 Hz, 2H), 7.21 (d, J=8.6 Hz, 2H), 6.71 (d, J=9.2 Hz, 2H), 3.92 (s, 4H), 3.61 (bs, 2H); EIMS 307 (M⁺).

Example 59

Preparation of 4-[6-(4-trifluoromethoxyphenyl)-pyridazin-3-yl]-phenylamine

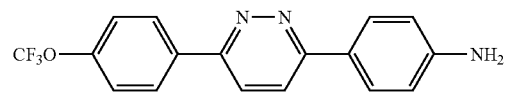

Step 1. 3-Chloro-6-(4-trifluoromethoxyphenyl)-pyridazine. To a solution containing 3,6-dichloropyridazine (0.3 g, 2.01 mmol), 4-trifluoromethoxyphenyl-boronic acid (0.50 g, 2.42 mmol) and 2 M $K_2CO_3$ (2 mL, 4.03 mmol) dissolved in 11 mL of dry 1,4-dioxane was added dichlorobis(triphenylphosphine)palladium(II) (14 mg, 0.02 mmol). The mixture was irradiated using a CEM Discover microwave at 190° C. for 30 min. The mixture was diluted with 100 mL of ether and washed with brine (30 mL). The organic phase was then dried over $MgSO_4$, filtered and concentrated. The residue was purified via radial chromatography using a 3:1 hexane/EtOAc solution as the eluent. Two fractions were isolated. The first fraction ($R_f$=0.63) was shown to be the bis-Suzuki product (95 mg, 12%). The second fraction isolated ($R_f$=0.34) was identified as 3-chloro-6-(4-trifluoromethoxyphenyl)-pyridazine (174 mg, 32%). $^1$H NMR (400 MHz, $CDCl_3$) δ 8.10 (d, J=9.2 Hz, 2H), 7.83 (d, J=8.9 Hz, 2H), 7.60 (d, J=8.9 Hz, 2H), 7.37 (d, J=9.2 Hz, 2H); EIMS 274 (M$^+$).

Step 2. 4-[6-(4-Trifluoromethoxyphenyl)-pyridazin-3-yl]-phenylamine.

To a solution containing 3-chloro-6-(4-trifluoromethoxyphenyl)-pyridazine (157 mg, 0.57 mmol), 4-aminophenylboronic acid (118 mg, 0.86 mmol) and 2 M $K_2CO_3$ (0.57 mL, 1.14 mmol) dissolved in 3.5 mL of dry 1,4-dioxane was added dichlorobis(triphenylphosphine)palladium(II) (4 mg, 0.006 mmol). The mixture was irradiated using a CEM Discover microwave at 190° C. for 30 min. The mixture was diluted with 100 mL of ether and washed with brine (30 mL). The organic phase was then dried over $MgSO_4$, filtered and concentrated. The residue was purified via radial chromatography using a 97:3 $CHCl_3/CH_3OH$ solution as the eluent ($R_f$=0.26) to afford the title compound (105 mg, 56%). $^1$H NMR (400 MHz, $CDCl_3$) δ 8.18 (d, J=8.6 Hz, 2H), 8.01 (d, J=8.6 Hz, 2H), 7.30-7.45 (m, 4H), 6.82 (d, J=8.6 Hz, 2H), 3.96 (bs, 2H); EIMS 331 (M$^+$).

Example 60

Preparation of 4-[3-(4-Trifluoromethoxyphenyl)-4-5-dihydro-[1,2,4]oxadiazol-5-yl]-benzaldehyde

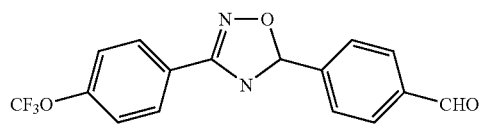

The compound was prepared according to the general procedure of Srivastava et al. *J. Heterocycl. Chem.* 1987, 24, 101 with slight modifications. To a stirred solution of 4-(trifluoromethoxy)benzamidoxime (Acros) (300 mg, 1.36 mmol) dissolved in 1.4 mL of acetic acid was added 1,4-terephthaldehyde (1.1 g, 8.18 mmol) and the reaction was stirred at room temperature for 4 d. The mixture was then dissolved in $CHCl_3$ (20 mL) followed by addition of 10 mL of heptane. This solution was concentrated under reduced pressure. This procedure was repeated twice. The residue was purified via radial chromatography using a 99:1 $CHCl_3/CH_3OH$ solution as the eluent. Two fractions were isolated. The first fraction isolated ($R_f$=0.30) was shown to be starting material (20 mg). The second fraction isolated ($R_f$=0.17) was shown to be the title compound (23 mg, 5%). $^1$H NMR (400 MHz, $CDCl_3$) δ 10.02 (s, 1H), 7.91 (d, J=8.2 Hz, 2H), 7.77 (d, J=9.2 Hz, 2H), 7.70 (d, J=8.2 Hz, 2H), 7.27 (d, J=8.2 Hz, 2H), 6.64 (d, J=4.3 Hz, 1H), 5.18 (d, J=4.3 Hz, 1H); EIMS 336 (M$^+$).

Example 61

Preparation of 4-[5-(4-Trifluoromethoxyphenyl)-[1,2,4]oxadiazol-3-yl]-phenylamine

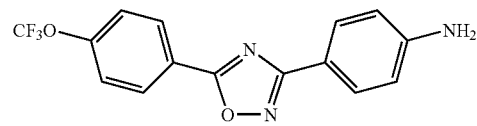

Step 1. {4-[5-(4-Trifluoromethoxyphenyl)-[1,2,4]oxadiazol-3-yl]-phenyl}-carbamic acid tert-butyl ester. To a stirred solution of tert-butyl-4-(N-hydroxycarbamimidoyl)-phenyl-carbamate (Ace Synthesis) (500 mg; 1.99 mmol) dissolved in 2.5 mL of acetic acid was added 4-trifluoromethoxybenzaldehyde (1.7 mL; 11.94 mmol), and the reaction mixture was stirred at room temperature for 4 d. The mixture was diluted with $CHCl_3$ (20 mL) and filtered through a pad of Celite®. The pad was washed with $CHCl_3$ (20 mL). Heptane (20 mL) was then added to the solution and the solution was concentrated under reduced pressure. This procedure was repeated twice. The residue was purified via radial chromatography using a 3:1 hexane/EtOAc solution as the eluent. Two fractions were isolated. The first fraction isolated ($R_f$=0.42) was shown to be the title compound (127 mg; 15%). $^1$H NMR (300 MHz, $CDCl_3$) δ 8.26 (d, J=8.9 Hz, 2H), 8.09 (d, J=8.9 Hz, 2H), 7.52 (d, J=8.6 Hz, 2H), 7.39 (d, J=8.3 Hz, 2H), 6.70 (s, 1H), 1.54 (s, 9H); EI/MS 421 [M]$^+$. The second fraction isolated ($R_f$=0.11) was shown to be the 4,5-dihydro-1,2,4-oxadiazole (96 mg; 11%). $^1$H NMR (300 MHz, $CDCl_3$) δ 8.40 (d, J=8.9 Hz, 2H), 8.00 (d, J=8.9 Hz, 2H), 7.51 (d, J=8.9 Hz, 2H), 7.22-7.31 (m, 3H), 6.87 (s, 1H), 1.54 (s, 9H); EI/MS 423 [M]$^+$.

Step 2. 4-[5-(4-Trifluoromethoxyphenyl)-[1,2,4]oxadiazol-3-yl]-phenylamine. To a stirred solution of {4-[5-(4-trifluoromethoxyphenyl)-[1,2,4]oxadiazol-3-yl]-phenyl}-carbamic acid tert-butyl ester (198 mg; 0.47 mmol) in $CH_2Cl_2$ (4.7 mL) was added trifluoroacetic acid (11.76 mmol; 0.87 mL) and the reaction was stirred at room temperature for 3 h. The solution was concentrated and the residue was taken up in 10 mL of saturated $KHCO_3$ solution and stirred for 30 min. The mixture was then extracted with $CH_2Cl_2$ (3×10 mL). The organic phase was then dried over $MgSO_4$, filtered and concentrated to afford 4-[5-(4-trifluoromethoxyphenyl)-[1,2,4]oxadiazol-3-yl]-phenylamine (127 mg; 84%). $^1$H NMR (300 MHz, $CDCl_3$) δ 8.26 (d, J=8.9 Hz, 2H), 7.97 (d, J=8.9 Hz, 2H), 7.39 (d, J=8.6 Hz, 2H), 6.77 (d, J=8.6 Hz, 2H), 3.40-3.80 (bs, 2H); EI/MS 321 [M]$^+$.

Example 62

Preparation of 1-(4-amin-phenyl)-4-(4-trifluoromethoxy-phenyl)-piperazine-2,5-dione

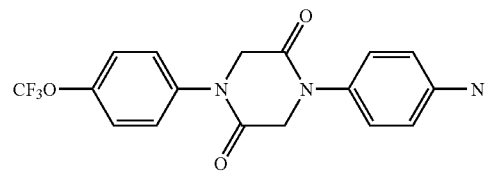

Step 1. 4-Nitrophenylamino acetic acid, methyl ester. To a solution of ethyl bromoacetate (60 g, 0.36 mol) and 4-nitroaniline (5 g, 0.036 mol) in 100 mL of DMF was added NaHCO₃ (60 g, 0.71 mol) and tetra-n-butylammonium iodide (500 mg, cat). The solution was heated to 90° C. for 16 h, and then it was cooled and poured onto 300 mL of water. The resulting yellow solid was filtered and air-dried. Recrystallization from MeOH furnished 5 g of the methyl ester as a light yellow solid. ¹H NMR (400 MHz, CDCl₃) δ 8.36 (d, J=8 Hz, 2H), 7.65 (d, J=8 Hz, 2H), 4.42 (2, 2H), 3.93 (s, 2H), 3.79 (s, 2H); mp 179-182° C.

Step 2. [(2-Chloroacetyl)-(4-trifluoromethoxyphenyl)-amino]-acetic acid methyl ester. To a suspension of 4-nitrophenylamino acetic acid, methyl ester (3.0 g, 14.2 mmol) in 30 mL of toluene was added chloroacetyl chloride (3 mL, excess). The solution was heated to 80° C. for 1 h, whereupon the solid dissolved. The solution was then cooled and concentrated, and then the residual solid was recrystallized from MeOH to give 3.5 g of the ester as a light yellow solid. ¹H NMR (400 MHz, CDCl₃) δ 8.36 (d, J=8 Hz, 2H), 7.65 (d, J=8 Hz, 2H), 4.42 (2, 2H), 3.93 (s, 2H), 3.79 (s, 3H); MS 286 (M⁺); mp 106-109° C.

Step 3. 1-(4-Aminophenyl)-4-(4-trifluoromethoxyphenyl)-piperazine-2,5-dione. The product of step 2 (0.6 g, 2.3 mmol) was combined with 4-trifluoromethoxyaniline (0.81 g, 4.6 mmol) and the materials were heated to 140° C. for 90 min. The residual solid was stirred with 50 mL of DCM and filtered to remove the hydrochloride salt of the aniline, and then the residue was concentrated and purified. Chromatography (elution with EtOAc-hexanes) furnished 0.44 g of the nitrophenyl piperazinedione as a white solid, mp 223-224° C. Reduction of the nitro group using a Pd/C catalyst under conditions described above gave the title amine as a white solid. ¹H NMR (400 MHz, CDCl₃) δ 7.4 (d, J=8.5 Hz, 2H), 7.33 (d, J=8.6 Hz, 2H), 7.12 (d, J=8.7 Hz, 2H), 6.75 (d, J=8.7 Hz, 2H), 4.5 (s, 2H), 4 45 (s, 2H); MS 366.2 (M+H⁺); mp 250° C. (dec.).

Example 63

Preparation of 5-(4-aminophenyl)-3-(4-trifluoromethylphenyl)-3H-[1,3,4]oxadiazol-2-one

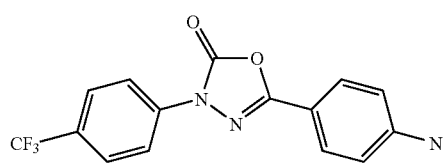

5-(4-Nitrophenyl)-3-(4-trifluoromethylphenyl) 3H-[1,3,4] oxadiazole-2-one was prepared by treating the corresponding 4-nitrobenzoic acid, N'-(4-trifluoromethylphenyl)-hydrazide with phosgene, using conditions described by Reimlinger, et al, in Chemische Berichte 1970, 103, 1934. The nitro group was then reduced to the amine by treatment with hydrogen and Pd/C in EtOH. ¹H NMR (400 MHz, CDCl₃) δ 8.1 (d, J=8.4 Hz, 2H), 7.75 (m, 4H), 6.75 (d, J=8.4 Hz, 2H), 4.1 (br s, 2H); MS 322.6 (M+H⁺); mp 160-163° C.

Example 64

Preparation of 4-[1-(4-Trifluoromethoxyphenyl)-1H-imidazol-4-yl]-benzaldehyde O-((2S,3R,4R,5S,6S)-3,4,5-trimethoxy-6-methyl-tetrahydropyran-2-yl)-oxime (Compound 26)

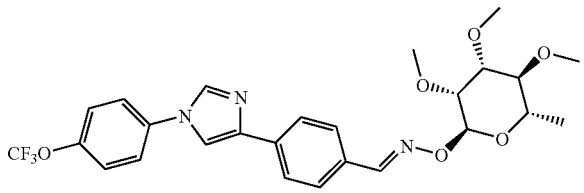

A solution of 4-[1-(4-trifluoromethoxyphenyl)-1H-imidazol-4-yl]-benzaldehyde (50 mg, 0.15 mmol) and O-(2S,3R,4R,5S,6S)-(3,4,5-trimethoxy-6-methyl-tetrahydropyran-2-yl)-hydroxylamine (45 mg, 0.20 mmol) were combined in 5 mL of dry EtOH, and the solution heated at reflux under a N₂ atmosphere for 12 h. The resulting solution was concentrated in vacuo and purified by chromatography (Biotage, 1:1:1 Hexanes/EtOAc/DCM) to furnish 35 mg (44%) of Compound 26 as a white solid. ¹H NMR (300 MHz, CDCl₃) δ 8.15 (s, 1H), 7.90 (s, 1H), 7.85 (d, J=6 Hz, 2H), 7.68 (d, J=6 Hz, 2H), 7.60 (s, 1H), 7.68 (s, 1H), 7.50 (d, J=6 Hz, 2H), 7.38 (d, J=6 Hz, 2H), 3.77 (dd, J=3.2, 2.0 Hz, 1H), 3.68 (dd, J=9.6, 6.2 Hz, 1H), 3.59 (s, 3H), 3.56 (s, 3H), 3.55 (s, 3H), 3.51 (m, 1H), 3.21 (t, J=9.3 Hz, 1H), 1.33 (d, J=6.1 Hz, 3H); MS 536.1 (M+H); mp 178° C. Anal. Calcd. for C₁₆H₁₀F₃N₃O₂: C, 59.01; H, 5.50; N, 7.65. Found: C, 58.86; H, 5.58; N, 7.63.

The compounds of this invention in Table 4 were prepared by the routes described earlier and illustrated in Example 64.

Example 65

Preparation of 2,2,2-trifluoro-1-{4-[1-(4-trifluoromethyl-phenyl)-1H-[1,2,4]triazol-3-yl]-phenyl}-ethanone, O-((2S,3R,4R,5S,6S) 4-ethoxy-3,5-dimethoxy-6-methyl-tetrahydropyran-2-yl)-oxime (Compound 169)

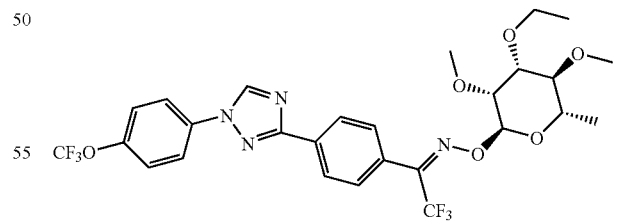

The oxime was prepared from the corresponding trifluoromethylacetophenone using the conditions described in the previous Examples. ¹H NMR (300 MHz, CDCl₃) δ 8.68 (s, 1H), 8.26 (d, J=8.30 Hz, 2H), 7.88 (d, J=8.26 Hz, 2H), 7.81 (d, J=8.26 Hz, 2H), 7.68 (d, J=8.30 Hz, 2H), 5.63 (d, J=1.85 Hz, 1H), 3.79-3.61 (m, 4H), 3.57 (s, 3H), 3.56 (s, 3H), 3.44 (dd, J=9.31, 3.36 Hz, 1H), 3.18 (t, J=9.48 Hz, 1H), 1.36-1.23 (m, 6H); MS 602 ([M+H]⁺).

The compounds of this invention in Table 5 were prepared by the routes described earlier and illustrated in Examples 64 and 65.

Example 66

Preparation of 5-[1-(4-trifluoromethoxyphenyl)-1H-[1,2,4]triazol-3-yl]-indan-1-one O-((2S,3R,4R,5S,6S)-4-ethoxy-3,5-dimethoxy-6-methyl-tetrahydropyran-2-yl)-oxime (Compound 170)

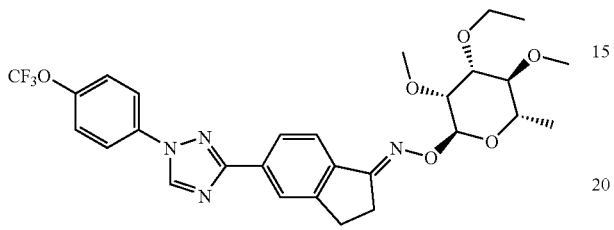

The oxime was prepared from the corresponding 2-indanone using the conditions described in Example 64. $^1$H NMR (300 MHz, CDCl$_3$) δ 8.62 (s, 1H), 8.22-8.16 (m, 2H), 7.84-7.78 (m, 3H), 7.42-7.38 (m, 2H), 5.63 (d, J=1.85 Hz, 1H), 3.79-3.61 (m, 4H), 3.57 (s, 3H), 3.56 (s, 3H), 3.44 (dd, J=9.31, 3.36 Hz, 1H), 3.22-3.18 (m, 3H), 3.02-2.96 (m, 2H), 1.36-1.23 (m, 6H); MS 576 ([M+H]$^+$).

Example 67

Preparation of 4-{1-[5-(1,1,2,3,3,3-hexafluoropropoxy)-pyridinyl]-1H-[1,2,4]triazol-3-yl}-benzaldehyde O-((2S,3R,4R,5S,6S)-3,4,5-trimethoxy-6-methyl-tetrahydropyran-2-yl)-oxime (Compound 94)

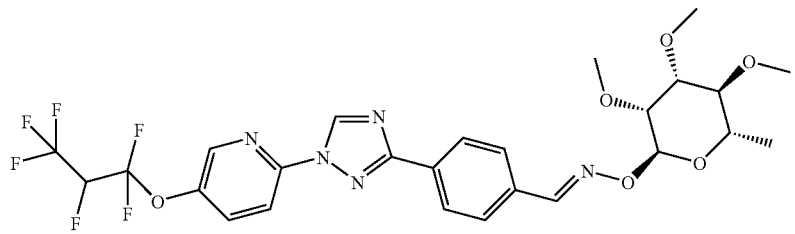

Fluoroalkylation conditions were based on a paper by Timperley et al. *J. Fluorine Chem.* 2006, 127, 249. A solution of 4-[1-(5-hydroxy-pyridin-2-yl)-1H-[1,2,4]triazol-3-yl]-benzaldehyde O-((2S,3R,4R,5S,6S)-3,4,5-trimethoxy-6-methyl-tetrahydropyran-2-yl)-oxime in 10 mL anhydrous DMF/THF (1:1) under a N$_2$ atmosphere was cooled at 0° C. while an excess of hexafluoropropylene gas was added over 15 min. Following addition, triethylamine (15 uL, 0.109 mmol) was added and the reaction mixture warmed to ambient temperature before concentration to dryness. Chromatography (EtOAc/hexanes, 1:1) afforded Compound 94 (16 mg, 24%). $^1$H NMR (CDCl$_3$) δ 9.17 (s, 1H), 8.39 (d, J=7.68 Hz, 1H), 8.21 (d, J=8.22 Hz, 2H), 8.19 (s, 1H), 8.08 (d, J=7.68 Hz, 1H), 7.74 (d, J=8.22 Hz, 2H), 6.97 (s, 1H), 5.63 (d, J=1.85 Hz, 1H), 5.17 (m, 1H), 3.78 (dd, J=3.28, 1.99 Hz, 1H), 3.63 (m, 1H), 3.59 (s, 3H), 3.57 (s, 3H), 3.56 (s, 3H), 3.43 (dd, J=9.31, 3.36 Hz, 1H), 3.18 (t, J=9.48 Hz, 1H), 1.29 (d, J=6.26 Hz, 3H); EIMS 619 m/z (M$^+$).

Example 68

Preparation of 4-[1-(4-trifluoromethanesulfinylphenyl)-1H-[1,2,4]triazol-3-yl]-benzaldehyde O-((2S,3R,4R,5S,6S)-3,4,5-trimethoxy-6-methyl-tetrahydropyran-2-yl)-oxime (Compound 103) and 4-[1-(4-trifluoromethanesulfonylphenyl)-1H-[1,2,4]triazol-3-yl]-benzaldehyde O-((2S,3R,4R,5S,6S)-3,4,5-trimethoxy-6-methyl-tetrahydropyran-2-yl)-oxime (Compound 104)

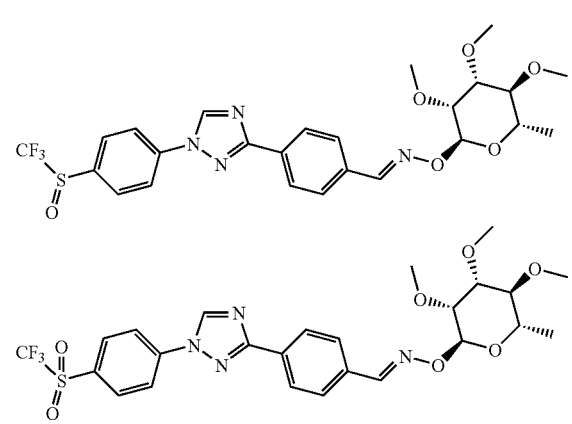

A solution of 4-[1-(4-trifluoromethylsulfanylphenyl)-1H-[1,2,4]triazol-3-yl]-benzaldehyde O-((2S,3R,4R,5S,6S)-3,4,5-trimethoxy-6-methyl-tetrahydropyran-2-yl)-oxime (100 mg, 0.18 mmol, 1.0 eq) and 3-chloroperoxybenzoic acid (124 mg, 0.72 mmol, 4.0 eq) in DCM (10 mL) was stirred under ambient conditions for 48 h. The solution was then washed with saturated NaHSO$_3$ (aq), extracted into DCM (100 mL), concentrated to dryness, and purified via chromatography (2:2:1, hexanes/EtOAc/acetone) to afford 55 mg of the sulfoxide (54%) and the sulfone (5.6 mg, 5%).

For the sulfoxide (Compound 103): $^1$H NMR (CDCl$_3$) δ 8.78 (s, 1H), 8.26 (d, J=8.24 Hz, 2H), 8.21 (s, 1H), 8.09 (d, J=8.38 Hz, 2H), 7.99 (d, J=8.38 Hz, 2H), 7.78 (d, J=8.24 Hz, 2H), 5.63 (d, J=1.85 Hz, 1H), 3.68 (dd, J=3.28, 1.99 Hz, 1H), 3.63 (m, 1H), 3.59 (s, 3H), 3.57 (s, 3H), 3.56 (s, 3H), 3.44 (dd, J=9.31, 3.36 Hz, 1H), 3.20 (t, J=9.48 Hz, 1H), 1.25 (d, J=6.26 Hz, 3H); EIMS 568 m/z (M$^+$).

For the sulfone (Compound 104): $^1$H NMR (CDCl$_3$) δ 8.79 (s, 1H), 8.24-8.18 (m, 5H), 8.15 (d, J=8.28 Hz, 2H), 7.79 (d, J=8.32 Hz, 2H), 5.63 (d, J=1.85 Hz, 1H), 3.68 (dd, J=3.28, 1.99 Hz, 1H), 3.63 (m, 1H), 3.59 (s, 3H), 3.57 (s, 3H), 3.56 (s, 3H), 3.44 (dd, J=9.31, 3.36 Hz, 1H), 3.20 (t, J=9.48 Hz, 1H), 1.25 (d, J=6.26 Hz, 3H); EIMS 584 m/z (M+).

Example 69

Preparation of 4-[1-(4-pentafluoroethyloxy-phenyl)-1H-[1,2,4]triazol-3-yl]-benzaldehyde, O-((2S,3R,4R,5S,6S)-3,4-dimethoxy-6-methyl-5-propoxy-tetrahydropyran-2-yl)-oxime (Compound 113)

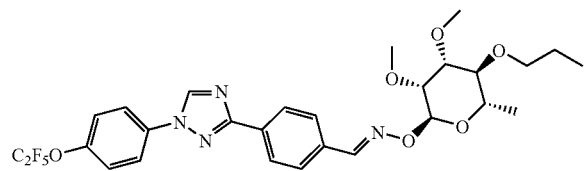

Compound III (60 mg, 0.1 mmol) was dissolved in 1 mL of bromopropane and treated with 50 mg of powdered KOH and 5 mg of powdered Bu₄NI (excess). The solution was stirred at ambient temperature for 16 h, and then was diluted with 10 mL of dry Et₂O, filtered and concentrated. The residue was eluted through a short silica column to give 25 mg of Compound 113. ¹H NMR (CDCl₃) δ 8.61 (s, 1H), 8.23 (d, J=8.1 Hz, 2H), 8.01 (s, 1H), 7.85 (d, J=9 Hz, 2H), 7.76 (d, J=8.1 Hz, 2H), 7.42 (d, J=9 Hz, 2H), 7.38 (d, J=8.2 Hz, 2H), 5.70 (d, J=1.8 Hz, 1H), 3.8-3.6 (m, 3H), 3.60-3.55 (m, 8H), 3.30 (t, J=9.6 Hz, 1H), 1.65 (m, 2H), 1.33 (d, J=7 Hz, 3H), 0.98 (t, J=7.5 Hz, 3H); EIMS 615.0 m/z (M+); mp 121-128° C.

Example 70

Preparation of 4-[2-(4-trifluoromethoxyphenyl)-pyridin-2-yl]-benzaldehyde, O-((2S,3R,4R,5S,6S)-3,4,5-trimethoxy-6-methyl-tetrahydropyran-2-yl)-oxime (Compound 132)

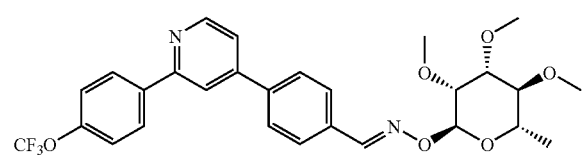

Step 1. 2-Chloro-4-iodopyridine (1.6 mmol), 4-cyanophenyl boronic acid (2.5 mmol), 2 M potassium carbonate (3.3 mmol), tetrakis(triphenyphosphine)palladium(0) (0.01 mmol) and dioxane (8 mL) were combined in a vial and heated by microwave for 10 min at 150° C. The crystallized product was filtered and subsequently dried in vacuo to yield 250 mg of 4-(2-chloropyridin-4-yl)-benzonitrile as yellow needles. ¹H NMR (400 MHz, CDCl₃) δ 8.52 (d, J=5.1 Hz, 1H), 7.81 (d, J=8.4 Hz, 2H), 7.72 (d, J=8.2 Hz, 2H), 7.55 (m, 1H), 7.43 (dd, J=5.2, 1.4 Hz, 1H); EIMS 214 m/z (M+).

Step 2. 4-(2-Chloropyridin-4-yl)-benzonitrile (4.65 mmol) was reduced with DIBAL under conditions described earlier to give the aldehyde as a tan solid. ¹H NMR (400 MHz, CDCl₃) δ 10.11 (s, 1H), 8.50 (d, J=4.8 Hz, 1H), 8.02 (d, J=8.3 Hz, 2H), 7.78 (d, J=8.2 Hz, 2H), 7.59 (d, J=1.4 Hz, 1H), 7.47 (dd, J=5.2, 1.5 Hz, 1H); EIMS 217 m/z (M+).

Step 3. 4-(2-Chloropyridin-4-yl)-benzaldehyde (1.5 mmol) and O-((2S,3R,4R,5S,6S)-3,4,5-trimethoxy-6-methyl-tetrahydropyran-2-yl)-hydroxylamine (1.5 mmol) were combined in EtOH under conditions described above in the preparation of compound 26 to yield the oxime. ¹H NMR (400 MHz, CDCl₃) δ 8.45 (d, J=5.9 Hz, 1H), 8.21 (s, 1H), 7.76 (d, J=8.3 Hz, 2H), 7.65 (d, J=8.3 Hz, 2H), 7.55 (m, 1H), 7.44 (dd, J=5.4, 1.6 Hz, 1H), 5.68 (d, J=1.8 Hz, 1H), 3.78 (d, J=3.1, 2.0 Hz, 1H), 3.68 (dd, J=9.6, 6.3 Hz, 1H), 3.59 (s, 3H), 3.56 (s, 3H), 3.55 (s, 3H), 3.52 (m, 1H), 3.21 (t, J=9.5 Hz, 1H), 1.32 (d, J=6.2 Hz, 3H); EIMS 420 m/z (M+).

Step 4. 4-[2-(4-Trifluoromethoxyphenyl)-pyridin-4-yl]-benzaldehyde O-((2S,3R,4R,5S,6S)-3,4,5-trimethoxy-6-methyl-tetrahydropyran-2-yl)-oxime. 4-(2-Chloropyridin-4-yl)-benzaldehyde O-((2S,3R,4R,5S,6S)-3,4,5-trimethoxy-6-methyl-tetrahydropyran-2-yl)-oxime (0.24 mmol), 4-trifluoromethoxyphenyl boronic acid (0.36 mmol), (Ph₃P)₄Pd(0) (0.002 mmol), 2 M K₂CO₃ (0.475 mmol) and dioxane (1 mL) were combined in a vial and heated by microwave for 10 min at 150° C. The reaction mixture was taken up in ether and washed with brine. The ether layer was dried over magnesium sulfate, was filtered and the solvent was removed in vacuo. The crude mixture was purified by silica gel chromatography to yield 48 mg of Compound 132 as a tan oil. ¹H NMR (400 MHz, CDCl₃) δ 8.76 (d, J=5.0 Hz, 1H), 8.21 (s, 1H), 8.09 (d, J=8.8 Hz, 2H), 7.91 (s, 1H), 7.78 (d, J=8.6 Hz, 2H), 7.72 (d, J=8.7 Hz, 2H), 7.48 (dd, J=5.3, 1.7 Hz, 1H), 7.34 (d, J=8.6 Hz, 2H), 5.69 (d, J=1.7 Hz, 1H), 3.78 (m, 1H), 3.69 (m, 1H), 3.59 (s, 3H), 3.57 (s, 3H), 3.55 (s, 3H), 3.52 (d, J=3.3 Hz, 1H), 3.22 (t, J=9.4 Hz, 1H), 1.33 (d, J=6.2 Hz, 3H); EIMS 546 m/z (M+).

Example 71

Preparation of {4-[2-(4-trifluoromethylphenyl)-pyrimidin-4-yl]-phenyl}-carbamic acid (2S,3R,4R,5S,6S)-3,4,5-trimethoxy-6-methyl-tetrahydropyran-2-yl ester (Compound 232)

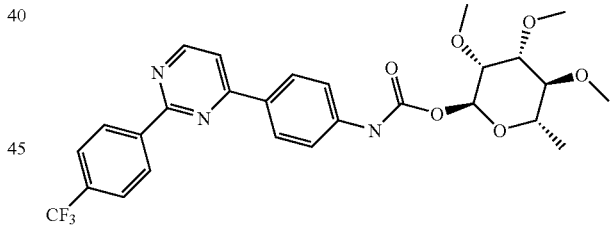

Step 1. Carbonic acid 4-nitrophenyl ester (2S,3R,4R,5S,6S)-3,4,5-trimethoxy-6-methyl-tetrahydropyran-2-yl ester. To a solution cooled in an ice bath of 509 mg (2.52 mmol) of 4-nitrophenyl chloroformate in 2 mL of dioxane was added dropwise via syringe a solution of 0.50 g (2.42 mmol) of 3,4,5-trimethoxy-6-methyl-tetrahydropyran-2-ol in 3 mL of pyridine. The contents were allowed to gradually warm to room temperature and stir overnight. The pyridine was removed in vacuo at room temperature and the residue was triturated with ethyl ether. The mixture was filtered and the filtrate was dried (MgSO₄). Concentration gave 840 mg of an oil which was purified by chromatography on silica gel using 3:2 hexanes/EtOAc as eluent to afford 337 mg (37%) of the α-anomeric carbamate as the higher R_f component; ¹H NMR (400 MHz, CDCl₃) δ 8.30 (d, J=9.3 Hz, 2H), 7.43 (d, J=9.2 Hz, 2H), 6.12 (d, J=2.3 Hz, 1H), 3.73-3.71 (m, 2H), 3.58 (s, 3H), 3.56 (s, 3H), 3.56 (s, 3H), 3.52 (m, 1H), 3.23 (t, J=9.2 Hz, 1H), 1.36 (d, J=6.2 Hz, 3H); and 157 mg (17%) of the β-anomeric carbamate as the lower R$_f$ component; $^1$HNMR NMR (300 MHz, CDCl$_3$) δ 8.32 (d, J=9.3 Hz, 2H), 7.42 (d, J=9.3 Hz, 2H), 5.57 (d, J=2.1 Hz, 1H), 3.87 (m, 1H), 3.71 (s, 3H), 3.59 (s, 3H), 3.56 (s, 3H), 3.43 (m, 1H), 3.31-3.18 (m, 2H), 1.43 (d, J=6.2 Hz, 3H); mp 113-116° C.

Step 2. To a mixture cooled in an ice bath of 126 mg (0.40 mmol) of 4-[2-(4-trifluoromethylphenyl)-pyrimidin-4-yl]-phenylamine in 1 mL of dry toluene was added dropwise via syringe 1.6 mL (0.80 mmol) of a 0.5 M solution of potassium hexamethyldisilazide in toluene over a 10-15 minute period. To this mixture was then added dropwise a solution of 148 mg (0.400 mmol) of carbonic acid 4-nitrophenyl ester 3,4,5-trimethoxy-6-methyl-tetrahydropyran-2-yl ester in 2 mL of toluene. The contents were allowed to gradually warm to room temperature and stir overnight and were added to cold saturated sodium bicarbonate. The mixture was extracted two times with chloroform and the combined extracts were dried (MgSO$_4$). Concentration gave 130 mg which was purified by chromatography on silica gel using 9:1 DCM/EtOAc to afford 64 mg (29%) of Compound 232. $^1$HNMR (300 MHz, CDCl$_3$) δ 8.87 (d, J=5.2 Hz, 1H), 8.71 (d, J=8.2 Hz, 2H), 8.26 (d, J=8.8 Hz, 2H), 7.79 (d, J=8.2 Hz, 2H), 7.65 (d, J=5.2 Hz, 1H), 7.63 (d, 2H), 6.86 (br s, 1H), 6.26 (d, J=1.9 Hz, 1H), 3.74-3.70 (m, 2H), 3.61 (s, 3H), 3.60 (s, 3H), 3.57 (s, 3H), 3.53 (m, 1H), 3.24 (t, J=9.5 Hz, 1H), 1.36 (d, J=6.0 Hz, 3H); MS (API-ES+) 549 ([M+H]$^+$, 10), 358 (100); mp 176-179° C.

Example 72

Preparation of {4-[2-(4-methoxyphenyl)-pyrimidin-4-yl]-phenyl}-carbamic acid (2S,3R,4R,5S,6S)-3,4,5-trimethoxy-6-methyl-tetrahydropyran-2-yl ester (Compound 234)

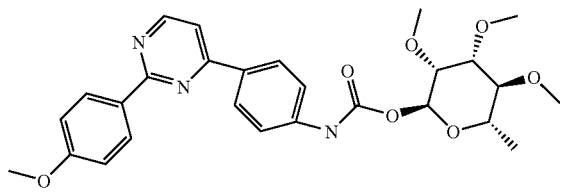

To a mixture cooled in an ice bath of 112 mg (0.404 mmol) of 4-[2-(4-methoxyphenyl)-pyrimidin-4-yl]-phenylamine in 1.5 mL of dry THF was added dropwise via syringe 0.81 mL (0.40 mmol) of a 0.5 M solution of potassium hexamethyldisilazide in toluene over a 10-15 minute period. This solution was then added dropwise via syringe to a solution cooled in an ice bath of 126 mg (0.386 mmol) of carbonic acid 4-nitrophenyl ester 3,4,5-trimethoxy-6-methyl-tetrahydropyran-2-yl ester in 2 mL of THF. The contents were allowed to gradually warm to room temperature and stir overnight and were added to cold saturated sodium bicarbonate. The mixture was extracted two times with ethyl ether and the combined extracts were dried (MgSO$_4$). Concentration gave a red oil which was purified by chromatography on silica gel using 1:1 hexanes/EtOAc to afford 16 mg (8%) of Compound 234. $^1$H NMR (300 MHz, CDCl$_3$) δ 8.79 (d, J=5.2 Hz, 1H), 8.55 (d, J=8.8 Hz, 2H), 8.25 (d, J=8.8 Hz, 2H), 7.62 (d, J=8.5 Hz, 2H), 7.53 (d, J=5.5 Hz, 1H), 7.05 (d, J=9.0 Hz, 2H), 6.84 (br s, 1H), 6.26 (d, J=1.7 Hz, 1H), 3.92 (s, 3H), 3.71-3.69 (m, 2H), 3.61 (s, 3H), 3.60 (s, 3H), 3.57 (s, 3H), 3.55-3.47 (m, 1H), 3.24 (t, J=9.4 Hz, 1H), 1.36 (d, J=6.1 Hz, 3H); MS (API-ES+) 510 ([M+H]$^+$, 100).

Example 73

Preparation of {2-chloro-4-[3-(4-trifluoromethylphenyl)-[1,2,4]triazol-1-yl]-phenyl}-carbamic acid (2S,3R,4R,5S,6S)-3,4,5-trimethoxy-6-methyl-tetrahydropyran-2-yl ester (α-anomer, Compound 189), and {2-chloro-4-[3-(4-trifluoromethylphenyl)-[1,2,4]triazol-1-yl]-phenyl}-carbamic acid (2R,3R,4R,5S,6S)-3,4,5-trimethoxy-6-methyl-tetrahydropyran-2-yl ester (β-anomer, Compound 190))

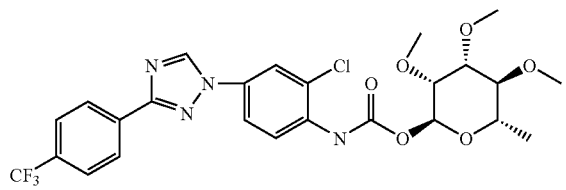

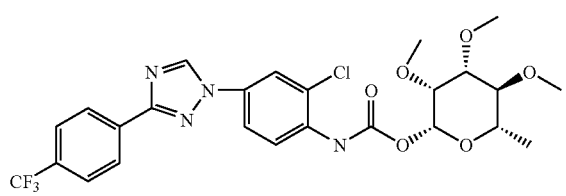

A solution of the aniline (0.45 g, 1.3 mmol) in dry THF (5 mL) was treated with 2 mL of a 20% solution of phosgene in toluene (4 mmol). The solution was capped and stored for 18 h, then concentrated and re-dissolved in 5 mL of dry THF. This solution, which was not completely dissolved, was treated with tri-O-methylrhamnopyranoside (0.3 g, 1.45 mmol) and triethylamine (0.2 mL, 1.6 mmol), and the solution was heated to reflux for 1 h. TLC showed the formation of two new, more polar products. The solution was concentrated in vacuo, then applied directly to a Biotage column and eluted with 1:1:1 solution of EtOAc/Hexanes/DCM. The two new products were isolated and concentrated to give 75 mg of the α-anomer (Compound 189) and 110 mg of the β-anomer (Compound 190). For the α-anomer: $^1$H NMR (300 MHz, CDCl$_3$) δ 8.60 (s, 1H), 8.41 (d, J=8 Hz, 1H), 8.33 (d, J=7.8 Hz, 2H), 7.90 (d, J=1 Hz, 1H), 7.75 (d, J=7.8 Hz, 2H), 7.65 (dd, J=1, 8 Hz, 1H), 6.22 (d, J=1.2 Hz, 1H), 3.8-3.65 (m, 2H), 3.65-3.5 (m, 10H), 3.22 (t, J=9.2 Hz, 1H), 1.36 (d, J=6.3 Hz, 3H); mp 175° C. For the β-anomer: $^1$H NMR (300 MHz, CDCl$_3$) δ 8.60 (s, 1H), 8.38 (d, J=8 Hz, 1H), 8.37 (d, J=7.8 Hz, 2H), 7.90 (d, J=1.5 Hz, 1H), 7.75 (d, J=7.8 Hz, 2H), 7.65 (dd, J=1.5, 8 Hz, 1H), 7.45 (s, 1H, NH), 5.72 (s, 1H), 3.85 (m, 1H), 3.75 (s, 3H), 3.62 (s, 3H), 3.58 (s, 3H), 3.45 (m, 1H), 3.35 (m, 1H), 3.22 (t, J=9.2 Hz, 1H), 1.36 (d, J=6.3 Hz, 3H).

Example 74

Preparation of {4-[1-(4-trifluoromethoxyphenyl)-1H-[1,2,4]triazol-3-yl]-phenyl}-carbamic acid (2S,3R,4R,5S,6S)-3,4,5-trimethoxy-6-methyl-tetrahydropyran-2-yl ester (Compound 191)

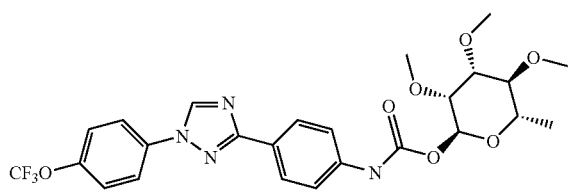

The aniline (0.15 g, 0.47 mmol) was taken up in 5 mL of DCM and treated with di-tert-butyl tricarbonate (0.15 g 0.57 mmol). The solution was allowed to stir magnetically for 1 h, and then it was concentrated in vacuo and redissolved in dry THF. To this solution was added tri-O-methyl rhamnopyranoside (0.13 g, 0.63 mmol) and triethylamine (0.1 g, 1 mmol), and the solution was heated to reflux for 1 h, then cooled, concentrated, and purified by chromatography (1:1:1 Hexanes/EtOAc/DCM) to afford 160 mg of Compound 191 as a white solid. $^1$H NMR (300 MHz, CDCl$_3$) δ 8.55 (s, 1H), 8.16 (d, J=8.7 Hz, 2H), 7.79 (d, J=9.1 Hz, 2H), 7.53 (d, J=8.7 Hz, 2H), 7.38 (d, J=8.8 Hz, 2H), 6.78 (s, 1H), 6.23 (d, J=1.9 Hz, 1H), 3.70 (m, 2H), 3.59 (s, 3H), 3.57 (s, 3H), 3.54 (s, 3H), 3.51 (m, 1H), 3.21 (t, J=9.4 Hz, 1H), 1.34 (d, J=6.2 Hz, 3H); MS 553.0 (M+H); mp 186-188° C.

Example 75

Preparation of {4-[1-(4-pentafluoroethyloxyphenyl)-1H-[1,2,4]triazol-3-yl]-phenyl}-carbamic acid (2S,3R,4R,5S,6S)-4-ethoxy-3,5-dimethoxy-6-methyl-tetrahydropyran-2-yl ester and {4-[1-(4-pentafluoroethyloxyphenyl)-1H-[1,2,4]triazol-3-yl]-phenyl}-carbamic acid (2R,3R,4R,5S,6S)-4-ethoxy-3,5-dimethoxy-6-methyl-tetrahydropyran-2-yl ester (Compounds 201 and 202)

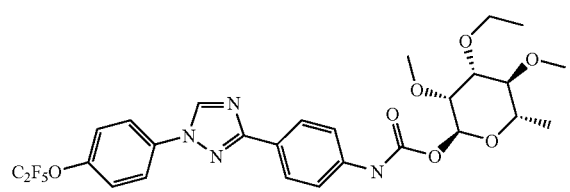

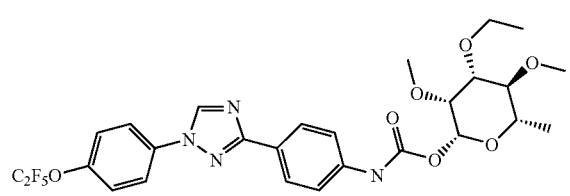

A solution of 4-[1-(4-pentafluoroethyloxyphenyl)-1H-[1,2,4]triazol-3-yl]-phenylamine (1.0 g, 2.7 mmol) in 8 mL of dry THF was stirred while p-nitrophenyl chloroformate (0.60 g, 3 mmol) was added in one portion and the solution was allowed to stir for 3 h. The resulting solid was filtered and air-dried, and then re-suspended in 15 mL of dry THF. The 3'-O-ethyl rhamnose (0.6 g, 2.7 mmol) was added, followed by 0.12 g of 60% NaH (2.7 mmol). The solution was then heated to reflux for 30 min, then another equivalent of NaH was added and heating resumed for another 60 min. The mixture was cooled and poured onto 50 mL of ice/water, extracted into ether, dried and concentrated. TLC shows Ca. 90:10 ratio of α- and β-anomers, which were separated by silica gel chromatography (30% acetone in hexanes). For the α-anomer (Compound 201): $^1$H NMR (CDCl$_3$) δ 8.59 (s, 1H), 8.20 (d, J=9 Hz, 2H), 7.81 (d, J=8 Hz, 2H), 7.5 (d, J=8 Hz, 2H), 7.40 (d, J=9 Hz, 2H), 6.90 (s, 1H), 6.22 (s, 1H), 3.80-3.52 (m, 1H), 3.20 (t, J=9.3 Hz, 1H), 1.33 (m, 6H); EIMS 617.0 m/z (M$^+$); mp 192-193° C. For the β-anomer (Compound 202): $^1$H NMR (CDCl$_3$) δ 8.59 (s, 1H), 8.20 (d, J=9 Hz, 2H), 7.81 (d, J=8 Hz, 2H), 7.5 (d, J=8 Hz, 2H), 7.40 (d, J=9 Hz, 2H), 7.0 (s, 1H), 5.72 (s, 1H), 3.80-3.20 (m, 12H), 1.33 (m, 6H); EIMS 617.0 m/z (M$^+$).

Example 76

Preparation of {4-[1-(4-pentafluoroethyloxyphenyl)-1H-[1,2,4]triazol-3-yl]-phenyl}-carbamic acid (2S,3R,4R,5S,6S)-4-propoxy-3,5-dimethoxy-6-methyl-tetrahydropyran-2-yl ester (Compound 207)

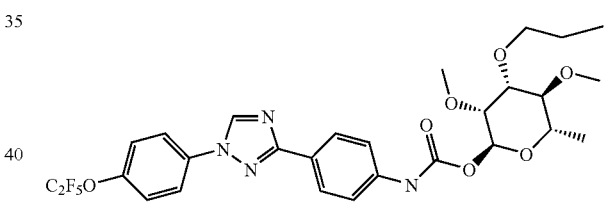

A solution of 4-[1-(4-pentafluoroethyloxyphenyl)-1H-[1,2,4]triazol-3-yl]-benzoyl azide (described in Example 27) (12.5 g, 29.5 mmol) in 150 mL of dry toluene was heated at 110° C. for 90 min, then cooled to room temperature and treated with 3-O-propyl-2,4-di-O-methyl L-rhamnose (6.9 g, 29.5 mmol) and 2.4 g of 60% NaH (60 mmol). The solution was then warmed to 40° C. for 1 h, and then it was cooled to ambient temperature and poured onto 150 mL of ice/water, extracted into ether, dried and concentrated. The crude product was purified by silica gel chromatography and then recrystallized from ether-hexanes to furnish 9.6 g of Compound 207. $^1$H NMR (300 MHz, CDCl$_3$) δ 8.58 (s, 1H), 8.2 (d, J=8 Hz, 2H), 7.82 (d, J=8 Hz, 2H), 7.55 (d, J=9 Hz, 2H), 7.41 (d, J=9 Hz, 2H), 6.81 (s, 1H), 6.22 (d, J=1.5 Hz, 1H), 3.75-3.44 (m, 11H), 3.23 (t, J=9.3 Hz, 1H), 1.71 (m, 2H), 1.35 (d, J=6.3 Hz, 3H), 1.00 (t, J=7.5 Hz, 3H); MS 630.0 (M+H); mp 158° C.

The compounds of this invention in Table 6 were prepared by the routes described earlier and illustrated in Examples 71 to 76.

Example 77

Preparation of {4-[1-(4-trifluoromethoxyphenyl)-1H-imidazolyl]-phenyl}-thiocarbamic acid (2S,3R,4R,5S,6S)-3,4,5-trimethoxy-6-methyl-tetrahydropyran-2-yl ester (Compound 176)

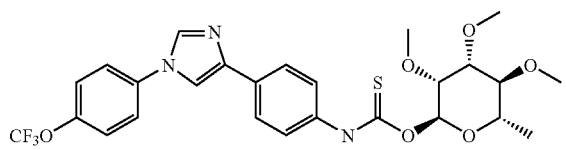

To a solution of 150 mg (0.47 mmol) of 4-[1-(4-trifluoromethoxyphenyl)-1H-imidazol-4-yl]-phenylamine in 5 mL of DCM cooled to 0° C. was added 0.09 g (0.50 mmol) of thiocarbonyldiimidazole (TDI) and 0.07 g (0.5 mmol) of diisopropylethylamine (Hunig's base). After 30 min, another equivalent of TDI and Hunig's base was added, and the solution was allowed to warm to ambient temperature before concentrating and purifying by chromatography (50:50 EtOAc-hexanes) to give 0.10 g of the isothiocyanate as an off-white solid. This material was then dissolved in 5 mL of dry THF and treated with 60 mg (0.29 mmol) of tri-O-methyl rhamnose and 20 mg (0.5 mmol) of 60% NaH. The solution was allowed to stir at ambient temperature for 3 h, before it was partitioned between water and EtOAc. The organic layer was then dried and concentrated. Chromatography gave 30 mg of Compound 176 as a colorless solid. $^1$H NMR (300 MHz, CDCl$_3$) δ 7.94 (s, 1H), 7.80 (d, J=7.5 Hz, 2H), 7.50 (m, 3H), 7.40 (d, J=7 Hz, 2H), 7.3 (s, 1H), 7.23 (br d, J=7 Hz, 2H), 6.80 (s, 1H), 3.90-3.20 (m, 13H), 1.39 (d, J=6.3 Hz, 3H); MS 568.9 (M+H); mp 129° C.

The following thiocarbamate was also prepared by the route described in the previous example.

Example 78

Preparation of {4-[1-(4-pentafluoroethyloxy-phenyl)-1H-[1,2,4]triazol-3-yl]-phenyl}-thiocarbamic acid (2S,3R,4R,5S,6S)-4-ethoxy-3,5-dimethoxy-6-methyl-tetrahydropyran-2-yl ester (Compound 203)

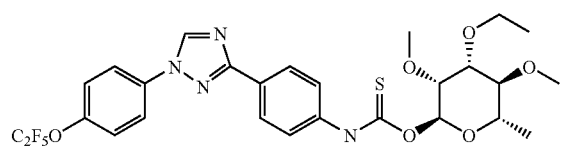

$^1$H NMR (400 MHz, CDCl$_3$) δ 8.59 (s, 1H), 8.24 (d, J=7.6 Hz, 2H), 7.80 (m, 4H), 7.40 (d, J=8.9 Hz, 2H), 6.79 (d, J=0.8 Hz, 1H), 3.90-3.40 (m, 10H), 3.22 (m, 1H), 3.18 (t, J=9.3 Hz, 1H), 1.3 (m, 6H); MS 633.0 (M+H); mp 126° C.

Example 79

Preparation of {4-[1-(4-pentafluoroethyloxy-phenyl)-1H-[1,2,4]triazol-3-yl]-phenyl}-thiocarbamic acid (2S,3R,4R,5S,6S)-3,4,5-trimethoxy-6-methyl-tetrahydropyran-2-yl ester (Compound 211)

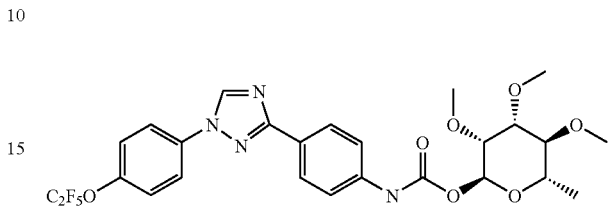

The azide prepared in Example 27 (0.22 g, 0.52 mmol) was dissolved in 5 mL of toluene and heated to 110° C. for 1 h, then it was cooled and treated with tri-O-methyl thiorhamnopyranoside (0.125 g, 0.56 mmol). The solution was heated to 40° C. for 1 h, then cooled, concentrated, and purified by chromatography (0-100% EtOAc/hexanes) to afford 75 mg of Compound 211 as a light yellow gummy solid. $^1$H NMR (300 MHz, CDCl$_3$) δ 8.58 (s, 1H), 8.18 (d, J=8.7 Hz, 2H), 7.79 (d, J=9.1 Hz, 2H), 7.53 (d, J=8.7 Hz, 2H), 7.38 (d, J=8.8 Hz, 2H), 6.78 (s, 1H), 6.23 (d, J=1.9 Hz, 1H), 3.70 (m, 2H), 3.59 (s, 3H), 3.57 (s, 3H), 3.54 (s, 3H), 3.51 (m, 1H), 3.21 (t, J=9.4 Hz, 1H), 1.34 (d, J=6.2 Hz, 3H).

Example 80

Preparation of {4-[1-(4-trifluoromethoxyphenyl)-1H-imidazol-4-yl]-phenyl}-thiocarbamic acid (2S,3R,4R,5S,6S)-4-ethoxy-3,5-dimethoxy-6-methyl-tetrahydropyran-2-yl ester (Compound 177)

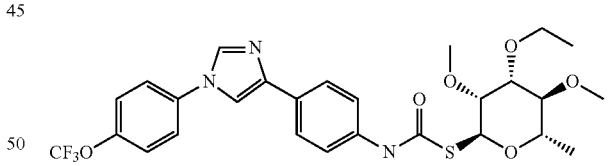

(2S,3R,4R,5S,6S)-4-Ethoxy-3,5-dimethoxy-6-methyl-tetrahydropyran-2-thiol (0.080 g, 0.34 mmol) was combined with {4-[1-(4-trifluoromethoxyphenyl)-1H-imidazol-4-yl]-phenyl}-carbamic acid 4-nitrophenyl ester (0.165 g, 0.34 mmol) and Hunig's base (0.06 g, 0.46 mmol) in 3 mL of THF, and the solution was heated at reflux for 2 h. Concentration and chromatography through a silica gel column then furnished the thiocarbamate (Compound 177) as a light yellow solid. $^1$H NMR δ 7.88 (s, 1H), 7.75 (d, J=7 Hz, 2H), 7.68 (s, 1H), 7.5 (d, J=7 Hz, 2H), 7.45 (s, 1H), 7.37 (d, J=8 Hz, 2H), 6.15 (d, J=1.5 Hz, 1H), 3.78-3.45 (m, 11H), 3.18 (t, J=9.2 Hz, 1H), 1.36 (d, J=6.2 Hz, 3H), 1.3 (t, J=7.5 Hz, 3H); mp 173-176° C.

Example 81

Preparation of 4-[1-(4-trifluoromethoxyphenyl)-1H-imidazol-4-yl]-N-((2S,3R,4R,5S,6S)-3,4,5-trimethoxy-6-methyl-tetrahydropyran-2-yloxy)-benzamide (Compound 171)

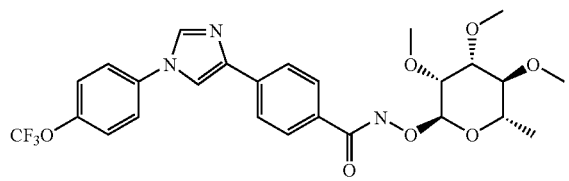

A solution of 4-[1-(4-trifluoromethoxyphenyl)-1H-imidazol-4-yl]-benzoic acid (50 mg, 0.14 mmol) was treated with excess thionyl chloride and heated briefly on a steam bath. The tan oil was then concentrated in vacuo and dissolved in 5 mL of THF. Compound E-30 (44 mg, 0.2 mmol) and ethyldiisopropylamine (52 mg, 0.4 mmol) were added and the solution was allowed to stir for 15 min. The solution was then partitioned between aqueous NaHCO$_3$ and ether, and the organic layer was dried, concentrated and purified by chromatography (50:50 EtOAc-hexanes) to give 20 mg of Compound 171 as a colorless solid. $^1$H NMR (400 MHz, CDCl$_3$) δ 7.90 (d, J=6.4 Hz, 2H), 7.89 (s, 1H), 7.80 (d, J=8.6 Hz, 2H), 7.63 (d, J=1.3 Hz, 1H), 7.49 (d, J=9.3 Hz, 2H), 7.38 (d, J=8.9 Hz, 2H), 5.31 (s, 1H), 3.97 (m, 1H), 3.80 (m, 1H), 3.57 (s, 3H), 3.56 (s, 3H), 3.53 (s, 3H), 3.50 (m, 1H), 3.21 (t, J=9.4 Hz, 1H), 1.36 (d, J=6.2 Hz, 3H); MS 552.0 (M$^+$); mp 185° C.

Example 82

Preparation of methyl {4-[1-(4-trifluoromethoxyphenyl)-1H-[1,2,4]triazol-3-yl]-phenyl}-carbamic acid (2S,3R,4R,5S,6S)-4-ethoxy-3,5-dimethoxy-6-methyl-tetrahydropyran-2-yl ester (Compound 250)

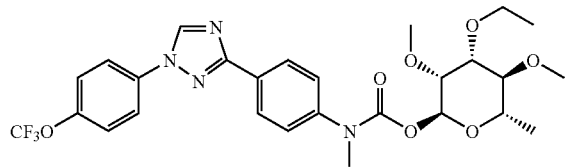

Compound 193 (0.15 g, 0.26 mmol) and iodomethane were combined in 5 mL of dry DMF, and the solution was stirred under N$_2$ and treated with 0.025 g (0.62 mmol) of NaH (60% in oil). The solution was allowed to stir at ambient temperature overnight, and then it was partitioned between water and Et$_2$O. Drying, concentration and chromatography of the organic layer furnished 73 mg of Compound 250 as a colorless solid foam. $^1$H NMR (300 MHz, CDCl$_3$) δ 8.61 (s, 1H), 8.2 (d, J=8 Hz, 2H), 7.82 (d, J=8 Hz, 2H), 7.55 (d, J=9 Hz, 2H), 7.41 (d, J=9 Hz, 2H), 6.17 (s, 1H), 3.7-3.4 (m, 11H), 3.39 (s, 3H, N—CH$_3$), 3.18 (t, J=9 Hz, 1H), 1.35 (d, J=6.3 Hz, 3H), 1.2 (t, J=7 Hz, 3H); MS 581.9 ([M+H]$^+$).

Example 83

Preparation of methyl {4-[1-(4-pentafluoroethoxyphenyl)-1H-[1,2,4]triazol-3-yl]-phenyl}-carbamic acid (2S,3R,4R,5S,6S)-4-ethoxy-3,5-dimethoxy-6-methyl-tetrahydropyran-2-yl ester (Compound 251)

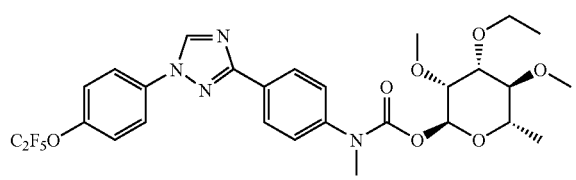

Compound 207 was methylated as in Example 82 to give Compound 251. $^1$H NMR (300 MHz, CDCl$_3$) δ 8.60 (s, 1H), 8.20 (d, J=68 Hz, 2H), 7.83 (d, J=8.8 Hz, 2H), 7.41 (d, J=9 Hz, 2H), 7.39 (d, J=8.6 Hz, 2H), 6.17 (s, 1H), 3.70-3.40 (m, 11H), 3.39 (s, 3H, NCH$_3$), 1.38 (d, J=6.0 Hz, 3H), 1.20 (t, J=7.5 Hz, 3H); MS 630.99 ([M+H]$^+$).

Example 84

Preparation of methyl-{4-[1-(4-pentafluoroethyloxyphenyl)-4,5-dihydro-1H-pyrazol-4-yl]-phenyl}-carbamic acid (2S,3R,4R,5S,6S)-4-ethoxy-3,5-dimethoxy-6-methyl-tetrahydropyran-2-yl ester (Compound 252)

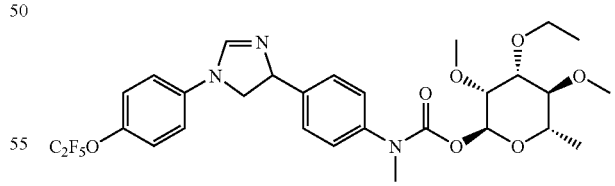

Compound 179 was methylated as in Example 82 to give Compound 252. $^1$H NMR (300 MHz, CDCl$_3$) δ 7.68 (d, J=8.24 Hz, 2H), 7.24 (d, J=8.24 Hz, 2H), 7.12 (d, J=8.28 Hz, 2H), 7.08 (d, J=8.28 Hz, 2H), 6.12 (d, J=1.85 Hz, 1H), 3.92 (t, J=9.44 Hz, 2H), 3.79-3.61 (m, 4H), 3.57 (s, 3H), 3.56 (s, 3H), 3.44 (dd, J=9.31, 3.36 Hz, 1H), 3.38 (s, 3H), 3.32-3.18 (m, 3H), 1.36-1.23 (m, 6H); EI/MS 631 (M$^+$).

Example 85

Preparation of ethyl {4-[1-(4-pentafluoroethoxyphenyl)-1H-[1,2,4]triazol-3-yl]-phenyl}-carbamic acid (2S,3R,4R,5S,6S)-4-propoxy-3,5-dimethoxy-6-methyl-tetrahydropyran-2-yl ester (Compound 253)

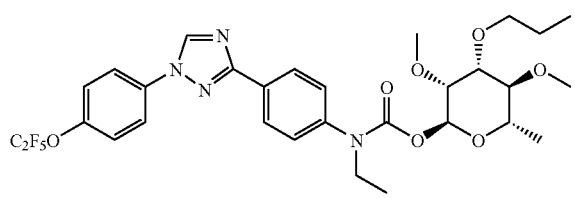

Compound 207 was N-ethylated as in Example 82, using iodoethane instead of iodomethane, to give Compound 253. $^1$H NMR (300 MHz, CDCl$_3$) δ 8.60 (s, 1H), 8.22 (d, J=68 Hz, 2H), 7.83 (d, J=8.8 Hz, 2H), 7.41 (d, J=9 Hz, 2H), 7.39 (d, J=8.6 Hz, 2H), 6.17 (s, 1H), 3.8 (q, J=7.5 Hz, 2H), 3.60-3.30 (m, 11H), 3.10 (br s, 1H), 1.38 (d, J=6.0 Hz, 3H), 1.20 (t, J=7.5 Hz, 3H); MS 659.12 ([M+H]$^+$).

Example 86

Preparation of methoxymethyl {4-[1-(4-trifluoromethoxyphenyl)-1H-[1,2,4]triazol-3-yl]-phenyl}-carbamic acid (2S,3R,4R,5S,6S)-4-ethoxy-3,5-dimethoxy-6-methyl-tetrahydropyran-2-yl ester (Compound 254)

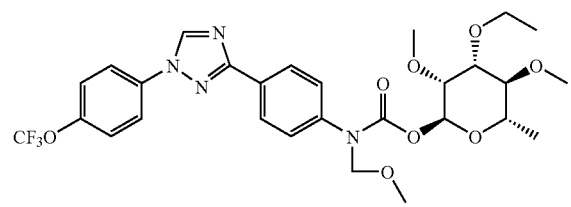

Compound 193 (0.15 g, 0.26 mmol) and bromomethyl methyl ether (78 mg, 0.6 mmol) were combined in 5 mL of dry THF, and the solution was stirred under N$_2$ and treated with 0.025 g (0.6 mmol) of NaH (60% in oil). The solution was allowed to stir at ambient temperature overnight, and then it was partitioned between water and Et$_2$O. Drying, concentration and chromatography of the organic layer furnished 110 mg of Compound 254 as a colorless solid foam. $^1$H NMR (300 MHz, CDCl$_3$) δ 8.61 (s, 1H), 8.24 (d, J=8 Hz, 2H), 7.82 (d, J=8 Hz, 2H), 7.4 (overlapping d, J=8 Hz, 4H), 6.17 (s, 1H), 5.05 (br s, 2H), 3.6-3.3 (m, 14H), 3.18 (t, J=9 Hz, 1H), 1.35 (d, J=6.3 Hz, 3H), 1.2 (t, J=7 Hz, 3H); MS 611.8 ([M+H]$^+$).

Example 87

Preparation of methoxymethyl {4-[1-(4-pentafluoroethoxyphenyl)-1H-[1,2,4]triazol-3-yl]-phenyl}-carbamic acid (2S,3R,4R,5S,6S)-4-ethoxy-3,5-dimethoxy-6-methyl-tetrahydropyran-2-yl ester (Compound 255).

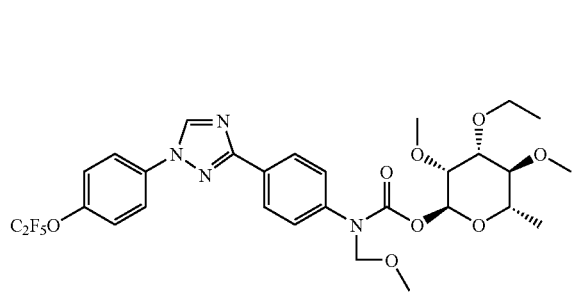

Methoxymethylation of Compound 201, using conditions described in Example 86, gave Compound 255 as a viscous foam. $^1$H NMR (300 MHz, CDCl$_3$) δ 8.61 (s, 1H), 8.22 (d, J=8 Hz, 2H), 7.82 (d, J=8 Hz, 2H), 7.4 (m, 4H), 6.17 (s, 1H), 5.05 (br s, 2H), 3.6-3.3 (m, 14H), 3.18 (t, J=9 Hz, 1H), 1.35 (d, J=6.3 Hz, 3H), 1.2 (t, J=7 Hz, 3H); MS 661.8 ([M+H]$^+$).

Example 88

Preparation of allyl {4-[1-(4-pentafluoroethoxy-phenyl)-1H-[1,2,4]triazol-3-yl]-phenyl}-carbamic acid (2S,3R,4R,5S,6S)-4-ethoxy-3,5-dimethoxy-6-methyl-tetrahydropyran-2-yl ester (Compound 256)

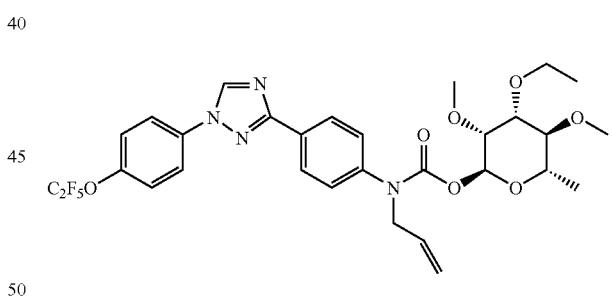

60% NaH (0.015 g, 0.40 mmol) was added to a solution of Compound 201 (0.15 g, 0.24 mmol) and allyl bromide (0.41 g, 0.34 mmol) in dry DMF (1.1 mL) at 0° C. under N$_2$. The reaction mixture was then allowed to warm to 25° C. and stirred for 5 h, at which point it was poured onto ice-H$_2$O (50 mL) and was extracted with EtOAc (3×50 mL). The combined organic extracts were washed with H$_2$O (50 mL) and were dried (Na$_2$SO$_4$), filtered and concentrated. Chromatography afforded Compound 256 (0.040 g, 25%) as a white gummy solid. $^1$H NMR (300 MHz, CDCl$_3$) δ 8.59 (s, 1H), 8.21 (d, J=8.1 Hz, 2H), 7.83 (d, J=9.0 Hz, 2H), 7.42 (d, J=9.3 Hz, 2H), 7.35 (br, 2H), 6.17 (br, 1H), 6.00-5.92 (m, 1H), 5.27-5.17 (m, 2H), 4.34 (br, 2H), 3.80-3.30 (m, 11H), 3.08 (br, 1H), 1.44 (br, 3H), 1.30 (br, 3H); MS 657 ([M]$^+$).

Example 89

Preparation of hydroxymethyl {4-[1-(4-pentafluoro-ethoxy-phenyl)-1H-[1,2,4]triazol-3-yl]-phenyl}-carbamic acid (2S,3R,4R,5S,6S)-4-propoxy-3,5-dimethoxy-6-methyl-tetrahydropyran-2-yl ester (Compound 257)

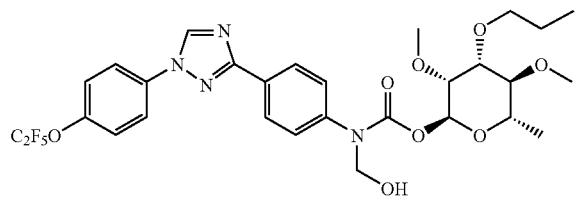

A solution of Compound 207 (0.15 g, 0.24 mmol) was dissolved in 4 mL of DCM and treated with paraformaldehyde (50 mg, excess) and trifluoroacetic acid (250 µL, excess). The solution was stirred at ambient temperature for 20 h, and then it was concentrated in vacuo. Chromatography (0 to 100% EtOAc in hexanes) gave 25 mg of the hydroxymethyl derivative (Compound 257) as a solid foam. $^1$H NMR (300 MHz, CDCl$_3$) δ 8.60 (s, 1H), 8.20 (d, J=68 Hz, 2H), 7.83 (d, J=8.8 Hz, 2H), 7.41 (d, J=9 Hz, 4H), 7.39 6.17 (s, 1H), 5.15 (dd, J=6, 14 Hz, 2H), 3.65-3.20 (m, 12H), 3.15 (br s, 1H), 1.52 (m, 2H), 1.38 (d, J=6.0 Hz, 3H), 0.95 (t, J=7.5 Hz, 3H); MS 661.10 ([M+H]$^+$).

Example 90

Preparation of acetyl {4-[1-(4-pentafluoroethoxyphenyl)-1H-[1,2,4]triazol-3-yl]-phenyl}-carbamic acid (2S,3R,4R,5S,6S)-4-ethoxy-3,5-dimethoxy-6-methyl-tetrahydropyran-2-yl ester (Compound 258)

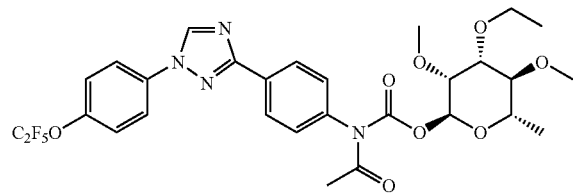

60% NaH (0.016 g, 0.40 mmol) was added to a solution of Compound 201 (0.15 g, 0.24 mmol) in dry DMF (1.1 mL) at 0° C. under N$_2$ and the mixture was stirred for ~5 min. Acetyl chloride (0.03 mL, 0.42 mmol) was then added, and the reaction mixture was allowed to warm to 25° C. and stirred for a total of 64 h. The mixture was poured onto ice-H$_2$O (50 mL) and was extracted with EtOAc (3×50 mL). The combined organic extracts were washed with H$_2$O (50 mL) and satd aq NaCl (75 mL) and were dried (Na$_2$SO$_4$), filtered and concentrated. Chromatography afforded Compound 258 (0.042 g, 26%) as a light yellow solid. $^1$H NMR (400 MHz, CDCl$_3$) δ 8.59 (s, 1H), 8.29 (d, J=8.1 Hz, 2H), 7.81 (d, J=9.0 Hz, 2H), 7.40 (d, J=9.1 Hz, 2H), 7.24 (d, J=8.5 Hz, 2H), 6.07 (d, J=2.0 Hz, 1H), 3.48 (s, 3H), 3.41 (s, 3H), 3.49-3.35 (m, 1H), 3.31-3.20 (m, 3H), 3.04 (t, J=9.4 Hz, 1H), 2.74 (dd, J=9.8, 3.4 Hz, 1H), 2.69 (s, 3H), 1.25 (d, J=6.1 Hz, 3H), 1.01 (t, J=7.0 Hz, 3H); MS 658 (M$^+$); mp 70-72° C.

Example 91

Preparation of 4-(((2S,3R,4R,5S,6S)-4-ethoxy-3,5-dimethoxy-6-methyl-tetrahydropyran-2-yloxycarbonyl)-{4-[1-(4-pentafluoroethoxy-phenyl)-1H-[1,2,4]triazol-3-yl]-phenyl}-amino)-4-oxo-butyric acid methyl ester (Compound 259)

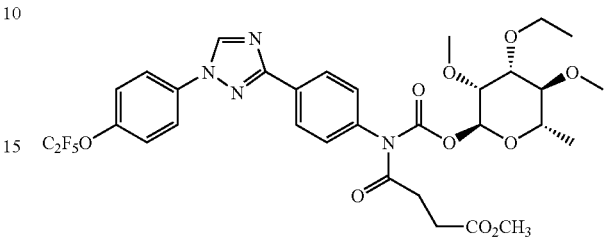

60% NaH (0.041 g, 1.0 mmol) was added in one portion to a solution of Compound 201 (0.500 g, 0.81 mmol) in dry DMF (3.6 mL) at 25° C. and the mixture was stirred for ~5 min. Methyl succinyl chloride (0.12 mL, 0.97 mmol) was then added, and the reaction mixture was allowed to stir at 60° C. for 3 h. The mixture was cooled, poured onto satd aq NH$_4$Cl (50 mL) and was extracted with EtOAc (3×50 mL). The combined organic extracts were washed with H$_2$O (50 mL) and satd aq NaCl (75 mL) and were dried (Na$_2$SO$_4$), filtered and concentrated. Chromatography afforded Compound 259 (0.079 g, 13%) as a white solid. $^1$H NMR (300 MHz, CDCl$_3$) δ 8.60 (s, 1H), 8.30 (d, J=9.0 Hz, 2H), 7.82 (d, J=9.0 Hz, 2H), 7.41 (d, J=8.7 Hz, 2H), 7.29-7.22 (m, 2H), 6.08 (d, J=1.8 Hz, 1H), 3.70 (s, 3H), 3.50-3.19 (m, 9H), 3.05 (t, J=9.3 Hz, 1H), 2.79-2.69 (m, 3H), 1.29-1.22 (m, 6H), 1.03 (t, J=6.9 Hz, 3H); MS 730 (M$^+$); mp 72-76° C.

Testing of Compounds

Bioassays on beet armyworm (BAW; *Spodoptera exigua*: Lepidoptera) were conducted using either a 96-well microtiter plate-based high throughput (HTS) bioassay or a 128-well diet tray assay. The HTS assay is a based on a modification of Lewer et al. *J. Nat. Prod.* 2006, 69, 1506. BAW eggs of were placed on top of artificial diet (100 µl) in each well of 96-well microtiter plate. The diet was pretreated with test compounds (12 µg dissolved in 30 µL of DMSO-acetone-water mixture) layered on top of the diet using a liquid handling system and then allowed to dry for several hours. Infested plates were then covered with a layer of sterile cotton batting and the plate lid, and then held in the dark at 29° C. Mortality was recoded at 6 d post-treatment. Each plate had six replicates. The percent mortality was calculated from the average of the six replicates. In the case of the 128-well diet assay, three to five second instar BAW larvae were placed in each well (3 mL) of the diet tray that had been previously filled with 1 mL of artificial diet to which 50 µg/cm$^2$ of the test compound (dissolved in 50 µL of 90:10 acetone-water mixture) had been applied (to each of eight wells) and then allowed to dry. Trays were covered with a clear self-adhesive cover, and held at 25° C., 14:10 light-dark for six days. Percent mortality was recorded for the larvae in each well; activity in the eight wells was then averaged. The results for both bioassays are indicated in Table 7. In Table 7, under the BAW HTS or BAW 50 heading, an "A" means that the compound was tested and at least 50 percent mortality was observed whereas, "B" means that either (1) the compound was tested and less than 50 percent mortality was observed or (2) the compound was not tested.

TABLE 1

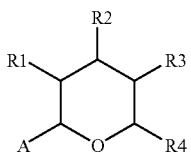

General Formula

| # | A | R1 | R2 | R3 | R4 | Sugar | M.S. | bp | $^1$H NMR (CDCl$_3$, δ) |
|---|---|---|---|---|---|---|---|---|---|
| E-1 | OCH$_3$ | OCH$_3$ | OCH$_3$ | OCH$_3$ | CH$_3$ | L-rhamnose | — | 150° C. (0.5 mm Hg) | 5.28 (m, 1 H), 3.85 (m, 1 H), 3.66 (m, 1 H), 3.60-3.50 (m, 1 H), 3.58 (s, 3 H), 3.53 (s, 6 H), 3.37 (s, 3 H), 3.16 (t, 1 H), 1.31 (d, 3 H) |
| E-2 | OH | OCH$_3$ | OCH$_3$ | OCH$_3$ | CH$_3$ | L-rhamnose | — | 145-155° C. (1 mm Hg) | 5.28 (s, 1 H), 3.83 (m, 1 H), 3.7-3.45 (m, 11 H), 3.16 (t, J = 9.2 Hz, 1 H), 3.0 (s, 1 H), 1.31 (d, J = 6 Hz, 3 H) |
| E-3 | OCH$_3$ | OC$_2$H$_5$ | OCH$_3$ | OCH$_3$ | CH$_3$ | L-rhamnose | 202.9 (M-MeOH) | 165° C. (10 mTorr) | 4.71 (d, J = 1.8 Hz, 1 H), 3.77-3.50 (m, 11 H), 3.37 (s, 3 H), 3.13 (t, J = 9.4 Hz, 1 H), 1.32 (d, J = 6.3 Hz, 3 H), 1.27 (t, J = 7.0 Hz, 3 H) |
| E-4 | OC$_2$H$_5$ | OC$_2$H$_5$ | OC$_2$H$_5$ | OC$_2$H$_5$ | CH$_3$ | L-rhamnose | 299.1 (M + Na) | 180° C. (10 mTorr) | 4.72 (d, J = 1.8 Hz) and 4.30 (s), total 1 H, 4.0-3.35 (series of m, 10 H), 3.2 (m, 2 H), 1.3-1.1 (m, 15 H) |
| E-5 | OCH$_3$ | OCH$_3$ | OC$_3$H$_7$ | OCH$_3$ | CH$_3$ | L-rhamnose | | 175° C. (10 mTorr) | 4.70 (d, J = 1.8 Hz, 1 H), 3.77-3.50 (m, 11 H), 3.37 (s, 3 H), 3.13 (t, J = 9.4 Hz, 1 H), 1.62 (m, 2 H), 1.32 (d, J = 6.3 Hz, 3 H), 0.98 (t, J = 7.5 Hz, 3 H) |
| E-6 | OCH$_3$ | OCH$_3$ | O-allyl | OCH$_3$ | CH$_3$ | L-rhamnose | | 175° C. (10 mTorr) | 5.98 (m, 1 H), 5.32 (d, 1 H), 5.20 (d, 1 H), 4.50 (s, 1 H), 4.18 (d, 2 H), 3.62-3.50 (m, 9 H), 3.28 (s, 3 H), 3.17 (t, J = 6.3 Hz, 1 H), 1.33 (d, J = 6.3 Hz, 3 H) |
| E-7 | OCH$_3$ | OCH$_3$ | OC$_4$H$_9$ | OCH$_3$ | CH$_3$ | L-rhamnose | | 165° C. (5 mTorr) | 4.71 (s, 1 H), 3.62-3.50 (m, 11 H), 3.35 (s, 3 H), 3.17 (t, 1 H), 1.6 (m, 2 H), 1.4 (m, 2 H), 1.33 (d, J = 6.3 Hz, 3 H), 0.98 (t, J = 7.5 Hz, 3 H) |
| E-8 | OH | OCH$_3$ | OC$_2$H$_5$ | OCH$_3$ | CH$_3$ | L-rhamnose | 202.9 (M + H$_2$O) | 165° C. (9 mTorr) | 5.35 (m, J = 3.2, 2.0 Hz, 1 H), 3.84-3.62 (m, 5 H), 3.59 (s, 3 H), 3.53 (s, 3 H), 3.16 (t, J = 9.5 Hz, 1 H), 2.73 (d, J = 3.4 Hz, 1 H), 1.33-1.26 (m, 6 H) |
| E-9 | OH | OC$_2$H$_5$ | OC$_2$H$_5$ | OC$_2$H$_5$ | CH$_3$ | L-rhamnose | 248.2 (M+) | 203° C. (5 mTorr) | 5.2 (s) and 4.65 (dd, J = 1.2, 9 Hz, anomeric proton signals, total 1 H, ratio 64:36 α:β); 4.10-3.45 (m, 8 H), 3.36-3.20 (m, 2 H), 1.37-1.13 (m, 12 H) |
| E-10 | OH | OCH$_3$ | OC$_3$H$_7$ | OCH$_3$ | CH$_3$ | L-rhamnose | 220.2 (M+) | 185° C. (5 mTorr) | 5.25 (dd, J = 3.2, 2.0 Hz) and 4.61 (m, total 1 H), 3.80 (m, 1 H), 3.70-3.50 (m, 9 H), 3.36-3.05 (m, 1 H), 1.60 (m, 2 H), 1.30 (m, 5 H), 0.95 (t, J = 7.5 Hz, 3 H) |
| E-11 | OH | OCH$_3$ | O-allyl | OCH$_3$ | CH$_3$ | L-rhamnose | 254.9 (M + Na) | 175° C. (10 mTorr) | 5.95 (m, 1 H), 5.3 (m, 1 H), 5.19 (m, 1 H), 5.21 and 4.61 (both m, α and β anomers, total 1 H), 4.20 (m, 2 H), 3.80 (m, 1 H), 3.70-3.50 (m, 7 H), 3.40-3.10 (m, 3 H), 1.3 (m, 3 H) |
| E-12 | OH | OCH$_3$ | OC$_4$H$_9$ | OCH$_3$ | CH$_3$ | L-rhamnose | 248.2 (M+) | 189° C. (5 mTorr) | 5.35 (dd, J = 3.2, 2.0 Hz) and 4.45 (m, total 1 H), 3.80 (m, 1 H), 3.70-3.50 (m, 10 H), 3.36-3.05 (m, 1 H), 2.73 (d, J = 3.4 Hz, 1 H), 1.60 (m, 2 H), 1.40 (m, 2 H), 1.33 (d, J = 6 Hz, 3 H), 0.95 (t, J = 7.5 Hz, 3 H) |
| E-13 | —OH | —OCH$_3$ | —OCH$_3$ | —OCH$_3$ | CH$_2$O—CH$_3$ | L-mannose | | | 5.32 (s, 1 H), 3.9 (m, 1 H), 3.66-3.53 (series of m, 4 H) 3.52 (s, 3 H), 3.51 (s, 3 H), 3.49 (s, 3 H), 3.40 (s, 3 H), 3.35 (m, 1 H), 3.18 (d, J = 3 Hz, 1 H) |
| E-14 | —OH | —OCH$_3$ | —OCH$_3$ | —OCH$_3$ | CH$_2$O—CH$_3$ | D-glucose | | | 5.33 (d, J = 3.6 Hz) and 4.60 (d, J = 4 Hz), α and β anomers, total 1 H), 3.9 (m, 1 H), 3.6-3.3 (series of s and m, 14 H), 3.28 (m, 3 H), 1.7 (s, 1 H) |
| E-15 | —OCH$_3$ | —OCH$_3$ | —OCH$_3$ | —OCH$_3$ | —H$_2$ | L-xylose | 207 (M + H) | | 4.77 (d, J = 3.5 Hz) and 4.15 (d, J = 7.4 Hz, total 1 H in a 0.27:1 α:β ratio), 4.00 (dd, J = 11.6, 5.0 Hz, 1 H), 4.03-2.93 (series of s and m, 16 H) |
| E-16 | —OH | —OCH$_3$ | —OCH$_3$ | —OCH$_3$ | —H$_2$ | L-xylose | 175 (M − H$_2$O) | | 5.23 (t, J = 3.4 Hz) and 4.60 (t, J = 6.3 Hz, total 1 H in a 1.5:1 α:β ratio), 4.01-2.97 (series of s and m, 15 H) |
| E-17 | —OCH$_3$ | —OCH$_3$ | —OCH$_3$ | —OCH$_3$ | —H$_2$ | L-lyxose | 207 (M + H) | | 4.69 (d, J = 3.0 Hz, 1 H, α anomer), 3.77 (dd, J = 10.8, 4.7 Hz, 1 H), 3.62-3.32 (series of s and m, 16 H) |
| E-18 | —OH | —OCH$_3$ | —OCH$_3$ | —OCH$_3$ | —H$_2$ | L-lyxose | 175 (M − H$_2$O) | | 5.18-5.11 (m, 1 H, mixture of α and β anomers), 4.84 (d, J = 10.1 Hz, 0.4 H), 3.98-3.37 (series of s and m, 14 H), 3.11 (d, J = 4.2 Hz, 0.6 H) |
| E-19 | —OCH$_3$ | —OCH$_3$ | —OCH$_3$ | —OCH$_3$ | CH$_2$O—CH$_3$ | L-glucose | 205 (M − CH$_2$OCH$_3$) | | (600 MHz, CDCl$_3$) 4.83 (d, J = 4.1 Hz) and 4.14 (d, J = 7.8 Hz, total 1 H in a 0.2:1 α:β ratio), 3.66-3.36 (series of s and m, 18 H), 3.29-3.26 (m, 1 H), 3.17-3.13 (m, 1 H), 3.01-2.94 (m, 1 H) |

TABLE 1-continued

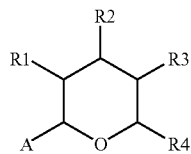

General Formula

| # | A | R1 | R2 | R3 | R4 | Sugar | M.S. | bp | $^1$H NMR (CDCl$_3$, δ) |
|---|---|---|---|---|---|---|---|---|---|
| E-20 | —OH | —OCH$_3$ | —OCH$_3$ | —OCH$_3$ | CH$_2$O—CH$_3$ | L-glucose | 191 (M − CH$_2$OCH$_3$) | Mp 63-67° C. | 5.33 (d, J = 3.7 Hz) and 4.58 (d, J = 7.9 Hz, total 1 H in a 2.5:1 α:β ratio), 3.92-3.86 (m, 0.8 H), 3.65-3.08 (series of s and m, 18 H), 2.96 (dd, J = 8.8, 7.8 Hz, 0.2 H) |
| E-21 | —OCH$_3$ | —H$_2$ | —OCH$_3$ | —OCH$_3$ | CH$_2$O—CH$_3$ | 2-deoxy-D-glucose | 220 (M$^+$) | | 4.81 (dd, J = 3.6, 1.1 Hz) and 4.34 (dd, J = 9.5, 1.9 Hz, total 1 H in a 0.29:1 α:β ratio), 3.71-3.23 (m, 16 H), 3.18-3.05 (m, 1 H), 2.33-2.16 (m, 1 H), 1.60-1.41 (m, 1 H) |
| E-22 | —OCH$_3$ | —H$_2$ | —OCH$_3$ | OH | CH$_3$ | L-oleandrose | | | 4.78 (d, J = 3.3 Hz, 1 H), 3.52 (m, 1 H), 3.47 (m, 1 H), 3.45 (s, 3 H), 3.30 (s, 3 H), 3.19 (m, 1 H), 2.67 (brs, 1 H), 2.29 (dd, J = 4.8, 12.9 Hz, 1 H), 1.51 (m, 1 H), 1.32 (d, J = 6.3 Hz, 3 H) |

TABLE 2

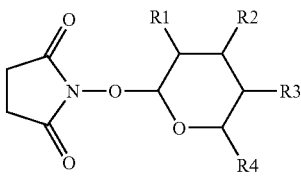

| # | R1 | R2 | R3 | R4 | Sugar | M.S. | mp | $^1$H NMR (CDCl$_3$, δ) |
|---|---|---|---|---|---|---|---|---|
| E-23 | OCH$_3$ | OCH$_3$ | OCH$_3$ | CH$_3$ | L-rhamnose | 326.1 [M + Na]$^+$ | 135° C. | 5.35 (d, J = 2.0 Hz, 1 H), 4.29 (m, 1 H), 3.89 (dd, J = 3.3, 2.1 Hz, 1 H), 3.55 (s, 3 H), 3.54 (s, 3 H), 3.52 (s, 3 H), 3.51 (m, 1 H), 3.18 (t, J = 9.3 Hz, 1 H), 2.74 (s, 4 H), 1.27 (d, J = 6.1 Hz, 3 H) |
| E-24 | OCH$_3$ | OCH$_3$ | OH | CH$_3$ | L-rhamnose | 288 [M − H] | 163-166° C. | 5.42 (s, 1 H), 4.40 (m, 1 H), 4.0 (m, 1 H), 3.63 (d, J = 8 Hz, 1 H), 3.55-3.45 (m, 7 H), 2.78 (s, 4 H), 2.2 (br s, 1 H), 1.30 (d, J = 6.3 Hz, 3 H) |
| E-25 | OCH$_3$ | OC$_2$H$_5$ | OCH$_3$ | CH$_3$ | L-rhamnose | | | 5.35 m, 1 H), 4.29 (m, 1 H), 3.85 (m, 1 H), 3.78-3.50 (m, 9 H), 3.19 (t, J = 9.5 Hz, 1 H), 2.75 (s, 4 H), 1.33-1.26 (m, 6 H) |
| E-26 | OCH$_3$ | OC$_3$H$_7$ | OCH$_3$ | CH$_3$ | L-rhamnose | 354. [M + Na]$^+$ | 69-71° C. | 5.35 (s, 1 H), 4.29 (m, 1 H), 3.84 (m, 1 H), 3.78-3.50 (m, 9 H), 3.19 (t, J = 9.5 Hz, 1 H), 2.75 (s, 4 H), 1.64 (m, 2 H), 1.25 (d, J = 6.1 Hz, 3 H), 0.95 (t, J = 7.5 Hz, 3 H)) |
| E-27 | OCH$_3$ | OC$_4$H$_9$ | OCH$_3$ | CH$_3$ | L-rhamnose | | | 5.32 (d, J = 1.8 Hz, 1 H), 4.29 (m, 1 H), 3.84 (m, 1 H), 3.6-3.45 (m, 9 H), 3.17 (t, J = 9.3 Hz, 1 H), 2.73 (s, 4 H), 1.6 (m, 2 H), 1.4 (m, 2 H), 1.26 (d, J = 5.7 Hz, 3 H), 0.93 (t, J = 7.5 Hz, 3 H) |
| E-28 | OCH$_3$ | OCH$_3$ | OCH$_3$ | CH$_2$OCH$_3$ | D-glucose | | | 5.52 (d, J = 4 Hz, 1 H), 4.45 (d, J = 10 Hz, 1 H), 3.68-3.47 (m, 12 H), 3.4-3.27, series of m, 5 H), 2.72 (s, 4 H) |
| E-29 | OCH$_3$ | OCH$_3$ | OCH$_3$ | CH$_2$OCH$_3$ | L-mannose | | | 5.44 (s, 1 H), 4.29 (m, 1 H), 3.90 (m, 1 H), 3.7-3.55 (m, 3 H), 3.54 (s, 3 H), 3.53 (s, 3 H), 3.52 (s, 3 H), 3.53 (m, 1 H), 3.38 (s, 3 H), 2.73 (s, 4 H) |

TABLE 3

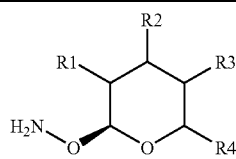

| # | R1 | R2 | R3 | R4 | Sugar | M.S. | Mp | $^1$H NMR (CDCl$_3$, δ) |
|---|---|---|---|---|---|---|---|---|
| E-30 | OCH$_3$ | OCH$_3$ | OCH$_3$ | CH$_3$ | L-rhamnose | 221.7 (M + H$^+$) | 55° C. | 5.51 (s, 2 H), 4.98 (d, J = 1.8 Hz, 1 H), 3.60 (m, 2 H), 3.55 (s, 3 H), 3.50 (s, 3 H), 3.48 (s, 3 H), 3.35 |

TABLE 3-continued

| # | R1 | R2 | R3 | R4 | Sugar | M.S. | Mp | $^1$H NMR (CDCl$_3$, δ) |
|---|----|----|----|----|-------|------|-----|------------------------|
| E-31 | OCH$_3$ | OC$_2$H$_5$ | OCH$_3$ | CH$_3$ | L-rhamnose | 258.1 (M + Na$^+$) | 88° C. | (dd, J = 9.2, 3.3 Hz, 1 H), 3.13 (t, J = 9.4 Hz, 1 H), 1.34 (d, J = 6.2 Hz, 3 H) 5.51 (s, 2 H), 4.98 (d, J = 1.8 Hz, 1 H), 3.60 (m, 4 H), 3.55 3.50 (s, 3 H), 3.48 (s, 3 H), 3.35 (dd, J = 9.2, 3.3 Hz, 1 H), 3.13 (t, J = 9.4 Hz, 1 H), 1.34-1.26 (m, 6 H) |
| E-32 | OCH$_3$ | OC$_3$H$_7$ | OCH$_3$ | CH$_3$ | L-rhamnose | 249.1 (M + H$^+$) | 49° C. | 5.6 (s, 2 H), 4.95 (d, J = 1.8 Hz, 1 H), 3.6-3.3 (m, 11 H), 3.13 (t, J = 9.3 Hz, 1 H), 1.65 (m, 2 H), 1.34 (d, J = 6.2 Hz, 3 H), 0.97 (t, J = 7.5 Hz, 3 H) |
| E-33 | OCH$_3$ | OC$_4$H$_9$ | OCH$_3$ | CH$_3$ | L-rhamnose |  | 40-42° C. | 5.6 (s, 2 H), 4.97 (d, J = 1.8 Hz, 1 H), 3.6-3.3 (m, 11 H), 3.13 (t, J = 9.3 Hz, 1 H), 1.62 (m, 2 H), 1.40 (m, 2 H), 1.34 (d, J = 6.2 Hz, 3 H), 0.94 (t, J = 7.5 Hz, 3 H) |
| E-34 | OC$_2$H$_5$ | OC$_2$H$_5$ | OC$_2$H$_5$ | CH$_3$ | L-rhamnose | 264.1 (M + Na$^+$) | Oil | 5.5 (s, 2 H), 4.90 (s, 1 H), 3.9 (m, 1 H), 3.80-3.50 (m, 7 H), 3.4 (m, 1 H), 3.25 (t, J = 9 Hz, 1 H), 1.35 (d, J = 6.3 Hz, 3 H), 1.27 (m, 9 H) |
| E-35 | OCH$_3$ | OCH$_3$ | OH | CH$_3$ | L-rhamnose | 268 (M + AcOH) | Oil | 5.6 (br s, 2 H), 4.96 (s, 1 H), 3.7-3.5 (m, 3 H), 3.48 (s, 3 H), 3.42 (s, 3 H), 3.25 (dd, J = 10, 3 Hz, 1 H), 2.75 (br s, 1 H), 1.7 (d, J = 7 Hz, 3 H) |
| E-36 | OCH$_3$ | OCH$_3$ | OCH$_3$ | CH$_2$OCH$_3$ | L-mannose | 251.1 (M + H$^+$) | 58° C. | 5.5 (br s, 2 H), 5.04 (d, J = 2 Hz, 1 H), 3.65-3.58 (m, 4 H), 3.52 (s, 3 H), 3.48 (two s, 6 H), 3.42 (s, 3 H), 3.45-3.39 (m, 2 H). |
| E-37 | OCH$_3$ | OCH$_3$ | OCH$_3$ | CH$_3$ | L-fucose |  | 91° C. | 5.58 (s, 2 H), 5.1 (d, J = 4 Hz, 1 H), 3.60 (q, J = 6.8 Hz, 1 H), 3.66 (m, 1 H), 3.60 (s, 3 H), 3.53 (s, 3 H), 3.51 (s, 3 H), 3.5-3.4 (m, 2 H), 1.34 (d, J = 6.4 Hz, 3 H) |
| E-38 | OCH$_3$ | OCH$_3$ | OCH$_3$ | CH$_2$OCH$_3$ | D-glucose | 251.8 (M + H)$^+$ | 82° C. | 5.6 (br. s, 2 H), 5.1 (d, J = 4 Hz, 1 H), 3.7 (s, 3 H), 3.55 (s, 3 H), 3.53 (s, 3 H), 3.41 (s, 3 H), 3.65-3.35 (series of m, 3 H), 3.4 (m, 1 H), 3.2 (m, 2 H) |

TABLE 4

| # | Ar$_1$ | Het link[1] | Het | Ar$_2$ | Sugar[2] | M.S. | Mp ° C. | $^1$H NMR (CDCl$_3$, δ)[3] |
|---|--------|-------------|-----|--------|----------|------|---------|---------------------------|
| 1 | 3-OCH$_3$ phenyl | 4,1 | pyrazole | 1,4 Phenyl | A | 481.0 [M]$^+$ |  | 8.22 (d, J = 8.24 Hz, 2 H), 8.06 (s, 1 H), 7.82-7.78 (m, 5 H), 7.39-7.36 (m, 1 H), 7.21-7.17 (m, 1 H), 6.87 (m, 1 H), 5.63 (d, J = 1.85 Hz, 1 H), 3.84 (s, 3 H), 3.68 (dd, J = 3.28, 1.99 Hz, 1 H), 3.63 (m, 1 H), 3.59 (s, 3 H), 3.57 (s, 3 H), 3.56 (s, 3 H), 3.44 (dd, J = 9.31, 3.36 Hz, 1 H), 3.20 (t, J = 9.48 Hz, 1 H), 1.25 (d, J = 6.26 Hz, 3 H) |
| 2 | 4-Cl phenyl | 3,1 | pyrazole | 1,4 Phenyl | A | 485.0 [M + H]$^+$ |  | 8.18 (s, 1 H), 8.02 (d, J = 2.01 Hz, 1 H), 7.81 (d, J = 8.32 Hz, 2 H), 7.78 (d, J = 8.32 Hz, 2 H), 7.47 (d, J = 8.22 Hz, 2 H), 7.29 (d, J = 8.22 Hz, 2 H), 7.01 (d, J = 2.01 Hz, 1 H), 5.63 (d, J = 1.85 Hz, 1 H), 3.68 (dd, J = 3.28, 1.99 Hz, 1 H), 3.63 (m, 1 H), 3.59 (s, 3 H), 3.57 (s, 3 H), 3.56 (s, 3 H), 3.44 (dd, J = 9.31, 3.36 Hz, 1 H), 3.20 (t, J = 9.48 Hz, 1 H), 1.25 (d, J = 6.26 Hz, 3 H) |
| 3 | 2-pyridyl | 3,1 | pyrazole | 1,4 Phenyl | A | 452.0 [M]$^+$ |  | 8.64 (m, 1 H), 8.19 (s, 1 H), 8.16-8.11 (m, 1 H), 8.04 (d, J = 1.98 Hz, 1 H), 7.81 (d, J = 8.34 Hz, 2 H), 7.78-7.69 (m, 4 H), 7.13 (d, J = 1.98 Hz, 1 H), 5.63 (d, J = 1.85 Hz, 1 H), 3.68 (dd, J = 3.28, 1.99 Hz, 1 H), 3.63 (m, 1 H), 3.59 (s, 3 H), 3.57 (s, 3 H), 3.56 (s, 3 H), 3.44 (dd, J = 9.31, 3.36 Hz, 1 H), 3.20 (t, J = 9.48 Hz, 1 H), 1.25 (d, J = 6.26 Hz, 3 H) |
| 4 | 2-thienyl | 3,1 | pyrazole | 1,4 Phenyl | A | 457.0 [M]$^+$ |  | 8.16 (s, 1 H), 7.94 (d, J = 1.91 Hz, 1 H), 7.79 (d, J = 8.30 Hz, 2 H), 7.69 (d, J = 8.30 Hz, 2 H), 7.42 (m, 1 H), 7.31 (m, 1 H), 7.07 (m, 1 H), 6.68 (d, J = 1.91 Hz, 1 H), 5.63 (d, J = 1.85 Hz, 1 H), 3.68 (dd, J = 3.28, 1.99 Hz, 1 H), 3.63 (m, 1 H), 3.59 (s, 3 H), 3.57 (s, 3 H), 3.56 (s, 3 H), 3.44 (dd, J = 9.31, 3.36 Hz, 1 H), 3.20 (t, J = 9.48 Hz, 1 H), 1.25 (d, J = 6.26 Hz, 3 H) |
| 5 | 4-(1-OH-propyl) phenyl | 1,3 | pyrazole | 1,4 Phenyl | A | 509.0 [M + H]$^+$ |  | 8.17 (s, 1 H), 7.96 (d, J =3.34 Hz, 1 H), 7.92 (d, J = 8.23 Hz, 2 H), 7.74 (d, J = 8.30 Hz, 2 H), 7.66 (d, J = 8.23 Hz, 2 H), 7.42 (d, J = 8.30 Hz, 2 H), 6.79 (d, J = 3.34 Hz, 1 H), 5.63 (d, J = 1.85 Hz, 1 H), 4.62 (t, J = 7.26 Hz, 1 H), 3.73 (dd, J = 3.28, 1.99 Hz, 1 H), 3.63 (m, 1 H), 3.59 (s, 3 H), 3.57 (s, 3 H), 3.56 |

TABLE 4-continued $$Ar_1\text{-Het-}Ar_2\text{-C(H)=N-O-Sugar}$$

| # | Ar₁ | Het link[1] | Het | Ar₂ | Sugar[2] | M.S. | Mp °C. | ¹H NMR (CDCl₃, δ)[3] |
|---|---|---|---|---|---|---|---|---|
| | | | | | | | | (s, 3 H), 3.44 (dd, J = 9.31, 3.36 Hz, 1 H), 3.18 (t, J = 9.48 Hz, 1 H), 1.79 (m, 3 H), 1.31 (d, J = 6.26 Hz, 3 H), 0.94 (t, J = 7.40, 3 H) |
| 6 | 4-SCF₃ phenyl | 1,3 | pyrazole | 1,4 Phenyl | A | 551.0 [M + H]⁺ | | 8.18 (s, 1 H), 7.99 (d, J = 3.32 Hz, 1 H), 7.94 (d, J = 8.22 Hz, 2 H), 7.82 (d, J = 8.29 Hz, 2 H), 7.74 (d, J = 8.29 Hz, 2 H), 7.68 (d, J = 8.22 Hz, 2 H), 6.83 (d, J = 3.32 Hz, 1 H), 5.63 (d, J = 1.85 Hz, 1 H), 3.72 (dd, J = 3.28, 1.99 Hz, 1 H), 3.63 (m, 1 H), 3.59 (s, 3 H), 3.57 (s, 3 H), 3.56 (s, 3 H), 3.42 (dd, J = 9.31, 3.36 Hz, 1 H), 3.20 (t, J = 9.48 Hz, 1 H), 1.28 (d, J = 6.26 Hz, 3 H) |
| 7 | 4-OC₂F₄H phenyl | 1,3 | pyrazole | 1,4 Phenyl | A | 567.0 [M + H]⁺ | | 8.18 (s, 1 H), 7.97 (d, J = 3.22 Hz, 1 H), 7.91 (d, J = 8.28 Hz, 2 H), 7.78 (d, J = 8.31 Hz, 2 H), 7.69 (d, J = 8.28 Hz, 2 H), 7.31 (d, J = 8.31 Hz, 2 H), 6.81 (d, J = 3.22 Hz, 1 H), 5.94 (tt, J = 52.72, 2.64 Hz, 1 H), 5.63 (d, J = 1.85 Hz, 1 H), 3.77 (dd, J = 3.28, 1.99 Hz, 1 H), 3.63 (m, 1 H), 3.59 (s, 3 H), 3.57 (s, 3 H), 3.56 (s, 3 H), 3.44 (dd, J = 9.31, 3.36 Hz, 1 H), 3.18 (t, J = 9.48 Hz, 1 H), 1.31 (d, J = 6.26 Hz, 3 H) |
| 8 | 4-OC₂F₅ phenyl | 1,3 | pyrazole | 1,4 Phenyl | A | 585.0 [M + H]⁺ | | 8.17 (s, 1 H), 7.95 (d, J = 3.30 Hz, 1 H), 7.91 (d, J = 8.21 Hz, 2 H), 7.79 (d, J = 8.29 Hz, 2 H), 7.70 (d, J = 8.21 Hz, 2 H), 7.31 (d, J = 8.29 Hz, 2 H), 6.81 (d, J = 3.30 Hz, 1 H), 5.63 (d, J = 1.85 Hz, 1 H), 3.74 (dd, J = 3.28, 1.99 Hz, 1 H), 3.63 (m, 1 H), 3.59 (s, 3 H), 3.57 (s, 3 H), 3.56 (s, 3 H), 3.41 (dd, J = 9.31, 3.36 Hz, 1 H), 3.19 (t, J = 9.48 Hz, 1 H), 1.32 (d, J = 6.26 Hz, 3 H) |
| 9 | 4-SCH₃ phenyl | 1,3 | pyrazole | 1,4 Phenyl | A | 497.0 [M + H]⁺ | | 8.18 (s, 1 H), 7.94 (d, J = 3.36 Hz, 1 H), 7.91 (d, J = 8.21 Hz, 2 H), 7.71 (d, J = 8.20 Hz, 2 H), 7.69 (d, J = 8.21 Hz, 2 H), 7.36 (d, J = 8.20 Hz, 2 H), 6.78 (d, J = 3.36 Hz, 1 H), 5.63 (d, J = 1.85 Hz, 1 H), 3.72 (dd, J = 3.28, 1.99 Hz, 1 H), 3.63 (m, 1 H), 3.59 (s, 3 H), 3.57 (s, 3 H), 3.56 (s, 3 H), 3.44 (dd, J = 9.31, 3.36 Hz, 1 H), 3.20 (t, J = 9.48 Hz, 1 H), 2.52 (s, 3 H), 1.28 (d, J = 6.26 Hz, 3 H) |
| 10 | 4-i-Pr phenyl | 1,3 | pyrazole | 1,4 Phenyl | A | 493.0 [M + H]⁺ | | 8.18 (s, 1 H), 7.93 (d, J = 8.25 Hz, 2 H), 7.90 (d, J = 3.34 Hz, 1 H), 7.69 (d, J = 8.29 Hz, 2 H), 7.66 (d, J = 8.25 Hz, 2 H), 7.33 (d, J = 8.29 Hz, 2 H), 6.78 (d, J = 3.34 Hz, 1 H), 5.63 (d, J = 1.85 Hz, 1 H), 3.79 (dd, J = 3.28, 1.99 Hz, 1 H), 3.63 (m, 1 H), 3.59 (s, 3 H), 3.57 (s, 3 H), 3.56 (s, 3 H), 3.44 (dd, J = 9.31, 3.36 Hz, 1 H), 3.19 (t, J = 9.48 Hz, 1 H), 2.97 (m, 1 H), 1.28 (d, J = 6.43 Hz, 6 H), 1.31 (d, J = 6.26 Hz, 3 H) |
| 11 | 4-t-Bu | 1,3 | pyrazole | 1,4 Phenyl | A | 507.0 [M + H]⁺ | | 8.17 (s, 1 H), 7.94 (d, J = 8.21 Hz, 2 H), 7.91 (d, J = 3.29 Hz, 1 H), 7.68 (d, J = 8.19 Hz, 2 H), 7.65 (d, J = 8.21 Hz, 2 H), 7.46 (d, J = 8.19 Hz, 2 H), 6.77 (d, J = 3.29 Hz, 1 H), 5.63 (d, J = 1.85 Hz, 1 H), 3.75 (dd, J = 3.28, 1.99 Hz, 1 H), 3.63 (m, 1 H), 3.59 (s, 3 H), 3.57 (s, 3 H), 3.56 (s, 3 H), 3.44 (dd, J = 9.31, 3.36 Hz, 1 H), 3.20 (t, J = 9.48 Hz, 1 H), 1.34 (s, 9 H), 1.29 (d, J = 6.26 Hz, 3 H) |
| 12 | 4-OCF₃ phenyl | 1,3 | pyrazole | 1,4 Phenyl | A | 535.0 [M + H]⁺ | | 8.17 (s, 1 H), 7.95 (d, J = 3.34 Hz, 1 H), 7.91 (d, J = 8.25 Hz, 2 H), 7.78 (d, J = 8.28 Hz, 2 H), 7.69 (d, J = 8.25 Hz, 2 H), 7.34 (d, J = 8.28 Hz, 2 H), 6.81 (d, J = 3.34 Hz, 1 H), 5.63 (d, J = 1.85 Hz, 1 H), 3.74 (dd, J = 3.28, 1.99 Hz, 1 H), 3.63 (m, 1 H), 3.59 (s, 3 H), 3.57 (s, 3 H), 3.56 (s, 3 H), 3.44 (dd, J = 9.31, 3.36 Hz, 1 H), 3.18 (t, J = 9.48 Hz, 1 H), 1.31 (d, J = 6.26 Hz, 3 H) |
| 13 | 4-OCF₃ phenyl | 1,3 | 5-CO₂Et-pyrazoline | 1,4 Phenyl | A | 609.0 [M + H]⁺ | | 8.19 (s, 1 H), 7.72 (d, J = 8.34 Hz, 2 H), 7.66 (d, J = 8.34 Hz, 2 H), 7.16 (d, J = 8.68 Hz, 2 H), 7.08 (d, J = 8.68 Hz, 2 H), 5.63 (d, J = 1.85 Hz, 1 H), 4.87 (dd, J = 2.54, 2.12 Hz, 1 H), 4.25 (q, J = 7.12 Hz, 2 H), 3.68 (dd, J = 3.28, 1.99 Hz, 1 H), 3.65 (m, 3 H), 3.59 (s, 3 H), 3.57 (s, 3 H), 3.56 (s, 3 H), 3.44 (dd, J = 9.31, 3.36 Hz, 1 H), 3.20 (t, J = 9.48 Hz, 1 H), 1.32 (d, J = 6.26 Hz, 3 H), 1.27 (t, J = 7.64 Hz, 3 H) |
| 14 | 4-OCF₃ phenyl | 1,3 | 5-CO₂-i-Bu-pyrazoline | 1,4 Phenyl | A | 637.0 [M + H]⁺ | | 8.17 (s, 1 H), 7.70 (d, J = 8.36 Hz, 2 H), 7.64 (d, J = 8.36 Hz, 2 H), 7.12 (m, 4 H), 5.63 (d, J = 1.85 Hz, 1 H), 4.89 (dd, J = 2.42, 2.02 Hz, 1 H), 3.99-3.91 (m, 4 H), 3.68 (dd, J = 3.28, 1.99 Hz, 1 H), 3.63 (m, 1 H), 3.59 (s, 3 H), 3.57 (s, 3 H), 3.56 (s, 3 H), 3.44 (dd, J = 9.31, 3.36 Hz, 1 H), 3.20 (t, J = 9.48 Hz, 1 H), 1.86 (m, 1 H), 1.31 (d, J = 6.26 Hz, 3 H), 0.82 (d, J = 7.12 Hz, 6 H) |
| 15 | 4-OCF₃ phenyl | 1,3 | pyrazoline | 1,4 Phenyl | A | 537.0 [M + H]⁺ | | 8.17 (s, 1 H), 7.73 (d, J = 8.40 Hz, 2 H), 7.64 (d, J = 8.40 Hz, 2 H), 7.12 (d, J = 8.26 Hz, 2 H), 7.09 (d, J = 8.26 Hz, 2 H), 5.63 (d, J = 1.85 Hz, 1 H), 3.89 (t, J = 7.34 Hz, 2 H), 3.68 (dd, J = 3.28, 1.99 Hz, 1 H), 3.63 (m, 1 H), 3.59 (s, 3 H), 3.57 (s, 3 H), 3.56 (s, 3 H), 3.44 (dd, J = 9.31, 3.36 Hz, 1 H), 3.28 (t, J = 7.7 Hz, 2 H), 3.20 (t, J = 9.48 Hz, 1 H), 1.25 (d, J = 6.26 Hz, 3 H) |

TABLE 4-continued $$Ar_1\text{-Het-}Ar_2\text{-CH=N-O-Sugar}$$

| # | Ar₁ | Het link[1] | Het | Ar₂ | Sugar[2] | M.S. | Mp °C. | ¹H NMR (CDCl₃, δ)[3] |
|---|---|---|---|---|---|---|---|---|
| 16 | 4-Br phenyl | 4,1 | Imidazole | 1,4 Phenyl | A | 530.0 [M]⁺ | | 8.19 (s, 1 H), 7.97 (s, 1 H), 7.78 (d, J = 8.26 Hz, 2 H), 7.71 (d, J = 8.22 Hz, 2 H), 7.62 (s, 1 H), 7.66 (d, J = 8.26 Hz, 2 H), 7.49 (d, J = 8.22 Hz, 2 H), 5.63 (d, J = 1.85 Hz, 1 H), 3.68 (dd, J = 3.28, 1.99 Hz, 1 H), 3.63 (m, 1 H), 3.59 (s, 3 H), 3.57 (s, 3 H), 3.56 (s, 3 H), 3.44 (dd, J = 9.31, 3.36 Hz, 1 H), 3.20 (t, J = 9.48 Hz, 1 H), 1.25 (d, J = 6.26 Hz, 3 H) |
| 17 | 2-CN-3-Cl phenyl | 1,4 | imidazole | 1,4 Phenyl | A | 510 [M]⁺ | | 8.13 (s, 1 H), 7.91 (s, 1 H), 7.81 (d, J = 8.38 Hz, 2 H), 7.71 (d, J = 8.42 Hz, 1 H), 7.70 (d, J = 8.38 Hz, 2 H), 7.68 (s, 1 H), 7.60 (t, 9.51, 1 H), 7.42 (d, J = 8.42 Hz, 1 H), 5.61 (d, J = 1.85 Hz, 1 H), 3.78 (dd, J = 3.28, 1.99 Hz, 1 H), 3.69 (m, 1 H), 3.59 (s, 3 H), 3.57 (s, 3 H), 3.56 (s, 3 H), 3.49 (dd, J = 9.31, 3.36 Hz, 1 H), 3.20 (t, J = 9.48 Hz, 1 H), 1.25 (d, J = 6.26 Hz, 3 H) |
| 18 | 4-OCF₃ phenyl | 1,4 | imidazole | 5-OCH₃-1,2 Phenyl | A | 566.0 [M + H]⁺ | | 8.70 (s, 1 H), 7.95 (d, J = 8.9 Hz, 2 H), 7.51 (d, J = 9.2 Hz, 2 H), 7.39 (d, J = 9.0 Hz, 2 H), 7.32 (d, J = 1.2 Hz, 1 H), 7.16 (d, J = 2.3 Hz, 1 H), 6.91 (d, J = 9.2 Hz, 1 H), 5.66 (d, J = 3.3 Hz, 1 H), 3.88 (s, 3 H), 3.76 (dd, J = 3.2, 1.9 Hz, 1 H), 3.71-3.66 (m, 1 H), 3.57 (s, 3 H), 3.55 (s, 3 H), 3.51 (s, 3 H), 3.50-3.49 (m, 1 H), 3.18 (t, J = 9.5 Hz, 1 H), 1.29 (d, J = 6.6 Hz, 3 H) |
| 19 | 4-OCF₃ phenyl | 1,4 | imidazole | 1,2 Phenyl | A | 536.0 [M + H]⁺ | | 8.82 (s, 1 H), 8.01 (d, J = 8.0 Hz, 1 H), 7.93 (d, J = 1.5 Hz, 1 H), 7.63 (d, J = 7.9 Hz, 1 H), 7.51 (d, J = 9.2 Hz, 2 H), 7.44 (t, J = 7.7 Hz, 1 H), 7.39 (d, J = 8.9 Hz, 2 H), 7.34 (d, J = 1.3 Hz, 2 H), 5.68 (d, J = 2.5 Hz, 1 H), 3.77 (dd, J = 3.2, 1.8 Hz, 1 H), 3.72-3.67 (m, 1 H), 3.57 (s, 3 H), 3.54 (s, 3 H), 3.51 (s, 3 H), 3.49 (d, J = 3.5 Hz, 1 H), 3.19 (t, J = 9.5 Hz, 1 H), 1.29 (d, J = 6.2 Hz, 3 H) |
| 20 | 4-OCF₃ phenyl | 1,4 | imidazole | 4-OCH₃-1,2 Phenyl | A | 566.0 [M + H]⁺ | | 8.78 (s, 1 H), 7.92 (s, 1 H), 7.91 (d, J = 1.3 Hz, 1 H), 7.54-7.48 (m, 3 H), 7.38 (d, J = 8.8 Hz, 2 H), 7.25 (d, J = 1.1 Hz, 1 H), 7.01 (dd, J = 8.6, 2.7 Hz, 1 H), 5.69 (d, J = 1.8 Hz, 1 H), 3.89 (s, 3 H), 3.76 (dd, J = 3.6, 1.6 Hz, 1 H), 3.70-3.67 (m, 1 H), 3.57 (s, 3 H), 3.55 (s, 3 H), 3.51 (s, 3 H), 3.49 (d, J = 3.3 Hz, 1 H), 3.19 (t, J = 9.2 Hz, 1 H), 1.29 (d, J = 6.1 Hz, 3 H) |
| 21 | 4-OCF₃ phenyl | 1,4 | imidazole | 2,4-difluoro-1,3 Phenyl | A | 572.0 [M]⁺ | | 8.41 (s, 1 H), 8.29-8.22 (m, 1 H), 7.89 (d, J = 1.1 Hz, 1 H), 7.75 (dd, J = 3.8, 1.2 Hz, 1 H), 7.49 (d, J = 8.9 Hz, 2 H), 7.38 (d, J = 8.6 Hz, 2 H), 7.05 (t, J = 9.2 Hz, 1 H), 5.62 (dd, J = 57.8, 1.7 Hz, 1 H), 3.80 (dd, J = 3.4, 2.0 Hz, 1 H), 3.71-3.69 (m, 1 H), 3.59 (s, 3 H), 3.57 (s, 3 H), 3.55 (d, J = 1.8 Hz, 3 H), 3.51 (d, J = 1.0 Hz, 1 H), 3.19 (dd, J = 9.1, 4.0 Hz, 1 H), 1.32 (t, J = 6.1 Hz, 3 H) |
| 22 | 6-fluoro-pyrid-2-yl | 1,4 | imidazole | 1,4 Phenyl | A | 470 [M]⁺ | | 8.37 (s, 1 H), 8.09 (s, 1 H), 7.92 (s, 1 H), 7.90 (t, J = 9.32 Hz, 1 H), 7.83 (d, J = 8.30 Hz, 2 H), 7.62 (d, J = 8.30 Hz, 2 H), 7.26 (m, 1 H), 6.86 (m, 1 H), 5.63 (d, J = 1.85 Hz, 1 H), 3.73 (dd, J = 3.28, 1.99 Hz, 1 H), 3.64 (m, 1 H), 3.59 (s, 3 H), 3.57 (s, 3 H), 3.56 (s, 3 H), 3.44 (dd, J = 9.31, 3.36 Hz, 1 H), 3.17 (t, J = 9.48 Hz, 1 H), 1.28 (d, J = 6.26 Hz, 3 H) |
| 23 | 4-iodo-pyrid-2-yl | 1,4 | imidazole | 1,4 Phenyl | A | 578 [M]⁺ | | 8.37 (s, 1 H), 8.13 (s, 1 H), 8.11 (d, J = 8.29 Hz, 1 H), 7.91 (s, 1 H), 7.82 (d, J = 8.26 Hz, 2 H), 7.74 (s, 1 H), 7.63 (d, J = 8.26 Hz, 2 H), 7.59 (d, J = 8.29 Hz, 1 H), 5.63 (d, J = 1.85 Hz, 1 H), 3.72 (dd, J = 3.28, 1.99 Hz, 1 H), 3.63 (m, 1 H), 3.59 (s, 3 H), 3.57 (s, 3 H), 3.56 (s, 3 H), 3.42 (dd, J = 9.31, 3.36 Hz, 1 H), 3.18 (t, J = 9.48 Hz, 1 H), 1.27 (d, J = 6.26 Hz, 3 H) |
| 24 | 3,5-difluoro phenyl | 1,4 | imidazole | 1,4 Phenyl | A | 487 [M]⁺ | | 8.11 (s, 1 H), 7.89 (s, 1 H), 7.79 (d, J = 8.26 Hz, 2 H), 7.65 (d, J = 8.26 Hz, 2 H), 7.58 (s, 1 H), 6.99 (m, 2 H), 6.84 (m, 1 H), 5.63 (d, J = 1.85 Hz, 1 H), 3.76 (dd, J = 3.28, 1.99 Hz, 1 H), 3.63 (m, 1 H), 3.59 (s, 3 H), 3.57 (s, 3 H), 3.56 (s, 3 H), 3.44 (dd, J = 9.31, 3.36 Hz, 1 H), 3.18 (t, J = 9.48 Hz, 1 H), 1.28 (d, J = 6.26 Hz, 3 H) |
| 25 | 4-OCF₃ phenyl | 1,4 | imidazole | 4-OCH₃-1,3 Phenyl | A | 566.0 [M]⁺ | | 8.59 (s, 1 H), 8.22 (d, J = 1.8 Hz, 1 H), 7.96 (dd, J = 8.6, 2.7 Hz, 1 H), 7.88 (d, J = 1.3 Hz, 1 H), 7.58 (d, J = 1.3 Hz, 1 H), 7.49 (d, J = 8.8 Hz, 2 H), 7.37 (d, J = 8.5 Hz, 2 H), 6.80 (d, J = 7.7 Hz, 1 H), 5.69 (d, J = 1.8 Hz, 1 H), 3.91 (s, 3 H), 3.77 (dd, J = 3.6, 1.6 Hz, 1 H), 3.72-3.67 (m, 1 H), 3.57 (s, 3 H), 3.55 (s, 3 H), 3.51 (s, 3 H), 3.48 (d, J = 3.3 Hz, 1 H), 3.19 (t, J = 9.2 Hz, 1 H), 1.32 (d, J = 6.1 Hz, 3 H) |
| 27 | 4-n-Pr phenyl | 1,4 | imidazole | 1,4 Phenyl | A | | 188 | 8.18 (s, 1 H), 7.90 (s, 1 H), 7.87 (d, J = 7.8 Hz, 2 H), 7.69 (d, J = 7.8 Hz, 2 H), 7.63 (s, 1 H), 7.37 (d, J = 8.4 Hz, 2 H), 7.32 (d, J = 8.4 Hz, 2 H), 5.69 (d, J = 1.8 Hz, 1 H), 3.79 (m, 1 H), 3.7 (m, 1 H), 3.63-3.5 (m, 10 H), 3.22 (t, J = 6.3 Hz, 1 H), 2.68 (t, J = 8.1 Hz, 2 H), 1.6 (m, 2 H), 1.34 (d, J = 6 Hz, 3 H), 1.0 (t, J = 7.5 Hz, 3 H) |
| 28 | 4-OCF₃ phenyl | 1,4 | imidazole | 1,4 Phenyl | B | 563.0 [M]⁺ | 181 | 8.20 (s, 1 H), 7.90 (s, 1 H), 7.85 (d, J = 8.5 Hz, 2 H), 7.70 (d, J = 8.5 Hz, 2 H), 7.61 (s, 1 H), 7.42 (d, J = 8.4 Hz, 2 H), 7.40 |

TABLE 4-continued $$Ar_1\text{-Het-}Ar_2\text{-CH=N-O-Sugar}$$

| # | Ar₁ | Het link[1] | Het | Ar₂ | Sugar[2] | M.S. | Mp °C. | ¹H NMR (CDCl₃, δ)[3] |
|---|---|---|---|---|---|---|---|---|
| 29 | 4-n-Pr phenyl | 1,4 | imidazole | 1,4 Phenyl | B | | 194-195 | (d, J = 8.4 Hz, 2 H), 5.62 (d, J = 1.8 Hz, 1 H), 3.80-3.5 (m, 9 H), 3.20 (t, J = 9.5 Hz, 1 H), 1.25 (m, 6 H) 8.17 (s, 1 H), 7.90 (s, 1 H), 7.88 (d, J =8.4 Hz, 2 H), 7.68 (d, J = 8.4 Hz, 2 H), 7.62 (s, 1 H), 7.38 (d, J = 8.4 Hz, 2 H), 7.29 (d, J = 8.4 Hz, 2 H), 5.66 (d, J = 1.5 Hz, 1 H), 3.74-3.5 (m, 11 H), 3.22 (t, J = 8 Hz, 1 H), 2.68 (t, J = 7.4 Hz, 2 H), 1.69 (m, 2 H), 1.33 (m, 6 H), 0.99 (t, J = 7.5 Hz, 3 H) |
| 30 | 4-OCF₃ phenyl | 1,4 | imidazole | 1,4 Phenyl | A | 535.0 [M + H]⁺ | | 8.17 (s, 1 H), 7.93 (s, 1 H), 7.82 (d, J = 8.25 Hz, 2 H), 7.77 (d, J = 8.27 Hz, 2 H), 7.58 (s, 1 H), 7.45 (d, J = 8.25 Hz, 2 H), 7.23 (d, J = 8.27 Hz, 2 H), 5.63 (d, J = 1.8 Hz, 1 H), 3.7 (dd, J = 3.28, 1.99 Hz, 1 H), 3.63 (m, 1 H), 3.59 (s, 3 H), 3.57 (s, 3 H), 3.56 (s, 3 H), 3.44 (dd, J = 9.31, 3.36 Hz, 1 H), 3.20 (t, J = 9.48 Hz, 1 H), 1.25 (d, J = 6.3 Hz, 3 H) |
| 31 | 4-OCF₃ phenyl | 1,4 | imidazole | 1,4 Phenyl | G | 577.6 [M]⁺ | | 8.12 (s, 1 H), 7.86 (s, 1 H), 7.81 (d, J = 8.23 Hz, 2 H), 7.66 (d, J = 8.29 Hz, 2 H), 7.63 (s, 1 H), 7.58 (d, J = 8.29 Hz, 2 H), 7.33 (d, J = 8.23 Hz, 2 H), 5.59 (d, J = 1.92 Hz, 1 H), 3.91 (dd, J = 9.16, 7.24 Hz, 1 H), 3.83 (dd, J = 3.40, 1.92 Hz, 1 H), 3.71-3.57 (m, 7 H), 3.29 (t, J = 9.44 Hz, 1 H), 1.33 (d, J = 6.42 Hz, 3 H), 1.26 (td, J = 7.06, 3.66 Hz, 6 H), 1.18 (t, J = 7.20 Hz, 3 H) |
| 32 | 5-CF₃-pyrid-2-yl | 1,4 | imidazole | 1,4 Phenyl | A | 521.0 [M + H]⁺ | 235 | 8.79 (s, 1 H), 8.47 (s, 1 H), 8.20-8.00 (m, 3 H), 7.90 (d, J = 8.4 Hz, 2 H), 7.69 (d, J = 8.7 Hz, 2 H), 7.53 (d, J = 8.6 Hz, 1 H), 5.67 (d, J = 1.9 Hz, 1 H), 3.77 (dd, J = 3.3, 2.0 Hz, 1 H), 3.69 (dd, J = 9.7, 6.3 Hz, 1 H), 3.58 (s, 3 H), 3.56 (s, 3 H), 3.54 (s, 3 H), 3.52 (m, 1 H), 3.20 (t, J = 9.5 Hz, 1 H), 1.32 (d, J = 6.5 Hz, 3 H) |
| 33 | 5-CF₃-pyrid-2-yl | 1,4 | imidazole | 1,4 Phenyl | G | 563.0 [M + H]⁺ | 194 | 8.78 (d, J = 2.2 Hz, 1 H), 8.47 (d, J = 1.4 Hz, 1 H), 8.17-8.01 (m, 3 H), 7.89 (d, J = 8.5 Hz, 2 H), 7.68 (d, J = 8.5 Hz, 2 H), 7.53 (d, J = 8.7 Hz, 2 H), 5.58 (d, J = 1.9 Hz, 1 H), 3.93 (dd, J = 9.2, 7.2 Hz, 1 H), 3.82 (dd, J = 3.4, 1.9 Hz, 1 H), 3.78-3.55 (m, 6 H), 3.32 (t, J = 9.5 Hz, 1 H), 1.31 (d, J = 6.4 Hz, 3 H), 1.27 (td, J = 7.0, 3.6 Hz, 6 H), 1.20 (t, J = 7.1 Hz, 3 H) |
| 34 | 2-Cl, 5-Br phenyl | 1,4 | imidazole | 1,4 Phenyl | A | 564 [M]⁺ | | 8.15 (s, 1 H), 7.93 (s, 1 H), 7.79 (m, 2 H), 7.68 (s, 1 H), 7.56 (s, 1 H), 7.52 (d, J = 8.26 Hz, 2 H), 7.43 (d, J = 8.26 Hz, 2 H), 5.61 (d, J = 1.85 Hz, 1 H), 3.78 (dd, J = 3.28, 1.99 Hz, 1 H), 3.69 (m, 1 H), 3.59 (s, 3 H), 3.57 (s, 3 H), 3.56 (s, 3 H), 3.49 (dd, J = 9.31, 3.36 Hz, 1 H), 3.20 (t, J = 9.48 Hz, 1 H), 1.25 (d, J = 6.26 Hz, 3 H) |
| 35 | 4-OCF₃ phenyl | 1,4 | imidazole | 6-OCH₃-1,3 Phenyl | A | 566.0 [M]⁺ | | 8.42 (d, J = 1.7 Hz, 1 H), 8.18 (s, 1 H), 7.89 (d, J = 1.5 Hz, 1 H), 7.86 (s, 1 H), 7.66 (dd, J = 8.7, 2.1 Hz, 1 H), 7.50 (d, J = 8.9 Hz, 2 H), 7.36 (d, J = 9.0 Hz, 2 H), 6.99 (d, J = 8.6 Hz, 2 H), 5.66 (d, J = 2.1 Hz, 1 H), 4.01 (s, 3 H), 3.77 (dd, J = 3.2, 2.1 Hz, 1 H), 3.72-3.67 (m, 1 H), 3.58 (s, 3 H), 3.56-3.53 (m, 6 H), 3.52-3.50 (m, 1 H), 3.20 (t, J = 9.5 Hz, 1 H), 1.32 (d, J = 5.8 Hz, 3 H) |
| 36 | 4-OCF₃ phenyl | 1,4 | imidazole | 3-fluoro-1,4 Phenyl | A | 553.0 [M]⁺ | | 8.41 (s, 1 H), 7.92 (t, J = 7.7 Hz, 1 H), 7.88 (d, J = 1.3 Hz, 1 H), 7.61 (d, J = 1.1 Hz, 2 H), 7.57 (s, 1 H), 7.49 (d, J = 9.1 Hz, 2 H), 7.38 (d, J = 8.6 Hz, 2 H), 5.67 (d, J = 2.9 Hz, 1 H), 3.77 (dd, J = 3.3, 2.0 Hz, 1 H), 3.72-3.67 (m, 1 H), 3.58 (s, 3 H), 3.56 (s, 3 H), 3.54 (s, 3 H), 3.51 (d, J = 3.8 Hz, 1 H), 3.20 (t, J = 9.5 Hz, 1 H), 1.32 (d, J = 6.5 Hz, 3 H) |
| 37 | 4-OCH₂CF₃ phenyl | 1,4 | imidazole | 1,4 Phenyl | A | 549 [M]⁺ | | 8.17 (s, 1 H), 7.83 (s, 1 H), 7.82 (d, J = 8.22 Hz, 2 H), 7.64 (d, J = 8.22 Hz, 2 H), 7.57 (s, 1 H), 7.39 (d, J = 8.23 Hz, 2 H), 7.07 (d, J = 8.23 Hz, 2 H), 5.63 (d, J = 1.85 Hz, 1 H), 4.41 (q, J = 8.24 Hz, 2 H), 3.74 (dd, J = 3.28, 1.99 Hz, 1 H), 3.63 (m, 1 H), 3.59 (s, 3 H), 3.57 (s, 3 H), 3.56 (s, 3 H), 3.44 (dd, J = 9.31, 3.36 Hz, 1 H), 3.20 (t, J = 9.48 Hz, 1 H), 1.29 (d, J = 6.26 Hz, 3 H) |
| 38 | 3,4,5,6-tetrafluoro-pyrid-2-yl | 1,4 | imidazole | 1,4 Phenyl | A | 524 [M]⁺ | | 8.08 (s, 1 H), 7.98 (s, 1 H), 7.78 (d, J = 8.29 Hz, 2 H), 7.61 (s, 1 H), 7.59 (d, J = 8.29 Hz, 2 H), 5.58 (d, J = 1.85 Hz, 1 H), 3.68 (dd, J = 3.28, 1.99 Hz, 1 H), 3.63 (m, 1 H), 3.59 (s, 3 H), 3.57 (s, 3 H), 3.56 (s, 3 H), 3.44 (dd, J = 9.31, 3.36 Hz, 1 H), 3.16 (t, J = 9.48 Hz, 1 H), 1.22 (d, J = 6.26 Hz, 3 H) |
| 39 | 5-iodo-pyrid-2-yl | 1,4 | imidazole | 1,4 Phenyl | A | 578 [M]⁺ | | 8.67 (s, 1 H), 8.33 (s, 1 H), 8.14 (s, 1 H), 8.08 (d, J = 8.32 Hz, 1 H), 7.91 (s, 1 H), 7.83 (d, J = 8.24 Hz, 2 H), 7.62 (d, J = 8.24 Hz, 2 H), 7.21 (d, J = 8.32 Hz, 1 H), 5.63 (d, J = 1.85 Hz, 1 H), 3.74 (dd, J = 3.28, 1.99 Hz, 1 H), 3.63 (m, 1 H), 3.59 (s, 3 H), 3.57 (s, 3 H), 3.56 (s, 3 H), 3.44 (dd, J = 9.31, 3.36 Hz, 1 H), 3.16 (t, J = 9.48 Hz, 1 H), 1.29 (d, J = 6.26 Hz, 3 H) |

TABLE 4-continued $$Ar_1-Het-Ar_2-CH=N-O-Sugar$$

| # | Ar₁ | Het link[1] | Het | Ar₂ | Sugar[2] | M.S. | Mp °C. | ¹H NMR (CDCl₃, δ)[3] |
|---|---|---|---|---|---|---|---|---|
| 40 | 4-CF₃ phenyl | 1,4 | imidazole | 6-OCH₃-1,3 Phenyl | A | 550.0 [M + H]⁺ | 176-178 | 8.43 (s, 1 H), 8.18 (s, 1 H), 7.95 (d, J = 15.4 Hz, #H), 7.78 (d, J = 7.4 Hz, 2 H), 7.64-7.58 (m, 2 H), 7.25 (d, J = 3.8 Hz, 1 H), 6.99 (d, J = 7.7 Hz, 1 H), 5.66 (s, 1 H), 4.02 (s, 3 H), 3.78-3.75 (m, 2 H), 3.58-3.53 (m, 10 H), 3.22-3.20 (m, 1 H), 1.31 (d, J = 5.8 Hz, 3 H) |
| 41 | 4-CH₃ phenyl | 1,4 | imidazole | 1,4 Phenyl | A | 465 [M]⁺ | | 8.12 (s, 1 H), 7.84 (s, 1 H), 7.82 (d, J = 8.31 Hz, 2 H), 7.63 (d, J = 8.31 Hz, 2 H), 7.56 (s, 1 H), 7.28 (s, 4 H), 5.63 (d, J = 1.85 Hz, 1 H), 3.73 (dd, J = 3.28, 1.99 Hz, 1 H), 3.65 (m, 1 H), 3.59 (s, 3 H), 3.57 (s, 3 H), 3.56 (s, 3 H), 3.32 (dd, J = 9.31, 3.36 Hz, 1 H), 3.17 (t, J = 9.48 Hz, 1 H), 2.39 (s, 3 H), 1.29 (d, J = 6.26 Hz, 3 H) |
| 42 | 4-CF₃ phenyl | 1,4 | imidazole | 1,4 Phenyl | A | 519 [M]⁺ | | 8.14 (s, 1 H), 7.96 (s, 1 H), 7.81 (d, J = 8.27 Hz, 2 H), 7.74 (d, J = 8.22 Hz, 2 H), 7.65 (d, J = 8.27 Hz, 2 H), 7.63 (s, 1 H), 7.55 (d, J = 8.22 Hz, 2 H), 5.63 (d, J = 1.85 Hz, 1 H), 3.75 (dd, J = 3.28, 1.99 Hz, 1 H), 3.67 (m, 1 H), 3.59 (s, 3 H), 3.57 (s, 3 H), 3.56 (s, 3 H), 3.31 (dd, J = 9.31, 3.36 Hz, 1 H), 3.18 (t, J = 9.48 Hz, 1 H), 1.31 (d, J = 6.26 Hz, 3 H) |
| 43 | 4-Cl phenyl | 1,4 | imidazole | 1,4 Phenyl | A | 485 [M]⁺ | | 8.09 (s, 1 H), 7.86 (s, 1 H), 7.81 (d, J = 8.22 Hz, 2 H), 7.64 (d, J = 8.22 Hz, 2 H), 7.57 (s, 1 H), 7.45 (d, J = 8.29 Hz, 2 H), 7.37 (d, J = 8.29 Hz, 2 H), 5.63 (d, J = 1.85 Hz, 1 H), 3.74 (dd, J = 3.28, 1.99 Hz, 1 H), 3.63 (m, 1 H), 3.59 (s, 3 H), 3.57 (s, 3 H), 3.56 (s, 3 H), 3.44 (dd, J = 9.31, 3.36 Hz, 1 H), 3.17 (t, J = 9.48 Hz, 1 H), 1.28 (d, J = 6.26 Hz, 3 H) |
| 44 | 4-OCH₃ phenyl | 1,4 | imidazole | 1,4 Phenyl | A | 481 [M]⁺ | | 8.09 (s, 1 H), 7.83 (d, J = 8.23 Hz, 2 H), 7.76 (s, 1 H), 7.61 (d, J = 8.23 Hz, 2 H), 7.51 (s, 1 H), 7.29 (d, J = 8.20 Hz, 2 H), 6.97 (d, J = 8.20 Hz, 2 H), 5.63 (d, J = 1.85 Hz, 1 H), 3.82 (s, 3 H), 3.73 (dd, J = 3.28, 1.99 Hz, 1 H), 3.63 (m, 1 H), 3.59 (s, 3 H), 3.57 (s, 3 H), 3.56 (s, 3 H), 3.42 (dd, J = 9.31, 3.36 Hz, 1 H), 3.16 (t, J = 9.48 Hz, 1 H), 1.29 (d, J = 6.26 Hz, 3 H) |
| 45 | 4-Br phenyl | 1,4 | imidazole | 1,4 Phenyl | A | 530 [M]⁺ | | 8.12 (s, 1 H), 7.86 (s, 1 H), 7.81 (d, J = 8.23 Hz, 2 H), 7.66 (d, J = 8.29 Hz, 2 H), 7.63 (s, 1 H), 7.58 (d, J = 8.29 Hz, 2 H), 7.33 (d, J = 8.23 Hz, 2 H), 5.63 (d, J = 1.85 Hz, 1 H), 3.74 (dd, J = 3.28, 1.99 Hz, 1 H), 3.63 (m, 1 H), 3.59 (s, 3 H), 3.57 (s, 3 H), 3.56 (s, 3 H), 3.33 (dd, J = 9.31, 3.36 Hz, 1 H), 3.18 (t, J = 9.48 Hz, 1 H), 1.29 (d, J = 6.26 Hz, 3 H) |
| 46 | 4-i-Pr phenyl | 1,4 | imidazole | 1,4 Phenyl | A | 493 [M]⁺ | | 8.37 (s, 1 H), 8.31 (s, 1 H), 8.28 (s, 1 H), 7.79 (d, J = 8.23 Hz, 2 H), 7.62 (d, J = 8.23 Hz, 2 H), 7.57 (d, J = 8.25 Hz, 2 H), 7.38 (d, J = 8.25 Hz, 2 H), 5.63 (d, J = 1.85 Hz, 1 H), 3.75 (dd, J = 3.28, 1.99 Hz, 1 H), 3.63 (m, 1 H), 3.59 (s, 3 H), 3.57 (s, 3 H), 3.56 (s, 3 H), 3.44 (dd, J = 9.31, 3.36 Hz, 1 H), 3.05 (t, J = 9.48 Hz, 1 H), 2.92 (m, 1 H) 1.27 (d, J = 6.46 Hz, 6 H), 1.21 (d, J = 6.26 Hz, 3 H) |
| 47 | 4-I phenyl | 1,4 | imidazole | 1,4 Phenyl | A | 577 [M]⁺ | | 8.16 (s, 1 H), 7.87 (s, 1 H), 7.83 (d, J = 8.29 Hz, 2 H), 7.68 (d, J = 8.29 Hz, 2 H), 7.57 (s, 1 H), 7.18 (d, J = 8.24 Hz, 2 H), 6.87 (d, J = 8.24 Hz, 2 H), 5.63 (d, J = 1.85 Hz, 1 H), 3.78 (dd, J = 3.28, 1.99 Hz, 1 H), 3.69 (m, 1 H), 3.59 (s, 3 H), 3.57 (s, 3 H), 3.56 (s, 3 H), 3.48 (dd, J = 9.31, 3.36 Hz, 1 H), 3.20 (t, J = 9.48 Hz, 1 H), 1.31 (d, J = 6.26 Hz, 3 H) |
| 48 | 4-t-Bu phenyl | 1,4 | imidazole | 1,4 Phenyl | A | 507 [M]⁺ | | 8.13 (s, 1 H), 7.86 (s, 1 H), 7.82 (d, J = 8.28 Hz, 2 H), 7.62 (d, J = 8.28 Hz, 2 H), 7.58 (s, 1 H), 7.48 (d, J = 8.26 Hz, 2 H), 7.36 (d, J = 8.26 Hz, 2 H), 5.63 (d, J = 1.85 Hz, 1 H), 3.73 (dd, J = 3.28, 1.99 Hz, 1 H), 3.65 (m, 1 H), 3.59 (s, 3 H), 3.57 (s, 3 H), 3.56 (s, 3 H), 3.45 (dd, J = 9.31, 3.36 Hz, 1 H), 3.18 (t, J = 9.48 Hz, 1 H), 1.37 (s, 9 H), 1.25 (d, J = 6.26 Hz, 3 H) |
| 49 | 4-OCF₃ phenyl | 1,4 | imidazole | 2,3-difluoro-1,4 Phenyl | A | 554.0 [M]⁺ | | 8.40 (s, 1 H), 7.99 (t, J = 8.0 Hz, 1 H), 7.93 (s, 1 H), 7.79 (dd, J = 3.2, 1.1 Hz, 1 H), 7.72 (t, J = 7.5 Hz, 1 H), 7.51 (d, J = 8.9 Hz, 2 H), 7.39 (d, J = 8.4 Hz, 2 H), 5.67 (s, 1 H), 3.77 (dd, J = 3.2, 1.9 Hz, 1 H), 3.71-3.67 (m, 1 H), 3.58-3.55 (m, 6 H), 3.51 (s, 3 H), 3.42 (dd, J = 9.5, 3.5 Hz, 1 H), 3.21 (t, J = 9.8 Hz, 1 H), 1.32 (d, J = 5.7 Hz, 3 H) |
| 50 | 4-OCF₃ phenyl | 1,4 | imidazole | 6-Cl-1,3 Phenyl | A | 570.0 [M + H]⁺ | | 8.38 (d, J = 3.1 Hz, 1 H), 8.19 (s, 1 H), 8.03 (d, J = 1.0 Hz, 1 H), 7.91 (d, J = 1.1 Hz, 1 H), 7.60 (dd, J = 8.2, 2.2 Hz, 1 H), 7.51 (d, J = 8.7 Hz, 2 H), 7.45 (d, J = 8.4 Hz, 1 H), 7.38 (d, J = 9.5 Hz, 2 H), 5.66 (d, J = 3.0 Hz, 1 H), 3.76 (dd, J = 3.2, 1.9 Hz, 1 H), 3.70-3.65 (m, 1 H), 3.58 (s, 3 H), 3.55 (s, 3 H), 3.54 (s, 3 H), 3.50 (dd, J = 6.4, 3.3 Hz, 1 H), 3.20 (t, J = 9.5 Hz, 1 H), 1.31 (d, J = 5.5 Hz, 3 H) |

TABLE 4-continued $$Ar_1-Het-Ar_2-CH=N-O-Sugar$$

| # | Ar₁ | Het link[1] | Het | Ar₂ | Sugar[2] | M.S. | Mp °C. | ¹H NMR (CDCl₃, δ)[3] |
|---|---|---|---|---|---|---|---|---|
| 51 | 4-OCF₂CF₃ phenyl | 1,4 | imidazole | 1,4 Phenyl | A | 585 [M]⁺ | | 8.17 (s, 1 H), 8.91 (s, 1 H), 7.84 (d, J = 8.22 Hz, 2 H), 7.68 (d, J = 8.22 Hz, 2 H), 7.61 (s, 1 H), 7.47 (d, J = 8.27 Hz, 2 H), 7.39 (d, J = 8.27 Hz, 2 H), 5.63 (d, J = 1.85 Hz, 1 H), 3.79 (dd, J = 3.28, 1.99 Hz, 1 H), 3.63 (m, 1 H), 3.59 (s, 3 H), 3.57 (s, 3 H), 3.56 (s, 3 H), 3.44 (dd, J = 9.31, 3.36 Hz, 1 H), 3.20 (t, J = 9.48 Hz, 1 H), 1.30 (d, J = 6.26 Hz, 3 H) |
| 52 | 4-OCF₂CF₃ phenyl | 1,4 | imidazole | 1,4 Phenyl | G | 627 [M]⁺ | | 8.12 (s, 1 H), 7.91 (s, 1 H), 7.84 (d, J = 8.26 Hz, 2 H), 7.63 (d, J = 8.26 Hz, 2 H), 7.61 (s, 1 H), 7.49 (d, J = 8.34 Hz, 2 H), 7.37 (d, J = 8.34 Hz, 2 H), 5.59 (d, J = 1.9 Hz, 1 H), 3.91 (dd, J = 9.16, 7.24 Hz, 1 H), 3.83 (dd, J = 3.40, 1.92 Hz, 1 H), 3.71-3.57 (m, 7 H), 3.29 (t, J = 9.44 Hz, 1 H), 1.33 (d, J = 6.42 Hz, 3 H), 1.26 (td, J = 7.06, 3.66 Hz, 6 H), 1.18 (t, J = 7.20 Hz, 3 H) |
| 53 | 4-OCF₃ phenyl | 1,3 | 4-5-di(CO₂Et) pyrazoline | 1,4 Phenyl | A | 681.0 [M + H]⁺ | | 8.18 (s, 1 H), 7.85 (d, J = 8.26 Hz, 2 H), 7.66 (d, J = 8.26 Hz, 2 H), 7.18 (s, 4 H), 5.63 (d, J = 1.85 Hz, 1 H), 5.20 (d, 5.34 Hz, 1 H), 4.58 (d, J = 5.34 Hz, 1 H), 4.21 (m, 4 H), 3.68 (dd, J = 3.28, 1.99 Hz, 1 H), 3.63 (m, 1 H), 3.59 (s, 3 H), 3.57 (s, 3 H), 3.56 (s, 3 H), 3.44 (dd, J = 9.31, 3.36 Hz, 1 H), 3.20 (t, J = 9.48 Hz, 1 H), 1.25 (d, J = 6.26 Hz, 3 H), 1.23 (m, 6 H) |
| 54 | 4-OCF₃ phenyl | 1,3 | 5-CO₂Me-pyrazoline | 1,4 Phenyl | A | 595.0 [M + H]⁺ | | 8.17 (s, 1 H), 7.71 (d, J = 8.38 Hz, 2 H), 7.65 (d, J = 8.38 Hz, 2 H), 7.17 (d, J = 8.30 Hz, 2 H), 7.08 (d, J = 8.30 Hz, 2 H), 5.63 (d, J = 1.85 Hz, 1 H), 4.83 (dd, J = 2.42, 1.98 Hz, 1 H), 3.79 (s, 3 H), 3.77-3.62 (m, 4 H), 3.59 (s, 3 H), 3.57 (s, 3 H), 3.56 (s, 3 H), 3.44 (dd, J = 9.31, 3.36 Hz, 1 H), 3.20 (t, J = 9.48 Hz, 1 H), 1.25 (d, J = 6.26 Hz, 3 H) |
| 55 | 4-OCF₃ phenyl | 1,3 | 4-n-Pr-5-CO₂Et-pyrazoline | 1,4 Phenyl | A | 651.0 [M]⁺ | | 8.16 (s, 1 H), 7.74 (d, J = 8.22 Hz, 2 H), 7.62 (d, J = 8.22 Hz, 2 H), 7.14 (d, J = 8.18 Hz, 2 H), 7.07 (d, J = 8.18 Hz, 2 H), 5.63 (d, J = 1.85 Hz, 1 H), 4.59 (d, J = 5.36 Hz, 1 H), 4.19 (q, J = 7.20 Hz, 2 H), 3.78 (dd, J = 3.28, 1.99 Hz, 1 H), 3.72-3.49 (m, 15 H), 3.44 (dd, J = 9.31, 3.36 Hz, 1 H), 3.20 (t, J = 9.48 Hz, 1 H), 1.36-1.24 (m, 6 H), 1.21 (t, J = 9.40 Hz, 3 H) |
| 56 | 4-OCF₃ phenyl | 1,3 | 4-CH₃-5-CO₂Et-pyrazoline | 1,4 Phenyl | A | 623.0 [M]⁺ | | 8.16 (s, 1 H), 7.72 (d, J = 8.22 Hz, 2 H), 7.63 (d, J = 8.22 Hz, 2 H), 7.12 (d, J = 8.34 Hz, 2 H), 7.08 (d, J = 8.34 Hz, 2 H), 5.63 (d, J = 1.85 Hz, 1 H), 4.42 (d, J = 5.22 Hz, 1 H), 4.19 (q, J = 7.02 Hz, 2 H), 3.71-3.63 (m, 3 H), 3.59 (s, 3 H), 3.57 (s, 3 H), 3.56 (s, 3 H), 3.44 (dd, J = 9.31, 3.36 Hz, 1 H), 3.20 (t, J = 9.48 Hz, 1 H), 1.28 (d, J = 6.26 Hz, 3 H), 1.22-1.17 (m, 6 H) |
| 57 | 4-CF₃ | 4,1 | imidazole | 1,4 Phenyl | A | 519.0 [M + H]⁺ | 104 | 8.21 (s, 1 H), 7.98 (s, 1 H), 7.91 (d, J = 8.2 Hz, 2 H), 7.80 (d, J = 8.0 Hz, 2 H), 7.70 (d, J = 8.2 Hz, 2 H), 7.68 (d, J = 8.2 Hz, 2 H), 7.5 (d, J = 8.3 Hz, 2 H), 5.68 (d, J = 1.8 Hz, 1 H), 3.78 (m, 1 H), 3.68 (m, 1 H), 3.59 (s, 3 H), 3.57 (s, 3 H), 3.56 (s, 3 H), 3.44 (dd, J = 9.31, 3.36 Hz, 1 H), 3.20 (t, J = 9.48 Hz, 1 H), 1.25 (d, J = 6.3 Hz, 3 H) |
| 58 | 4-OCF₃ phenyl | 1,4 | imidazole | 1,3 Phenyl | A | 536.4 [M + H]⁺ | | 8.21 (s, 1 H), 8.12 (s, 1 H), 7.91 (s, 1 H), 7.89 (s, 1 H), 7.62 (s, 1 H), 7.53 (d, J = 7.9 Hz, 1 H), 7.50 (d, J = 8.9 Hz, 2 H), 7.45 (d, J = 7.3 Hz, 1 H), 7.37 (d, J = 8.6 Hz, 2 H), 5.68 (d, J = 2.6 Hz, 1 H), 3.78 (dd, J = 2.8, 2.0 Hz, 1 H), 3.72-3.67 (m, 1 H), 3.58 (s, 3 H), 3.56 (s, 3 H), 3.55 (s, 3 H), 3.52-3.49 (m, 1 H), 3.21 (t, J = 9.3 Hz, 1 H), 1.32 (d, J = 6.5 Hz, 3 H) |
| 59 | 3-CF₃, 4-OCF₃ phenyl | 1,4 | imidazole | 1,4 Phenyl | A | 604.5 [M + H]⁺ | | 8.18 (s, 1 H), 7.92 (d, J = 2 Hz, 1 H), 7.88 (d, J = 8.4 Hz, 2 H), 7.8 (d, J = 3 Hz, 1 H), 7.74-7.68 (m, 3 H), 7.64 (d, J = 2 Hz, 1 H), 7.6 (d, J = 8 Hz, 2 H), 5.64 (d, J = 1.9 Hz, 1 H), 3.81 (dd, J = 9.2, 7.24 Hz, 1 H), 3.75 (dd, J = 3.40, 1.9 Hz, 1 H), 3.71-3.57 (m, 7 H), 3.21 (t, J = 9.4 Hz, 1 H), 1.33 (d, J = 6.4 Hz, 3 H) |
| 60 | 4-n-Pr phenyl | 5,3 | isoxazole | 1,4 Phenyl | A | 494.0 [M]⁺ | | 8.18 (s, 1 H), 7.89 (d, J = 8.22 Hz, 2 H), 7.74 (d, J = 8.44 Hz, 2 H), 7.71 (d, J = 8.22 Hz, 2 H), 7.31 (d, J = 8.44 Hz, 2 H), 6.81 (s, 1 H), 5.63 (d, J = 1.85 Hz, 1 H), 3.68 (dd, J = 3.28, 1.99 Hz, 1 H), 3.63 (m, 1 H), 3.59 (s, 3 H), 3.57 (s, 3 H), 3.56 (s, 3 H), 3.44 (dd, J = 9.31, 3.36 Hz, 1 H), 3.20 (t, J = 9.48 Hz, 1 H), 2.68 (t, J = 7.24 Hz, 2 H), 1.68 (m, 2 H), 1.31 (d, J = 6.26 Hz, 3 H), 0.98 (t, J = 7.12 Hz, 3 H) |
| 61 | 4-n-BuO-phenyl | 5,3 | isoxazole | 1,4 Phenyl | A | 524.0 [M]⁺ | | 8.19 (s, 1 H), 7.89 (d, J = 8.34 Hz, 2 H), 7.74 (d, J = 8.46 Hz, 2 H), 7.71 (d, J = 8.34 Hz, 2 H), 6.98 (d, J = 8.46 Hz, 2 H), 6.67 (s, 1 H), 5.63 (d, J = 1.85 Hz, 1 H), 4.04 (t, J = 7.88 Hz, 2 H), 3.68 (dd, J = 3.28, 1.99 Hz, 1 H), 3.63 (m, 1 H), 3.59 (s, 3 H), 3.57 (s, 3 H), 3.56 (s, 3 H), 3.44 (dd, J = 9.31, 3.36 Hz, 1 H), 3.20 (t, J = 9.48 Hz, 1 H), 1.79 (m, 2 H), 1.54 (m, 2 H), 1.32 (d, J = 6.26 Hz, 3 H), 0.99 (t, J = 7.26 Hz, 3 H) |
| 62 | 4-CH₃O-phenyl | 2,4 | thiazole | 1,4 Phenyl | A | 499.0 [M + H]⁺ | 74-80 | 8.18 (s, 1 H), 8.02 (d, J = 6.0 Hz, 2 H), 7.98 (d, J = 6.0 Hz, 2 H), 7.70 (d, J = 6.0 Hz, 2 H), 7.48 (s, 1 H), 6.98 (d, J = 6.0 Hz, 2 H), 5.68 (d, J = 3.0 Hz, 1 H), 3.88 (s, 3 H), 3.77-3.76 (m, 1 H), 3.71-3.67 (m, 1 H), 3.58 (s, 3 H), 3.56 (s, 3 H), 3.54 (s, 3 |

TABLE 4-continued $$Ar_1 - Het - Ar_2 - CH = N - O - Sugar$$

| # | Ar₁ | Het link[1] | Het | Ar₂ | Sugar[2] | M.S. | Mp °C. | ¹H NMR (CDCl₃, δ)[3] |
|---|---|---|---|---|---|---|---|---|
| | | | | | | | | H), 3.54-3.50 (m, 1 H), 3.20 (t, J = 9.0 Hz, 1 H), 1.32 (d, J = 6.0 Hz, 3 H) |
| 63 | 3-Cl-5-CF₃-pyrid-2-yl | 2,4 | thiazole | 1,4 Phenyl | A | 574.0 [M + H]⁺ | | 8.78 (s, 1 H), 8.19 (s, 1 H), 8.13 (d, J = 3.0 Hz, 1 H), 8.05 (d, J = 9.0 Hz, 2 H), 7.81 (s, 1 H), 7.73 (d, J = 6.0 Hz, 2 H), 5.69 (d, J = 3.0 Hz, 1 H), 3.78-3.77 (m, 1 H), 3.72-3.68 (m, 1 H), 3.59 (s, 3 H), 3.56 (s, 3 H), 3.55 (s, 3 H), 3.53 (dd, J = 6.0, 3.0 Hz, 1 H), 3.21 (t, J = 9.0 Hz, 1 H), 1.33 (d, J = 6.0 Hz, 3 H) |
| 64 | 6-CF₃CH₂O-pyrid-3-yl | 2,4 | thiazole | 1,4 Phenyl | A | 569.0 [M + H]⁺ | 142-145 | 8.78 (d, J = 3 Hz, 1 H), 8.32 (dd, J = 6.0, 3.0 Hz, 1 H), 8.2 (s, 1 H), 8.01 (d, J = 6.0 Hz, 2 H), 7.71 (d, J = 6.0 Hz, 2 H), 7.55 (s, 1 H), 6.98 (d, J = 6.0 Hz, 1 H), 5.68 (d, J = 3.0 Hz, 1 H), 4.83 (q, J = 6.0 Hz, 2 H), 3.77 (m, 1 H), 3.69 (m, 1 H), 3.58 (s, 3 H), 3.56 (s, 3 H), 3.54 (s, 3 H), 3.52 (dd, J = 6.0, 3.0 Hz, 1 H), 3.20 (t, J = 9.0 Hz, 1 H), 1.32 (d, J = 6.0 Hz, 3 H) |
| 65 | 4-CF₃-phenyl | 2,4 | thiazole | 1,4 Phenyl | A | 537.0 [M + H]⁺ | 166-168 | 8.19 (s, 1 H), 8.16 (d, J = 6.0 Hz, 2 H), 8.03 (d, J = 6.0 Hz, 2 H), 7.74-7.71 (m, 4 H), 7.63 (s, 1 H), 5.68 (s, 1 H), 3.78-3.76 (m, 1 H), 3.71-3.67 (m, 1 H), 3.58 (s, 3 H), 3.56 (s, 3 H), 3.54 (s, 3 H), 3.53-3.50 (m, 1 H), 3.21 (t, J = 9.0 Hz, 1 H), 1.33 (d, J = 3.0 Hz, 3 H) |
| 66 | 6-CF₃-pyrid-3-yl | 2,4 | thiazole | 1,4 Phenyl | A | 539.0 [M + H]⁺ | 167-169 | 9.33 (s, 1 H), 8.52 (dd, J = 7.5, 3.0 Hz, 1 H), 8.19 (s, 1 H), 8.03 (d, J = 6.0 Hz, 2 H), 7.81 (d, J = 6.0 Hz, 1 H), 7.74 (d, J = 6.0 Hz, 2 H), 7.70 (s, 1 H), 5.69 (d, J = 3.0 Hz, 1 H), 3.78-3.77 (m, 1 H), 3.71-3.67 (m, 1 H), 3.59 (s, 3 H), 3.56 (s, 3 H), 3.55 (s, 3 H), 3.52 (dd, J =9.0, 3.0 Hz, 1 H), 1.33 (d, J = 3.0 Hz, 3 H) |
| 67 | 4-OCF₃ phenyl | 1,3 | pyrrole | 1,4 Phenyl | A | 534 [M]⁺ | | 8.15 (s, 1 H), 7.63 (s, 1 H), 7.60 (d, J = 8.48 Hz, 2 H), 7.49 (d, J = 8.48 Hz, 2 H), 7.25-7.19 (m, 4 H), 6.98 (d, J = 5.88 Hz, 1 H), 6.71 (d, J = 5.86 Hz, 1 H), 5.63 (d, J = 1.85 Hz, 1 H), 3.68 (dd, J = 3.28, 1.99 Hz, 1 H), 3.63 (m, 1 H), 3.59 (s, 3 H), 3.57 (s, 3 H), 3.56 (s, 3 H), 3.44 (dd, J = 9.31, 3.36 Hz, 1 H), 3.20 (t, J = 9.48 Hz, 1 H), 1.25 (d, J = 6.26 Hz, 3 H) |
| 68 | 4-OCF₃ phenyl | 4,2 | 4,5-dihydro-1,3-oxazole | 1,4 Phenyl | B | 552 [M + H]⁺ | | 8.19 (s, 1 H), 8.08 (d, J = 8.26 Hz, 2 H), 7.72 (d, J = 8.26 Hz, 2 H), 7.32 (d, J = 8.24 Hz, 2 H), 7.20 (d, J = 8.24 Hz, 2 H), 5.63 (d, J = 1.85 Hz, 1 H), 5.42 (t, J = 9.42 Hz, 1 H), 8.84 (t, J = 9.46, 1 H), 4.28 (t, J = 9.46 Hz, 1 H), 3.79-3.61 (m, 4 H), 3.57 (s, 3 H), 3.56 (s, 3 H), 3.44 (dd, J = 9.31, 3.36 Hz, 1 H), 3.18 (t, J = 9.48 Hz, 1 H), 1.36-1.23 (m, 6 H) |
| 69 | 5-Cl-pyrid-2-yl | 3,1 | 1,2,4-triazole | 1,4 Phenyl | A | 487.0 [M + H]⁺ | | 8.77-8.69 (m, 2 H), 8.21-8.17 (m, 2 H), 7.89-7.73 (m, 5 H), 5.63 (d, J = 1.85 Hz, 1 H), 3.68 (dd, J = 3.28, 1.99 Hz, 1 H), 3.63 (m, 1 H), 3.59 (s, 3 H), 3.57 (s, 3 H), 3.56 (s, 3 H), 3.44 (dd, J = 9.31, 3.36 Hz, 1 H), 3.20 (t, J = 9.48 Hz, 1 H), 1.25 (d, J = 6.26 Hz, 3 H) |
| 70 | 2-F phenyl | 3,1 | 1,2,4-triazole | 1,4 Phenyl | A | 470.0 [M]⁺ | | 9.41 (s, 1 H), 8.24 (s, 1 H), 8.19-8.17 (m, 1 H), 7.91 (d, J = 8.25 Hz, 2 H), 7.79-7.69 (m, 1 H), 7.58 (d, J = 8.25 Hz, 2 H), 7.16-7.08 (m, 1 H), 6.89-6.84 (m, 1 H), 5.63 (d, J = 1.85 Hz, 1 H), 3.68 (dd, J = 3.28, 1.99 Hz, 1 H), 3.63 (m, 1 H), 3.59 (s, 3 H), 3.57 (s, 3 H), 3.56 (s, 3 H), 3.44 (dd, J = 9.31, 3.36 Hz, 1 H), 3.20 (t, J = 9.48 Hz, 1 H), 1.25 (d, J = 6.26 Hz, 3 H) |
| 71 | pyrid-3-yl | 3,1 | 1,2,4-triazole | 1,4 Phenyl | A | 453.0 [M]⁺ | | 9.51 (s, 1 H), 9.28 (s, 1 H), 8.69-8.67 (m, 1 H), 8.48 (s, 1 H), 8.42-8.40 (m, 1 H), 8.08 (d, J = 8.30 Hz, 2 H), 7.84 (d, J = 8.30 Hz, 2 H), 7.58-7.52 (m, 1 H), 5.63 (d, J = 1.85 Hz, 1 H), 3.68 (dd, J = 3.28, 1.99 Hz, 1 H), 3.63 (m, 1 H), 3.59 (s, 3 H), 3.57 (s, 3 H), 3.56 (s, 3 H), 3.44 (dd, J = 9.31, 3.36 Hz, 1 H), 3.20 (t, J = 9.48 Hz, 1 H), 1.25 (d, J = 6.26 Hz, 3 H) |
| 72 | 4-CF₃ phenyl | 3,1 | 1,2,4-triazole | 1,4 Phenyl | A | 522.0 [M + H]⁺ | 166 | 8.66 (s, 1 H), 8.33 (d, J =7.9 Hz, 2 H), 8.20 (s, 1 H), 7.81 (s, 4 H), 7.74 (d, J = 8.4 Hz, 2 H), 5.68 (d, J = 1.9 Hz, 1 H), 3.77 (dd, J = 3.2, 2.0 Hz, 1 H), 3.68 (d, J = 9.6, 6.2 Hz, 1 H), 3.59 (s, 3 H), 3.56 (s, 3 H), 3.55 (s, 3 H), 3.51 (m, 1 H), 3.21 (t, J = 9.3 Hz, 1 H), 1.33 (d, J = 6.1 Hz, 3 H) |
| 73 | phenyl | 1,3 | pyrazoline | 1,4 Phenyl | A | 454.2 [M + H]⁺ | | 8.17 (s, 1 H), ) 7.73 (d, J = 8.40 Hz, 2 H), 7.64 (d, J = 8.40 Hz, 2 H), 7.33 (m, 2 H), 7.18 (d, J = 7 Hz, 2 H), 6.89 (t, J = 7 Hz, 1 H), 5.68 (s, 1 H), 3.95 (t, J = 9 Hz, 2 H), 3.78 (m, 1 H), 3.6 (m, 1 H), 3.6-3.5 (m, 10 H), 3.28 (t, J = 9 Hz, 2 H), 3.21 (t, J = 8 Hz, 1 H), 1.34 (d, J = 6.3 Hz, 3 H) |
| 74 | 4-CF₃ phenyl | 3,1 | 1,2,4-triazole | 1,4 Phenyl | C | 549.0 [M + H]⁺ | 170-175 | 8.66 (s, 1 H), 8.35 (d, J = 7.9 Hz, 2 H), 8.20 (s, 1 H), 7.81 (s, 4 H), 7.74 (d, J = 8.4 Hz, 2 H), 5.66 (d, J = 1.8 Hz, 1 H), 3.77 (m, 1 H), 3.68-3.5 (m, 10 H), 3.21 (t, J = 9.2 Hz, 1 H), 1.7 (m, 2 H), 1.33 (d, J = 6.2 Hz, 3 H), 0.98 (t, J = 7.5 Hz, 3 H) |
| 75 | 4-Cl phenyl | 1,4 | 1,2,3-triazole | 1,4 Phenyl | A | 486.0 [M]⁺ | | 8.19 (s, 1 H), 8.17 (s, 1 H), 7.93 (d, J = 8.22 Hz, 2 H), 7.72 (d, J = 8.20 Hz, 2 H), 7.60 (d, J = 8.22 Hz, 2 H), 7.51 (d, J = 8.20 Hz, 2 H), 5.63 (d, J = 1.85 Hz, 1 H), 3.68 (dd, J = 3.28, 1.99 Hz, 1 H), 3.63 (m, 1 H), 3.59 (s, 3 H), 3.57 (s, 3 H), 3.56 (s, 3 H), 3.44 (dd, J = 9.31, 3.36 Hz, 1 H), 3.20 (t, J = 9.48 Hz, 1 H), 1.25 (d, J = 6.26 Hz, 3 H) |

TABLE 4-continued

Ar$_1$—Het—Ar$_2$—CH=N—O—Sugar

| # | Ar$_1$ | Het link[1] | Het | Ar$_2$ | Sugar[2] | M.S. | Mp °C. | $^1$H NMR (CDCl$_3$, δ)[3] |
|---|---|---|---|---|---|---|---|---|
| 76 | 4-CH$_3$ phenyl | 1,4 | 1,2,3-triazole | 1,4 Phenyl | A | 466.0 [M]$^+$ | | 8.19 (s, 1 H), 8.18 (s, 1 H), 7.96 (d, J = 8.26 Hz, 2 H), 7.70 (d, J = 8.26 Hz, 2 H), 7.67 (d, J = 8.30 Hz, 2 H), 7.37 (d, J = 8.30 Hz, 2 H), 5.63 (d, J = 1.85 Hz, 1 H), 3.68 (dd, J = 3.28, 1.99 Hz, 1 H), 3.63 (m, 1 H), 3.59 (s, 3 H), 3.57 (s, 3 H), 3.56 (s, 3 H), 3.44 (dd, J = 9.31, 3.36 Hz, 1 H), 3.20 (t, J = 9.48 Hz, 1 H), 2.42 (s, 3 H), 1.25 (d, J = 6.26 Hz, 3 H) |
| 77 | 4-OCH$_3$ phenyl | 1,4 | 1,2,3-triazole | 1,4 Phenyl | A | 482.0 [M]$^+$ | | 8.17 (s, 1 H), 8.16 (s, 1 H), 7.92 (d, J = 8.32 Hz, 2 H), 7.69 (d, J = 8.32 Hz, 2 H), 7.64 (d, J = 8.23 Hz, 2 H), 7.04 (d, J = 8.23 Hz, 2 H), 5.63 (d, J = 1.85 Hz, 1 H), 3.86 (s, 3 H), 3.71 (dd, J = 3.28, 1.99 Hz, 1 H), 3.63 (m, 1 H), 3.59 (s, 3 H), 3.57 (s, 3 H), 3.56 (s, 3 H), 3.42 (dd, J = 9.31, 3.36 Hz, 1 H), 3.19 (t, J = 9.48 Hz, 1 H), 1.29 (d, J = 6.26 Hz, 3 H) |
| 78 | 4-CF$_3$ phenyl | 1,4 | 1,2,3-triazole | 1,4 Phenyl | A | 520.0 [M]$^+$ | | 8.28 (s, 1 H), 8.18 (s, 1 H), 7.97 (d, J = 8.48 Hz, 2 H), 7.92 (d, J = 8.36 Hz, 2 H), 7.83 (d, J = 8.48 Hz, 2 H), 7.76 (d, J = 8.36 Hz, 2 H), 5.63 (d, J = 1.85 Hz, 1 H), 3.74 (dd, J = 3.28, 1.99 Hz, 1 H), 3.63 (m, 1 H), 3.59 (s, 3 H), 3.57 (s, 3 H), 3.56 (s, 3 H), 3.44 (dd, J = 9.31, 3.36 Hz, 1 H), 3.20 (t, J = 9.48 Hz, 1 H), 1.28 (d, J = 6.26 Hz, 3 H) |
| 79 | 4-OCF$_3$ phenyl | 1,4 | 1,2,3-triazole | 1,4 Phenyl | A | 536.0 [M]$^+$ | | 9.39 (s, 1 H), 8.41 (s, 1 H), 8.08 (d, J = 8.22 Hz, 2 H), 7.98 (d, J = 8.28 Hz, 2 H), 7.78 (d, J = 8.22 Hz, 2 H), 7.66 (d, J = 8.28 Hz, 2 H), 5.63 (d, J = 1.85 Hz, 1 H), 3.77 (dd, J = 3.28, 1.99 Hz, 1 H), 3.63 (m, 1 H), 3.59 (s, 3 H), 3.57 (s, 3 H), 3.56 (s, 3 H), 3.44 (dd, J = 9.31, 3.36 Hz, 1 H), 3.17 (t, J = 9.48 Hz, 1 H), 1.26 (d, J = 6.26 Hz, 3 H) |
| 80 | 4-CF$_3$ phenyl | 1,3 | 1,2,4-triazole | 1,4 Phenyl | A | 521.0 [M + H]$^+$ | 175-176 | 8.69 (s, 1 H), 8.25 (d, J = 8.7 Hz, 2 H), 8.20 (s, 1 H), 7.93 (d, J = 8.4 Hz, 2 H), 7.82 (d, J = 8.7 Hz, 2 H), 7.76 (d, J = 8.4 Hz, 2 H), 5.67 (d, J = 2.1 Hz, 1 H), 3.8-3.65 (m, 2 H), 3.65 (s, 3 H), 3.58 (s, 3 H), 3.56 (s, 3 H), 3.6 (m, 1 H), 3.25 (t, J = 9.3 Hz, 1 H), 1.33 (d, J = 6.3 Hz, 3 H) |
| 81 | 4-n-Bu phenyl | 1,3 | 1,2,4-triazole | 1,4 Phenyl | A | 509.1 [M + H]$^+$ | 142 | 8.51 (s, 1 H), 8.33 (d, J = 8 Hz, 2 H), 8.20 (s, 1 H), 7.75 (d, J = 8 Hz, 2 H), 7.65 (d, J = 8.2 Hz, 2 H), 7.33 (d, J = 8.2 Hz, 2 H), 5.68 (d, J = 1.9 Hz, 1 H), 3.77 (dd, J = 3.2, 2.0 Hz, 1 H), 3.68 (dd, J = 9.6, 6.2 Hz, 1 H), 3.59 (s, 3 H), 3.56 (s, 3 H), 3.55 (s, 3 H), 3.51 (m, 1 H), 3.21 (t, J = 9.3 Hz, 1 H), 2.70 (t, J = 7.8 Hz, 2 H), 1.65 (m, 2 H), 1.38 (m, 2 H), 1.33 (d, J = 6.1 Hz, 3 H), 0.95 (t, J = 7.5 Hz, 3 H) |
| 82 | 4-OCF$_3$ phenyl | 1,3 | 1,2,4-triazole | 1,4 Phenyl | A | 536 [M]$^+$ | | 8.59 (s, 1 H), 8.22 (d, J = 8.3 Hz, 2 H), 8.18 (s, 1 H), 7.81 (d, J = 8.3 Hz, 2 H), 7.67 (d, J = 8.3 Hz, 2 H), 7.39 (d, J = 8.3 Hz, 2 H), 5.63 (d, J = 1.8 Hz, 1 H), 3.78 (dd, J = 3.3, 2.0 Hz, 1 H), 3.63 (m, 1 H), 3.59 (s, 3 H), 3.57 (s, 3 H), 3.56 (s, 3 H), 3.44 (dd, J = 9.31, 3.4 Hz, 1 H), 3.20 (t, J = 9.48 Hz, 1 H), 1.28 (d, J = 6.26 Hz, 3 H) |
| 83 | 4-i-Pr phenyl | 1,3 | 1,2,4-triazole | 1,4 Phenyl | A | 494.0 [M]$^+$ | | 8.53 (s, 1 H), 8.21 (d, J = 8.29 Hz, 2 H), 8.17 (s, 1 H), 7.72 (d, J = 8.29 Hz, 2 H), 7.63 (d, J = 8.25 Hz, 2 H), 7.36 (d, J = 8.25 Hz, 2 H), 5.63 (d, J = 1.85 Hz, 1 H), 3.70 (dd, J = 3.28, 1.99 Hz, 1 H), 3.63 (m, 1 H), 3.59 (s, 3 H), 3.57 (s, 3 H), 3.56 (s, 3 H), 3.44 (dd, J = 9.31, 3.36 Hz, 1 H), 3.20 (t, J = 9.48 Hz, 1 H), 2.97 (m, 1 H), 1.31 (d, J = 6.12 Hz, 3 H), 1.29 (d, J = 6.12 Hz, 3 H), 1.25 (d, J = 6.26 Hz, 3 H) |
| 84 | 4-Cl phenyl | 1,3 | 1,2,4-triazole | 1,4 Phenyl | A | 487 [M + H]$^+$ | | 8.58 (s, 1 H), 8.21 (d, J = 8.26 Hz, 2 H), 8.18 (s, 1 H), 7.74 (d, J = 8.24 Hz, 2 H), 7.72 (d, J = 8.26 Hz, 2 H), 7.49 (d, J = 8.24 Hz, 2 H), 5.63 (d, J = 1.85 Hz, 1 H), 3.71 (dd, J = 3.28, 1.99 Hz, 1 H), 3.63 (m, 1 H), 3.59 (s, 3 H), 3.57 (s, 3 H), 3.56 (s, 3 H), 3.41 (dd, J = 9.31, 3.36 Hz, 1 H), 3.17 (t, J = 9.48 Hz, 1 H), 1.29 (d, J = 6.26 Hz, 3 H) |
| 85 | 4-OCH$_3$ phenyl | 1,3 | 1,2,4-triazole | 1,4 Phenyl | A | 482 [M]$^+$ | | 8.41 (s, 1 H), 8.22 (s, 1 H), 8.18 (d, J = 8.27 Hz, 2 H), 7.69 (d, J = 8.26 Hz, 2 H), 7.59 (d, J = 8.27 Hz, 2 H), 6.99 (d, J = 8.26 Hz, 2 H), 5.63 (d, J = 1.85 Hz, 1 H), 3.82 (s, 3 H), 3.76 (dd, J = 3.28, 1.99 Hz, 1 H), 3.63 (m, 1 H), 3.59 (s, 3 H), 3.57 (s, 3 H), 3.56 (s, 3 H), 3.44 (dd, J = 9.31, 3.36 Hz, 1 H), 3.19 (t, J = 9.48 Hz, 1 H), 1.32 (d, J = 6.26 Hz, 3 H) |
| 86 | 4-t-Bu phenyl | 1,3 | 1,2,4-triazole | 1,4 Phenyl | A | 508 [M]$^+$ | | 8.52 (s, 1 H), 8.21 (d, J = 8.23 Hz, 2 H), 8.17 (s, 1 H), 7.71 (d, J = 8.23 Hz, 2 H), 7.62 (d, J = 8.26 Hz, 2 H), 7.51 (d, J = 8.26 Hz, 2 H), 5.63 (d, J = 1.85 Hz, 1 H), 3.72 (dd, J = 3.28, 1.99 Hz, 1 H), 3.63 (m, 1 H), 3.59 (s, 3 H), 3.57 (s, 3 H), 3.56 (s, 3 H), 3.44 (dd, J = 9.31, 3.36 Hz, 1 H), 3.19 (t, J = 9.48 Hz, 1 H), 1.34 (s, 9 H), 1.28 (d, J = 6.26 Hz, 3 H) |
| 87 | 4-SCF$_3$ phenyl | 1,3 | 1,2,4-triazole | 1,4 Phenyl | A | 552.0 [M]$^+$ | | 8.66 (s, 1 H), 8.24 (d, J = 8.28 Hz, 2 H), 8.19 (s, 1 H), 7.87 (s, 4 H), 7.78 (d, J = 8.28 Hz, 2 H), 5.63 (d, J = 1.85 Hz, 1 H), 3.78 (dd, J = 3.28, 1.99 Hz, 1 H), 3.63 (m, 1 H), 3.59 (s, 3 H), 3.57 (s, 3 H), 3.56 (s, 3 H), 3.42 (dd, J = 9.31, 3.36 Hz, 1 H), 3.18 (t, J = 9.48 Hz, 1 H), 1.29 (d, J = 6.26 Hz, 3 H) |

TABLE 4-continued

Ar₁―Het―Ar₂―CH=N―O―Sugar

| # | Ar₁ | Het link[1] | Het | Ar₂ | Sugar[2] | M.S. | Mp °C. | ¹H NMR (CDCl₃, δ)[3] |
|---|---|---|---|---|---|---|---|---|
| 88 | 4-OC₂F₄H phenyl | 1,3 | 1,2,4-triazole | 1,4 Phenyl | A | 568.0 [M]⁺ | | 8.59 (s, 1 H), 8.22 (d, J = 8.26 Hz, 2 H), 8.19 (s, 1 H), 7.81 (d, J = 8.22 Hz, 2 H), 7.76 (d, J = 8.26 Hz, 2 H), 7.41 (d, J = 8.22 Hz, 2 H), 5.97 (tt, J = 52.72, 2.64 Hz, 1 H), 5.63 (d, J = 1.85 Hz, 1 H), 3.68 (dd, J = 3.28, 1.99 Hz, 1 H), 3.63 (m, 1 H), 3.59 (s, 3 H), 3.57 (s, 3 H), 3.56 (s, 3 H), 3.44 (dd, J = 9.31, 3.36 Hz, 1 H), 3.20 (t, J = 9.48 Hz, 1 H), 1.25 (d, J = 6.26 Hz, 3 H) |
| 89 | 4-OC₂F₅ phenyl | 1,3 | 1,2,4-triazole | 1,4 Phenyl | A | 586.0 [M]⁺ | | 8.59 (s, 1 H), 8.21 (d, J = 8.28 Hz, 2 H), 8.18 (s, 1 H), 7.81 (d, J = 8.22 Hz, 2 H), 7.77 (d, J = 8.28 Hz, 2 H), 7.39 (d, J = 8.22 Hz, 2 H), 5.63 (d, J = 1.85 Hz, 1 H), 3.79 (dd, J = 3.28, 1.99 Hz, 1 H), 3.63 (m, 1 H), 3.59 (s, 3 H), 3.57 (s, 3 H), 3.56 (s, 3 H), 3.43 (dd, J = 9.31, 3.36 Hz, 1 H), 3.18 (t, J = 9.48 Hz, 1 H), 1.30 (d, J = 6.26 Hz, 3 H) |
| 90 | 4-SCH₃ phenyl | 1,3 | 1,2,4-triazole | 1,4 Phenyl | A | 498.0 [M]⁺ | | 8.57 (s, 1 H), 8.21 (d, J = 8.24 Hz, 2 H), 8.17 (s, 1 H), 7.73 (d, J = 8.24 Hz, 2 H), 7.64 (d, J = 8.23 Hz, 2 H), 7.38 (d, J = 8.23 Hz, 2 H), 5.63 (d, J = 1.85 Hz, 1 H), 3.70 (dd, J = 3.28, 1.99 Hz, 1 H), 3.63 (m, 1 H), 3.59 (s, 3 H), 3.57 (s, 3 H), 3.56 (s, 3 H), 3.42 (dd, J = 9.31, 3.36 Hz, 1 H), 3.18 (t, J = 9.48 Hz, 1 H), 2.56 (s, 3 H), 1.28 (d, J = 6.26 Hz, 3 H) |
| 91 | 3-OCF₃ phenyl | 1,3 | 1,2,4-triazole | 1,4 Phenyl | A | 536.0 [M]⁺ | | 8.62 (s, 1 H), 8.25 (d, J = 8.28 Hz, 2 H), 8.20 (s, 1 H), 7.78 (d, J = 8.28 Hz, 2 H), 7.73 (m, 2 H), 7.58 (t, J = 9.54, 1 H), 7.26 (s, 1 H), 5.63 (d, J = 1.85 Hz, 1 H), 3.72 (dd, J = 3.28, 1.99 Hz, 1 H), 3.63 (m, 1 H), 3.59 (s, 3 H), 3.57 (s, 3 H), 3.56 (s, 3 H), 3.44 (dd, J = 9.31, 3.36 Hz, 1 H), 3.17 (t, J = 9.48 Hz, 1 H), 1.31 (d, J = 6.26 Hz, 3 H) |
| 92 | 4-OC₂F₅ phenyl | 1,3 | 1,2,4-triazole | 1,4 Phenyl | G | 628.0 [M]⁺ | | 8.59 (s, 1 H), 8.21 (d, J = 8.26 Hz, 2 H), 8.17 (s, 1 H), 7.84 (d, J = 8.24 Hz, 2 H), 7.74 (d, J = 8.24 Hz, 2 H), 7.39 (d, J = 8.34 Hz, 2 H), 5.62 (d, J = 1.92 Hz, 1 H), 3.91 (dd, J = 9.16, 7.24 Hz, 1 H), 3.85 (dd, J = 3.40, 1.92 Hz, 1 H), 3.69-3.49 (m, 7 H), 3.29 (t, J = 9.44 Hz, 1 H), 1.33 (d, J = 6.42 Hz, 3 H), 1.26 (td, J = 7.06, 3.66 Hz, 6 H), 1.18 (t, J = 7.20 Hz, 3 H) |
| 93 | 4-OC₂F₅ phenyl | 1,3 | 1,2,4-triazole | 1,4 Phenyl | B | 600.0 [M]⁺ | 107 | 8.58 (s, 1 H), 8.21 (d, J = 8.40 Hz, 2 H), 8.16 (s, 1 H), 7.79 (d, J = 8.24 Hz, 2 H), 7.72 (d, J = 8.40 Hz, 2 H), 7.38 (d, J = 8.24 Hz, 2 H), 5.63 (d, J = 1.85 Hz, 1 H), 3.79-3.61 (m, 4 H), 3.57 (s, 3 H), 3.56 (s, 3 H), 3.44 (dd, J = 9.31, 3.36 Hz, 1 H), 3.18 (t, J = 9.48 Hz, 1 H), 1.36-1.23 (m, 6 H) |
| 95 | 4-CF₃ phenyl | 3,5 | 1,2,4-triazole | 1,4 Phenyl | A | 520.0 [M]⁺ | | 8.21 (d, J = 8.41 Hz, 2 H), 8.13 (s, 1 H), 8.06 (d, J = 8.41 Hz, 2 H), 7.69 (d, J = 7.96 Hz, 2 H), 7.62 (d, J = 7.96 Hz, 2 H), 7.59 (s, 1 H), 5.63 (d, J = 1.85 Hz, 1 H), 3.78 (dd, J = 3.28, 1.99 Hz, 1 H), 3.63 (m, 1 H), 3.59 (s, 3 H), 3.57 (s, 3 H), 3.56 (s, 3 H), 3.44 (dd, J = 9.31, 3.36 Hz, 1 H), 3.18 (t, J = 9.48 Hz, 1 H), 1.29 (d, J = 6.26 Hz, 3 H) |
| 96 | 4-Cl | 3,5 | 1,2,4-triazole | 1,4 Phenyl | A | 486.0 [M]⁺ | | 8.17 (s, 1 H), 8.08 (d, J = 8.22 Hz, 2 H), 7.99 (d, J = 8.45 Hz, 2 H), 7.69 (d, J = 8.22 Hz, 2 H), 7.61 (s, 1 H), 7.41 (d, J = 8.45 Hz, 2 H), 5.63 (d, J = 1.85 Hz, 1 H), 3.71 (dd, J = 3.28, 1.99 Hz, 1 H), 3.63 (m, 1 H), 3.59 (s, 3 H), 3.57 (s, 3 H), 3.56 (s, 3 H), 3.44 (dd, J = 9.31, 3.36 Hz, 1 H), 3.20 (t, J = 9.48 Hz, 1 H), 1.31 (d, J = 6.26 Hz, 3 H) |
| 97 | 4-t-Bu phenyl | 3,5 | 1,2,4-triazole | 1,4 Phenyl | A | 508.0 [M]⁺ | | 8.15 (s, 1 H), 8.13 (d, J = 8.34 Hz, 2 H), 7.93 (d, J = 8.32 Hz, 2 H), 7.62 (d, J = 8.32 Hz, 2 H), 7.59 (s, 1 H), 7.41 (d, J = 8.34 Hz, 2 H), 5.63 (d, J = 1.85 Hz, 1 H), 3.71 (dd, J = 3.28, 1.99 Hz, 1 H), 3.63 (m, 1 H), 3.59 (s, 3 H), 3.57 (s, 3 H), 3.56 (s, 3 H), 3.44 (dd, J = 9.31, 3.36 Hz, 1 H), 3.20 (t, J = 9.48 Hz, 1 H), 1.29 (s, 9 H), 1.29 (d, J = 6.26 Hz, 3 H) |
| 98 | 3,4-Cl₂ phenyl | 2,5 | 1,2,4-triazolin-3-one | 1,4 Phenyl | A | 537 [M]⁺ | | 8.19 (d, J = 3.36 Hz, 1 H), 8.16 (s, 1 H), 7.94 (d, J = 3.36 Hz, 1 H), 7.79 (d, J = 8.42 Hz, 2 H), 7.69 (d, J = 8.42 Hz, 2 H), 7.45 (s, 1 H), 5.63 (d, J = 1.85 Hz, 1 H), 3.74 (dd, J = 3.28, 1.99 Hz, 1 H), 3.63 (m, 1 H), 3.59 (s, 3 H), 3.57 (s, 3 H), 3.56 (s, 3 H), 3.44 (dd, J = 9.31, 3.36 Hz, 1 H), 3.18 (t, J = 9.48 Hz, 1 H), 1.27 (d, J = 6.26 Hz, 3 H) |
| 99 | Perfluoro-4-tolyl | 2,5 | 1,2,4-triazolin-3-one | 1,4 Phenyl | A | 608 [M]⁺ | | 8.16 (s, 1 H), 7.84 (d, J = 8.23 Hz, 2 H), 7.75 (d, J = 8.23 Hz, 2 H), 5.63 (d, J = 1.85 Hz, 1 H), 3.73 (dd, J = 3.28, 1.99 Hz, 1 H), 3.63 (m, 1 H), 3.59 (s, 3 H), 3.57 (s, 3 H), 3.56 (s, 3 H), 3.44 (dd, J = 9.31, 3.36 Hz, 1 H), 3.21 (t, J = 9.48 Hz, 1 H), 1.27 (d, J = 6.26 Hz, 3 H) |
| 100 | 2,4-F₂ phenyl | 2,5 | 1,2,4-triazolin-3-one | 1,4 Phenyl | A | 504 [M]⁺ | | 8.14 (s, 1 H), 7.86 (d, J = 8.26 Hz, 2 H), 7.67 (d, J = 8.26 Hz, 2 H), 7.58 (m, 1 H), 7.03 (m, 2 H), 5.63 (d, J = 1.85 Hz, 1 H), 3.77 (dd, J = 3.28, 1.99 Hz, 1 H), 3.63 (m, 1 H), 3.59 (s, 3 H), 3.57 (s, 3 H), 3.56 (s, 3 H), 3.41 (dd, J = 9.31, 3.36 Hz, 1 H), 3.21 (t, J = 9.48 Hz, 1 H), 1.31 (d, J = 6.26 Hz, 3 H) |
| 101 | 4-OCF₃ phenyl | 2,5 | 1,2,4-triazolin-3-one | 1,4 Phenyl | A | 552 [M]⁺ | | 8.09 (s, 1 H), 8.02 (d, J = 8.21 Hz, 2 H), 7.88 (d, J = 8.44 Hz, 2 H), 7.63 (d, J = 8.44 Hz, 2 H), 7.24 (d, J = 8.21 Hz, 2 H), 5.63 (d, J = 1.85 Hz, 1 H), 3.72 (dd, J = 3.2, 1.99 Hz, 1 H), 3.63 (m, |

TABLE 4-continued $$Ar_1 \diagdown Het \diagup Ar_2 \diagdown C(H) = N \diagdown O \diagdown Sugar$$

| # | Ar₁ | Het link[1] | Het | Ar₂ | Sugar[2] | M.S. | Mp °C. | ¹H NMR (CDCl₃, δ)[3] |
|---|---|---|---|---|---|---|---|---|
| | | | | | | | | 1 H), 3.59 (s, 3 H), 3.57 (s, 3 H), 3.56 (s, 3 H), 3.41 (dd, J = 9.31, 3.36 Hz, 1 H), 3.20 (t, J = 9.48 Hz, 1 H), 1.30 (d, J = 6.26 Hz, 3 H) |
| 102 | 4-Br phenyl | 1,3 | 1,2,4-triazole | 1,4 Phenyl | A | 531.0 [M]⁺ | | 8.59 (s, 1 H), 8.21 (d, J = 8.26 Hz, 2 H), 8.18 (s, 1 H), 7.72 (d, J = 8.26 Hz, 2 H), 7.69 (s, 4 H), 5.63 (d, J = 1.85 Hz, 1 H), 3.73 (dd, J = 3.28, 1.99 Hz, 1 H), 3.63 (m, 1 H), 3.59 (s, 3 H), 3.57 (s, 3 H), 3.56 (s, 3 H), 3.41 (dd, J = 9.31, 3.36 Hz, 1 H), 3.19 (t, J = 9.48 Hz, 1 H), 1.28 (d, J = 6.26 Hz, 3 H) |
| 105 | 4-SC₂F₅ phenyl | 1,3 | 1,2,4-triazole | 1,4 Phenyl | A | 602.0 [M]⁺ | | 8.65 (s, 1 H), 8.22 (d, J = 8.28 Hz, 2 H), 8.17 (s, 1 H), 7.88-7.81 (m, 4 H), 7.76 (d, J = 8.28 Hz, 2 H), 5.63 (d, J = 1.85 Hz, 1 H), 3.68 (dd, J = 3.28, 1.99 Hz, 1 H), 3.63 (m, 1 H), 3.59 (s, 3 H), 3.57 (s, 3 H), 3.56 (s, 3 H), 3.44 (dd, J = 9.31, 3.36 Hz, 1 H), 3.20 (t, J = 9.48 Hz, 1 H), 1.25 (d, J = 6.26 Hz, 3 H) |
| 106 | 4-OC₂F₅ phenyl | 1,3 | 1,2,4-triazole | 1,4 Phenyl | C | 614.0 [M]⁺ | | 8.59 (s, 1 H), 8.20 (d, J = 8.38 Hz, 2 H), 8.18 (s, 1 H), 7.79 (d, J = 8.24 Hz, 2 H), 7.75 (d, J = 8.38 Hz, 2 H), 7.38 (d, J = 8.24 Hz, 2 H), 5.63 (d, J = 1.85 Hz, 1 H), 3.71-3.62 (m, 4 H), 3.59 (s, 3 H), 3.57 (s, 3 H), 3.44 (dd, J = 9.31, 3.36 Hz, 1 H), 3.20 (t, J = 9.48 Hz, 1 H), 1.68 (m, 2 H), 1.31 (d, J = 6.26 Hz, 3 H), 0.98 (t, J = 7.88 Hz, 3 H) |
| 107 | 4-CF₃ phenyl | 1,3 | 1,2,4-triazole | 1,4 Phenyl | C | 549.0 [M + H]⁺ | 188-190 | 8.69 (s, 1 H), 8.25 (d, J = 8.7 Hz, 2 H), 8.20 (s, 1 H), 7.93 (d, J = 8.7 Hz, 2 H), 7.82 (d, J = 8.7 Hz, 2 H), 7.76 (d, J = 8.4 Hz, 2 H), 5.67 (d, J = 2.1 Hz, 1 H), 3.8-3.65 (m, 2 H), 3.65 (s, 3 H), 3.58 (s, 3 H), 3.6 (m, 3 H), 3.25 (t, J = 9.3 Hz, 1 H), 1.7 (m, 2 H), 1.33 (d, J = 6.3 Hz, 3 H), 1.01 (t, J = 7.5 Hz, 3 H) |
| 108 | 4-C₂F₅ phenyl | 1,3 | 1,2,4-triazole | 1,4 Phenyl | C | 598.0 [M]⁺ | | 8.62 (s, 1 H), 8.27 (d, J = 8.26 Hz, 2 H), 8.20 (s, 1 H), 7.94 (d, J = 8.33 Hz, 2 H), 7.78 (d, J = 8.33 Hz, 2 H), 7.70 (d, J = 8.26 Hz, 2 H), 5.62 (d, J =1.85 Hz, 1 H), 3.87-3.62 (m, 4 H), 3.59 (s, 3 H), 3.56 (s, 3 H), 3.46 (dd, J = 9.32, 3.34 Hz, 1 H), 3.14 (t, J = 9.46 Hz, 1 H), 1.65-1.62 (m, 2 H), 1.26 (d, J = 6.10 Hz, 3 H), 0.99 (t, J = 7.62 Hz, 3 H) |
| 109 | 4-OC₂F₅ phenyl | 1,3 | 1,2,4-triazole | 1,4 Phenyl | D | 651.1 [M + Na]⁺ | 128 | 8.61 (s, 1 H), 8.23 (d, J = 8.4 Hz, 2 H), 8.21 (s, 1 H), 7.79 (d, J = 8.2 Hz, 2 H), 7.75 (d, J = 8.4 Hz, 2 H), 7.38 (d, J = 8.2 Hz, 2 H), 5.67 (d, J = 1.85 Hz, 1 H), 3.71-3.62 (m, 5 H), 3.59 (s, 3 H), 3.57 (s, 3 H), 3.20 (t, J = 9.5 Hz, 1 H), 1.68 (m, 2 H), 1.45 (m, 2 H), 1.33 (d, J = 7 Hz, 3 H), 0.98 (t, J = 7.9 Hz, 3 H) |
| 110 | 4-C₃F₇ phenyl | 1,3 | 1,2,4-triazole | 1,4 Phenyl | C | 648.0 [M]⁺ | 126 | 8.71 (s, 1 H), 8.23 (d, J = 8.30 Hz, 2 H), 8.19 (s, 1 H), 7.94 (d, J = 8.28 Hz, 2 H), 7.78-7.69 (m, 4 H), 5.62 (d, J = 1.85 Hz, 1 H), 3.87-3.62 (m, 4 H), 3.59 (s, 3 H), 3.56 (s, 3 H), 3.46 (dd, J = 9.32, 3.34 Hz, 1 H), 3.14 (t, J = 9.46 Hz, 1 H), 1.65-1.62 (m, 2 H), 1.26 (d, J = 6.10 Hz, 3 H), 0.99 (t, J = 7.62 Hz, 3 H) |
| 111 | 4-OC₂F₅ phenyl | 1,3 | 1,2,4-triazole | 1,4 Phenyl | B | 573.0 [M]⁺ | 134-137 | 8.59 (s, 1 H), 8.23 (d, J = 8.7 Hz, 2 H), 8.20 (s, 1 H), 7.79 (d, J = 9.3 Hz, 2 H), 7.75 (d, J = 8.7 Hz, 2 H), 7.39 (d, J = 9.3 Hz, 2 H), 5.71 (d, J = 1.8 Hz, 1 H), 3.82 (m, 1 H), 3.77 (m, 1 H), 3.63 (m, 1 H), 3.55 (s, 3 H), 3.51 (s, 3 H), 3.45 (m, 1 H), 2.4 (s, 1 H), 1.33 (d, J = 7 Hz, 3 H) |
| 112 | 4-CF₃SO₂O-phenyl | 1,3 | 1,2,4-triazole | 1,4 Phenyl | B | 614.0 [M]⁺ | | 8.61 (s, 1 H), 8.22 (d, J = 8.34 Hz, 2 H), 8.19 (s, 1 H), 7.91 (d, J = 8.30 Hz, 2 H), 7.74 (d, J = 8.30 Hz, 2 H), 7.48 (d, J = 8.34 Hz, 2 H), 5.63 (d, J = 1.85 Hz, 1 H), 3.79-3.61 (m, 4 H), 3.57 (s, 3 H), 3.56 (s, 3 H), 3.44 (dd, J = 9.31/3.36 Hz, 1 H), 3.18 (t, J = 9.48 Hz, 1 H), 1.36-1.23 (m, 6 H) |
| 114 | 4-OC₂F₅ phenyl | 1,3 | 1,2,4-triazole | 1,4 Phenyl | H | 617.0 [M]⁺ | | 8.61 (s, 1 H), 8.27 (s, 1 H), 8.23 (d, J = 8.4 Hz, 2 H), 7.82 (d, J = 8.2 Hz, 2 H), 7.75 (d, J = 8.4 Hz, 2 H), 7.42 (d, J = 8.2 Hz, 2 H), 5.80 (d, J = 3 Hz, 1 H), 3.68-3.30 (m, 18 H) |
| 115 | 2-Cl, 4-CF₃ phenyl | 1,3 | 1,2,4-triazole | 1,4 Phenyl | B | 568.0 [M]⁺ | 94 | 8.69 (s, 1 H), 8.20 (d, J = 8.26 Hz, 2 H), 8.16 (s, 1 H), 7.91-7.86 (m, 3 H), 7.71 (d, J = 8.26 Hz, 2 H), 5.63 (d, J = 1.85 Hz, 1 H), 3.79-3.61 (m, 4 H), 3.57 (s, 3 H), 3.56 (s, 3 H), 3.44 (dd, J = 9.31, 3.36 Hz, 1 H), 3.18 (t, J = 9.48 Hz, 1 H), 1.36-1.23 (m, 6 H) |
| 116 | 5-CF₃ pyrid-2-yl | 1,3 | 1,2,4-triazole | 1,4 Phenyl | B | 535.0 [M]⁺ | 194 | 9.23 (s, 1 H), 8.78 (s, 1 H), 8.29 (d, J = 8.31 Hz, 2 H), 8.24 (s, 1 H), 8.18-8.16 (m, 2 H), 7.78 (d, J = 8.31 Hz, 2 H), 5.63 (d, J = 1.85 Hz, 1 H), 3.79-3.61 (m, 4 H), 3.57 (s, 3 H), 3.56 (s, 3 H), 3.44 (dd, J = 9.31, 3.36 Hz, 1 H), 3.18 (t, J = 9.48 Hz, 1 H), 1.36-1.23 (m, 6 H) |
| 117 | 6-Cl-pyridazin-3-yl | 1,3 | 1,2,4-triazole | 1,4 Phenyl | B | 502.0 [M]⁺ | | 9.39 (s, 1 H), 8.26 (d, J = 8.28 Hz, 2 H), 8.19-8.16 (m, 3 H), 7.78 (d, J = 8.28 Hz, 2 H), 5.63 (d, J = 1.85 Hz, 1 H), 3.79-3.61 (m, 4 H), 3.57 (s, 3 H), 3.56 (s, 3 H), 3.44 (dd, J = 9.31, 3.36 Hz, 1 H), 3.18 (t, J = 9.48 Hz, 1 H), 1.36-1.23 (m, 6 H) |
| 118 | 5-CF₃-pyrid-2-yl | 1,3 | 1,2,4-triazole | 1,4 Phenyl | C | 549.0 [M]⁺ | 204 | 9.21 (s, 1 H), 8.76 (s, 1 H), 8.25 (d, J = 8.34 Hz, 2 H), 8.17 (s, 1 H), 8.15-8.08 (m, 2 H), 7.75 (d, J = 8.34 Hz, 2 H), 5.62 (d, J = 1.85 Hz, 1 H), 3.87-3.62 (m, 4 H), 3.59 (s, 3 H), 3.56 (s, 3 H), 3.46 (dd, J = 9.32, 3.34 Hz, 1 H), 3.14 (t, J = 9.46 Hz, 1 H), |

TABLE 4-continued $$Ar_1 - Het - Ar_2 - C(H) = N - O - Sugar$$

| # | Ar₁ | Het link[1] | Het | Ar₂ | Sugar[2] | M.S. | Mp °C. | ¹H NMR (CDCl₃, δ)[3] |
|---|-----|-----|-----|-----|-----|-----|-----|-----|
| | | | | | | | | 1.65-1.62 (m, 2 H), 1.26 (d, J = 6.10 Hz, 3 H), 0.99 (t, J = 7.62 Hz, 3 H) |
| 119 | 4-OC₂F₅ phenyl | 1,3 | 1,2,4-triazole | 1,4 Phenyl | I | 616.9 [M]⁺ | | 8.61 (s, 1 H), 8.24 (d, J = 8.4 Hz, 2 H), 8.21 (s, 1 H), 7.79 (d, J = 8.2 Hz, 2 H), 7.75 (d, J = 8.4 Hz, 2 H), 7.42 (d, J = 8.2 Hz, 2 H), 5.77 (d, J = 1.7 Hz, 1 H), 3.79 (m, 1 H), 3.70 (m, 1 H), 3.61 (m, 2 H), 3.6-3.5 (m, 11 H), 3.40 (s, 3 H) |
| 120 | 4-OCF₃ phenyl | 1,3 | 1,2,4-triazole | 1,4 Phenyl | B | 551 [M + H]⁺ | 131-134 | 8.60 (s, 1 H), 8.24 (d, J = 8.4 Hz, 2 H), 8.21 (s, 1 H), 7.83 (d, J = 8.7 Hz, 2 H), 7.77 (d, J = 8.4 Hz, 2 H), 7.39 (d, J = 8.7 Hz, 2 H), 5.63 (d, J = 1.6 Hz, 1 H), 3.78 -3.5 (m, 5 H), 3.61 (s, 3 H), 3.58 (s, 3 H), 3.22 (t, J = 9.2 Hz, 1 H), 1.3 (m, 6 H) |
| 121 | 6-CF₃ pyrid-3-yl | 1,3 | 1,2,4-triazole | 1,4 Phenyl | B | 535 [M + H]⁺ | 217-219 | 9.21 (s, 1 H), 8.78 (s, 1 H), 8.36 (d, J = 8.20 Hz, 1 H), 8.22 (d, J = 8.26 Hz, 2 H), 8.19 (s, 1 H), 7.90 (d, J = 8.20 Hz, 1 H), 7.78 (d, J = 8.26 Hz, 2 H), 5.63 (d, J = 1.85 Hz, 1 H), 3.79-3.61 (m, 4 H), 3.57 (s, 3 H), 3.56 (s, 3 H), 3.44 (dd, J = 9.31, 3.36 Hz, 1 H), 3.18 (t, J = 9.48 Hz, 1 H), 1.36-1.23 (m, 6 H) |
| 122 | 4-OC₂F₅ phenyl | 1,3 | 1,2,4-triazole | 1,4 Phenyl | J | 586.9 [M]⁺ | 100-108 | 8.58 (s, 1 H), 8.25 (s, 1 H), 8.19 (d, J = 8.7 Hz, 2 H), 7.8 (m, 4 H), 7.4 (d, J = 8 Hz, 2 H), 5.78 (d, J = 4.2 Hz, 1 H), 4.0 (m, 1 H), 3.8 (m, 1 H), 3.65-3.45 (m, 11 H), 1.28 (d, J = 6.3 Hz, 3 H) |
| 123 | 4-OCF₃ phenyl | 1,3 | 1,2,4-triazole | 5,2-pyridyl | B | 551 [M + H]⁺ | | 9.41 (s, 1 H), 8.60 (s, 1 H), 8.46 (d, J = 8.18 Hz, 1 H), 8.32 (s, 1 H), 8.08 (d, J = 8.18 Hz, 1 H), 7.78 (d, J = 8.22 Hz, 2 H), 7.41 (d, J = 8.22 Hz, 2 H), 5.63 (d, J = 1.85 Hz, 1 H), 3.79-3.61 (m, 4 H), 3.57 (s, 3 H), 3.56 (s, 3 H), 3.44 (dd, J = 9.31, 3.36 Hz, 1 H), 3.18 (t, J = 9.48 Hz, 1 H), 1.36-1.23 (m, 6 H) |
| 124 | 4-OCF₂CF₂Br phenyl | 1,3 | 1,2,4-triazole | 1,4 Phenyl | B | 661 [M + H]⁺ | | 8.59 (s, 1 H), 8.21 (d, J = 8.28 Hz, 2 H), 8.18 (s, 1 H), 7.78 (d, J = 8.30 Hz, 2 H), 7.72 (d, J = 8.28 Hz, 2 H), 7.38 (d, J = 8.30 Hz, 2 H), 5.63 (d, J = 1.85 Hz, 1 H), 3.79-3.61 (m, 4 H), 3.57 (s, 3 H), 3.56 (s, 3 H), 3.44 (dd, J = 9.31, 3.36 Hz, 1 H), 3.18 (t, J = 9.48 Hz, 1 H), 1.36-1.23 (m, 6 H) |
| 125 | 4-OCH₂CH₃ phenyl | 1,3 | 1,2,4-triazole | 1,4 Phenyl | B | 510 [M + H]⁺ | 136-138 | 8.46 (s, 1 H), 8.24 (d, J = 8.26 Hz, 2 H), 8.18 (s, 1 H), 7.74 (d, J = 8.26 Hz, 2 H), 7.62 (d, J = 8.22 Hz, 2 H), 7.04 (d, J = 8.22 Hz, 2 H), 5.63 (d, J = 1.85 Hz, 1 H), 4.12 (q, 7.22 Hz, 2 H), 3.79-3.61 (m, 4 H), 3.57 (s, 3 H), 3.56 (s, 3 H), 3.44 (dd, J = 9.31, 3.36 Hz, 1 H), 3.18 (t, J = 9.48 Hz, 1 H), 1.48 (t, J = 9.46 Hz, 3 H), 1.36-1.23 (m, 6 H) |
| 126 | 4-CN phenyl | 1,3 | 1,2,4-triazole | 1,4 Phenyl | B | 491 [M + H]⁺ | | 8.72 (s, 1 H), 8.24 (s, 1 H), 8.21 (d, J = 8.28 Hz, 2 H), 7.96 (d, J = 8.22 Hz, 2 H), 7.82 (d, J = 8.28 Hz, 2 H), 7.78 (d, J = 8.22 Hz, 2 H), 5.63 (d, J = 1.85 Hz, 1 H), 3.79-3.61 (m, 4 H), 3.57 (s, 3 H), 3.56 (s, 3 H), 3.44 (dd, J = 9.31, 3.36 Hz, 1 H), 3.18 (t, J = 9.48 Hz, 1 H), 1.36-1.23 (m, 6 H) |
| 127 | 4-NO₂ phenyl | 1,3 | 1,2,4-triazole | 1,4 Phenyl | B | 511 [M + H]⁺ | 178-180 | 8.79 (s, 1 H), 8.44 (d, J = 8.20 Hz, 2 H), 8.22 (d, J = 8.22 Hz, 2 H), 8.18 (s, 1 H), 8.02 (d, J = 8.20 Hz, 2 H), 7.78 (d, J = 8.22 Hz, 2 H), 5.63 (d, J = 1.85 Hz, 1 H), 3.79-3.61 (m, 4 H), 3.57 (s, 3 H), 3.56 (s, 3 H), 3.44 (dd, J = 9.31, 3.36 Hz, 1 H), 3.18 (t, J = 9.48 Hz, 1 H), 1.36-1.23 (m, 6 H) |
| 128 | 4-OCF₃ phenyl | 3,5 | 1,2,4-thiadiazole | 1,4 Phenyl | B | 567 [M + H]⁺ | 146-148 | 8.44 (d, J = 8.20 Hz, 2 H), 8.20 (s, 1 H), 8.09 (d, J = 8.24 Hz, 2 H), 7.79 (d, J = 8.20 Hz, 2 H), 7.38 (d, J = 8.24 Hz, 2 H), 5.63 (d, J = 1.85 Hz, 1 H), 3.79-3.61 (m, 4 H), 3.57 (s, 3 H), 3.56 (s, 3 H), 3.44 (dd, J = 9.31, 3.36 Hz, 1 H), 3.18 (t, J = 9.48 Hz, 1 H), 1.36-1.23 (m, 6 H) |
| 129 | 4-OCF₃ phenyl | 5,3 | 1,2,4-thiadiazole | 1,4 Phenyl | B | 567 [M + H]⁺ | 139-141 | 8.42 (d, J = 8.26 Hz, 2 H), 8.20 (s, 1 H), 8.12 (d, J = 8.22 Hz, 2 H), 7.78 (d, J = 8.26 Hz, 2 H), 7.38 (d, J = 8.22 Hz, 2 H), 5.63 (d, J = 1.85 Hz, 1 H), 3.79-3.61 (m, 4 H), 3.57 (s, 3 H), 3.56 (s, 3 H), 3.44 (dd, J = 9.31, 3.36 Hz, 1 H), 3.18 (t, J = 9.48 Hz, 1 H), 1.36-1.23 (m, 6 H) |
| 130 | 4-OCF₃ phenyl | 3,5 | 4,5-dihydro-1,2,4-oxadiazole | 1,4 Phenyl | B | 553 [M]⁺ | | 8.15 (s, 1 H), 7.78 (d, J = 8.9 Hz, 2 H), 7.68 (d, J = 8.2 Hz, 2 H), 7.57 (d, J = 8.6 Hz, 2 H), 7.28 (d, J = 8.6 Hz, 2 H), 6.58 (d, J = 4.3 Hz, 1 H), 5.62 (bs, 1 H), 4.95 (d, J = 4.3 Hz, 1 H), 3.80-3.50 (m, 5 H), 3.58 (s, 3 H), 3.54 (s, 3 H), 3.19 (t, J = 9.6 Hz, 1 H), 1.35-1.20 (m, 6 H) |
| 131 | 4-CF₃ phenyl | 5,2 | tetrazole | 1,4 Phenyl | A | 521 [M]⁺ | 156-158 | 8.39 (d, J = 9.0 Hz, 2 H), 8.26 (d, J = 8.7 Hz, 2 H), 8.23 (s, 1 H), 7.86 (d, J = 8.9 Hz, 2 H), 7.80 (d, J = 8.5 Hz, 2 H), 5.70 (d, J = 1.8 Hz, 1 H), 3.78 (m, 1 H), 3.69 (m, 1 H), 3.59 (s, 3 H), 3.57 (s, 3 H), 3.56 (s, 3 H), 3.52 (m, 1 H), 3.22 (t, J = 9.4 Hz, 1 H), 1.34 (d, J = 6.2 Hz, 3 H) |
| 133 | 4-OCF₃ phenyl | 4,2 | pyridine | 1,4 Phenyl | A | 546 [M]⁺ | 112-120 | 8.78 (d, J = 5.3 Hz, 1 H), 8.23 (s, 1 H), 8.11 (d, J = 8.2 Hz, 2 H), 7.93 (s, 1 H), 7.78 (d, J = 8.6 Hz, 2 H), 7.73 (d, J = 9.1 Hz, 2 H), 7.45 (m, 1 H), 7.38 (d, J = 8.2 Hz, 2 H), 5.70 (d, J = 1.9 Hz, 1 H), 3.79 (m, 1 H), 3.71 (m, 1 H), 3.60 (s, 3 H), 3.58 (s, 3 H), 3.56 (s, 3 H), 3.53 (m, 1 H), 3.23 (t, J = 9.4 Hz, 1 H), 1.34 (d, J = 6.0 Hz, 3 H) |

TABLE 4-continued $$Ar_1\text{—}Het\text{—}Ar_2\text{—}CH=N\text{—}O\text{—}Sugar$$

| # | Ar₁ | Het link[1] | Het | Ar₂ | Sugar[2] | M.S. | Mp °C. | ¹H NMR (CDCl₃, δ)[3] |
|---|---|---|---|---|---|---|---|---|
| 134 | 4-OCF₃ phenyl | 2,6 | pyridine | 1,4 Phenyl | A | 546 [M]⁺ | | 8.23 (s, 1 H), 8.19 (d, J = 8.5 Hz, 2 H), 7.86 (t, J = 7.9 Hz, 1 H), 7.76 (m, 3 H), 7.70 (d, J = 7.7 Hz, 1 H), 7.36 (d, J = 8.7 Hz, 2 H), 5.71 (d, J = 1.7 Hz, 1 H), 3.80 (m, 1 H), 3.72 (m, 1 H), 3.61 (s, 3 H), 3.58 (s, 3 H), 3.57 (s, 3 H), 3.53 (m, 1 H), 3.23 (t, J = 9.4 Hz, 1 H), 1.35 (d, J = 6.1 Hz, 3 H) |
| 135 | 4-OCF₃ phenyl | 3,5 | pyridine | 1,4 Phenyl | A | 546 [M]⁺ | | 8.85 (d, J = 17.1 Hz, 2 H), 8.21 (s, 1 H), 8.03 (t, J = 1.9 Hz, 1 H), 7.78 (d, J = 8.5 Hz, 2 H), 7.68 (d, J = 3.4 Hz, 2 H), 7.66 (d, J = 3.7 Hz, 2 H), 7.36 (d, J = 8.7 Hz, 2 H), 5.68 (d, J = 2.0 Hz, 1 H), 3.78 (m, 1 H), 3.69 (m, 1 H), 3.59 (s, 3 H), 3.57 (s, 3 H), 3.55 (s, 3 H), 3.51 (d, J = 3.4 Hz, 1 H), 3.21 (t, J = 9.5 Hz, 1 H), 1.33 (d, J = 6.2 Hz, 3 H) |
| 136 | 4-OCF₃ phenyl | 5,2 | pyrimidine | 1,4 Phenyl | A | 547 [M]⁺ | | (in acetone) 9.27 (s, 2 H), 8.68 (d, J = 8.7 Hz, 2 H), 8.42 (s, 1 H), 7.97 (d, J = 8.7 Hz, 2 H), 7.90 (d, J = 8.5 Hz, 2 H), 7.55-7.47 (m, 2 H), 5.58 (d, J = 2.0 Hz, 1 H), 3.83 (m, 1 H), 3.62 (m, 1 H), 3.53 (s, 3 H), 3.52 (s, 3 H), 3.47 (s, 3 H), 3.46 (m, 1 H), 3.13 (t, J = 9.3 Hz, 1 H), 1.22 (d, J = 6.3 Hz, 3 H) |
| 137 | 4-OCF₃ phenyl | 2,5 | pyrimidine | 1,4 Phenyl | A | 547 [M]⁺ | | (in acetone) 9.27 (s, 2 H), 8.68 (d, J = 9.3 Hz, 2 H), 8.42 (s, 1 H), 7.97 (d, J = 8.5 Hz, 2 H), 7.90 (d, J = 8.4 Hz, 2 H), 7.52 (d, J = 8.4 Hz, 2 H), 5.58 (d, J = 2.2 Hz, 1 H), 3.83 (m, 1 H), 3.62 (m, 1 H), 3.53 (s, 3 H), 3.52 (s, 3 H), 3.47 (s, 3 H), 3.45 (m, 1 H), 3.13 (t, J = 9.3 Hz, 1 H), 1.22 (d, J = 6.3 Hz, 3 H) |
| 138 | 4-OCF₃ phenyl | 4,2 | pyrimidine | 1,4 Phenyl | A | 547 [M]⁺ | | 8.87 (d, J = 5.3 Hz, 1 H), 8.62 (d, J = 8.5 Hz, 2 H), 8.29-8.20 (m, 3 H), 7.81 (d, J = 8.5 Hz, 2 H), 7.64 (d, J = 5.3 Hz, 1 H), 7.35 (d, J = 8.7 Hz, 2 H), 5.70 (d, J = 1.9 Hz, 1 H), 3.78 (m, 1 H), 3.69 (m, 1 H), 3.59 (s, 3 H), 3.57 (s, 3 H), 3.55 (s, 3 H), 3.52 (m, 1 H), 3.22 (t, J = 9.4 Hz, 1 H), 1.33 (d, J = 6.3 Hz, 3 H) |
| 139 | 4-OCF₃ phenyl | 2,4 | pyrimidine | 1,4 Phenyl | A | 547 [M]⁺ | | 8.88 (d, J = 5.3 Hz, 1 H), 8.60 (d, J = 8.4 Hz, 2 H), 8.27 (d, J = 9.0 Hz, 2 H), 8.23 (s, 1 H), 7.78 (d, J = 8.5 Hz, 2 H), 7.60 (d, J = 5.1 Hz, 1 H), 7.39 (d, J = 8.8 Hz, 2 H), 5.70 (d, J = 1.8 Hz, 1 H), 3.78 (m, 1 H), 3.70 (m, 1 H), 3.59 (s, 3 H), 3.57 (s, 3 H), 3.55 (s, 3 H), 3.52 (m, 1 H), 3.22 (t, J = 9.5 Hz, 1 H), 1.33 (d, J = 6.2 Hz, 3 H) |
| 140 | 4-OCF₃ phenyl | 4,6 | pyrimidine | 1,4 Phenyl | A | 547 [M]⁺ | | 9.34 (s, 1 H), 8.26-8.16 (m, 5 H), 8.10 (s, 1 H), 7.81 (d, J = 8.6 Hz, 2 H), 7.41-7.36 (m, 2 H), 5.70 (d, J = 1.9 Hz, 1 H), 3.78 (m, 1 H), 3.69 (m, 1 H), 3.59 (s, 3 H), 3.57 (s, 3 H), 3.55 (s, 3 H), 3.52 (m, 1 H), 3.22 (t, J = 9.4 Hz, 1 H), 1.33 (d, J = 6.3 Hz, 3 H) |
| 141 | 4-OC₂H₅ phenyl | 5,2 | pyrimidine | 1,4 Phenyl | A | 597 [M]⁺ | | 9.04 (s, 2 H), 8.55 (d, J = 8.5 Hz, 2 H), 8.24 (s, 1 H), 7.81 (d, J = 8.5 Hz, 2 H), 7.70 (d, J = 8.5 Hz, 2 H), 7.43 (d, J = 8.52 Hz, 2 H), 5.71 (d, J = 1.9 Hz, 1 H), 3.79-3.81 (m, 1 H), 3.74-3.69 (m, 1 H), 3.61 (s, 3 H), 3.59 (s, 3 H), 3.57 (s, 3 H), 3.54-3.53 (m, 1 H), 3.23 (t, J = 9.3 Hz, 1 H), 1.35 (d, J = 6.2 Hz, 3 H) |
| 142 | 4-OC₂F₅ phenyl | 5,2 | pyrimidine | 1,4 Phenyl | B | 611 [M]⁺ | | 9.04 (s, 2 H), 8.55 (d, J = 8.5 Hz, 2 H), 8.24 (s, 1 H), 7.81 (d, J = 8.5 Hz, 2 H), 7.70 (d, J = 8.7 Hz, 2 H), 7.43 (d, J = 8.79 Hz, 2 H), 5.70 (d, J = 1.6 Hz, 1 H), 3.82-3.64 (m, 5 H), 3.62 (s, 3 H), 3.59 (s, 3 H), 3.23 (t, J = 9.3 Hz, 1 H), 1.35-1.32 (m, 6 H) |
| 143 | 3-OCF₃ phenyl | 5,2 | pyrimidine | 1,4 Phenyl | B | | | |
| 144 | 4-OCF₃ phenyl | 5,2 | pyrimidine | 1,4 Phenyl | C | | | |
| 145 | 4-OCF₃ phenyl | 5,2 | pyrimidine | 1,4 Phenyl | D | | | |
| 146 | 4-OCF₃ phenyl | 5,2 | pyrimidine | 1,3 Phenyl | B | | | |
| 147 | 2-OCF₃ phenyl | 5,2 | pyrimidine | 1,3 Phenyl | B | | | |
| 148 | 4-OCF₃ phenyl | 5,2 | pyrimidine | 3-F, 1,4 Phenyl | B | | | |
| 149 | 3-OCF₃ phenyl | 5,2 | pyrimidine | 1,3 Phenyl | B | | | |
| 150 | 4-CH₃ Phenyl | 5,2 | pyrimidine | 1,4 Phenyl | B | | 223-225 | |
| 151 | 4-CF₃ Phenyl | 5,2 | pyrimidine | 1,4 Phenyl | B | | 228-229 | |
| 152 | 2-CH₃ Phenyl | 5,2 | pyrimidine | 1,4 Phenyl | B | | | |
| 153 | 4-F Phenyl | 5,2 | pyrimidine | 1,4 Phenyl | B | | 226-227 | |
| 154 | 4-CN Phenyl | 5,2 | pyrimidine | 1,4 Phenyl | B | | 207-211 | |
| 155 | 4-OCH₃ phenyl | 5,2 | pyrimidine | 3-CH₃, 1,4 Phenyl | B | | 121-125 | |

TABLE 4-continued

Ar₁—Het—Ar₂—CH=N—O—Sugar

| # | Ar₁ | Het link[1] | Het | Ar₂ | Sugar[2] | M.S. | Mp °C. | ¹H NMR (CDCl₃, δ)[3] |
|---|---|---|---|---|---|---|---|---|
| 156 | 2-OCF₃ phenyl | 5,2 | pyrimidine | 1,4 Phenyl | B | | | |
| 157 | 4-CF₃ phenyl | 2,4 | 1,3,5-triazine | 1,4 Phenyl | A | 532 [M]⁺ | | 9.32 (s, 1 H), 8.76 (d, J = 8.1 Hz, 2 H), 8.67 (d, J = 8.6 Hz, 2 H), 8.24 (s, 1 H), 7.83 (d, J = 8.3 Hz, 4 H), 5.70 (d, J = 1.7 Hz, 1 H), 3.78 (dd, J = 2.0, 3.3 Hz, 1 H), 3.73-3.66 (m, 1 H), 3.59 (s, 3 H), 3.57 (s, 3 H), 3.55 (s, 3 H), 3.49-3.51 (m, 1 H), 3.22 (t, J = 9.3 Hz, 1 H), 1.33 (d, J = 6.1 Hz, 3 H) |
| 158 | 4-OCF₃ phenyl | 2,4 | 1,3,5-triazine | 1,4 Phenyl | A | 548 [M]⁺ | | 9.28 (s, 1 H), 8.71-8.64 (m, 4 H), 8.24 (s, 1 H), 7.82 (d, J = 8.3 Hz, 2 H), 7.39 (d, J = 9.6 Hz, 2 H), 5.70 (d, J = 1.7 Hz, 1 H), 3.78 (dd, J = 2.0, 3.3 Hz, 1 H), 3.72-3.65 (m, 1 H), 3.59 (s, 3 H), 3.57 (s, 3 H), 3.55 (s, 3 H), 3.53-3.50 (m, 1 H), 3.22 (t, J = 9.4 Hz, 1 H), 1.33 (d, J = 6.1 Hz, 3 H) |
| 159 | 4-OCF₃ phenyl | 2,6 | pyrazine | 1,4 Phenyl | A | 547 [M]⁺ | | 9.00 (d, J = 8.6 Hz 2 H), 8.23 (s, 1 H), 8.21-8.18 (m, 4 H), 7.81 (d, J = 8.5 Hz, 2 H), 7.40 (d, 2 H), 5.70 (d, J = 1.9 Hz, 1 H), 3.78 (m, 1 H), 3.69 (m, 1 H), 3.59 (s, 3 H), 3.57 (s, 3 H), 3.55 (s, 3 H), 3.52 (m, 1 H), 3.22 (t, J = 9.4 Hz, 1 H), 1.33 (d, J = 6.3 Hz, 3 H) |
| 160 | 4-OCF₃ phenyl | 1,4 | piperazine | 2,5-pyridyl | B | 568 [M + H]⁺ | | 8.22 (s, 1 H), 8.08 (s, 1 H), 7.92 (d, J = 8.28 Hz, 1 H), 7.12 (d, J = 8.22 Hz, 2 H), 6.94 (d, J = 8.22 Hz, 2 H), 6.64 (d, J = 8.28 Hz, 1 H), 5.63 (d, J = 1.85 Hz, 1 H), 3.82-3.61 (m, 8 H), 3.57 (s, 3 H), 3.56 (s, 3 H), 3.44 (dd, J = 9.31, 3.36 Hz, 1 H), 3.31-3.22 (m, 4 H), 3.18 (t, J = 9.48 Hz, 1 H), 1.36-1.23 (m, 6 H) |
| 161 | 5-CF₃-pyrid-2-yl | 1,4 | piperazine | 1,4 Phenyl | B | 552 [M + H]⁺ | | 8.42 (s, 1 H), 8.08 (s, 1 H), 7.68 (d, J = 8.30 Hz, 1 H), 7.58 (d, J = 8.24 Hz, 2 H), 6.96 (d, J = 8.24 Hz, 2 H), 6.68 (d, J = 8.30 Hz, 1 H), 5.63 (d, J = 1.85 Hz, 1 H), 3.82-3.61 (m, 8 H), 3.57 (s, 3 H), 3.56 (s, 3 H), 3.44 (dd, J = 9.31, 3.36 Hz, 1 H), 3.42-3.38 (m, 4 H), 3.18 (t, J = 9.48 Hz, 1 H), 1.36-1.23 (m, 6 H) |
| 162 | 4-OCF₃ phenyl | 1,4 | piperazine | 1,4 Phenyl | C | 581 [M + H]⁺ | | 8.04 (s, 1 H), 7.52 (d, J = 8.22 Hz, 2 H), 7.14 (d, J = 8.28 Hz, 2 H), 6.98-6.92 (m, 4 H), 5.62 (d, J = 1.85 Hz, 1 H), 3.87-3.62 (m, 4 H), 3.59 (s, 3 H), 3.56 (s, 3 H), 3.46 (dd, J = 9.32, 3.34 Hz, 1 H), 3.42-3.40 (m, 4 H), 3.38-3.34 (m, 4 H), 3.14 (t, J = 9.46 Hz, 1 H), 1.65-1.62 (m, 2 H), 1.26 (d, J = 6.10 Hz, 3 H), 0.99 (t, J = 7.62 Hz, 3 H) |
| 163 | 4-SCH₃ phenyl | 5,2 | pyrimidine | 1,4-phenyl | B | | 210-220 | 9.03 (s, 2 H), 8.53 (d, J = 8.4 Hz, 2 H), 8.2 (s, 1 H), 7.79 (d, J = 8.7 Ha, 2 H), 7.48 (d, J = 8.7 Hz, 2 H), 7.41 (d, J = 8.7 Hz, 2 H), 5.68 (s, 1 H), 3.8-3.5 (series of s and m, 11 H), 3.22 (t, J = 9 Hz, 1 H), 2.57 (s, 3 H), 1.33 (m, 6 H) |

[1] Het link: Positions on Het to which Ar₁ and Ar₂ are attached respectively.
[2] Key to Sugars: see below. (Tables 4 and 6)
[3] All NMR data measured in CDCl₃ at 300 or 400 MHz unless otherwise noted.

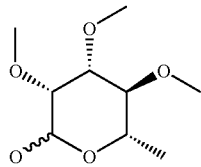

A
(3R,4R,5S,6S)-3,4,5-Trimethoxy-6-methyl-tetrahydropyran-2-yl

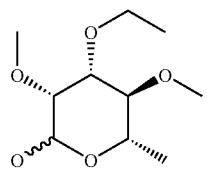

B
(3R,4R,5S,6S)-3,5-Dimethoxy-4-ethoxy-6-methyl-tetrahydropyran-2-yl

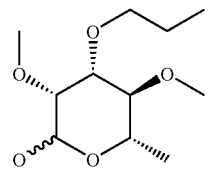

C
(3R,4R,5S,6S)-3,5-Dimethoxy-4-propoxy-6-methyl-tetrahydropyran-2-yl

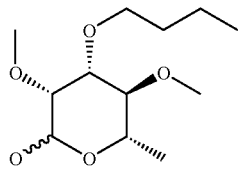

D
(3R,4R,5S,6S)-3,5-Dimethoxy-4-butoxy-6-methyl-tetrahydropyran-2-yl

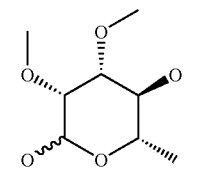

E
(3R,4R,5S,6S)-3,4-Dimethoxy-5-hydroxy-6-methyl-tetrahydropyran-2-yl

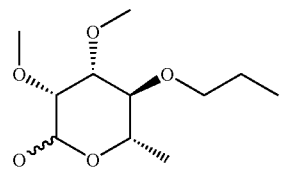

F
(3R,4R,5S,6S)-3,4-Dimethoxy-5-propoxy-6-methyl-tetrahydropyran-2-yl

TABLE 4-continued

Ar₁—Het—Ar₂—CH=N—O—Sugar

| # | Ar₁ | Het link[1] | Het | Ar₂ | Sugar[2] | M.S. | Mp °C. | ¹H NMR (CDCl₃, δ)[3] |
|---|-----|-------------|-----|-----|----------|------|--------|----------------------|

G
(3R,4R,5S,6S)-3,4,5-
Triethoxy-6-methyl-
tetrahydropyran-2-yl

H
(3R,4S,5R,6R)-3,4,5-
Trimethoxy-6-
methoxymethyl-
tetrahydropyran-2-yl

I
(3R,4R,5S,6S)-
3,4,5-Trimethoxy-6-
methoxymethyl-
tetrahydropyran-2-yl

J
(3S,4R,5R,6S)-3,4,5-
Trimethoxy-6-methyl-
tetrahydropyran-2-yl

K
(3R,4R,5S,
6S)-3,5-Dimethoxy-4-
allyloxy-6-methyl-
tetrahydropyran-2-yl

L
(3S,4R,5S)-3,4,5-
Trimethoxy-
tetrahydropyran-2-ol

M
(3R,4R,5S)-3,4,5-
Trimethoxy-tetra-
hydropyran-2-ol

N
(3R,4R,5S,6S)-3,4,5-
Trimethoxy-6-methyl-
tetrahydropyran-2-thiol

O
(2R,3S,4R,5S,6S)-3,4,5-
Trimethoxy-6-
methoxymethyl-
tetrahydro-
pyran-2-ol

P
(5S,6R)-5-Dimethyl-
amino-6-methyl-
tetrahydropyran-2-ol

Q
(4S,5S,6S)-4,5-
Dimethoxy-6-methyl-
tetrahydropyran-2-ol

R
(4S,5S,6S)-4-Methoxy-
6-methyl-tetrahydro-
pyran-2,5-diol

TABLE 5

Ar₁—Het—Ar₂—C(R5)=N—O—Sugar

| # | Ar₁ | Het link[1] | Het | Ar₂ | Sugar[2] | R5 | MS | ¹H NMR (CDCl₃, δ)[3] |
|---|-----|-------------|-----|-----|----------|-----|-----|----------------------|
| 164 | 4-OCF₃ Phenyl | 1,4 | imidazole | 2,5 Thienyl | A | CH₃ | 556 [M + 1]⁺ | |
| 165 | 4-OCF₃ Phenyl | 1,4 | imidazole | 1,4 Phenyl | A | CH₃ | 550 [M + 1]⁺ | 7.87(dd, J = 8.4, 1.8 Hz, 2 H), 7.85(s, 1 H), 7.75(d, J = 8.9 Hz, 2 H), 7.59(s, 1 H), 7.49(d, J = 9.0 Hz, 2 H), 7.37(d, J = 8.7 Hz, 2 H), 5.72(s, 1 H), 3.81(dd, J = |

TABLE 5-continued

Ar₁—Het—Ar₂—C(R5)=N—O—Sugar

| # | Ar₁ | Het link[1] | Het | Ar₂ | Sugar[2] | R5 | MS | ¹H NMR (CDCl₃)[3] |
|---|---|---|---|---|---|---|---|---|
| | | | | | | | | 3.1, 2.1 Hz, 1 H), 3.71-3.67(m, 1 H), 3.59(s, 3 H), 3.56 (s, 3 H), 3.53-3.49(m, 4 H), 3.24(d, J = 9.2 Hz, 1 H), 2.30(s, 3 H), 1.33(d, J = 6.0 Hz, 3 H) |
| 166 | 4-OCF₃ Phenyl | 1,4 | imidazole | 1,3 Phenyl | A | CH₃ | 550 [M + 1]⁺ | 8.15(s, 1 H), 7.89(d, J = 1.3 Hz, 1 H), 7.85-7.84(m, 1 H), 7.65-7.63(m, 1 H), 7.60(d, J = 1.3 Hz, 1 H), 7.50 (d, J = 8.9 Hz, 2 H), 7.45-7.42(m, 1 H), 7.37(d, J = 8.9 Hz, 2 H), 5.74(d, J = 1.5 Hz, 1 H), 3.81(dd, J = 3.4, 2.0 Hz, 1 H), 3.67-3.64(m, 1 H), 3.59(s, 3 H), 3.56(d, J = 2.2 Hz, 3 H), 3.53(s, 3 H), 3.50(dd, J = 4.5, 1.3 Hz, 1 H), 3.22(t, J = 9.3 Hz, 1 H), 2.33(s, 3 H), 1.33(d, J = 6.8 Hz, 3 H) |
| 167 | 4-OCF₃ phenyl | 1,4 | imidazole | 6-Cl, 1,3 Phenyl | A | CH₃ | 585 [M + 1]⁺ | |
| 168 | 4-OCF₃ Phenyl | 1,4 | imidazole | 6-F, 1,3 Phenyl | A | CH₃ | 568 [M + 1]⁺ | 8.45(dd, J = 7.4, 1.9 Hz, 1 H), 7.92(s, 1 H), 7.75(dd, J = 4.0, 1.1 Hz, 1 H), 7.70-7.65(m, 1 H), 7.51(d, J = 9.0 Hz, 2 H), 7.38(d, J = 9.3 Hz, 2 H), 7.16-7.09(m, 1 H), 5.73(s, 1 H), 3.80(dd, J = 3.4, 2.2 Hz, 1 H), 3.70-3.68 (m, 1 H), 3.59(s, 3 H), 3.56(s, 3 H), 3.50(d, J = 5.7 Hz, 3 H), 3.42(dd, J = 9.8, 3.2 Hz, 1 H), 3.21(t, J = 9.4 Hz, 1 H), 2.33(s, 3 H), 1.32(d, J = 6.2 Hz, 3 H) |
| 169 | 4-CF₃ Phenyl | 1,3 | triazole | 1,4 Phenyl | A | CF₃ | 602 [M + 1]⁺ | 8.68(s, 1 H), 8.26(d, J = 8.30 Hz, 2 H), 7.88(d, J = 8.26 Hz, 2 H), 7.81(d, J = 8.26 Hz, 2 H), 7.68(d, J = 8.30 Hz, 2 H), 5.63(d, J = 1.85 Hz, 1 H), 3.79-3.61(m, 4 H), 3.57(s, 3 H), 3.56(s, 3 H), 3.44(dd, J = 9.31, 3.36 Hz, 1 H), 3.18(t, J = 9.48 Hz, 1 H), 1.36-1.23(m, 6 H); |

Het link: refers to atom positions on Het to which Ar₁ and Ar₂ are attached respectively.
[2]See Key to Sugars, Table 4.
[3]All NMR data measured in CDCl₃ at 300 or 400 MHz unless otherwise noted.

TABLE 6

Ar₁—Het—Ar₂—N(H)—C(=O)—Sugar

| # | Ar₁ | Het link[1] | Het | Ar₂ | Anomer | Sugar[2] | M.S. | Mp (° C.) | ¹H NMR (CDCl₃, δ)[3] |
|---|---|---|---|---|---|---|---|---|---|
| 172 | 3-Cl phenyl | 1,3 | 4,5-dihydro-1H-pyrazole | 1,4-phenyl | α | A | 504.0 [M + H]⁺ | | 7.96-6.69(m, 9 H), 6.22(t, J = 2.3 Hz, 1 H), 3.75-3.64(m, 3 H), 3.6-3.45(m, 11 H), 3.21(m, 3 H), 1.34(d, J = 6.0 Hz, 3 H) |
| 173 | 4-OCF₃ phenyl | 1,4 | imidazole | 1,4-phenyl | α | A | 552.0 [M + H]⁺ | | 7.87(d, J = 1.0 Hz, 1 H), 7.79(d, J = 8.9 Hz, 2 H), 7.52-7.41(m, 5 H), 7.36(d, J = 8.9 Hz, 2 H), 6.90(s, 1 H), 6.24(d, J = 1.7 Hz, 1 H), 3.68(m, 2 H), 3.6-3.45 (m, 10 H), 3.15(t, J = 9.2 Hz, 1 H), 1.36(d, J = 6.3 Hz, 3 H) |
| 174 | 4-OCF₃ phenyl | 1,4 | imidazole | 1,4-phenyl | β | A | 552 [M + H]⁺ | | 7.87(d, J = 1.3 Hz, 1 H), 7.80(d, J = 8.8 Hz, 2 H), 7.53-7.43(m, 5 H), 7.39-7.34(m, 2 H), 6.89(s, 1 H), 5.62(s, 1 H), 3.80(m, 1 H), 3.65(s, 3 H), 3.56(s, 3 H), 3.52(s, 3 H), 3.37(m, 1 H), 3.28(m, 1 H), 3.19(t, J = 9.6 Hz, 1 H), 1.33 (d, J = 6.2 Hz, 3 H) |
| 175 | 4-OCF₃ phenyl | 1,4 | imidazole | 1,4-phenyl | α | D | 594.0 [M + H]⁺ | | 7.87(d, J = 1.1 Hz, 1 H), 7.79(d, J = 8.7 Hz, 2 H), 7.50(d, J = 1.2 Hz, 1 H), 7.50-7.44(m, 4 H), 7.37(d, J = 8.8 Hz, 2 H), 6.77(s, 1 H), 6.19(d, J = 1.8 Hz, 1 H), 3.68(m, 1 H), 3.62(m, 1 H), 3.59(s, 3 H), 3.58(m, 1 H), 3.56(s, 3 H), 3.20(t, J = 9.6 Hz, 1 H), 1.69-1.59(m, 4 H), 1.44(sext, J = 7.4 Hz, 2 H), 1.33 (d, J = 6.3 Hz, 3 H), 0.95(t, J = 7.4 Hz, 3 H) |
| 178 | 4-OCF₃ phenyl | 1,3 | 4,5-dihydro-1H-pyrazole | 1,4-phenyl | α | B | 567 [M + H]⁺ | 197-199 | 8.72(d, J = 8.22 Hz, 2 H), 7.44(d, J = 8.22 Hz, 2 H), 7.16(d, J = 8.28 Hz, 2 H), 7.08(d, J = 8.28 Hz, 2 H), 6.88(s, 1 H), 6.20(d, J = 1.85 Hz, 1 H), 3.92(t, J = 9.46 Hz, 2 H), 3.79-3.61(m, 4 H), 3.57(s, 3 H), 3.56(s, 3 H), 3.44(dd, J = 9.31, 3.36 Hz, 1 H), 3.24-3.18(m, 3 H), 1.36-1.23(m, 6 H) |

TABLE 6-continued

Ar₁–Het–Ar₂–NH–C(=O)–Sugar

| # | Ar₁ | Het link[1] | Het | Ar₂ | Anomer | Sugar[2] | M.S. | Mp (° C.) | ¹H NMR (CDCl₃, δ)[3] |
|---|---|---|---|---|---|---|---|---|---|
| 179 | 4-OC₂F₅ phenyl | 1,3 | 4,5-dihydro-1H-pyrazole | 1,4-phenyl | α | B | 617 [M + H]⁺ | — | 7.72(d, J = 8.28 Hz, 2 H), 7.44(d, J = 8.28 Hz, 2 H), 7.16(d, J = 8.26 Hz, 2 H), 7.08(d, J = 8.26 Hz, 2 H), 6.78(s, 1 H), 6.20(d, J = 1.85 Hz, 1 H), 3.88(t, J = 9.48 Hz, 2 H), 3.79-3.61(m, 4 H), 3.57(s, 3 H), 3.56(s, 3 H), 3.44(dd, J = 9.31, 3.36 Hz, 1 H), 3.34-3.20(m, 3 H), 1.36-1.23(m, 6 H) |
| 180 | 4-OC₂F₅ phenyl | 1,3 | 4-dimethyl-aminomethyl-4,5-dihydro-1H-pyrazole | 1,4-phenyl | α | B | 674 [M + H]⁺ | — | 7.68(d, J = 8.26 Hz, 2 H), 7.44(d, J = 8.26 Hz, 2 H), 7.14-7.08(m, 4 H), 6.92 (s, 1 H), 6.20(d, J = 1.85 Hz, 1 H), 3.79-3.61(m, 7 H), 3.57(s, 3 H), 3.56(s, 3 H), 3.44(dd, J = 9.31, 3.36 Hz, 1 H), 3.18(t, J = 9.48 Hz, 1 H), 2.56-2.52(m, 2 H), 2.40(s, 6 H), 1.36-1.23(m, 6 H) |
| 181 | 4-CF₃ phenyl | 5,3 | 4,5-dihydro-isoxazole | 1,4-phenyl | α | B | 552 [M]⁺ | — | 7.45-7.63(m, 8 H), 6.94(bs, 1 H), 6.17(bs, 1 H), 5.79(dd, J = 10.7, 7.6 Hz, 1 H), 3.50-3.90(m, 5 H), 3.58(s, 3 H), 3.54(s, 3 H), 3.10-3.40(m, 3 H), 1.2-1.4 (m, 6 H) |
| 182 | 4-CF₃ phenyl | 5,3 | 4,5-dihydro-isoxazole | 1,4-phenyl | β | B | 552 [M]⁺ | — | 7.40-7.70(m, 8 H), 6.98(bs, 1 H), 5.79(dd, J = 11.2, 7.9 Hz, 1 H), 5.63(bs, 1 H), 3.50-3.90(m, 4 H), 3.66(s, 3 H), 3.57(s, 3 H), 3.20-3.40(m, 3 H), 3.14(t, J = 9.4 Hz, 1 H), 1.20-1.40(m, 6 H) |
| 183 | 4-OCF₃ phenyl | 3,5 | 4,5-dihydro-isoxazole | 1,4-phenyl | α | B | 568 [M]⁺ | — | 7.72(d, J = 8.9 Hz, 2 H), 7520-7.20(m, 6 H), 6.74(s, 1 H), 6.16(s, 1 H), 5.73 (dd, J = 11.0, 8.4 Hz, 1 H), 3.80-3.45(m, 6 H), 3.58(s, 3 H), 3.54(s, 3 H), 3.30 (dd, J = 16.6, 8.4 Hz, 1 H), 3.19(t, J = 9.2 Hz, 1 H), 1.20-1.35(m, 6 H) |
| 184 | 4-OCF₃ phenyl | 3,5 | 4,5-dihydro-isoxazole | 1,4-phenyl | β | B | 568 [M]⁺ | — | 7.72(d, J = 8.9 Hz, 2 H), 7.40(d, J = 8.6 Hz, 2 H), 7.33(d, J = 8.9 Hz, 2 H) 7.26(d, J = 8.6 Hz, 2 H), 6.84(s, 1 H), 5.73(dd, J = 11.2, 8.2 Hz, 1 H), 5.63 (bs, 1 H), 3.55-3.80(m, 4 H), 3.66(s, 3 H), 3.57(s, 3 H), 3.20-3.40(m, 3 H), 3.14(t, J = 9.2 Hz, 1 H), 1.20-1.40(m, 6 H) |
| 185 | 4-OCF₃ phenyl | 5,2 | 4,5-dihydro-oxazole | 1,4-phenyl | α | B | 568 [M + H]⁺ | 130-132 | 7.68(d, J = 8.22 Hz, 2 H), 7.44(d, J = 8.22 Hz, 2 H), 7.22(d, J = 8.26 Hz, 2 H), 7.16(d, J = 8.26 Hz, 2 H), 6.96(s, 1 H), 6.20(d, J = 1.85 Hz, 1 H), 3.79-3.61(m, 6 H), 3.57(s, 3 H), 3.56(s, 3 H), 3.44(dd, J = 9.31, 3.36 Hz, 1 H), 3.18 (t, J = 9.48 Hz, 1 H), 2.92(t, J = 9.60 Hz, 2 H), 1.36-1.23(m, 6 H) |
| 186 | 4-OCF₃ phenyl | 2,4 | 4,5-dihydro-oxazole | 1,4-phenyl | α | B | 568 [M + H]⁺ | 137-139 | 8.02(d, J = 8.20 Hz, 2 H), 7.52(d, J = 8.20 Hz, 2 H), 7.38(d, J = 8.24 Hz, 2 H), 7.22(d, J = 8.24 Hz, 2 H), 6.84(s, 1 H), 6.20(d, J = 1.85 Hz, 1 H), 5.44(t, J = 9.42 Hz, 1 H), 4.82(t, J = 9.48 Hz, 1 H), 4.28(t, J = 8.48 Hz, 1 H), 3.79-3.61(m, 4 H), 3.57(s, 3 H), 3.56(s, 3 H), 3.44(dd, J = 9.31, 3.36 Hz, 1 H), 3.18 (t, J = 9.48 Hz, 1 H), 1.36-1.23(m, 6 H) |
| 187 | 4-OCF₃ phenyl | 1,3 | 1,3-dihydro-imidazol-2-one | 1,4-phenyl | α | B | 581 [M]⁺ | — | 7.70(d, J = 8.9 Hz, 2 H), 7.40-7.60(m, 4 H), 7.31(d, J = 8.6 Hz, 2 H), 7.03 (bs, 1 H), 6.70(dd, J = 5.3, 3.3 Hz, 1 H), 6.18(bs, 1 H), 3.50-3.80(m, 6 H), 3.58(s, 3 H), 3.55(s, 3 H), 3.19(t, J = 9.2 Hz, 1 H), 1.20-1.35(m, 6 H) |
| 188 | 4-OCF₃ phenyl | 1,3 | imidazolidin-2-one | 1,4-phenyl | α | B | 583[M]⁺ | — | 7.62(d, J = 8.9 Hz, 2 H), 7.53(d, J = 8.9 Hz, 2 H), 7.35-7.45(m, 2 H), 7.23(d, J = 8.6 Hz, 2 H), 6.69(bs, 1 H), 6.17(bs, 1 H), 3.97(s, 4 H), 3.50-3.80(m, 5 H), 3.59(s, 3 H) 3.55(s, 3 H), 3.20(t, J = 9.2 Hz, 1 H), 1.20-1.35(m, 6 H) |
| 192 | 4-CF₃ phenyl | 1,3 | 1,2,4-triazole | 1,4-phenyl | α | B | 551 [M + H]⁺ | 185 | 8.65(s, 1 H), 8.18(d, J = 8.4 Hz, 2 H), 7.91(d, J = 8.5 Hz, 2 H), 7.79(d, J = 9.0 Hz, 2 H), 7.54(d, J = 8.4 Hz, 2 H), 6.84(s, 1 H), 6.20(d, J = 1.7 Hz, 1 H), 3.78-3.50(m, 11 H), 3.22(t, J = 9.3 Hz, 1 H), 1.33(d, J = 6.3 Hz, 3 H), 1.29(t, J = 7.0 Hz, 3 H) |
| 193 | 4-OCF₃ phenyl | 1,3 | 1,2,4-triazole | 1,4-phenyl | α | B | 566.9 [M + H]⁺ | — | 8.56(s, 1 H), 8.16(d, J = 8.4 Hz, 2 H), 7.79(d, J = 9.1 Hz, 2 H), 7.53(d, J = 8.6 Hz, 2 H), 7.38(d, J = 9.1 Hz, 2 H), 6.79(s, 1 H), 6.20(d, J = 1.7 Hz, 1 H), 3.80-3.50(m, 11 H), 3.21(t, J = 9.2 Hz, 1 H), 1.37-1.23(m, 6 H) |
| 194 | 4-OCF₃ phenyl | 1,3 | 5-CH₃-1,2,4-triazole | 1,4-phenyl | α | A | 566.9 [M + H]⁺ | — | 8.10(d, J = 8.8 Hz, 2 H), 7.57(d, J = 9.3 Hz, 2 H), 7.50(d, J = 7.3 Hz, 2 H), 7.38(d, J = 8.5 Hz, 2 H), 6.80(s, 1 H), 6.22(d, J = 2.0 Hz, 1 H), 3.68(m, 2 H), 3.58(s, 3 H), 3.56(s, 3 H), 3.53(s, 3 H), 3.49(m, 1 H), 3.21(t, J = 9.5 Hz, 1 H), 2.59(s, 3 H), 1.33(d, J = 6.2 Hz, 3 H) |

TABLE 6-continued

Structure: Ar₁–Het–Ar₂–N(H)–C(=O)–Sugar

| # | Ar₁ | Het link[1] | Het | Ar₂ | Anomer | Sugar[2] | M.S. | Mp (° C.) | ¹H NMR (CDCl₃, δ)[3] |
|---|---|---|---|---|---|---|---|---|---|
| 195 | 4-OCF₃ phenyl | 1,3 | 5-CH₃-1,2,4-triazole | 1,4-phenyl | β | A | 566.9 [M + H]⁺ | | 8.10(d, J = 8.8 Hz, 2 H), 7.57(d, J = 9.3 Hz, 2 H), 7.50(d, J = 7.3 Hz, 2 H), 7.38(d, J = 8.5 Hz, 2 H), 6.80(s, 1 H), 6.22(d, J = 2.0 Hz, 1 H), 3.68(m, 2 H(, 3.58(s, 3 H), 3.56(s, 3 H), 3.53(s, 3 H), 3.49(m, 1 H), 3.21(t, J = 9.5 Hz, 1 H), 2.59(s, 3 H), 1.33(d, J = 6.2 Hz, 3 H) |
| 196 | 4-O-(4-ClPh)-phenyl | 1,3 | 1,2,4-triazole | 1,4-phenyl | α | A | 595.0 [M]⁺ | | 8.50(s, 1 H), 8.16(d, J = 9.1 Hz, 2 H), 7.69(d, J = 9.1 Hz, 2 H), 7.53(d, J = 8.5 Hz, 2 H), 7.33(d, J = 8.9 Hz, 2 H), 7.12(d, J = 9.1 Hz, 2 H), 6.99(d, J = 8.9 Hz, 2 H), 6.87(s, 1 H), 6.22(d, J = 2.0 Hz, 1 H), 3.70(m, 2 H), 3.58(s, 3 H), 3.56(s, 3 H), 3.53(s, 3 H), 3.50(m, 1 H), 3.21(t, J = 9.4 Hz, 1 H), 1.33(d, J = 6.1 Hz, 3 H) |
| 197 | 4-CH₃ phenyl | 3,1 | 1,2,4-triazole | 1,4-phenyl | α | D | | | 8.58(s, 1 H), 8.15(d, 2 H), 7.75(d, 2 H), 7.62(d, 2 H), 7.32(d, 2 H), 7.05(s, 1 H), 6.22(d, 1 H), 3.7-3.5(m, 11 H), 3.21(t, 1 H), 2.41(s, 3 H), 1.65(m, 2 H), 1.45(m, 2 H), 1.33(d, 3 H), 0.95(t, J = 7.5 Hz, 3 H) |
| 198 | 4-CF₃ phenyl | 3,1 | 1,2,4-triazole | 1,4-phenyl | α | D | 579.0 [M + H]⁺ | 175 | 8.59(s, 1 H), 8.56(d, J = 7.6 Hz, 2 H), 7.77-7.71(m, 4 H), 7.60(d, J = 8.9 Hz, 2 H), 6.90(s, 1 H), 6.20(d, J = 1.8 Hz, 1 H), 3.75-3.57(m, 11 H), 3.20(t, J = 9.3 Hz, 1 H), 1.66(m, 2 H), 1.47(sext, J = 7.4 Hz, 2 H), 1.39(t, J = 6.3 Hz, 3 H), 0.98(t, J = 7.3 Hz, 3 H) |
| 199 | 4-CF₃ phenyl | 3,1 | 1,2,4-triazole | 1,4-phenyl | β | D | 579.0 [M + H]⁺ | 179 | 8.59(s, 1 H), 8.34(d, J = 7.6 Hz, 2 H), 7.77-7.71(m, 4 H), 7.60(d, J = 8.9 Hz, 2 H), 7.0(s, 1 H), 5.68(d, J = 0.8 Hz, 1 H), 3.80-3.78(m, 1 H), 3.75-3.57(m, 8 H), 3.41(dd, J = 9.2, 6.1 Hz, 1 H), 3.37(dd, J = 9.4, 3.0 Hz, 1 H), 3.18(t, J = 9.3 Hz, 1 H), 1.66(m, 2 H), 1.47(sext, J = 7.4 Hz, 2 H), 1.39(d, J = 6.3 Hz, 3 H), 0.98(t, J = 7.3 Hz, 3 H) |
| 200 | 4-OC₂F₅ phenyl | 1,3 | 1,2,4-triazole | 1,4-phenyl | α | A | 603.0 [M + H]⁺ | 207-210 | 8.59(s, 1 H), 8.20(d, J = 8.7 Hz, 2 H), 7.85(d, J = 8 Hz, 2 H), 7.5(d, J = 8 Hz, 2 H), 7.30(t, J = 8.7 Hz, 2 H), 6.80(s, 1 H), 6.22(d, J = 1.8 Hz, 1 H), 3.65-3.45(m, 12 H), 3.20(t, J = 9.3 Hz, 1 H), 1.33(d, J = 6.2 Hz, 3 H) |
| 204 | 4-OC₂F₅ phenyl | 1,3 | 1,2,4-triazole | 1,4-phenyl | α | K | 629.0 [M + H]⁺ | | 8.6(s, 1 H), 8.20(d, J = 8.7 Hz, 2 H), 7.81(d, J = 8.7 Hz, 2 H), 7.55(d, J = 8.4 Hz, 2 H), 7.38(d, J = 8.7 Hz, 2 H), 6.95(s, 1 H), 6.21(d, J = 1.8 Hz, 1 H), 6.0 (m, 1 H), 5.35(d, J = 12 Hz, 1 H), 5.21(d, J = 8 Hz, 1 H), 4.20(d, J = 6 Hz, 2 H), 3.75-3.50(m, 9 H), 3.23(t, J = 9.5 Hz, 1 H), 1.33(d, J = 7 Hz, 3 H) |
| 205 | 4-OCF₃ phenyl | 1,3 | 1,2,4-triazole | 1,4-phenyl | α | K | 579.0 [M + H]⁺ | | 8.55(s, 1 H), 8.17(d, J = 8.7 Hz, 2 H), 7.80(d, J = 8.7 Hz, 2 H), 7.55(d, J = 8.4 Hz, 2 H), 7.38(d, J = 8.7 Hz, 2 H), 6.85(s, 1 H), 6.20(d, J = 1.8 Hz, 1 H), 6.0(m, 1 H), 5.35(d, J = 12 Hz, 1 H), 5.21(d, J = 8 Hz, 1 H), 4.20(d, J = 6 Hz, 2 H), 3.75-3.50(m, 9 H), 3.23(t, J = 9.5 Hz, 1 H), 1.33(d, J = 7 Hz, 3 H) |
| 206 | 4-OC₂F₅ phenyl | 1,3 | 1,2,4-triazole | 1,4-phenyl | α | G | 644.97 [M + H]⁺ | 142-144 | 8.58(s, 1 H), 8.2(d, J = 8 Hz, 2 H), 7.82(d, J = 8 Hz, 2 H), 7.55(d, J = 9 Hz, 2 H), 7.41(d, J = 9 Hz, 2 H), 6.81(s, 1 H), 6.16(d, J = 1.5 Hz, 1 H), 3.98-3.82 (m, 1 H), 3.8-3.55(m, 8 H), 3.32(t, J = 9.3 Hz, 1 H), 1.35(d, J = 6.3 Hz, 3 H), 1.3-1.11(m, 9 H) |
| 208 | 4-OC₂F₅ phenyl | 1,3 | 1,2,4-triazole | 1,4-phenyl | β | A | 602.8 [M + H]⁺ | — | 8.6(s, 1 H), 8.2(d, J = 8 Hz, 2 H), 7.8(d, J = 8 Hz, 2 H), 7.55(d, J = 9 Hz, 2 H), 7.39(d, J = 9 Hz, 2 H), 6.84(s, 1 H), 6.21(d, J = 1.5 Hz, 1 H), 3.65-3.44 (m, 12 H), 3.22(t, J = 9.3 Hz, 1 H), 1.35(d, J = 6.3 Hz, 3 H) |
| 209 | 4-OCF₃ phenyl | 1,3 | 1,2,4-triazole | 1,4-phenyl | α | C | | 144-147 | 8.58(s, 1 H), 8.2(d, J = 8.6 Hz, 2 H), 7.82(d, J = 8 Hz, 2 H), 7.56(d, J = 9 Hz, 2 H), 7.41(d, J = 9 Hz, 2 H), 6.85(s, 1 H), 6.22(d, J = 1.5 Hz, 1 H), 3.75-3.48(m, 11 H), 3.23(t, J = 9.3 Hz, 1 H), 1.69(m, 2 H), 1.35(d, J = 6.3 Hz, 3 H), 1.00(t, J = 7.5 Hz, 3 H) |
| 210 | 4-OCF₃ phenyl | 1,3 | 1,2,4-triazole | 1,4-phenyl | β | B | 566 [M]⁺ | — | 8.55(s, 1 H), 8.2(d, J = 8 Hz, 2 H), 7.82(d, J = 8 Hz, 2 H), 7.55(d, J = 9 Hz, 2 H), 7.41(d, J = 9 Hz, 2 H), 6.95(s, 1 H), 5.66(s, 1 H), 3.7-3.3(m, 11 H), |

TABLE 6-continued

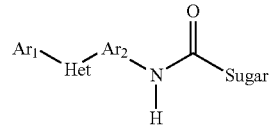

| # | Ar₁ | Het link[1] | Het | Ar₂ | Anomer | Sugar[2] | M.S. | Mp (° C.) | ¹H NMR (CDCl₃, δ)[3] |
|---|---|---|---|---|---|---|---|---|---|
| | | | | | | | | | 3.18(t, J = 9 Hz, 1 H), 1.35(d, J = 6.3 Hz, 3 H), 1.25(t, J = 7.5 Hz, 3 H) |
| 212 | 4-OCF₃ phenyl | 1,3 | 1,2,4-triazole | 1,4-phenyl | α/β | L | 538 [M]⁺ | — | 8.55(s, 1 H), 8.16(d, J = 8.4 Hz, 2 H), 7.79(d, J = 8.8 Hz, 2 H), 7.53(d, J = 8.8 Hz, 2 H), 7.38(d, J = 8.7 Hz, 2 H), 6.94 and 6.89(2 s, 1 H), 6.27(d, J = 3.7 Hz, major) and 5.56(d, J = 7.7 Hz, minor, total 1 H in a 1.6:1 α:β ratio), 4.04-3.16(series of s and m, 14 H) |
| 213 | 4-OC₂F₅ phenyl | 1,3 | 1,2,4-triazole | 1,4-phenyl | α/β | L | 588 [M]⁺ | — | 8.56(s, 1 H), 8.16(d, J = 8.8 Hz, 2 H), 7.81(d, J = 9.1 Hz, 2 H), 7.54(d, J = 8.8 Hz, 2 H), 7.39(d, J = 9.0 Hz, 2 H), 6.95 and 6.90(br, total 1 H), 6.27(d, J = 3.7 Hz, major) and 5.57(d, J = 7.5 Hz, minor, total 1 H in a 3.8:1 α:β ratio), 4.08-2.96(series of s and m, 14 H) |
| 214 | 4-OCF₃ phenyl | 1,3 | 1,2,4-triazole | 1,4-phenyl | α | M | 538 [M]⁺ | 176-179 | 8.55(s, 1 H), 8.16(d, J = 8.4 Hz, 2 H), 7.79(d, J = 9.0 Hz, 2 H), 7.53(d, J = 8.3 Hz, 2 H), 7.38(d, J = 8.8 Hz, 2 H), 6.89(s, 1 H), 6.15(d, J = 3.4 Hz, 1 H), 4.00-3.93(m, 1 H), 3.69-3.39(series of s and m, 13 H) |
| 215 | 4-OCF₃ phenyl | 1,3 | 1,2,4-triazole | 1,4-phenyl | β | M | 538 [M]⁺ | 77-80 | 8.54(s, 1 H), 8.14(d, J = 9.0 Hz, 2 H), 7.79(d, J = 9.0 Hz, 2 H), 7.54(d, J = 9.0 Hz, 2 H), 7.37(d, J = 9.1 Hz, 2 H), 7.08(br, 1 H), 6.19(d, J = 3.1 Hz, 1 H), 4.05(dd, J = 12.8, 1.7 Hz, 1 H), 3.74(t, J = 3.5 Hz, 1 H), 3.72-3.66(m, 2 H), 3.57-3.51(2 s and m, 7 H), 3.46(s, 3 H) |
| 216 | 4-OC₃F₇ phenyl | 1,3 | 1,2,4-triazole | 1,4-phenyl | α | C | 681.12 [M + H]⁺ | | 8.7(s, 1 H), 8.2(d, J = 8 Hz, 2 H), 7.83(d, J = 8 Hz, 2 H), 7.55(d, J = 9 Hz, 2 H), 7.41(d, J = 9 Hz, 2 H), 6.93(s, 1 H), 6.21(br s, 1 H), 3.7-3.44(m, 11 H), 3.23(t, J = 9.3 Hz, 1 H), 1.71(m, 2 H), 1.35(d, J = 6.3 Hz, 3 H), 0.98(t, J = 7.5 Hz, 3 H) |
| 217 | 4-OC₂F₅ phenyl | 1,3 | 1,2,4-triazole | 1,4-phenyl | α | O | 633 [M + H]⁺ | 71-81 | 8.57(s, 1 H), 8.15(d, J = 8.7 Hz, 2 H), 7.80(d, J = 9.0 Hz, 2 H), 7.53(d, J = 8.5 Hz, 2 H), 7.38(d, J = 8.9 Hz, 2 H), 6.97(s, 1 H), 6.35(d, J = 4.0 Hz, 1 H), 3.78-3.46(m, 13 H), 3.42-3.16(m, 5 H) |
| 218 | 4-OCF₃ phenyl | 1,3 | 5-vinyl-1,2,4-triazole | 1,4-phenyl | α | β | 592 [M]⁺ | | 8.18(d, J = 8.20 Hz, 2 H), 7.58(d, J = 8.24 Hz, 2 H), 7.52(d, J = 8.20 Hz, 2 H), 7.40(d, J = 8.24 Hz, 2 H), 6.78(s, 1 H), 7.62-7.58(m, 2 H), 6.20(d, J = 1.85 Hz, 1 H), 7.78-7.72(m, 1 H), 3.79-3.61(m, 4 H), 3.57(s, 3 H), 3.56(s, 3 H), 3.44(dd, J = 9.31, 3.36 Hz, 1 H), 3.18(t, J = 9.48 Hz, 1 H), 1.36-1.23(m, 6 H) |
| 219 | 4-OCF₃ phenyl | 1,3 | 5-isobutyl-1,2,4-triazole | 1,4-phenyl | α | B | 622 [M]⁺ | | 8.08(d, J = 8.28 Hz, 2 H), 7.58-7.48(m, 4 H), 7.38(d, J = 8.28 Hz, 2 H), 7.06 (s, 1 H), 6.20(d, J = 1.85 Hz, 1 H), 3.79-3.61(m, 4 H), 3.57(s, 3 H), 3.56(s, 3 H), 3.44(dd, J = 9.31, 3.36 Hz, 1 H), 3.18(t, J = 9.48 Hz, 1 H), 2.68(d, J = 6.32 Hz, 2 H), 2.24-2.18(m, 1 H), 1.36-1.23(m, 6 H), 0.98-0.90(m, 6 H) |
| 220 | 4-OCF₃ phenyl | 1,3 | 5-propen-2-yl)-1,2,4-triazole | 1,4-phenyl | α | B | 606 [M]⁺ | | 8.14(d, J = 8.24 Hz, 2 H), 7.58(d, J = 8.28 Hz, 2 H), 7.52(d, J = 8.24 Hz, 2 H), 7.38(d, J = 8.28 Hz, 2 H), 6.88(s, 1 H), 6.20(d, J = 1.85 Hz, 1 H), 5.44 (s, 1 H), 5.32(s, 1 H), 3.79-3.61(m, 4 H), 3.57(s, 3 H), 3.56(s, 3 H), 3.44(dd, J = 9.31, 3.36 Hz, 1 H), 3.18(t, J = 9.48 Hz, 1 H), 2.08(s, 3 H), 1.36-1.23(m, 6 H) |
| 221 | 4-OCF₃ phenyl | 1,3 | 5-(methylthio-ethyl)-1,2,4-triazole | 1,4-phenyl | α | B | 640 [M]⁺ | | 8.08(d, J = 8.22 Hz, 2 H), 7.60(d, J = 8.26 Hz, 2 H), 7.52(d, J = 8.22 Hz, 2 H), 7.42(d, J = 8.26 Hz, 2 H), 6.92(s, 1 H), 6.20(d, J = 1.85 Hz, 1 H), 3.79-3.61(m, 4 H), 3.57(s, 3 H), 3.56(s, 3 H), 3.44(dd, J = 9.31, 3.36 Hz, 1 H), 3.22-3.08(m, 3 H), 2.98(t, J = 9.42 Hz, 2 H), 2.04(s, 3 H), 1.36-1.23(m, 6 H) |
| 222 | 4-OCF₃ phenyl | 1,3 | 5-trifluoro-methyl-1,2,4-triazole | 1,4-phenyl | α | B | 634 [M]⁺ | | 8.12(d, J = 8.28 Hz, 2 H), 7.58(d, J = 8.28 Hz, 2 H), 7.52(d, J = 8.28 Hz, 2 H), 7.42(d, J = 8.28 Hz, 2 H), 6.84(s, 1 H), 6.20(d, J = 1.85 Hz, 1 H), 3.79-3.61(m, 4 H), 3.57(s, 3 H), 3.56(s, 3 H), 3.44(dd, J = 9.31, 3.36 Hz, 1 H), 3.18 (t, J = 9.48 Hz, 1 H), 1.36-1.23(m, 6 H) |
| 223 | 4-OCF₃ phenyl | 1,3 | 1,2,4-triazole | 2-Br, 1,4-phenyl | α | B | 645 [M]⁺ | | 8.58(s, 1 H), 8.38(s, 1 H), 8.32(d, J = 8.30 Hz, 1 H), 8.18(d, J = 8.30 Hz, 1 H), 7.80(d, J = 8.22 Hz, 2 H), 7.42(d, J = 8.22 Hz, 2 H), 7.28(s, 1 H), 6.20 (d, J = 1.85 Hz, 1 H), 3.79-3.61(m, 4 H), 3.57(s, 3 |

TABLE 6-continued

Ar₁–Het–Ar₂–N(H)–C(=O)–Sugar

| # | Ar₁ | Het link[1] | Het | Ar₂ | Anomer | Sugar[2] | M.S. | Mp (° C.) | ¹H NMR (CDCl₃, δ)[3] |
|---|---|---|---|---|---|---|---|---|---|
| | | | | | | | | | H), 3.56(s, 3 H), 3.44(dd, J = 9.31, 3.36 Hz, 1 H), 3.18(t, J = 9.48 Hz, 1 H), 1.36-1.23(m, 6 H) |
| 224 | 4-OC₂F₅ phenyl | 1,3 | 1,2,4-tirazole | 2-Br, 1,4-phenyl | α | B | 695 [M]⁺ | | 8.56(s, 1 H), 8.38(s, 1 H), 8.36(d, J = 8.26 Hz, 1 H), 8.18(d, J = 8.26 Hz, 1 H), 7.82(d, J = 8.28 Hz, 2 H), 7.42(d, J = 8.28 Hz, 2 H), 7.28(s, 1 H), 6.20 (d, J = 1.85 Hz, 1 H), 3.79-3.61(m, 4 H), 3.57(s, 3 H), 3.56(s, 3 H), 3.44(dd, J = 9.31, 3.36 Hz, 1 H), 3.18(t, J = 9.48 Hz, 1 H), 1.36-1.23(m, 6 H) |
| 225 | 4-OC₃F₇ phenyl | 1,3 | 1,2,4-triazole | 1,4-phenyl | α | B | | 158-162 | 8.59(s, 1 H), 8.18(d, J = 8.7 Hz, 2 H), 7.84(d, J = 8 Hz, 2 H), 7.58(d, J = 8 Hz, 2 H), 7.38(d, J = 8.7 Hz, 2 H), 6.85(s, 1 H), 6.22(d, J = 1.8 Hz, 1 H), 3.65-3.45(m, 11 H), 3.20(t, J = 9.3 Hz, 1 H), 1.33(m, 6 H) |
| 226 | 4-OCF₃ phenyl | 2,4 | 5-MeO₂C—1,2,4-triazolin-3-one | 1,4-phenyl | α | B | 639 [M − H]⁺ | 113-120 dec | 8.10(d, J = 10.1 Hz, 2 H), 7.60-7.51(m, 2 H), 7.34-7.27(m, 4 H), 6.85(br H), 6.18(d, J = 1.7 Hz, 0.9 H), 5.65(d, J = 0.9 Hz, 0.1 H), 3.90(s, 3 H), 3.78-3.33(m, 11 H), 3.21(t, J = 9.4 Hz, 1 H), 1.38-1.25(m, 6 H) (9:1 mixture of α:β) |
| 227 | 4-OCF₃ phenyl | 2,4 | 5-MeO₂C—1,2,4-triazolin-3-one | 1,4-phenyl | β | B | 639 [M − H]⁺ | 122-128 | 8.09(d, J = 9.5 Hz, 2 H), 7.56(d, J = 8.9 Hz, 2 H), 7.31(d, J = 8.7 Hz, 4 H), 6.94(br, 1 H), 5.65(d, J = 0.8 Hz, 1 H), 3.90(s, 3 H), 3.79-3.54(m, 9 H), 3.41-3.34(m, 2 H), 3.16(t, J = 9.2 Hz, 1 H), 1.36(d, J = 6.1 Hz, 3 H), 1.29(t, J = 7.0 Hz, 3 H) |
| 228 | 4-OCF₃ phenyl | 2,4 | 1,2,4-triazolin-3-one | 1,4-phenyl | α | B | 581 [M − H]⁺ | 166-168 | 8.06(d, J = 9.0 Hz, 2 H), 7.81(s, 1 H), 7.58-7.46(m, 4 H), 7.29(d, J = 8.9 Hz, 2 H), 6.89(s, 1 H), 6.17(d, J = 1.8 Hz, 1 H), 3.79-3.52(m, 11 H), 3.19(t, J = 9.3 Hz, 1 H), 1.31(d, J = 6.3 Hz, 3 H), 1.27(t, J = 7.0 Hz, 3 H) |
| 229 | 4-CF₃ phenyl | 3.1 | 1,2,4-triazole | 1,4-phenyl | α | A | 536.0 [M + H]⁺ | 207 | 8.56(s, 1 H), 8.31(d, J = 8.3 Hz, 2 H), 7.76-7.69(m, 4 H), 7.60(d, J = 8.4 Hz, 2 H), 6.83(s, 1 H), 6.23(d, J = 1.9 Hz, 1 H), 3.74-3.66(m, 2 H), 3.59(s, 3 H), 3.57(s, 3 H), 3.54(s, 3 H), 3.50(dd, J = 9.5, 3.4 Hz, 1 H), 3.22(t, J = 9.5 Hz, 1 H), 1.34(d, J = 6.2 Hz, 3 H) |
| 230 | 2,4-Cl₂ phenyl | 2,5 | 1,3,4-oxadiazole | 1,4-phenyl | α | A | | | 8.15(d, 1 H), 7.93(d, 2 H), 7.9(m, 1 H), 7.55(d, 2 H), 7.22(d, 1 H), 8.80(br s, 1 H), 6.22(d, J = 1.7 Hz, 1 H), 3.7-3.4(m, 12 H), 3.22(t, J = 9.3 Hz, 1 H), 1.33 (d, J = 6.3 Hz, 3 H) |
| 231 | 3-Cl, 4-F phenyl | 2,4 | thiazole | 1,4-phenyl | | | | 110 | 8.15(m, 4 H), 7.66(d, J = 8 Hz, 2 H), 7.62(d, J = 1.5 Hz, 1 H), 7.44(d, J = 8 Hz, 1 H), 7.22(s, 1 H), 6.22(d, J = 1.5 Hz, 1 H), 4.8-4.5(m, 12 H), 3.2(t, J = 9.3 Hz, 1 H), 1.34(d, J = 6.3 Hz, 3 H) |
| 233 | 4-CF₃ phenyl | 2,4 | pyrimidine, 6-(C₃F₇) | 1,4-phenyl | α | A | 715.8 [M]⁺ | | 8.72(d, J = 8.6 Hz, 2 H), 8.29(d, J = 8.7 Hz, 2 H), 7.93(s, 1 H), 7.79(d, J = 8.4 Hz, 2 H), 7.66(d, J = 8.6 Hz, 2 H), 6.92(s, 1 H), 6.24(d, J = 1.9 Hz, 1 H), 3.71(m, 2 H), 3.59(s, 3 H), 3.58(s, 3 H), 3.55(s, 3 H), 3.51(m, 1 H), 3.23(t, J = 9.5 Hz, 1 H), 1.35(d, J = 6.2 Hz, 3 H) |
| 235 | 4-CF₃ phenyl | 2,4 | pyrimidine, 6-(CF₃) | 1,4-phenyl | α | A | 615.0 [M]⁺ | | 8.75(d, J = 8.7 Hz, 2 H), 8.3(d, J = 8.7 Hz, 2 H), 7.94(s, 1 H), 7.81(d, J = 8.7 Hz, 2 H), 7.67(d, J = 8.7 Hz, 2 H), 6.9(s, 1 H), 6.26(s, 1 H), 3.8-3.7(m, 1 H), 3.65-3.55(m, 11 H), 3.25(t, J = 9 Hz, 1 H), 1.36(d, J = 6.3 Hz, 3 H) |
| 236 | 4-OCF₃ phenyl | 5,2 | pyrimidine | 1,4-phenyl | α | C | 591.8 [M + H]⁺ | | 9.0(s, 2 H), 8.52(d, J = 8 Hz, 2 H), 7.68(d, J = 8 Hz, 2 H), 7.60(d, J = 9 Hz, 2 H), 7.38(d, J = 9 Hz, 2 H), 6.9(s, 1 H), 6.21(br s, 1 H), 3.7-3.44(m, 11 H), 3.23(t, J = 9.3 Hz, 1 H), 1.71(m, 2 H), 1.35(d, J = 6.3 Hz, 3 H), 0.98(t, J = 7.5 Hz, 3 H) |
| 237 | 4-OCF₃ phenyl | 5,3 | 1,2,4-triazine | 1,4-phenyl | α | B | 578 [M]⁺ | | 9.58(s, 1 H), 8.58(d, J = 8.26 Hz, 2 H), 8.32(d, J = 8.24 Hz, 2 H), 7.62(d, J = 8.26 Hz, 2 H), 7.38(d, J = 8.24 Hz, 2 H), 7.08(s, 1 H), 6.20(d, J = 1.85 Hz, 1 H), 3.79-3.61(m, 4 H), 3.57(s, 3 H), 3.56(s, 3 H), 3.44(dd, J = 9.31, 3.36 Hz, 1 H), 3.18(t, J = 9.48 Hz, 1 H), 1.36-1.23(m, 6 H) |
| 238 | 4-OCF₃ phenyl | 3,5 | 1,2,4-triazine | 1,4-phenyl | α | B | 578 [M]⁺ | | 9.58(s, 1 H), 8.72(d, J = 8.22 Hz, 2 H), 8.30(d, J = 8.26 Hz, 2 H), 7.72(d, J = 8.22 Hz, 2 H), 7.40(d, J = 8.26 Hz, 2 H), 7.12(s, 1 H), 6.20(d, J = 1.85 Hz, 1 H), 3.79-3.61(m, 4 H), 3.57(s, 3 H), 3.56(s, 3 H), 3.44(dd, J = 9.31, 3.36 Hz, 1 H), 3.18(t, J = 9.48 Hz, 1 H), 1.36-1.23(m, 6 H) |

TABLE 6-continued

Ar₁—Het—Ar₂—N(H)—C(=O)—Sugar

| # | Ar₁ | Het link[1] | Het | Ar₂ | Anomer | Sugar[2] | M.S. | Mp (° C.) | ¹H NMR (CDCl₃, δ)[3] |
|---|---|---|---|---|---|---|---|---|---|
| 239 | 4-OCF₃ phenyl | 5,2 | pyridine | 1,4-phenyl | α | B | | | |
| 240 | 4-OCF₃ phenyl | 5,3 | 1,2,4-oxadiazole | 1,4-phenyl | α | B | 567 [M]⁺ | | 8.27(d, J = 8.9 Hz, 2 H), 8.14(d, J = 8.6 Hz, 2 H), 7.58(d, J = 8.6 Hz, 2 H), 7.39(d, J = 8.6 Hz, 2 H), 6.88(d, 1 H), 6.20(s, 1 H), 3.50-3.80(m, 11 H), 3.21 (t, J = 9.6 Hz, 1 H), 1.33(d, J = 6.3 Hz, 3 H), 1.29(t, J = 6.9 Hz, 3 H) |
| 241 | 4-OCF₃ phenyl | 1,4 | piperazine | 1,4-phenyl | α | B | 583 [M]⁺ | 155-157 | 7.38(d, J = 8.24 Hz, 2 H), 7.16(d, J = 8.30 Hz, 2 H), 6.98-6.89(m, 4 H), 6.62 (s, 1 H), 6.20(d, J = 1.85 Hz, 1 H), 3.79-3.61(m, 4 H), 3.57(s, 3 H), 3.56(s, 3 H), 3.39-3.18(m, 9 H), 3.18(t, J = 9.48 Hz, 1 H), 1.36-1.23(m, 6 H) |
| 242 | 4-OCF₃ phenyl | 1,4 | 2,5-piperazine-dione | 1,4-phenyl | α | B | 611 [M]⁺ | 228-233 | 7.47(d, J = 9 Hz, 2 H), 7.42(d, J = 9 Hz, 2 H), 7.34(m, 4 H), 7.0(s, 1 H), 6.19 (d, J = 1.8 Hz, 1 H), 4.5(m, 4 H), 3.74(m, 1 H), 3.7-3.5(m, 10 H), 3.23(t, J = 9.5 Hz, 1 H), 1.35(d, J = 6.3 Hz, 3 H), 1.30(t, J = 7 Hz, 3 H) |
| 243 | 4-OC₂F₅ phenyl | 1,4 | 2,5-piperazine-dione | 1,4-phenyl | α | B | 661 [M]⁺ | | 8.20(d, J = 8.26 Hz, 2 H), 7.43(d, J = 8.30 Hz, 2 H), 7.36(d, J = 8.26 Hz, 2 H), 7.22(d, J = 8.30 Hz, 2 H), 6.89(s, 1 H), 6.20(d, J = 1.85 Hz, 1 H), 4.38 (s, 2 H), 4.18(s, 2 H), 3.79-3.61(m, 4 H), 3.57(s, 3 H), 3.56(s, 3 H), 3.44(dd, J = 9.31, 3.36 Hz, 1 H), 3.18(t, J = 9.48 Hz, 1 H), 1.36-1.23(m, 6 H) |
| 244 | 4-OC₂F₅ phenyl | 1,3 | 1,3,4-triazole | 1,4-phenyl | α/β | R | 559 [M]⁺ | 171-175 | 8.58(s, 1 H), 8.16(d, J = 8.7 Hz, 2 H), 7.81(d, J = 8.7 Hz, 2 H), 7.52(d, J = 8.7 Hz, 2 H), 7.4(d, J = 8.7 Hz, 2 H), 6.93(s, 1 H), 6.3(d, J = 2 Hz) and 5.79 (dd, J = 10, 2 Hz, total of 1 H in a 1:3 α:β ratio), 3.51(m, 1 H), 3.46(s, 3 H), 3.3(m, 1 H), 3.22(t, J = 9.3 Hz, 1 H), 2.58(s, 1 H), 2.43(m, 1 H), 1.64(m, 1 H), 1.39(d, J = 6 Hz, 3 H) |
| 245 | 4-OC₂F₅ phenyl | 1,3 | 1,2,4-triazole | 1,4-phenyl | β | Q | 572 [M]⁺ | 151-155 | 8.52(s, 1 H), 8.16(d, J = 8.7 Hz, 2 H), 7.81(d, J = 8.7 Hz, 2 H), 7.51(d, J = 8.4 Hz, 2 H), 7.40(d, J = 8.7 Hz, 2 H), 6.94(s, 1 H), 5.73(dd, J = 10.2, 2 Hz, 1 H), 3.7-3.3(series of m, 8 H), 2.81(t, J = 9 Hz, 1 H), 2.4(m, 1 H), 1.6(m, 1 H), 1.37(d, J = 6.3 Hz, 3 H) |
| 246 | 4-OCF₃ phenyl | 1,3 | 1,2,4-triazole | 1,4-phenyl | α | P | 505 [M]⁺ | 134-138 | 8.55(s, 1 H), 8.15(d, J = 7.9 Hz, 2 H), 7.79(d, J = 9.2 Hz, 2 H), 7.54(d, J = 8.9 Hz, 2 H), 7.38(d, J = 8.7 Hz, 2 H), 6.83(br s, 1 H), 6.13(d, J = 2.4 Hz, 1 H), 3.99-3.89(m, 1 H), 2.35-2.24(m, 7 H), 2.05-1.98(m, 1 H), 1.91-1.68(m, 3 H), 1.28(d, J = 6.0 Hz, 3 H) |
| 247 | 4-OCF₃ phenyl | 4,2 | 4,5-dihydro-oxazole | 1,4-phenyl | α | B | 568 [M⁺] | | 8.02(d, J = 8.20 Hz, 2 H), 7.52(d, J = 8.20 Hz, 2 H), 7.38(d, J = 8.24 Hz, 2 H), 7.22(d, J = 8.24 Hz, 2 H), 6.84(s, 1 H), 6.20(d, J = 1.85 Hz, 1 H), 5.44(t, J = 9.42 Hz, 1 H), 4.82(t, J = 9.48 Hz, 1 H), 4.28(t, J = 9.48 Hz, 1 H), 3.79-3.61(m, 4 H), 3.57(s, 3 H), 3.56(s, 3 H), 3.44(dd, J = 9.31, 3.36 Hz, 1 H), 3.18 (t, J = 9.48 Hz, 1 H), 1.36-1.23(m, 6 H) |
| 248 | 4-OCF₃ phenyl | 3,6 | pyridazine | 1,4-phenyl | α | B | 577 [M]⁺ | | 8.19(d, J = 8.9 Hz, 2 H), 8.16(d, J = 8.9 Hz, 2 H), 7.94(s, 1 H), 7.90(s, 1 H), 7.61(d, J = 8.6 Hz, 2 H), 7.39(d, J = 8.6 Hz, 2 H), 6.91(s, 1 H), 6.21(s, 1 H), 3.54-3.80(m, 5 H), 3.60(s, 3 H), 3.57(s, 3 H), 3.21(t, J = 9.2 Hz, 1 H), 1.20-1.35(m, 6 H) |
| 249 | 4-CF₃ phenyl | 4,2 | 1,3,4-oxadiazolin-5-one | 1,4-phenyl | α | B | 566 [M − H] | | 8.15(d, J = 8.7 Hz, 2 H), 7.95(d, J = 8.7 Hz, 2 H), 7.75(d, J = 8.7 Hz, 2 H), 7.61(d, J = 8.7 Hz, 2 H), 6.90(s, 1 H), 6.22(s, 1 H), 3.8-3.55(series of s and m, 11 H), 3.21(t, J = 9.3 Hz, 1 H), 1.5(m, 6 H) |

[1] Het link: Atoms on Het to which Ar₃ and Ar₂ are attached respectively.
[2] Key to Sugars: See Table 4
[3] All NMR data measured in CDCl₃ at 300 or 400 MHz unless otherwise noted TABLE 7
| BAW 50 ug/cm2 | BAW HTS | Compound | Ar1 | Het | Ar2 |
|---|---|---|---|---|---|
| B | A | 1 | 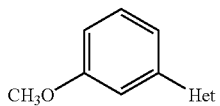 | 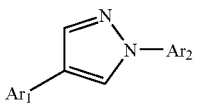 | 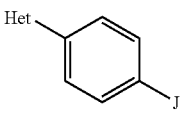 |
| B | A | 2 | 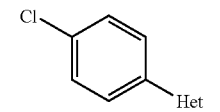 | 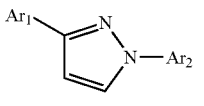 | 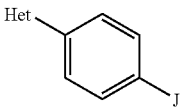 |
| B | A | 3 | 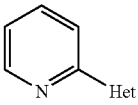 | 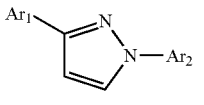 | 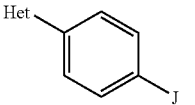 |
| B | B | 4 | 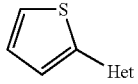 | 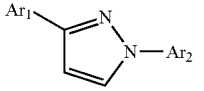 | 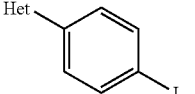 |
| A | B | 5 | 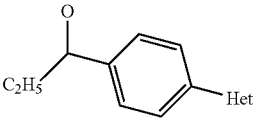 | 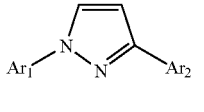 | 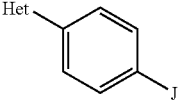 |
| A | B | 6 | 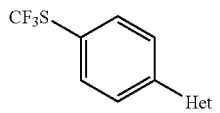 | 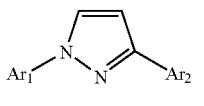 | 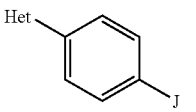 |
| A | B | 7 | 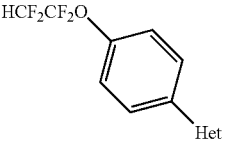 | 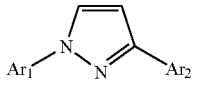 | 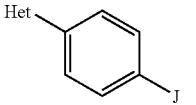 |
| A | B | 8 | 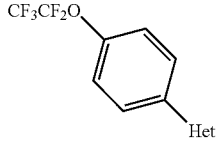 | 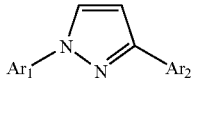 | 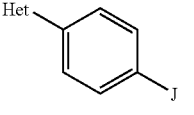 |
| A | B | 9 | 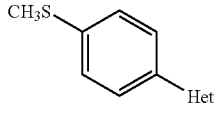 | 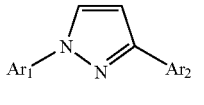 | 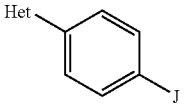 |
| A | B | 10 | 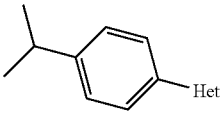 | 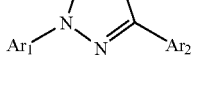 | 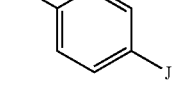 |
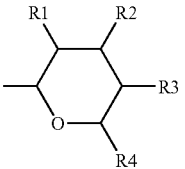

TABLE 7-continued
| | | | | | |
|---|---|---|---|---|---|
| A | B | 11 | 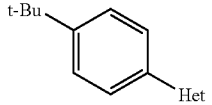 | 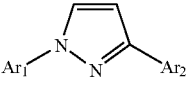 | 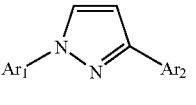 |
| A | B | 12 | 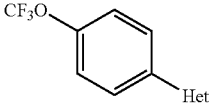 | 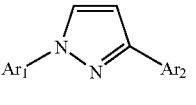 | 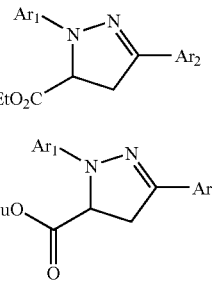 |
| A | B | 13 | 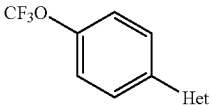 | 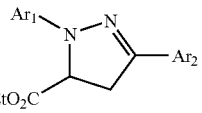 | 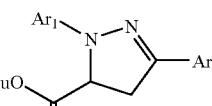 |
| B | B | 14 | 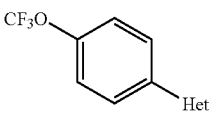 | 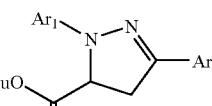 | 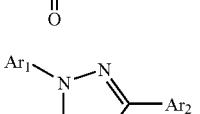 |
| A | B | 15 | 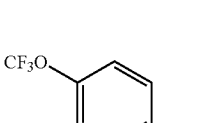 | 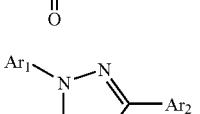 | 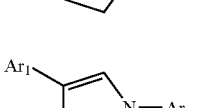 |
| B | A | 16 | 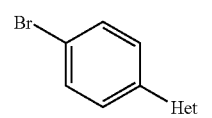 | 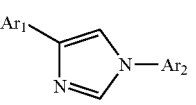 | 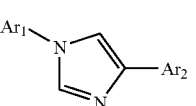 |
| B | A | 17 | 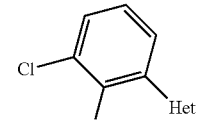 | 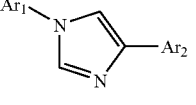 | 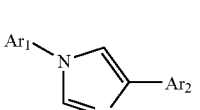 |
| B | A | 18 | 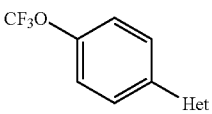 | 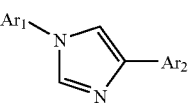 | 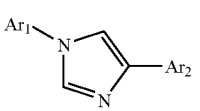 |
| B | B | 19 | 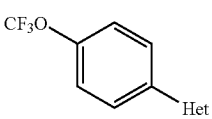 | 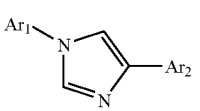 | 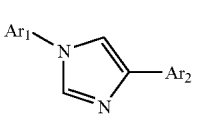 |
| B | A | 20 | 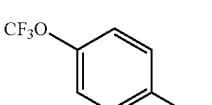 | 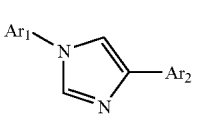 | 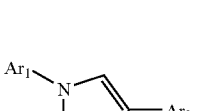 |
| B | A | 21 | 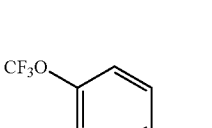 | 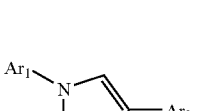 | 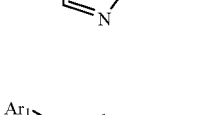 |
| B | B | 22 | 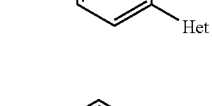 | 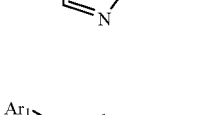 | 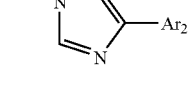 |

TABLE 7-continued

| | | | | | |
|---|---|---|---|---|---|
| B | B | 23 | 4-iodo-pyridin-2-yl—Het | Ar₁–N(imidazole)–Ar₂ (1,4) | Het—C₆H₄—J |
| B | A | 24 | 3,5-difluorophenyl—Het | Ar₁–N(imidazole)–Ar₂ (1,4) | Het—C₆H₄—J |
| B | B | 25 | 4-(CF₃O)-C₆H₄—Het | Ar₁–N(imidazole)–Ar₂ (1,4) | Het—C₆H₃(OMe)—J |
| A | A | 26 | 4-(CF₃O)-C₆H₄—Het | Ar₁–N(imidazole)–Ar₂ (1,5) | Het—C₆H₄—J |
| A | A | 27 | 4-(C₃H₇)-C₆H₄—Het | Ar₁–N(imidazole)–Ar₂ (1,4) | Het—C₆H₄—J |
| A | A | 28 | 4-(CF₃O)-C₆H₄—Het | Ar₁–N(imidazole)–Ar₂ (1,4) | Het—C₆H₄—J |
| A | B | 29 | 4-(C₃H₇)-C₆H₄—Het | Ar₁–N(imidazole)–Ar₂ (1,4) | Het—C₆H₄—J |
| A | A | 30 | 4-(CF₃O)-C₆H₄—Het | Ar₁–N(imidazole)–Ar₂ (1,4) | Het—C₆H₄—J |
| A | A | 31 | 4-(CF₃O)-C₆H₄—Het | Ar₁–N(imidazole)–Ar₂ (1,4) | Het—C₆H₄—J |
| A | A | 32 | 5-(CF₃)-pyridin-2-yl—Het | Ar₁–N(imidazole)–Ar₂ (1,4) | Het—C₆H₄—J |
| A | A | 33 | 5-(CF₃)-pyridin-2-yl—Het | Ar₁–N(imidazole)–Ar₂ (1,4) | Het—C₆H₄—J |
| A | B | 34 | 4-bromo-2-chloro-phenyl—Het | Ar₁–N(imidazole)–Ar₂ (1,4) | Het—C₆H₄—J |
| A | B | 35 | 4-(CF₃O)-C₆H₄—Het | Ar₁–N(imidazole)–Ar₂ (1,4) | Het—C₆H₃(OMe)—J |

TABLE 7-continued

| | | | | | |
|---|---|---|---|---|---|
| A | B | 36 | 4-(CF₃O)-C₆H₄-Het | Ar₁-imidazole-Ar₂ | Het-C₆H₃(F)-J |
| A | B | 37 | 4-(CF₃CH₂O)-C₆H₄-Het | Ar₁-imidazole-Ar₂ | Het-C₆H₄-J |
| A | B | 38 | 2,3,4,5-tetrafluoropyridin-6-yl-Het | Ar₁-imidazole-Ar₂ | Het-C₆H₄-J |
| A | B | 39 | 5-iodopyridin-2-yl-Het | Ar₁-imidazole-Ar₂ | Het-C₆H₄-J |
| A | B | 40 | 4-(CF₃)-C₆H₄-Het | Ar₁-imidazole-Ar₂ | Het-C₆H₃(OCH₃)-J |
| A | B | 41 | 4-(H₃C)-C₆H₄-Het | Ar₁-imidazole-Ar₂ | Het-C₆H₄-J |
| A | B | 42 | 4-(F₃C)-C₆H₄-Het | Ar₁-imidazole-Ar₂ | Het-C₆H₄-J |
| A | B | 43 | 4-Cl-C₆H₄-Het | Ar₁-imidazole-Ar₂ | Het-C₆H₄-J |
| A | B | 44 | 4-(CH₃O)-C₆H₄-Het | Ar₁-imidazole-Ar₂ | Het-C₆H₄-J |
| A | B | 45 | 4-Br-C₆H₄-Het | Ar₁-imidazole-Ar₂ | Het-C₆H₄-J |
| A | B | 46 | 4-iPr-C₆H₄-Het | Ar₁-imidazole-Ar₂ | Het-C₆H₄-J |
| A | B | 47 | 4-I-C₆H₄-Het | Ar₁-imidazole-Ar₂ | Het-C₆H₄-J |

TABLE 7-continued

| | | | | | |
|---|---|---|---|---|---|
| A | B | 48 | t-Bu—⟨phenyl⟩—Het | Ar₁–N(imidazole)–Ar₂ | Het—⟨phenyl⟩—J |
| A | B | 49 | CF₃O—⟨phenyl⟩—Het | Ar₁–N(imidazole)–Ar₂ | Het—⟨phenyl(2,3-diF)⟩—J |
| A | A | 50 | CF₃O—⟨phenyl⟩—Het | Ar₁–N(imidazole)–Ar₂ | Het—⟨phenyl(Cl)⟩—J |
| A | B | 51 | CF₃CF₂O—⟨phenyl⟩—Het | Ar₁–N(imidazole)–Ar₂ | Het—⟨phenyl⟩—J |
| A | B | 52 | CF₃CF₂O—⟨phenyl⟩—Het | Ar₁–N(imidazole)–Ar₂ | Het—⟨phenyl⟩—J |
| A | A | 53 | CF₃O—⟨phenyl⟩—Het | Ar₁–N–N=Ar₂ pyrazoline, EtO₂C, CO₂Et | Het—⟨phenyl⟩—J |
| A | A | 54 | CF₃O—⟨phenyl⟩—Het | Ar₁–N–N=Ar₂ pyrazoline, MeO₂C | Het—⟨phenyl⟩—J |
| A | A | 55 | CF₃O—⟨phenyl⟩—Het | Ar₁–N–N=Ar₂ pyrazoline, EtO₂C, nPr | Het—⟨phenyl⟩—J |
| A | A | 56 | CF₃O—⟨phenyl⟩—Het | Ar₁–N–N=Ar₂ pyrazoline, EtO₂C, Me | Het—⟨phenyl⟩—J |
| A | A | 57 | CF₃O—⟨phenyl⟩—Het | Ar₁–(imidazole)–N–Ar₂ | Het—⟨phenyl⟩—J |
| A | A | 58 | CF₃O—⟨phenyl⟩—Het | Ar₁–N(imidazole)–Ar₂ | Het—⟨phenyl(meta)⟩—J |

TABLE 7-continued
| | | | | | |
|---|---|---|---|---|---|
| A | A | 59 | 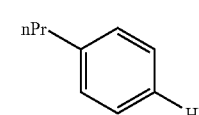 | 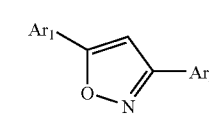 | 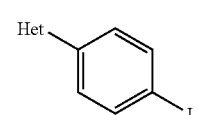 |
| A | A | 60 | 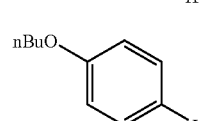 | 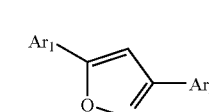 | 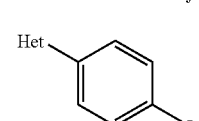 |
| A | A | 61 | 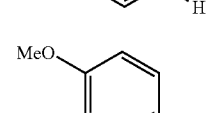 | 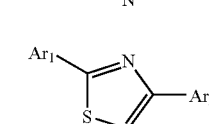 | 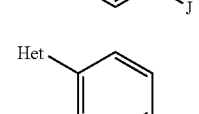 |
| A | A | 62 | 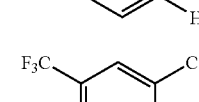 | 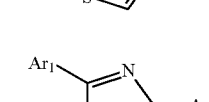 | 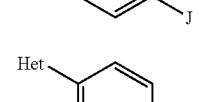 |
| A | A | 63 | 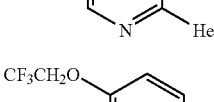 | 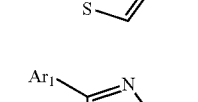 | 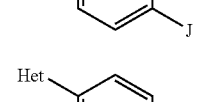 |
| A | A | 64 | 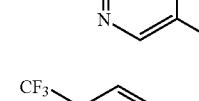 | 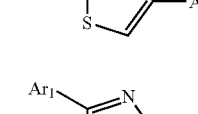 | 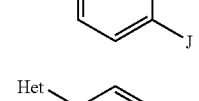 |
| A | A | 65 | 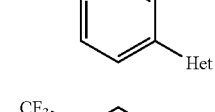 | 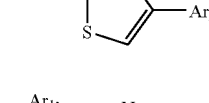 | 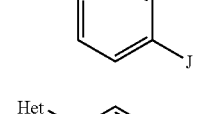 |
| A | A | 66 | 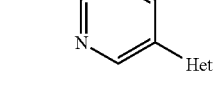 | 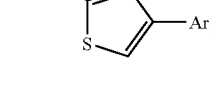 | 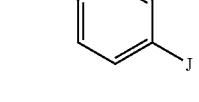 |
| A | B | 67 | 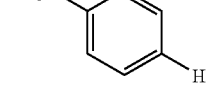 | 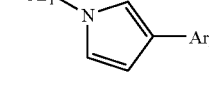 | 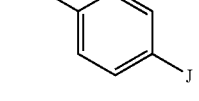 |
| A | B | 68 | 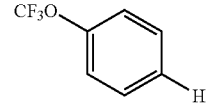 | 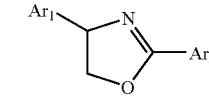 | 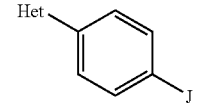 |
| B | B | 69 | 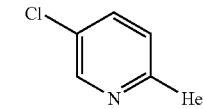 | 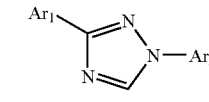 | 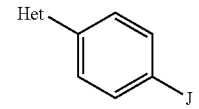 |
| B | A | 70 | 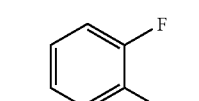 | 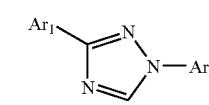 | 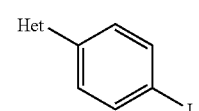 |
| B | A | 71 | | | |

TABLE 7-continued

| | | | | | |
|---|---|---|---|---|---|
| A | A | 72 | CF₃—⟨phenyl⟩—Het | Ar₁-triazole-Ar₂ | Het—⟨phenyl⟩—J |
| A | B | 73 | ⟨phenyl⟩—Het | Ar₁-pyrazoline-Ar₂ | Het—⟨phenyl⟩—J |
| A | B | 74 | CF₃—⟨phenyl⟩—Het | Ar₁-triazole-Ar₂ | Het—⟨phenyl⟩—J |
| B | A | 75 | Cl—⟨phenyl⟩—Het | Ar₁-triazole-Ar₂ | Het—⟨phenyl⟩—J |
| B | B | 76 | H₃C—⟨phenyl⟩—Het | Ar₁-triazole-Ar₂ | Het—⟨phenyl⟩—J |
| B | B | 77 | CH₃O—⟨phenyl⟩—Het | Ar₁-triazole-Ar₂ | Het—⟨phenyl⟩—J |
| A | B | 78 | CF₃—⟨phenyl⟩—Het | Ar₁-triazole-Ar₂ | Het—⟨phenyl⟩—J |
| A | B | 79 | CF₃O—⟨phenyl⟩—Het | Ar₁-triazole-Ar₂ | Het—⟨phenyl⟩—J |
| A | A | 80 | CF₃—⟨phenyl⟩—Het | Ar₁-triazole-Ar₂ | Het—⟨phenyl⟩—J |
| A | A | 81 | C₄H₉—⟨phenyl⟩—Het | Ar₁-triazole-Ar₂ | Het—⟨phenyl⟩—J |
| A | B | 82 | CF₃O—⟨phenyl⟩—Het | Ar₁-triazole-Ar₂ | Het—⟨phenyl⟩—J |
| A | B | 83 | iPr—⟨phenyl⟩—Het | Ar₁-triazole-Ar₂ | Het—⟨phenyl⟩—J |
| A | B | 84 | Cl—⟨phenyl⟩—Het | Ar₁-triazole-Ar₂ | Het—⟨phenyl⟩—J |

TABLE 7-continued

| | | | | | |
|---|---|---|---|---|---|
| A | B | 85 | 4-CH₃O-C₆H₄-Het | Ar₁-triazole-Ar₂ | Het-C₆H₄-J |
| A | B | 86 | 4-t-Bu-C₆H₄-Het | Ar₁-triazole-Ar₂ | Het-C₆H₄-J |
| A | B | 87 | 4-CF₃S-C₆H₄-Het | Ar₁-triazole-Ar₂ | Het-C₆H₄-J |
| A | B | 88 | 4-HCH₂CF₂O-C₆H₄-Het | Ar₁-triazole-Ar₂ | Het-C₆H₄-J |
| A | B | 89 | 4-CF₃CF₂O-C₆H₄-Het | Ar₁-triazole-Ar₂ | Het-C₆H₄-J |
| A | B | 90 | 4-CH₃S-C₆H₄-Het | Ar₁-triazole-Ar₂ | Het-C₆H₄-J |
| A | B | 91 | 3-CF₃O-C₆H₄-Het | Ar₁-triazole-Ar₂ | Het-C₆H₄-J |
| A | B | 92 | 4-CF₃CF₂O-C₆H₄-Het | Ar₁-triazole-Ar₂ | Het-C₆H₄-J |
| A | A | 93 | 4-CF₃CF₂O-C₆H₄-Het | Ar₁-triazole-Ar₂ | Het-C₆H₄-J |
| A | B | 94 | 5-CF₃CHFCF₂O-pyridin-2-yl-Het | Ar₁-triazole-Ar₂ | Het-C₆H₄-J |
| A | B | 95 | 4-CF₃-C₆H₄-Het | Ar₁-triazole-Ar₂ | Het-C₆H₄-J |
| A | B | 96 | 4-Cl-C₆H₄-Het | Ar₁-triazole-Ar₂ | Het-C₆H₄-J |

TABLE 7-continued

| | | | | | |
|---|---|---|---|---|---|
| A | B | 97 | t-Bu—⟨phenyl⟩—Het | Ar₁–[triazole]–Ar₂ | Het—⟨phenyl⟩—J |
| A | B | 98 | 3,4-Cl₂—⟨phenyl⟩—Het | Ar₁–[triazol-5(4H)-one]–Ar₂ | Het—⟨phenyl⟩—J |
| A | B | 99 | CF₃,F₄—⟨phenyl⟩—Het | Ar₁–[triazol-5(4H)-one]–Ar₂ | Het—⟨phenyl⟩—J |
| A | B | 100 | 2,4-F₂—⟨phenyl⟩—Het | Ar₁–[triazol-5(4H)-one]–Ar₂ | Het—⟨phenyl⟩—J |
| A | B | 101 | CF₃O—⟨phenyl⟩—Het | Ar₁–[triazol-5(4H)-one]–Ar₂ | Het—⟨phenyl⟩—J |
| B | B | 102 | Br—⟨phenyl⟩—Het | Ar₁–[triazole]–Ar₂ | Het—⟨phenyl⟩—J |
| A | B | 103 | CF₃S(O)—⟨phenyl⟩—Het | Ar₁–[triazole]–Ar₂ | Het—⟨phenyl⟩—J |
| A | B | 104 | CF₃SO₂—⟨phenyl⟩—Het | Ar₁–[triazole]–Ar₂ | Het—⟨phenyl⟩—J |
| A | B | 105 | CF₃CF₂S—⟨phenyl⟩—Het | Ar₁–[triazole]–Ar₂ | Het—⟨phenyl⟩—J |
| A | B | 106 | C₂F₅O—⟨phenyl⟩—Het | Ar₁–[triazole]–Ar₂ | Het—⟨phenyl⟩—J |
| A | A | 107 | CF₃—⟨phenyl⟩—Het | Ar₁–[triazole]–Ar₂ | Het—⟨phenyl⟩—J |
| A | B | 108 | C₂F₅—⟨phenyl⟩—Het | Ar₁–[triazole]–Ar₂ | Het—⟨phenyl⟩—J |

TABLE 7-continued

| | | | | | |
|---|---|---|---|---|---|
| A | A | 109 | C₂F₅O–⟨phenyl⟩–Het | Ar₁–(triazole)–Ar₂ | Het–⟨phenyl⟩–J |
| A | B | 110 | C₃F₇–⟨phenyl⟩–Het | Ar₁–(triazole)–Ar₂ | Het–⟨phenyl⟩–J |
| A | A | 111 | C₂F₅O–⟨phenyl⟩–Het | Ar₁–(triazole)–Ar₂ | Het–⟨phenyl⟩–J |
| A | B | 112 | CF₃SO₂O–⟨phenyl⟩–Het | Ar₁–(triazole)–Ar₂ | Het–⟨phenyl⟩–J |
| A | B | 113 | C₂F₅O–⟨phenyl⟩–Het | Ar₁–(triazole)–Ar₂ | Het–⟨phenyl⟩–J |
| A | A | 114 | C₂F₅O–⟨phenyl⟩–Het | Ar₁–(triazole)–Ar₂ | Het–⟨phenyl⟩–J |
| A | B | 115 | CF₃,Cl–⟨phenyl⟩–Het | Ar₁–(triazole)–Ar₂ | Het–⟨phenyl⟩–J |
| A | B | 116 | CF₃–⟨pyridyl⟩–Het | Ar₁–(triazole)–Ar₂ | Het–⟨phenyl⟩–J |
| B | B | 117 | Cl–⟨pyridazinyl⟩–Het | Ar₁–(triazole)–Ar₂ | Het–⟨phenyl⟩–J |
| A | B | 118 | CF₃–⟨pyridyl⟩–Het | Ar₁–(triazole)–Ar₂ | Het–⟨phenyl⟩–J |
| A | A | 119 | C₂F₅O–⟨phenyl⟩–Het | Ar₁–(triazole)–Ar₂ | Het–⟨phenyl⟩–J |
| A | A | 120 | CF₃O–⟨phenyl⟩–Het | Ar₁–(triazole)–Ar₂ | Het–⟨phenyl⟩–J |
| A | B | 121 | CF₃–⟨pyridyl⟩–Het | Ar₁–(triazole)–Ar₂ | Het–⟨phenyl⟩–J |

| | | | | | |
|---|---|---|---|---|---|
| A | A | 122 | 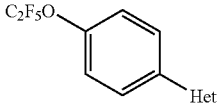 | 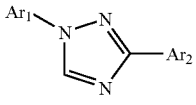 | 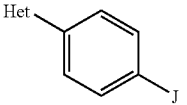 |
| A | B | 123 | 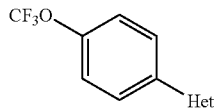 | 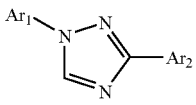 | 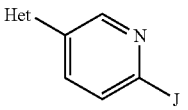 |
| A | B | 124 | 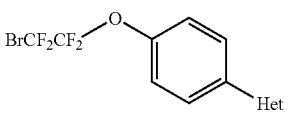 | 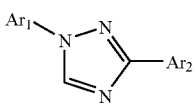 | 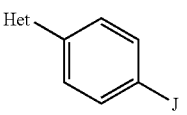 |
| A | B | 125 | 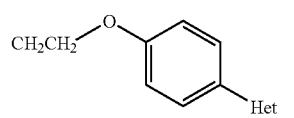 | 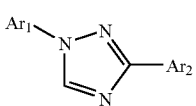 | 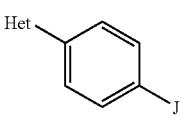 |
| A | B | 126 | 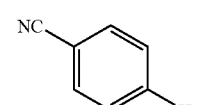 | 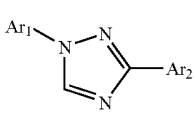 | 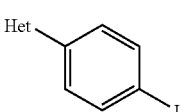 |
| A | B | 127 | 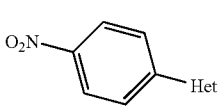 | 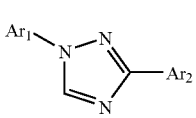 | 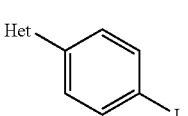 |
| A | B | 128 | 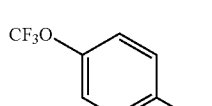 | 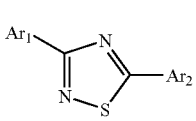 | 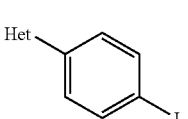 |
| A | B | 129 | 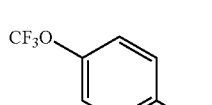 | 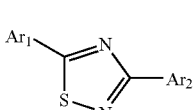 | 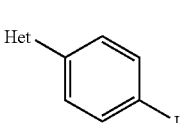 |
| A | A | 130 | 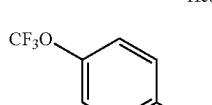 | 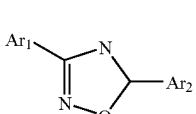 | 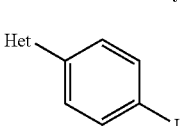 |
| B | B | 131 | 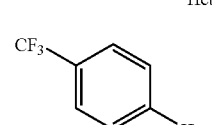 | 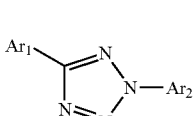 | 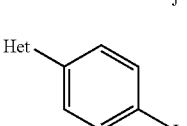 |
| A | B | 132 | 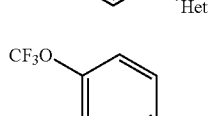 | 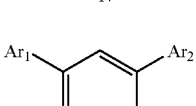 | 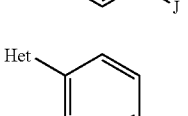 |
| A | B | 133 | 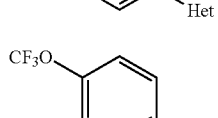 | 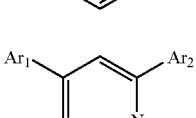 | 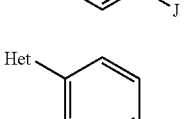 |
| A | B | 134 | 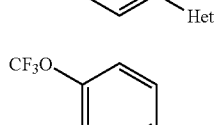 | 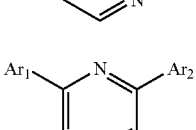 | 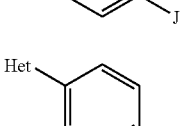 |

TABLE 7-continued

| | | | | | |
|---|---|---|---|---|---|
| A | B | 135 | CF₃O—⌬—Het | Ar₁—(pyridine-3,5-diyl)—Ar₂ | Het—⌬—J |
| A | B | 136 | CF₃O—⌬—Het | Ar₁—(pyrimidine-2,5-diyl)—Ar₂ | Het—⌬—J |
| A | B | 137 | CF₃O—⌬—Het | Ar₁—(pyrimidine-2,5-diyl)—Ar₂ | Het—⌬—J |
| A | A | 138 | CF₃O—⌬—Het | Ar₁—(pyrimidine-2,4-diyl)—Ar₂ | Het—⌬—J |
| A | A | 139 | CF₃O—⌬—Het | Ar₁—(pyrimidine-2,4-diyl)—Ar₂ | Het—⌬—J |
| A | B | 140 | CF₃O—⌬—Het | Ar₁—(pyrimidine-4,6-diyl)—Ar₂ | Het—⌬—J |
| A | A | 141 | C₂F₅O—⌬—Het | Ar₁—(pyrimidine-2,5-diyl)—Ar₂ | Het—⌬—J |
| A | A | 142 | C₂F₅O—⌬—Het | Ar₁—(pyrimidine-2,5-diyl)—Ar₂ | Het—⌬—J |
| A | B | 143 | CF₃O—⌬—Het (meta) | Ar₁—(pyrimidine-2,5-diyl)—Ar₂ | Het—⌬—J |
| A | B | 144 | CF₃O—⌬—Het | Ar₁—(pyrimidine-2,5-diyl)—Ar₂ | Het—⌬—J |
| A | B | 145 | CF₃O—⌬—Het | Ar₁—(pyrimidine-2,5-diyl)—Ar₂ | Het—⌬—J |
| A | B | 146 | CF₃O—⌬—Het | Ar₁—(pyrimidine-2,5-diyl)—Ar₂ | Het—⌬—J (meta) |
| B | B | 147 | OCF₃—⌬—Het (ortho) | Ar₁—(pyrimidine-2,5-diyl)—Ar₂ | Het—⌬—J (meta) |

TABLE 7-continued

| | | | | | |
|---|---|---|---|---|---|
| A | B | 148 | CF₃O–⟨⟩–Het | Ar₁–pyrimidine–Ar₂ | Het–⟨F⟩–J |
| A | B | 149 | CF₃O–⟨⟩–Het | Ar₁–pyrimidine–Ar₂ | Het–⟨⟩–J |
| B | B | 150 | H₃C–⟨⟩–Het | Ar₁–pyrimidine–Ar₂ | Het–⟨⟩–J |
| A | B | 151 | F₃C–⟨⟩–Het | Ar₁–pyrimidine–Ar₂ | Het–⟨⟩–J |
| A | B | 152 | ⟨CH₃⟩–Het | Ar₁–pyrimidine–Ar₂ | Het–⟨⟩–J |
| A | B | 153 | F–⟨⟩–Het | Ar₁–pyrimidine–Ar₂ | Het–⟨⟩–J |
| A | B | 154 | NC–⟨⟩–Het | Ar₁–pyrimidine–Ar₂ | Het–⟨⟩–J |
| A | B | 155 | CF₃O–⟨⟩–Het | Ar₁–pyrimidine–Ar₂ | Het–⟨CH₃⟩–J |
| A | B | 156 | ⟨OCF₃⟩–Het | Ar₁–pyrimidine–Ar₂ | Het–⟨⟩–J |
| B | A | 157 | CF₃–⟨⟩–Het | Ar₁–triazine–Ar₃ | Het–⟨⟩–J |
| A | A | 158 | CF₃O–⟨⟩–Het | Ar₁–triazine–Ar₂ | Het–⟨⟩–J |
| A | A | 159 | CF₃O–⟨⟩–Het | Ar₁–pyrimidine–Ar₂ | Het–pyridine–J |

TABLE 7-continued

| | | | | | |
|---|---|---|---|---|---|
| A | A | 160 | CF₃O-C₆H₄-Het | Ar₁-N(piperazine)-Ar₂ | Het-pyridine-J |
| A | A | 161 | CF₃-pyridine-Het | Ar₁-N(piperazine)-Ar₂ | Het-C₆H₄-J |
| A | B | 162 | CF₃O-C₆H₄-Het | Ar₁-N(piperazine)-Ar₂ | Het-C₆H₄-J |
| B | B | 163 | CH₃S-C₆H₄-Het | Ar₁-pyrimidine-Ar₂ | Het-C₆H₄-J |
| B | B | 164 | CF₃O-C₆H₄-Het | Ar₁-imidazole-Ar₂ | Het-thiophene-J |
| A | B | 165 | CF₃O-C₆H₄-Het | Ar₁-imidazole-Ar₂ | Het-C₆H₄-J |
| A | B | 166 | CF₃O-C₆H₄-Het | Ar₁-imidazole-Ar₂ | Het-C₆H₄-J (meta) |
| A | B | 167 | CF₃O-C₆H₄-Het | Ar₁-imidazole-Ar₂ | Het-C₆H₃(Cl)-J |
| A | A | 168 | CF₃O-C₆H₄-Het | Ar₁-imidazole-Ar₂ | Het-C₆H₃(F)-J |
| A | B | 169 | CF₃O-C₆H₄-Het | Ar₁-triazole-Ar₂ | Het-C₆H₄-J |
| A | B | 170 | CF₃O-pyridine-Het | Ar₁-triazole-Ar₂ | Het-indanylidene-K |
| A | A | 171 | CF₃O-C₆H₄-Het | Ar₁-imidazole-Ar₂ | Het-C₆H₄-J |
| A | B | 172 | Cl-C₆H₄-Het (meta) | Ar₁-dihydropyrazole-Ar₂ | Het-C₆H₄-J |

TABLE 7-continued

| | | | | | |
|---|---|---|---|---|---|
| A | A | 173 | CF₃O-Ph-Het | Ar₁-imidazole-Ar₂ | Het-Ph-J |
| A | A | 174 | CF₃O-Ph-Het | Ar₁-imidazole-Ar₂ | Het-Ph-J |
| A | A | 175 | CF₃O-Ph-Het | Ar₁-imidazole-Ar₂ | Het-Ph-J |
| A | B | 176 | CF₃O-Ph-Het | Ar₁-imidazole-Ar₂ | Het-Ph-J |
| B | A | 177 | CF₃O-Ph-Het | Ar₁-imidazole-Ar₂ | Het-Ph-J |
| A | B | 178 | CF₃O-Ph-Het | Ar₁-pyrazoline-Ar₁ | Het-Ph-J |
| A | B | 179 | C₂F₅O-Ph-Het | Ar₁-pyrazoline-Ar₁ | Het-Ph-J |
| A | B | 180 | C₂F₅O-Ph-Het | Ar₁-pyrazoline(Ar₂)(CH₂NMe₂) | Het-Ph-J |
| A | A | 181 | CF₃-Ph-Het | Ar₁-isoxazoline-Ar₂ | Het-Ph-J |
| B | B | 182 | CF₃-Ph-Het | Ar₁-isoxazoline-Ar₂ | Het-Ph-J |
| A | A | 183 | CF₃O-Ph-Het | Ar₁-isoxazoline-Ar₂ | Het-Ph-J |
| B | B | 184 | CF₃O-Ph-Het | Ar₁-isoxazoline-Ar₂ | Het-Ph-J |
| B | B | 185 | CF₃O-Ph-Het | Ar₁-oxazoline-Ar₂ | Het-Ph-J |

TABLE 7-continued

| | | | | | |
|---|---|---|---|---|---|
| A | B | 186 | CF₃O-C₆H₄-Het | Ar₁-oxazoline-Ar₂ | Het-C₆H₄-J |
| A | A | 187 | CF₃O-C₆H₄-Het | Ar₁-N(C=O)N-Ar₂ (imidazolone) | Het-C₆H₄-J |
| A | B | 188 | CF₃O-C₆H₄-Het | Ar₁-N(C=O)N-Ar₂ (imidazolidinone) | Het-C₆H₄-J |
| A | A | 189 | CF₃-C₆H₄-Het | Ar₁-triazole-Ar₂ | Het-C₆H₃(Cl)-J |
| A | A | 190 | CF₃-C₆H₄-Het | Ar₁-triazole-Ar₂ | Het-C₆H₃(Cl)-J |
| A | A | 191 | CF₃O-C₆H₄-Het | Ar₁-triazole-Ar₂ | Het-C₆H₄-J |
| A | A | 192 | CF₃-C₆H₄-Het | Ar₁-triazole-Ar₂ | Het-C₆H₄-J |
| A | B | 193 | CF₃O-C₆H₄-Het | Ar₁-triazole-Ar₂ | Het-C₆H₄-J |
| A | A | 194 | CF₃O-C₆H₄-Het | Ar₁-triazole(CH₃)-Ar₂ | Het-C₆H₄-J |
| A | B | 195 | CF₃O-C₆H₄-Het | Ar₁-triazole(CH₃)-Ar₂ | Het-C₆H₄-J |
| A | A | 196 | Cl-C₆H₄-O-C₆H₄-Het | Ar₁-triazole-Ar₂ | Het-C₆H₄-J |
| A | A | 197 | H₃C-C₆H₄-Het | Ar₁-triazole-Ar₂ | Het-C₆H₄-J |

TABLE 7-continued

| | | | | | |
|---|---|---|---|---|---|
| A | A | 198 | CF₃–⟨phenyl⟩–Het | Ar₁–(triazole, N1-Ar₂) | Het–⟨phenyl⟩–J |
| A | A | 199 | CF₃–⟨phenyl⟩–Het | Ar₁–(triazole, N1-Ar₂) | Het–⟨phenyl⟩–J |
| A | A | 200 | C₂F₅O–⟨phenyl⟩–Het | Ar₁–(triazole, C-Ar₂) | Het–⟨phenyl⟩–J |
| A | A | 201 | C₂F₅O–⟨phenyl⟩–Het | Ar₁–(triazole, C-Ar₂) | Het–⟨phenyl⟩–J |
| A | A | 202 | C₂F₅O–⟨phenyl⟩–Het | Ar₁–(triazole, C-Ar₂) | Het–⟨phenyl⟩–J |
| A | A | 203 | C₂F₅O–⟨phenyl⟩–Het | Ar₁–(triazole, C-Ar₂) | Het–⟨phenyl⟩–J |
| A | A | 204 | C₂F₅O–⟨phenyl⟩–Het | Ar₁–(triazole, C-Ar₂) | Het–⟨phenyl⟩–J |
| A | A | 205 | CF₃O–⟨phenyl⟩–Het | Ar₁–(triazole, C-Ar₂) | Het–⟨phenyl⟩–J |
| A | A | 206 | C₂F₅O–⟨phenyl⟩–Het | Ar₁–(triazole, C-Ar₂) | Het–⟨phenyl⟩–J |
| A | B | 207 | C₂F₅O–⟨phenyl⟩–Het | Ar₁–(triazole, C-Ar₂) | Het–⟨phenyl⟩–J |
| A | A | 208 | C₂F₅O–⟨phenyl⟩–Het | Ar₁–(triazole, C-Ar₂) | Het–⟨phenyl⟩–J |
| A | A | 209 | CF₃O–⟨phenyl⟩–Het | Ar₁–(triazole, C-Ar₂) | Het–⟨phenyl⟩–J |
| A | A | 210 | CF₃O–⟨phenyl⟩–Het | Ar₁–(triazole, C-Ar₂) | Het–⟨phenyl⟩–J |

TABLE 7-continued

| | | | | | |
|---|---|---|---|---|---|
| A | A | 211 | C₂F₅O–⟨phenyl⟩–Het | Ar₁–triazole–Ar₂ | Het–⟨phenyl⟩–J |
| A | A | 212 | CF₃O–⟨phenyl⟩–Het | Ar₁–triazole–Ar₂ | Het–⟨phenyl⟩–J |
| B | B | 213 | C₂F₅O–⟨phenyl⟩–Het | Ar₁–triazole–Ar₂ | Het–⟨phenyl⟩–J |
| A | A | 214 | CF₃O–⟨phenyl⟩–Het | Ar₁–triazole–Ar₂ | Het–⟨phenyl⟩–J |
| A | A | 215 | CF₃O–⟨phenyl⟩–Het | Ar₁–triazole–Ar₂ | Het–⟨phenyl⟩–J |
| A | A | 216 | C₃F₇O–⟨phenyl⟩–Het | Ar₁–triazole–Ar₂ | Het–⟨phenyl⟩–J |
| A | A | 217 | C₂F₅O–⟨phenyl⟩–Het | Ar₁–triazole–Ar₂ | Het–⟨phenyl⟩–J |
| A | B | 218 | CF₃O–⟨phenyl⟩–Het | Ar₁–triazole(vinyl)–Ar₂ | Het–⟨phenyl⟩–J |
| A | B | 219 | CF₃O–⟨phenyl⟩–Het | Ar₁–triazole(isobutyl)–Ar₂ | Het–⟨phenyl⟩–J |
| A | B | 220 | CF₃O–⟨phenyl⟩–Het | Ar₁–triazole(isopropenyl)–Ar₂ | Het–⟨phenyl⟩–J |
| A | B | 221 | CF₃O–⟨phenyl⟩–Het | Ar₁–triazole(CH₂CH₂SMe)–Ar₂ | Het–⟨phenyl⟩–J |
| A | B | 222 | CF₃O–⟨phenyl⟩–Het | Ar₁–triazole(CF₃)–Ar₂ | Het–⟨phenyl⟩–J |

TABLE 7-continued

| | | | | | |
|---|---|---|---|---|---|
| A | B | 223 | CF₃O–⟨phenyl⟩–Het | Ar₁–(triazole)–Ar₂ | Het–⟨phenyl(Br)⟩–J |
| A | B | 224 | C₂F₅O–⟨phenyl⟩–Het | Ar₁–(triazole)–Ar₂ | Het–⟨phenyl(Br)⟩–J |
| A | B | 225 | C₃F₇O–⟨phenyl⟩–Het | Ar₁–(triazole)–Ar₂ | Het–⟨phenyl⟩–J |
| B | B | 226 | F₃CO–⟨phenyl⟩–Het | Ar₁–(triazolone-CO₂CH₃)–Ar₂ | Het–⟨phenyl⟩–J |
| B | B | 227 | CF₃O–⟨phenyl⟩–Het | Ar₁–(triazolone-CO₂CH₃)–Ar₂ | Het–⟨phenyl⟩–J |
| B | B | 228 | CF₃O–⟨phenyl⟩–Het | Ar₁–(triazolone)–Ar₂ | Het–⟨phenyl⟩–J |
| A | A | 229 | CF₃–⟨phenyl⟩–Het | Ar₁–(triazole)–Ar₂ | Het–⟨phenyl⟩–J |
| A | B | 230 | 2,4-Cl₂–⟨phenyl⟩–Het | Ar₁–(oxadiazole)–Ar₂ | Het–⟨phenyl⟩–J |
| B | A | 231 | 3-Cl,4-F–⟨phenyl⟩–Het | Ar₁–(thiazole)–Ar₂ | Het–⟨phenyl⟩–J |
| A | A | 232 | CF₃–⟨phenyl⟩–Het | Ar₁–(pyrimidine)–Ar₂ | Het–⟨phenyl⟩–J |
| A | B | 233 | CF₃–⟨phenyl⟩–Het | Ar₁–(pyrimidine-C₃F₇)–Ar₂ | Het–⟨phenyl⟩–J |
| B | B | 234 | CH₃O–⟨phenyl⟩–Het | Ar₁–(pyrimidine)–Ar₂ | Het–⟨phenyl⟩–J |

TABLE 7-continued

| | | | | | |
|---|---|---|---|---|---|
| B | A | 235 | 4-CF₃-phenyl-Het | 2,4-Ar₁,Ar₂-6-CF₃-pyrimidine | 4-Het-phenyl-J |
| A | B | 236 | 4-CF₃O-phenyl-Het | 2,5-Ar₁,Ar₂-pyrimidine | 4-Het-phenyl-J |
| A | B | 237 | 4-CF₃O-phenyl-Het | 3,5-Ar₁,Ar₂-1,2,4-triazine | 4-Het-phenyl-J |
| A | B | 238 | 4-CF₃O-phenyl-Het | 3,5-Ar₁,Ar₂-1,2,4-triazine (isomer) | 4-Het-phenyl-J |
| B | B | 239 | 4-CF₃O-phenyl-Het | 2,5-Ar₁,Ar₂-pyridine | 4-Het-phenyl-J |
| A | A | 240 | 4-CF₃O-phenyl-Het | 3,5-Ar₁,Ar₂-1,2,4-oxadiazole | 4-Het-phenyl-J |
| B | B | 241 | 4-CF₃O-phenyl-Het | 1,4-Ar₁,Ar₂-piperazine | 4-Het-phenyl-J |
| A | B | 242 | 4-CF₃O-phenyl-Het | 1,4-Ar₁,Ar₂-piperazine-2,5-dione | 4-Het-phenyl-J |
| B | B | 243 | 4-C₂F₅O-phenyl-Het | 1,4-Ar₁,Ar₂-piperazine-2,5-dione | 4-Het-phenyl-J |
| A | B | 244 | 4-CF₃O-phenyl-Het | 1,3-Ar₁,Ar₂-1,2,4-triazole | 4-Het-phenyl-J |
| A | B | 245 | 4-CF₃O-phenyl-Het | 1,3-Ar₁,Ar₂-1,2,4-triazole | 4-Het-phenyl-J |
| A | B | 246 | 4-CF₃O-phenyl-Het | 1,5-Ar₁,Ar₂-1,2,4-triazole | 4-Het-phenyl-J |

TABLE 7-continued

| | | | Ar₁ group | Central ring | Ar₂-J group |
|---|---|---|---|---|---|
| A | B | 247 | CF₃O—⟨phenyl⟩—Het | Ar₁—[oxazoline]—Ar₂ | Het—⟨phenyl⟩—J |
| B | B | 248 | CF₃O—⟨phenyl⟩—Het | Ar₁—[pyridazine]—Ar₂ | Het—⟨phenyl⟩—J |
| B | B | 249 | CF₃—⟨phenyl⟩—Het | Ar₁—[1,3,4-oxadiazol-2(3H)-one]—Ar₂ | Het—⟨phenyl⟩—J |
| A | B | 250 | CF₃O—⟨phenyl⟩—Het | Ar₁—[1,2,4-triazole]—Ar₂ | Het—⟨phenyl⟩—J |
| A | B | 251 | C₂F₅O—⟨phenyl⟩—Het | Ar₁—[1,2,4-triazole]—Ar₂ | Het—⟨phenyl⟩—J |
| A | B | 252 | C₂F₅O—⟨phenyl⟩—Het | Ar₁—[pyrazoline]—Ar₂ | Het—⟨phenyl⟩—J |
| A | A | 253 | C₂F₅O—⟨phenyl⟩—Het | Ar₁—[1,2,4-triazole]—Ar₂ | Het—⟨phenyl⟩—J |
| A | A | 254 | CF₃O—⟨phenyl⟩—Het | Ar₁—[1,2,4-triazole]—Ar₂ | Het—⟨phenyl⟩—J |
| A | B | 255 | C₂F₅O—⟨phenyl⟩—Het | Ar₁—[1,2,4-triazole]—Ar₂ | Het—⟨phenyl⟩—J |
| A | A | 256 | C₂F₅O—⟨phenyl⟩—Het | Ar₁—[1,2,4-triazole]—Ar₂ | Het—⟨phenyl⟩—J |
| A | B | 257 | C₂F₅O—⟨phenyl⟩—Het | Ar₁—[1,2,4-triazole]—Ar₂ | Het—⟨phenyl⟩—J |
| A | A | 258 | C₂F₅O—⟨phenyl⟩—Het | Ar₁—[1,2,4-triazole]—Ar₂ | Het—⟨phenyl⟩—J |

TABLE 7-continued

| A | B | 259 | C₂F₅O-⌬-Het | Ar₁-[triazole]-Ar₂ | Het-⌬-J |
|---|---|---|---|---|---|

| BAW 50 ug/cm2 | BAW HTS | Compound | J | L | K | Q | R1 | R2 | R3 | R4 | anomer | sugar |
|---|---|---|---|---|---|---|---|---|---|---|---|---|
| B | A | 1 | CH | double | N | O | OCH₃ | OCH₃ | OCH₃ | CH₃ | α | L-rhamnose |
| B | A | 2 | CH | double | N | O | OCH₃ | OCH₃ | OCH₃ | CH₃ | α | L-rhamnose |
| B | A | 3 | CH | double | N | O | OCH₃ | OCH₃ | OCH₃ | CH₃ | α | L-rhamnose |
| B | B | 4 | CH | double | N | O | OCH₃ | OCH₃ | OCH₃ | CH₃ | α | L-rhamnose |
| A | B | 5 | CH | double | N | O | OCH₃ | OCH₃ | OCH₃ | CH₃ | α | L-rhamnose |
| A | B | 6 | CH | double | N | O | OCH₃ | OCH₃ | OCH₃ | CH₃ | α | L-rhamnose |
| A | B | 7 | CH | double | N | O | OCH₃ | OCH₃ | OCH₃ | CH₃ | α | L-rhamnose |
| A | B | 8 | CH | double | N | O | OCH₃ | OCH₃ | OCH₃ | CH₃ | α | L-rhamnose |
| A | B | 9 | CH | double | N | O | OCH₃ | OCH₃ | OCH₃ | CH₃ | α | L-rhamnose |
| A | B | 10 | CH | double | N | O | OCH₃ | OCH₃ | OCH₃ | CH₃ | α | L-rhamnose |
| A | B | 11 | CH | double | N | O | OCH₃ | OCH₃ | OCH₃ | CH₃ | α | L-rhamnose |
| A | B | 12 | CH | double | N | O | OCH₃ | OCH₃ | OCH₃ | CH₃ | α | L-rhamnose |
| A | B | 13 | CH | double | N | O | OCH₃ | OCH₃ | OCH₃ | CH₃ | α | L-rhamnose |
| B | B | 14 | CH | double | N | O | OCH₃ | OCH₃ | OCH₃ | CH₃ | α | L-rhamnose |
| A | B | 15 | CH | double | N | O | OCH₃ | OCH₃ | OCH₃ | CH₃ | α | L-rhamnose |
| B | A | 16 | CH | double | N | O | OCH₃ | OCH₃ | OCH₃ | CH₃ | α | L-rhamnose |
| B | A | 17 | CH | double | N | O | OCH₃ | OCH₃ | OCH₃ | CH₃ | α | L-rhamnose |
| B | A | 18 | CH | double | N | O | OCH₃ | OCH₃ | OCH₃ | CH₃ | α | L-rhamnose |
| B | B | 19 | CH | double | N | O | OCH₃ | OCH₃ | OCH₃ | CH₃ | α | L-rhamnose |
| B | A | 20 | CH | double | N | O | OCH₃ | OCH₃ | OCH₃ | CH₃ | α | L-rhamnose |
| B | A | 21 | CH | double | N | O | OCH₃ | OCH₃ | OCH₃ | CH₃ | α | L-rhamnose |
| B | B | 22 | CH | double | N | O | OCH₃ | OCH₃ | OCH₃ | CH₃ | α | L-rhamnose |
| B | B | 23 | CH | double | N | O | OCH₃ | OCH₃ | OCH₃ | CH₃ | α | L-rhamnose |
| B | A | 24 | CH | double | N | O | OCH₃ | OCH₃ | OCH₃ | CH₃ | α | L-rhamnose |
| B | B | 25 | CH | double | N | O | OCH₃ | OCH₃ | OCH₃ | CH₃ | α | L-rhamnose |
| A | A | 26 | CH | double | N | O | OCH₃ | OCH₃ | OCH₃ | CH₃ | α | L-rhamnose |
| A | A | 27 | CH | double | N | O | OCH₃ | OCH₃ | OCH₃ | CH₃ | α | L-rhamnose |
| A | A | 28 | CH | double | N | O | OCH₃ | OC₂H₅ | OCH₃ | CH₃ | α | L-rhamnose |
| A | B | 29 | CH | double | N | O | OCH₃ | OC₂H₅ | OCH₃ | CH₃ | α | L-rhamnose |
| A | A | 30 | CH | double | N | O | OCH₃ | OCH₃ | OCH₃ | CH₃ | α | L-rhamnose |
| A | A | 31 | CH | double | N | O | OC₂H₅ | OC₂H₅ | OC₂H₅ | CH₃ | α | L-rhamnose |
| A | A | 32 | CH | double | N | O | OCH₃ | OCH₃ | OCH₃ | CH₃ | α | L-rhamnose |
| A | A | 33 | CH | double | N | O | OC₂H₅ | OC₂H₅ | OC₂H₅ | CH₃ | α | L-rhamnose |
| A | B | 34 | CH | double | N | O | OCH₃ | OCH₃ | OCH₃ | CH₃ | α | L-rhamnose |
| A | B | 35 | CH | double | N | O | OCH₃ | OCH₃ | OCH₃ | CH₃ | α | L-rhamnose |
| A | B | 36 | CH | double | N | O | OCH₃ | OCH₃ | OCH₃ | CH₃ | α | L-rhamnose |
| A | B | 37 | CH | double | N | O | OCH₃ | OCH₃ | OCH₃ | CH₃ | α | L-rhamnose |
| A | B | 38 | CH | double | N | O | OCH₃ | OCH₃ | OCH₃ | CH₃ | α | L-rhamnose |
| A | B | 39 | CH | double | N | O | OCH₃ | OCH₃ | OCH₃ | CH₃ | α | L-rhamnose |
| A | B | 40 | CH | double | N | O | OCH₃ | OCH₃ | OCH₃ | CH₃ | α | L-rhamnose |
| A | B | 41 | CH | double | N | O | OCH₃ | OCH₃ | OCH₃ | CH₃ | α | L-rhamnose |
| A | B | 42 | CH | double | N | O | OCH₃ | OCH₃ | OCH₃ | CH₃ | α | L-rhamnose |
| A | B | 43 | CH | double | N | O | OCH₃ | OCH₃ | OCH₃ | CH₃ | α | L-rhamnose |
| A | B | 44 | CH | double | N | O | OCH₃ | OCH₃ | OCH₃ | CH₃ | α | L-rhamnose |
| A | B | 45 | CH | double | N | O | OCH₃ | OCH₃ | OCH₃ | CH₃ | α | L-rhamnose |
| A | B | 46 | CH | double | N | O | OCH₃ | OCH₃ | OCH₃ | CH₃ | α | L-rhamnose |
| A | B | 47 | CH | double | N | O | OCH₃ | OCH₃ | OCH₃ | CH₃ | α | L-rhamnose |
| A | B | 48 | CH | double | N | O | OCH₃ | OCH₃ | OCH₃ | CH₃ | α | L-rhamnose |
| A | B | 49 | CH | double | N | O | OCH₃ | OCH₃ | OCH₃ | CH₃ | α | L-rhamnose |
| A | A | 50 | CH | double | N | O | OCH₃ | OCH₃ | OCH₃ | CH₃ | α | L-rhamnose |
| A | B | 51 | CH | double | N | O | OCH₃ | OCH₃ | OCH₃ | CH₃ | α | L-rhamnose |
| A | B | 52 | CH | double | N | O | OC₂H₅ | OC₂H₅ | OC₂H₅ | CH₃ | α | L-rhamnose |
| A | A | 53 | CH | double | N | O | OCH₃ | OCH₃ | OCH₃ | CH₃ | α | L-rhamnose |
| A | A | 54 | CH | double | N | O | OCH₃ | OCH₃ | OCH₃ | CH₃ | α | L-rhamnose |
| A | A | 55 | CH | double | N | O | OCH₃ | OCH₃ | OCH₃ | CH₃ | α | L-rhamnose |
| A | A | 56 | CH | double | N | O | OCH₃ | OCH₃ | OCH₃ | CH₃ | α | L-rhamnose |
| A | A | 57 | CH | double | N | O | OCH₃ | OCH₃ | OCH₃ | CH₃ | α | L-rhamnose |
| A | A | 58 | CH | double | N | O | OCH₃ | OCH₃ | OCH₃ | CH₃ | α | L-rhamnose |
| A | A | 59 | CH | double | N | O | OCH₃ | OCH₃ | OCH₃ | CH₃ | α | L-rhamnose |
| A | A | 60 | CH | double | N | O | OCH₃ | OCH₃ | OCH₃ | CH₃ | α | L-rhamnose |
| A | A | 61 | CH | double | N | O | OCH₃ | OCH₃ | OCH₃ | CH₃ | α | L-rhamnose |
| A | A | 62 | CH | double | N | O | OCH₃ | OCH₃ | OCH₃ | CH₃ | α | L-rhamnose |
| A | A | 63 | CH | double | N | O | OCH₃ | OCH₃ | OCH₃ | CH₃ | α | L-rhamnose |
| A | A | 64 | CH | double | N | O | OCH₃ | OCH₃ | OCH₃ | CH₃ | α | L-rhamnose |
| A | A | 65 | CH | double | N | O | OCH₃ | OCH₃ | OCH₃ | CH₃ | α | L-rhamnose |
| A | A | 66 | OH | double | N | O | OCH₃ | OCH₃ | OCH₃ | CH₃ | α | L-rhamnose |
| A | B | 67 | CH | double | N | O | OCH₃ | OCH₃ | OCH₃ | CH₃ | α | L-rhamnose |
| A | B | 68 | CH | double | N | O | OCH₃ | OC₂H₅ | OCH₃ | CH₃ | α | L-rhamnose |
| B | B | 69 | CH | double | N | O | OCH₃ | OCH₃ | OCH₃ | CH₃ | α | L-rhamnose |

TABLE 7-continued

| | | | | | | | | | | | | |
|---|---|---|---|---|---|---|---|---|---|---|---|---|
| B | A | 70 | CH | double | N | O | OCH₃ | OCH₃ | OCH₃ | CH₃ | α | L-rhamnose |
| B | A | 71 | CH | double | N | O | OCH₃ | OCH₃ | OCH₃ | CH₃ | α | L-rhamnose |
| A | A | 72 | CH | double | N | O | OCH₃ | OCH₃ | OCH₃ | CH₃ | α | L-rhamnose |
| A | B | 73 | CH | double | N | O | OCH₃ | OCH₃ | OCH₃ | CH₃ | α | L-rhamnose |
| A | B | 74 | CH | double | N | O | OCH₃ | OC₃H₇ | OCH₃ | CH₃ | α | L-rhamnose |
| B | A | 75 | CH | double | N | O | OCH₃ | OCH₃ | OCH₃ | CH₃ | α | L-rhamnose |
| B | B | 76 | CH | double | N | O | OCH₃ | OCH₃ | OCH₃ | CH₃ | α | L-rhamnose |
| B | B | 77 | CH | double | N | O | OCH₃ | OCH₃ | OCH₃ | CH₃ | α | L-rhamnose |
| A | B | 78 | CH | double | N | O | OCH₃ | OCH₃ | OCH₃ | CH₃ | α | L-rhamnose |
| A | B | 79 | CH | double | N | O | OCH₃ | OCH₃ | OCH₃ | CH₃ | α | L-rhamnose |
| A | A | 80 | CH | double | N | O | OCH₃ | OCH₃ | OCH₃ | CH₃ | α | L-rhamnose |
| A | A | 81 | CH | double | N | O | OCH₃ | OCH₃ | OCH₃ | CH₃ | α | L-rhamnose |
| A | B | 82 | CH | double | N | O | OCH₃ | OCH₃ | OCH₃ | CH₃ | α | L-rhamnose |
| A | B | 83 | CH | double | N | O | OCH₃ | OCH₃ | OCH₃ | CH₃ | α | L-rhamnose |
| A | B | 84 | CH | double | N | O | OCH₃ | OCH₃ | OCH₃ | CH₃ | α | L-rhamnose |
| A | B | 85 | CH | double | N | O | OCH₃ | OCH₃ | OCH₃ | CH₃ | α | L-rhamnose |
| A | B | 86 | CH | double | N | O | OCH₃ | OCH₃ | OCH₃ | CH₃ | α | L-rhamnose |
| A | B | 87 | CH | double | N | O | OCH₃ | OCH₃ | OCH₃ | CH₃ | α | L-rhamnose |
| A | B | 88 | CH | double | N | O | OCH₃ | OCH₃ | OCH₃ | CH₃ | α | L-rhamnose |
| A | B | 89 | CH | double | N | O | OCH₃ | OCH₃ | OCH₃ | CH₃ | α | L-rhamnose |
| A | B | 90 | CH | double | N | O | OCH₃ | OCH₃ | OCH₃ | CH₃ | α | L-rhamnose |
| A | B | 91 | CH | double | N | O | OCH₃ | OCH₃ | OCH₃ | CH₃ | α | L-rhamnose |
| A | B | 92 | CH | double | N | O | OC₂H₅ | OC₂H₅ | OC₂H₅ | CH₃ | α | L-rhamnose |
| A | A | 93 | CH | double | N | O | OCH₃ | OC₂H₅ | OCH₃ | CH₃ | α | L-rhamnose |
| A | B | 94 | CH | double | N | O | OCH₃ | OCH₃ | OCH₃ | CH₃ | α | L-rhamnose |
| A | B | 95 | CH | double | N | O | OCH₃ | OCH₃ | OCH₃ | CH₃ | α | L-rhamnose |
| A | B | 96 | CH | double | N | O | OCH₃ | OCH₃ | OCH₃ | CH₃ | α | L-rhamnose |
| A | B | 97 | CH | double | N | O | OCH₃ | OCH₃ | OCH₃ | CH₃ | α | L-rhamnose |
| A | B | 98 | CH | double | N | O | OCH₃ | OCH₃ | OCH₃ | CH₃ | α | L-rhamnose |
| A | B | 99 | CH | double | N | O | OCH₃ | OCH₃ | OCH₃ | CH₃ | α | L-rhamnose |
| A | B | 100 | CH | double | N | O | OCH₃ | OCH₃ | OCH₃ | CH₃ | α | L-rhamnose |
| A | B | 101 | CH | double | N | O | OCH₃ | OCH₃ | OCH₃ | CH₃ | α | L-rhamnose |
| B | B | 102 | CH | double | N | O | OCH₃ | OCH₃ | OCH₃ | CH₃ | α | L-rhamnose |
| A | B | 103 | CH | double | N | O | OCH₃ | OCH₃ | OCH₃ | CH₃ | α | L-rhamnose |
| A | B | 104 | CH | double | N | O | OCH₃ | OCH₃ | OCH₃ | CH₃ | α | L-rhamnose |
| A | B | 105 | CH | double | N | O | OCH₃ | OCH₃ | OCH₃ | CH₃ | α | L-rhamnose |
| A | B | 106 | CH | double | N | O | OCH₃ | OC₃H₇ | OCH₃ | CH₃ | α | L-rhamnose |
| A | A | 107 | CH | double | N | O | OCH₃ | OC₃H₇ | OCH₃ | CH₃ | α | L-rhamnose |
| A | B | 108 | CH | double | N | O | OCH₃ | OC₃H₇ | OCH₃ | CH₃ | α | L-rhamnose |
| A | A | 109 | CH | double | N | O | OCH₃ | OC₄H₉ | OCH₃ | CH₃ | α | L-rhamnose |
| A | B | 110 | CH | double | N | O | OCH₃ | OC₃H₇ | OCH₃ | CH₃ | α | L-rhamnose |
| A | A | 111 | CH | double | N | O | OCH₃ | OCH₃ | CH | CH₃ | α | L-rhamnose |
| A | B | 112 | CH | double | N | O | OCH₃ | OC₂H₅ | OCH₃ | CH₃ | α | L-rhamnose |
| A | B | 113 | CH | double | N | O | OCH₃ | OCH₃ | OC₃H₇ | CH₃ | α | L-rhamnose |
| A | A | 114 | CH | double | N | O | OCH₃ | OCH₃ | OCH₃ | CH₂OCH₃ | α | D-glucose |
| A | B | 115 | CH | double | N | O | OCH₃ | OC₂H₅ | OCH₃ | CH₃ | α | L-rhamnose |
| A | B | 116 | CH | double | N | O | OCH₃ | OC₂H₅ | OCH₃ | CH₃ | α | L-rhamnose |
| B | B | 117 | CH | double | N | O | OCH₃ | OC₂H₅ | OCH₃ | CH₃ | α | L-rhamnose |
| A | B | 118 | CH | double | N | O | OCH₃ | OC₃H₇ | OCH₃ | CH₃ | α | L-rhamnose |
| A | A | 119 | CH | double | N | O | OCH₃ | OCH₃ | OCH₃ | CH₂OCH₃ | α | L-mannose |
| A | A | 120 | CH | double | N | O | OCH₃ | OC₂H₅ | OCH₃ | CH₃ | α | L-rhamnose |
| A | B | 121 | CH | double | N | O | OCH₃ | OC₂H₅ | OCH₃ | CH₃ | α | L-rhamnose |
| A | A | 122 | CH | double | N | O | OCH₃ | OCH₃ | OCH₃ | CH₃ | α | L-fucose |
| A | B | 123 | CH | double | N | O | OCH₃ | OC₂H₅ | OCH₃ | CH₃ | α | L-rhamnose |
| A | B | 124 | CH | double | N | O | OCH₃ | OC₂H₅ | OCH₃ | CH₃ | α | L-rhamnose |
| A | B | 125 | CH | double | N | O | OCH₃ | OC₂H₅ | OCH₃ | CH₃ | α | L-rhamnose |
| A | B | 126 | CH | double | N | O | OCH₃ | OC₂H₅ | OCH₃ | CH₃ | α | L-rhamnose |
| A | B | 127 | CH | double | N | O | OCH₃ | OC₂H₅ | OCH₃ | CH₃ | α | L-rhamnose |
| A | B | 128 | CH | double | N | O | OCH₃ | OC₂H₅ | OCH₃ | CH₃ | α | L-rhamnose |
| A | B | 129 | CH | double | N | O | OCH₃ | OC₂H₅ | OCH₃ | CH₃ | α | L-rhamnose |
| A | A | 130 | CH | double | N | O | OCH₃ | OC₂H₅ | OCH₃ | CH₃ | α | L-rhamnose |
| B | B | 131 | CH | double | N | O | OCH₃ | OCH₃ | OCH₃ | CH₃ | α | L-rhamnose |
| A | B | 132 | CH | double | N | O | OCH₃ | OCH₃ | OCH₃ | CH₃ | α | L-rhamnose |
| A | B | 133 | CH | double | N | O | OCH₃ | OCH₃ | OCH₃ | CH₃ | α | L-rhamnose |
| A | B | 134 | CH | double | N | O | OCH₃ | OCH₃ | OCH₃ | CH₃ | α | L-rhamnose |
| A | B | 135 | CH | double | N | O | OCH₃ | OCH₃ | OCH₃ | CH₃ | α | L-rhamnose |
| A | B | 136 | CH | double | N | O | OCH₃ | OCH₃ | OCH₃ | CH₃ | α | L-rhamnose |
| A | B | 137 | CH | double | N | O | OCH₃ | OCH₃ | OCH₃ | CH₃ | α | L-rhamnose |
| A | A | 138 | CH | double | N | O | OCH₃ | OCH₃ | OCH₃ | CH₃ | α | L-rhamnose |
| A | A | 139 | CH | double | N | O | OCH₃ | OCH₃ | OCH₃ | CH₃ | α | L-rhamnose |
| A | B | 140 | CH | double | N | O | OCH₃ | OCH₃ | OCH₃ | CH₃ | α | L-rhamnose |
| A | A | 141 | CH | double | N | O | OCH₃ | OCH₃ | OCH₃ | CH₃ | α | L-rhamnose |
| A | A | 142 | CH | double | N | O | OCH₃ | OC₂H₅ | OCH₃ | CH₃ | α | L-rhamnose |
| A | B | 143 | CH | double | N | O | OCH₃ | OC₂H₅ | OCH₃ | CH₃ | α | L-rhamnose |
| A | B | 144 | CH | double | N | O | OCH₃ | OC₃H₇ | OCH₃ | CH₃ | α | L-rhamnose |
| A | B | 145 | CH | double | N | O | OCH₃ | OC₄H₉ | OCH₃ | CH₃ | α | L-rhamnose |
| A | B | 146 | CH | double | N | O | OCH₃ | OC₂H₅ | OCH₃ | CH₃ | α | L-rhamnose |
| B | B | 147 | CH | double | N | O | OCH₃ | OC₂H₅ | OCH₂ | CH₃ | α | L-rhamnose |
| A | B | 148 | CH | double | N | O | CCH₃ | OC₂H₅ | OCH₃ | CH₃ | α | L-rhamnose |
| A | B | 149 | CH | double | N | O | OCH₃ | OC₂H₅ | OCH₃ | CH₃ | α | L-rhamnose |

TABLE 7-continued

| | | | | | | | | | | | |
|---|---|---|---|---|---|---|---|---|---|---|---|
| B | B | 150 | CH | double | N | O | OCH$_3$ | OC$_2$H$_5$ | OCH$_3$ | CH$_3$ | α | L-rhamnose |
| A | B | 151 | CH | double | N | O | OCH$_3$ | OC$_2$H$_5$ | OCH$_3$ | CH$_3$ | α | L-rhamnose |
| A | B | 152 | CH | double | N | O | OCH$_3$ | OC$_2$H$_5$ | OCH$_3$ | CH$_3$ | α | L-rhamnose |
| A | B | 153 | CH | double | N | O | OCH$_3$ | OC$_2$H$_5$ | OCH$_3$ | CH$_3$ | α | L-rhamnose |
| A | B | 154 | CH | double | N | O | OCH$_3$ | OC$_2$H$_5$ | OCH$_3$ | CH$_3$ | α | L-rhamnose |
| A | B | 155 | CH | double | N | O | OCH$_3$ | OC$_2$H$_5$ | OCH$_3$ | CH$_3$ | α | L-rhamnose |
| A | B | 156 | CH | double | N | O | OCH$_3$ | OC$_2$H$_5$ | OCH$_3$ | CH$_3$ | α | L-rhamnose |
| B | A | 157 | CH | double | N | O | OCH$_3$ | OCH$_3$ | OCH$_3$ | CH$_3$ | α | L-rhamnose |
| A | A | 158 | CH | double | N | O | OCH$_3$ | OCH$_3$ | OCH$_3$ | CH$_3$ | α | L-rhamnose |
| A | A | 159 | CH | double | N | O | OCH$_3$ | OCH$_3$ | OCH$_3$ | CH$_3$ | α | L-rhamnose |
| A | A | 160 | CH | double | N | O | OCH$_3$ | OC$_2$H$_5$ | OCH$_3$ | CH$_3$ | α | L-rhamnose |
| A | A | 161 | CH | double | N | O | OCH$_3$ | OC$_2$H$_5$ | OCH$_3$ | CH$_3$ | α | L-rhamnose |
| A | B | 162 | CH | double | N | O | OCH$_3$ | OC$_3$H$_7$ | OCH$_3$ | CH$_3$ | α | L-rhamnose |
| B | B | 163 | CH | double | N | O | OCH$_3$ | OC$_2$H$_5$ | OCH$_3$ | CH$_3$ | α | L-rhamnose |
| B | B | 164 | C—CH$_3$ | double | N | O | OCH$_3$ | OCH$_3$ | OCH$_3$ | CH$_3$ | α | L-rhamnose |
| A | B | 165 | C—CH$_3$ | double | N | O | OCH$_3$ | OCH$_3$ | OCH$_3$ | CH$_3$ | α | L-rhamnose |
| A | B | 166 | C—CH$_3$ | double | N | O | OCH$_3$ | OCH$_3$ | OCH$_3$ | CH$_3$ | α | L-rhamnose |
| A | B | 167 | C—CH$_3$ | double | N | O | OCH$_3$ | OCH$_3$ | OCH$_3$ | CH$_3$ | α | L-rhamnose |
| A | A | 168 | C—CH$_3$ | double | N | O | OCH$_3$ | OCH$_3$ | OCH$_3$ | CH$_3$ | α | L-rhamnose |
| A | B | 169 | C—CF$_3$ | double | N | O | OCH$_3$ | OC$_2$H$_5$ | OCH$_3$ | CH$_3$ | α | L-rhamnose |
| A | B | 170 | N/A | single | N | O | OCH$_3$ | OC$_2$H$_5$ | OCH$_3$ | CH$_3$ | α | L-rhamnose |
| A | A | 171 | C=O | single | NH | O | OCH$_3$ | OCH$_3$ | OCH$_3$ | CH$_3$ | α | L-rhamnose |
| A | B | 172 | NH | single | C=O | O | OCH$_3$ | OCH$_3$ | OCH$_3$ | CH$_3$ | α | L-rhamnose |
| A | A | 173 | NH | single | C=O | O | OCH$_3$ | OCH$_3$ | OCH$_3$ | CH$_3$ | α | L-rhamnose |
| A | A | 174 | NH | single | C=O | O | OCH$_3$ | OCH$_3$ | OCH$_3$ | CH$_3$ | β | L-rhamnose |
| A | A | 175 | NH | single | C=O | O | OCH$_3$ | OC$_4$H$_9$ | OCH$_3$ | CH$_3$ | α | L-rhamnose |
| A | B | 176 | NH | single | C=S | O | OCH$_3$ | OCH$_3$ | OCH$_3$ | CH$_3$ | α | L-rhamnose |
| B | A | 177 | NH | single | C=O | S | OCH$_3$ | OC$_2$H$_5$ | OCH$_3$ | CH$_3$ | α | L-rhamnose |
| A | B | 178 | NH | single | C=O | O | OCH$_3$ | OC$_2$H$_5$ | OCH$_3$ | CH$_3$ | α | L-rhamnose |
| A | B | 179 | NH | single | C=O | O | OCH$_3$ | OC$_2$H$_5$ | OCH$_3$ | CH$_3$ | α | L-rhamnose |
| A | B | 180 | NH | single | C=O | O | OCH$_3$ | OC$_2$H$_5$ | OCH$_3$ | CH$_3$ | α | L-rhamnose |
| A | A | 181 | NH | single | C=O | O | OCH$_3$ | OC$_2$H$_5$ | OCH$_3$ | CH$_3$ | α | L-rhamnose |
| B | B | 182 | NH | single | C=O | O | OCH$_3$ | OC$_2$H$_5$ | OCH$_3$ | CH$_3$ | β | L-rhamnose |
| A | A | 183 | NH | single | C=O | O | OCH$_3$ | OC$_2$H$_5$ | OCH$_3$ | CH$_3$ | α | L-rhamnose |
| B | B | 184 | NH | single | C=O | O | OCH$_3$ | OC$_2$H$_5$ | OCH$_3$ | CH$_3$ | β | L-glucose |
| B | B | 185 | NH | single | C=O | O | OCH$_3$ | OC$_2$H$_5$ | OCH$_3$ | CH$_3$ | α | L-rhamnose |
| A | B | 186 | NH | single | C=O | O | OCH$_3$ | OC$_2$H$_5$ | OCH$_3$ | CH$_3$ | α | L-rhamnose |
| A | A | 187 | NH | single | C=O | O | OCH$_3$ | OC$_2$H$_5$ | OCH$_3$ | CH$_3$ | α | L-rhamnose |
| A | B | 188 | NH | single | C=O | O | OCH$_3$ | OC$_2$H$_5$ | OCH$_3$ | CH$_3$ | α | L-rhamnose |
| A | A | 189 | NH | single | C=O | O | OCH$_3$ | OCH$_3$ | OCH$_3$ | CH$_3$ | α | L-rhamnose |
| A | A | 190 | NH | single | C=O | O | OCH$_3$ | OCH$_3$ | OCH$_3$ | CH$_3$ | β | L-rhamnose |
| A | A | 191 | NH | single | C=O | O | OCH$_3$ | OCH$_3$ | OCH$_3$ | CH$_3$ | α | L-rhamnose |
| A | A | 192 | NH | single | C=O | O | OCH$_3$ | OC$_2$H$_5$ | OCH$_3$ | CH$_3$ | α | L-rhamnose |
| A | B | 193 | NH | single | C=O | O | OCH$_3$ | OC$_2$H$_5$ | OCH$_3$ | CH$_3$ | α | L-rhamnose |
| A | A | 194 | NH | single | C=O | O | OCH$_3$ | OCH$_3$ | OCH$_3$ | CH$_3$ | α | L-rhamnose |
| A | B | 195 | NH | single | C=O | O | OCH$_3$ | OCH$_3$ | OCH$_3$ | CH$_3$ | β | L-rhamnose |
| A | A | 196 | NH | single | C=O | O | OCH$_3$ | OCH$_3$ | OCH$_3$ | CH$_3$ | α | L-rhamnose |
| A | A | 197 | NH | single | C=O | O | OCH$_3$ | OC$_4$H$_9$ | OCH$_3$ | CH$_3$ | α | L-rhamnose |
| A | A | 198 | NH | single | C=O | O | OCH$_3$ | OC$_4$H$_9$ | OCH$_3$ | CH$_3$ | α | L-rhamnose |
| A | A | 199 | NH | single | C=O | O | OCH$_3$ | OC$_4$H$_9$ | OCH$_3$ | CH$_3$ | β | L-rhamnose |
| A | A | 200 | NH | single | C=O | O | OCH$_3$ | OCH$_3$ | OCH$_3$ | CH$_3$ | α | L-rhamnose |
| A | A | 201 | NH | single | C=O | O | OCH$_3$ | OC$_2$H$_5$ | OCH$_3$ | CH$_3$ | α | L-rhamnose |
| A | A | 202 | NH | single | C=O | O | OCH$_3$ | OC$_2$H$_5$ | OCH$_3$ | CH$_3$ | β | L-rhamnose |
| A | A | 203 | NH | single | C=S | O | OCH$_3$ | OC$_2$H$_5$ | OCH$_3$ | CH$_3$ | α | L-rhamnose |
| A | A | 204 | NH | single | C=O | O | OCH$_3$ | OCH$_2$CH=CH$_2$ | OCH$_3$ | CH$_3$ | α | L-rhamnose |
| A | A | 205 | NH | single | C=O | O | OCH$_3$ | OCH$_2$CH=CH$_2$ | OCH$_3$ | CH$_3$ | α | L-rhamnose |
| A | A | 206 | NH | single | C=O | O | OC$_2$H$_5$ | OC$_2$H$_5$ | OC$_2$H$_5$ | CH$_3$ | α | L-rhamnose |
| A | B | 207 | NH | single | C=O | O | OCH$_3$ | OC$_3$H$_7$ | OCH$_3$ | CH$_3$ | α | L-rhamnose |
| A | A | 208 | NH | single | C=O | O | OCH$_3$ | OCH$_3$ | OCH$_3$ | CH$_3$ | β | L-rhamnose |
| A | A | 209 | NH | single | C=O | O | OCH$_3$ | OC$_3$H$_7$ | OCH$_3$ | CH$_3$ | α | L-rhamnose |
| A | A | 210 | NH | single | C=O | O | OCH$_3$ | OC$_2$H$_5$ | OCH$_3$ | CH$_3$ | β | L-rhamnose |
| A | A | 211 | NH | single | C=O | S | OCH$_3$ | OCH$_3$ | OCH$_3$ | CH$_3$ | α | L-rhamnose |
| A | A | 212 | NH | single | C=O | O | OCH$_3$ | OCH$_3$ | OCH$_3$ | H | α/β | L-xylose |
| B | B | 213 | NH | single | C=O | O | OCH$_3$ | OCH$_3$ | OCH$_3$ | H | α/β | L-xylose |
| A | A | 214 | NH | single | C=O | O | OCH$_3$ | OCH$_3$ | OCH$_3$ | H | α | L-lyxose |
| A | A | 215 | NH | single | C=O | O | OCH$_3$ | OCH$_3$ | OCH$_3$ | H | β | L-lyxose |
| A | A | 216 | NH | single | C=O | O | OCH$_3$ | OC$_3$H$_7$ | OCH$_3$ | CH$_3$ | α | L-rhamnose |
| A | A | 217 | NH | single | C=O | O | OCH$_3$ | OCH$_3$ | OCH$_3$ | OCH$_3$ | α | L-glucose |
| A | B | 218 | NH | single | C=O | O | OCH$_3$ | OC$_2$H$_5$ | OCH$_3$ | CH$_3$ | α | L-rhamnose |
| A | B | 219 | NH | single | C=O | O | OCH$_3$ | OC$_2$H$_5$ | OCH$_3$ | CH$_3$ | α | L-rhamnose |
| A | B | 220 | NH | single | C=O | O | OCH$_3$ | OC$_2$H$_5$ | OCH$_3$ | CH$_3$ | α | L-rhamnose |
| A | B | 221 | NH | single | C=O | O | OCH$_3$ | OC$_2$H$_5$ | OCH$_3$ | CH$_3$ | α | L-rhamnose |
| A | B | 222 | NH | single | C=O | O | OCH$_3$ | OC$_2$H$_5$ | OCH$_3$ | CH$_3$ | α | L-rhamnose |
| A | B | 223 | NH | single | C=O | O | OCH$_3$ | OC$_2$H$_5$ | OCH$_3$ | CH$_3$ | α | L-rhamnose |
| A | B | 224 | NH | single | C=O | O | OCH$_3$ | OC$_2$H$_5$ | OCH$_3$ | CH$_3$ | α | L-rhamnose |
| A | B | 225 | NH | single | C=O | O | OCH$_3$ | OC$_2$H$_5$ | OCH$_3$ | CH$_3$ | α | L-rhamnose |
| B | B | 226 | NH | single | C=O | O | OCH$_3$ | OC$_2$H$_5$ | OCH$_3$ | CH$_3$ | α | L-rhamnose |
| B | B | 227 | NH | single | C=O | O | OCH$_3$ | OC$_2$H$_5$ | OCH$_3$ | CH$_3$ | β | L-rhamnose |
| B | B | 228 | NH | single | C=O | O | OCH$_3$ | OC$_2$H$_5$ | OCH$_3$ | CH$_3$ | α | L-rhamnose |
| A | A | 229 | NH | single | C=O | O | OCH$_3$ | OCH$_3$ | OCH$_3$ | CH$_3$ | α | L-rhamnose |

TABLE 7-continued

| | | | | | | | | | | | | |
|---|---|---|---|---|---|---|---|---|---|---|---|---|
| A | B | 230 | NH | single | C=O | O | $OCH_3$ | $OCH_3$ | $OCH_3$ | $CH_3$ | α | L-rhamnose |
| B | A | 231 | NH | single | C=O | O | $OCH_3$ | $OCH_3$ | $OCH_3$ | $CH_3$ | α | L-rhamnose |
| A | A | 232 | NH | single | C=O | O | $OCH_3$ | $OCH_3$ | $OCH_3$ | $CH_3$ | α | L-rhamnose |
| A | B | 233 | NH | single | C=O | O | $OCH_3$ | $OCH_3$ | $OCH_3$ | $CH_3$ | α | L-rhamnose |
| B | B | 234 | NH | single | C=O | O | $OCH_3$ | $OCH_3$ | $OCH_3$ | $CH_3$ | α | L-rhamnose |
| B | A | 235 | NH | single | C=O | O | $OCH_3$ | $OCH_3$ | $OCH_3$ | $CH_3$ | α | L-rhamnose |
| A | B | 236 | NH | single | C=O | O | $CCH_3$ | $OC_3H_7$ | $OCH_3$ | $CH_3$ | α | L-rhamnose |
| A | B | 237 | NH | single | C=O | O | $OCH_3$ | $OC_2H_5$ | $OCH_3$ | $CH_3$ | α | L-rhamnose |
| A | B | 238 | NH | single | C=O | O | $OCH_3$ | $OC_2H_5$ | $OCH_3$ | $CH_3$ | α | L-rhamnose |
| B | B | 239 | NH | single | C=O | O | $CCH_3$ | $OC_2H_5$ | $OCH_3$ | $CH_3$ | α | L-rhamnose |
| A | A | 240 | NH | single | C=O | O | $OCH_3$ | $OC_2H_5$ | $OCH_3$ | $CH_3$ | α | L-rhamnose |
| B | B | 241 | NH | single | C=O | O | $OCH_3$ | $OC_2H_5$ | $OCH_3$ | $CH_3$ | α | L-rhamnose |
| A | B | 242 | NH | single | C=O | O | $OCH_3$ | $OC_2H_5$ | $OCH_3$ | $CH_3$ | α | L-rhamnose |
| B | B | 243 | NH | single | C=O | O | $OCH_3$ | $OC_2H_5$ | $OCH_3$ | $CH_3$ | α | L-rhamnose |
| A | B | 244 | NH | single | C=O | O | H | $OCH_3$ | CH | $CH_3$ | α/β | L-oleandrose |
| A | B | 245 | NH | single | C=O | O | H | $OCH_3$ | $OCH_3$ | $CH_3$ | β | L-oleandrose |
| A | B | 246 | NH | single | C=O | O | H | H | N(Me)2 | $CH_3$ | α | D-forosamine |
| A | B | 247 | NH | single | C=O | O | $OCH_3$ | $OC_2H_5$ | $OCH_3$ | $CH_3$ | α | L-rhamnose |
| B | B | 248 | NH | single | C=O | O | $OCH_3$ | $OC_2H_5$ | $OCH_3$ | $CH_3$ | α | L-rhamnose |
| B | B | 249 | NH | single | C=O | O | $OCH_3$ | $OC_2H_5$ | $OCH_3$ | $CH_3$ | α | L-rhamnose |
| A | B | 250 | $NCH_3$ | single | C=O | O | $OCH_3$ | $OC_2H_5$ | $OCH_3$ | $CH_3$ | α | L-rhamnose |
| A | B | 251 | $NCH_3$ | single | C=O | O | $OCH_3$ | $OC_2H_5$ | $OCH_3$ | $CH_3$ | α | L-rhamnose |
| A | B | 252 | $NCH_3$ | single | C=O | O | $OCH_3$ | $OC_2H_5$ | $OCH_3$ | $CH_3$ | α | L-rhamnose |
| A | A | 253 | $NCH_2CH_3$ | single | C=O | O | $OCH_3$ | $OC_3H_7$ | $OCH_3$ | $CH_3$ | α | L-rhamnose |
| A | A | 254 | $NCH_2OCH_3$ | single | C=O | O | $OCH_3$ | $OC_2H_5$ | $OCH_3$ | $CH_3$ | α | L-rhamnose |
| A | B | 255 | $NCH_2OCH_3$ | single | C=O | O | $OCH_3$ | $OC_2H_5$ | $OCH_3$ | $CH_3$ | α | L-rhamnose |
| A | A | 256 | $NCH_2CH=CH_2$ | single | C=O | O | $OCH_3$ | $OC_2H_5$ | $OCH_3$ | $CH_3$ | α | L-rhamnose |
| A | B | 257 | $NCH_2OH$ | single | C=O | O | $OCH_3$ | $OC_2H_5$ | $OCH_3$ | $CH_3$ | α | L-rhamnose |
| A | A | 258 | $NCOCH_3$ | single | C=O | O | $OCH_3$ | $OC_2H_5$ | $OCH_3$ | $CH_3$ | α | L-rhamnose |
| A | B | 259 | $NCOCH_2CH_2-CO_2CH_3$ | single | C=O | O | $OCH_3$ | $OC_2H_5$ | $OCH_3$ | $CH_3$ | α | L-rhamnose |

Acid & Salt Derivatives, and Solvates

The compounds disclosed in this invention can be in the form of pesticidally acceptable acid addition salts.

By way of non-limiting example, an amine function can form salts with hydrochloric, hydrobromic, sulfuric, phosphoric, acetic, benzoic, citric, malonic, salicylic, malic, fumaric, oxalic, succinic, tartaric, lactic, gluconic, ascorbic, maleic, aspartic, benzenesulfonic, methanesulfonic, ethanesulfonic, hydroxymethanesulfonic, and hydroxyethanesulfonic, acids.

Additionally, by way of non-limiting example, an acid function can form salts including those derived from alkali or alkaline earth metals and those derived from ammonia and amines. Examples of preferred cations include sodium, potassium, magnesium, and aminium cations.

The salts are prepared by contacting the free base form with a sufficient amount of the desired acid to produce a salt. The free base forms may be regenerated by treating the salt with a suitable dilute aqueous base solution such as dilute aqueous NaOH, potassium carbonate, ammonia, and sodium bicarbonate.

As an example, in many cases, a pesticide is modified to a more water soluble form e.g. 2,4-dichlorophenoxy acetic acid dimethyl amine salt is a more water soluble form of 2,4-dichlorophenoxy acetic acid, a well known herbicide.

The compounds disclosed in this invention can also form stable complexes with solvent molecules that remain intact after the non-complexed solvent molecules are removed from the compounds. These complexes are often referred to as "solvates".

Stereoisomers

Certain compounds disclosed in this invention can exist as one or more stereoisomers. The various stereoisomers include geometric isomers, diastereomers, and enantiomers. Thus, the compounds disclosed in this invention include racemic mixtures, individual stereoisomers, and optically active mixtures.

It will be appreciated by those skilled in the art that one stereoisomer may be more active than the others. Individual stereoisomers and optically active mixtures may be obtained by selective synthetic procedures, by conventional synthetic procedures using resolved starting materials, or by conventional resolution procedures.

Pests

In another embodiment, the invention disclosed in this document can be used to control pests.

In another embodiment, the invention disclosed in this document can be used to control pests of the Phylum Nematoda.

In another embodiment, the invention disclosed in this document can be used to control pests of the Phylum Arthropoda.

In another embodiment, the invention disclosed in this document can be used to control pests of the Subphylum Chelicerata.

In another embodiment, the invention disclosed in this document can be used to control pests of the Class Arachnida.

In another embodiment, the invention disclosed in this document can be used to control pests of the Subphylum Myriapoda.

In another embodiment, the invention disclosed in this document can be used to control pests of the Class Symphyla.

In another embodiment, the invention disclosed in this document can be used to control pests of the Subphylum Hexapoda.

In another embodiment, the invention disclosed in this document can be used to control pests of the Class Insecta.

In another embodiment, the invention disclosed in this document can be used to control *Coleoptera* (beetles). A non-exhaustive list of these pests includes, but is not limited to, *Acanthoscelides* spp. (weevils), *Acanthoscelides obtectus* (common bean weevil), *Agrilus planipennis* (emerald ash borer), *Agriotes* spp. (wireworms), *Anoplophora glabripennis* (Asian longhomed beetle), *Anthonomus* spp. (weevils), *Anthonomus grandis* (boll weevil), *Aphidius* spp., *Apion* spp. (weevils), *Apogonia* spp. (grubs), *Ataenius spretulus* (Black Turgrass Ataenius), *Atomaria linearis* (pygmy mangold beetle), *Aulacophore* spp., *Bothynoderes punctiventris* (beet root weevil), *Bruchus* spp. (weevils), *Bruchus pisorum* (pea weevil), *Cacoesia* spp., *Callosobruchus maculatus* (southern cow pea weevil), *Carpophilus hemipteras* (dried fruit beetle), *Cassida vittata, Cerosterna* spp, *Cerotoma* spp. (chrysomeids), *Cerotoma trifurcata* (bean leaf beetle), *Ceutorhynchus* spp. (weevils), *Ceutorhynchus assimilis* (cabbage seedpod weevil), *Ceutorhynchus napi* (cabbage curculio), *Chaetocnema* spp. (chrysomelids), *Colaspis* spp. (soil beetles), *Conoderus scalaris, Conoderus stigmosus, Conotrachelus nenuphar* (plum curculio), *Cotinus nitidis* (Green June beetle), *Crioceris asparagi* (asparagus beetle), *Cryptolestes ferrugineus* (rusty grain beetle), *Cryptolestes pusillus* (flat grain beetle), *Cryptolestes turcicus* (Turkish grain beetle), *Ctenicera* spp. (wireworms), *Curculio* spp. (weevils), *Cyclocephala* spp. (grubs), *Cylindrocpturus adspersus* (sunflower stem weevil), *Deporaus marginatus* (mango leaf-cutting weevil), *Dermestes lardarius* (larder beetle), *Dermestes maculates* (hide beetle), *Diabrotica* spp. (chrysolemids), *Epilachna varivestis* (Mexican bean beetle), *Faustinus cubae, Hylobius pales* (pales weevil), *Hypera* spp. (weevils), *Hypera postica* (alfalfa weevil), *Hyperdoes* spp. (Hyperodes weevil), *Hypothenemus hampei* (coffee berry beetle), *Ips* spp. (engravers), *Lasioderma serricorne* (cigarette beetle), *Leptinotarsa decemlineata* (Colorado potato beetle), *Liogenys fuscus, Liogenys suturalis, Lissorhoptrus oryzophilus* (rice water weevil), *Lyctus* spp. (wood beetles/powder post beetles), *Maecolaspis joliveti, Megascelis* spp., *Melanotus communis, Meligethes* spp., *Meligethes aeneus* (blossom beetle), *Melolontha melolontha* (common European cockchafer), *Oberea brevis, Oberea linearis, Oryctes rhinoceros* (date palm beetle), *Oryzaephilus mercator* (merchant grain beetle), *Oryzaephilus surinamensis* (sawtoothed grain beetle), *Otiorhynchus* spp. (weevils), *Oulema melanopus* (cereal leaf beetle), *Oulema oryzae, Pantomorus* spp. (weevils), *Phyllophaga* spp. (May/June beetle), *Phyllophaga cuyabana, Phyllotreta* spp. (chrysomelids), *Phynchites* spp., *Popillia japonica* (Japanese beetle), *Prostephanus truncates* (larger grain borer), *Rhizopertha dominica* (lesser grain borer), *Rhizotrogus* spp. (Eurpoean chafer), *Rhynchophorus* spp. (weevils), *Scolytus* spp. (wood beetles), *Shenophorus* spp. (Billbug), *Sitona lineatus* (pea leaf weevil), *Sitophilus* spp. (grain weevils), *Sitophilus granaries* (granary weevil), *Sitophilus oryzae* (rice weevil), *Stegobium paniceum* (drugstore beetle), *Tribolium* spp. (flour beetles), *Tribolium castaneum* (red flour beetle), *Tribolium confusum* (confused flour beetle), *Trogoderma variabile* (warehouse beetle), and *Zabrus tenebioides*.

In another embodiment, the invention disclosed in this document can be used to control *Dermaptera* (earwigs).

In another embodiment, the invention disclosed in this document can be used to control *Dictyoptera* (cockroaches). A non-exhaustive list of these pests includes, but is not limited to, *Blattella germanica* (German cockroach), *Blatta orientalis* (oriental cockroach), *Parcoblatta pennylvanica*, *Periplaneta americana* (American cockroach), *Periplaneta australoasiae* (Australian cockroach), *Periplaneta brunnea* (brown cockroach), *Periplaneta fuliginosa* (smokybrown cockroach), *Pyncoselus suninamensis* (Surinam cockroach), and *Supella longipalpa* (brownbanded cockroach).

In another embodiment, the invention disclosed in this document can be used to control *Diptera* (true flies). A non-exhaustive list of these pests includes, but is not limited to, *Aedes* spp. (mosquitoes), *Agromyza frontella* (alfalfa blotch leafminer), *Agromyza* spp. (leaf miner flies), *Anastrepha* spp. (fruit flies), *Anastrepha suspensa* (Caribbean fruit fly), *Anopheles* spp. (mosquitoes), *Batrocera* spp. (fruit flies), *Bactrocera cucurbitae* (melon fly), *Bactrocera dorsalis* (oriental fruit fly), *Ceratitis* spp. (fruit flies), *Ceratitis capitata* (Mediterranea fruit fly), *Chrysops* spp. (deer flies), *Cochliomyia* spp. (screwworms), *Contarinia* spp. (Gall midges), *Culex* spp. (mosquitoes), *Dasineura* spp. (gall midges), *Dasineura brassicae* (cabbage gall midge), *Delia* spp., *Delia platura* (seedcorn maggot), *Drosophila* spp. (vinegar flies), *Fannia* spp. (filth flies), *Fannia canicularis* (little house fly), *Fannia scalaris* (latrine fly), *Gasterophilus intestinalis* (horse bot fly), *Gracillia perseae, Haematobia irritans* (horn fly), *Hylemyia* spp. (root maggots), *Hypoderma lineatum* (common cattle grub), *Liriomyza* spp. (leafminer flies), *Liriomyza brassica* (serpentine leafminer), *Melophagus ovinus* (sheep ked), *Musca* spp. (muscid flies), *Musca autumnalis* (face fly), *Musca domestica* (house fly), *Oestrus ovis* (sheep bot fly), *Oscinella frit* (frit fly), *Pegomyia betae* (beet leafminer), *Phorbia* spp., *Psila rosae* (carrot rust fly), *Rhagoletis cerasi* (cherry fruit fly), *Rhagoletis pomonella* (apple maggot), *Sitodiplosis mosellana* (orange wheat blossom midge), *Stomoxys calcitrans* (stable fly), *Tabanus* spp. (horse flies), and *Tipula* spp. (crane flies).

In another embodiment, the invention disclosed in this document can be used to control *Hemiptera* (true bugs). A non-exhaustive list of these pests includes, but is not limited to, *Acrosternum hilare* (green stink bug), *Blissus leucopterus* (chinch bug), *Calocoris norvegicus* (potato mirid), *Cimex hemipterus* (tropical bed bug), *Cimex lectularius* (bed bug), *Dagbertus fasciatus, Dichelops furcatus, Dysdercus suturellus* (cotton stainer), *Edessa meditabunda, Eurygaster maura* (cereal bug), *Euschistus heros, Euschistus servus* (brown stink bug), *Helopeltis antonii, Helopeltis theivora* (tea blight plantbug), *Lagynotomus* spp. (stink bugs), *Leptocorisa oratorius, Leptocorisa varicornis, Lygus* spp. (plant bugs), *Lygus hesperus* (western tarnished plant bug), *Maconellicoccus hirsutus, Neurocolpus longirostris, Nezara viridula* (southern green stink bug), *Phytocoris* spp. (plant bugs), *Phytocoris californicus, Phytocoris relativus, Piezodorus guildingi, Poecilocapsus lineatus* (fourlined plant bug), *Psallus vaccinicola, Pseudacysta perseae, Scaptocoris castanea*, and *Triatoma* spp. (bloodsucking conenose bugs/kissing bugs).

In another embodiment, the invention disclosed in this document can be used to control *Homoptera* (aphids, scales, whiteflies, leafhoppers). A non-exhaustive list of these pests includes, but is not limited to, *Acrythosiphon pisum* (pea aphid), *Adelges* spp. (adelgids), *Aleurodes proletella* (cabbage whitefly), *Aleurodicus disperses, Aleurothrixus floccosus* (woolly whitefly), *Aluacaspis* spp., *Amrasca bigutella bigutella, Aphrophora* spp. (leafhoppers), *Aonidiella aurantii* (California red scale), *Aphis* spp. (aphids), *Aphis gossypii* (cotton aphid), *Aphis pomi* (apple aphid), *Aulacorthum solani* (foxglove aphid), *Bemisia* spp. (whiteflies), *Bemisia argentifolii, Bemisia tabaci* (sweetpotato whitefly), *Brachycolus noxius* (Russian aphid), *Brachycorynella asparagi* (asparagus aphid), *Brevennia rehi, Brevicoryne brassicae* (cabbage aphid), *Ceroplastes* spp. (scales), *Ceroplastes rubens* (red wax scale), *Chionaspis* spp. (scales), *Chrysomphalus* spp. (scales), *Coccus* spp. (scales), *Dysaphis plantaginea* (rosy apple aphid), *Empoasca* spp. (leafhoppers), *Eriosoma lanigerum* (woolly apple aphid), *Icerya purchasi* (cottony cushion scale), *Idioscopus nitidulus* (mango leafhopper), *Laodelphax striatellus* (smaller brown planthopper), *Lepidosaphes* spp., *Macrosiphum* spp., *Macrosiphum euphorbiae* (potato aphid), *Macrosiphum granarium* (English grain aphid), *Macrosiphum rosae* (rose aphid), *Macrosteles quadrilineatus* (aster leafhopper), *Mahanarva frimbiolata, Metopolophium dirhodum* (rose grain aphid), *Mictis longicornis, Myzus persicae* (green peach aphid), *Nephotettix* spp. (leafhoppers), *Nephotettix cinctipes* (green leafhopper), *Nilaparvata lugens* (brown planthopper), *Parlatoria pergandii* (chaff scale), *Parlatoria ziziphi* (ebony scale), *Peregrinus maidis* (corn delphacid), *Philaenus* spp. (spittlebugs), *Phylloxera vitifoliae* (grape phylloxera), *Physokermes piceae* (spruce bud scale), *Planococcus* spp. (mealybugs), *Pseudococcus* spp. (mealybugs), *Pseudococcus brevipes* (pine apple mealybug), *Quadraspidiotus perniciosus* (San Jose scale), *Rhapalosiphum* spp. (aphids), *Rhapalosiphum maida* (corn leaf aphid), *Rhapalosiphum padi* (oat bird-cherry aphid), *Saissetia* spp. (scales), *Saissetia oleae* (black scale), *Schizaphis graminum* (greenbug), *Sitobion avenae* (English grain aphid), *Sogatella furcifera* (white-backed planthopper), *Therioaphis* spp. (aphids), *Toumeyella* spp. (scales), *Toxoptera* spp. (aphids), *Trialeurodes* spp. (whiteflies), *Trialeurodes vaporariorum* (greenhouse whitefly), *Trialeurodes abutiloneus* (bandedwing whitefly), *Unaspis* spp. (scales), *Unaspis yanonensis* (arrowhead scale), and *Zulia entreriana*.

In another embodiment, the invention disclosed in this document can be used to control *Hymenoptera*(ants, wasps, and bees). A non-exhaustive list of these pests includes, but is not limited to, *Acromyrrmex* spp., *Athalia rosae, Atta* spp. (leafcutting ants), *Camponotus* spp. (carpenter ants), *Diprion* spp. (sawflies), *Formica* spp. (ants), *Iridomyrmex humilis* (Argentine ant), *Monomorium* ssp., *Monomorium minumum* (little black ant), *Monomorium pharaonis* (Pharaoh ant), *Neodiprion* spp. (sawflies), *Pogonomyrmex* spp. (harvester ants), *Polistes* spp. (paper wasps), *Solenopsis* spp. (fire ants), *Tapoinoma sessile* (odorous house ant), *Tetranomorium* spp. (pavement ants), *Vespula* spp. (yellow jackets), and *Xylocopa* spp. (carpenter bees).

In another embodiment, the invention disclosed in this document can be used to control *Isoptera*(termites). A non-exhaustive list of these pests includes, but is not limited to, *Coptotermes* spp., *Coptotermes curvignathus, Coptotermes frenchii, Coptotermes formosanus* (Formosan subterranean termite), *Cornitermes* spp. (nasute termites), *Cryptotermes* spp. (drywood termites), *Heterotermes* spp. (desert subterranean termites), *Heterotermes aureus, Kalotermes* spp. (drywood termites), *Incistitermes* spp. (drywood termites), *Macrotermes* spp. (fungus growing termites), *Marginitermes* spp. (drywood termites), *Microcerotermes* spp. (harvester termites), *Microtermes obesi, Procornitermes* spp., *Reticulitermes* spp. (subterranean termites), *Reticulitermes banyulensis, Reticulitermes grassei, Reticulitermes flavipes* (eastern subterranean termite), *Reticulitermes hageni, Reticulitermes hesperus* (western subterranean termite), *Reticulitermes santonensis, Reticulitermes speratus, Reticulitermes tibialis, Reticulitermes virginicus, Schedorhinotermes* spp., and *Zootermopsis* spp. (rotten-wood termites).

In another embodiment, the invention disclosed in this document can be used to control *Lepidoptera* (moths and butterflies). A non-exhaustive list of these pests includes, but is not limited to, *Achoea janata, Adoxophyes* spp., *Adoxophyes orana*, *Agrotis* spp. (cutworms), *Agrotis ipsilon* (black cutworm), *Alabama argillacea* (cotton leafworm), *Amorbia cuneana, Amyelosis transitella* (navel orangeworm), *Anacamptodes defectaria, Anarsia lineatella* (peach twig borer), *Anomis sabulifera* (jute looper), *Anticarsia gemmatalis* (velvetbean caterpillar), *Archips argyrospila* (fruittree leafroller), *Archips rosana* (rose leaf roller), *Argyrotaenia* spp. (tortricid moths), *Argyrotaenia citrana* (orange tortrix), *Autographa gamma, Bonagota cranaodes, Borbo cinnara* (rice leaf folder), *Bucculatrix thurberiella* (cotton leafperforator), *Caloptilia* spp. (leaf miners), *Capua reticulana, Carposina niponensis* (peach fruit moth), *Chilo* spp., *Chlumetia transversa* (mango shoot borer), *Choristoneura rosaceana* (obliquebanded leafroller), *Chrysodeixis* spp., *Cnaphalocerus medinalis* (grass leafroller), *Colias* spp., *Conpomorpha cramerella, Cossus cossus* (carpenter moth), *Crambus* spp. (Sod webworms), *Cydia funebrana* (plum fruit moth), *Cydia molesta* (oriental fruit moth), *Cydia nignicana* (pea moth), *Cydia pomonella* (codling moth), *Darna diducta, Diaphania* spp. (stem borers), *Diatraea* spp. (stalk borers), *Diatraea saccharalis* (sugarcane borer), *Diatraea graniosella* (southwester corn borer), *Earias* spp. (bollworms), *Earias insulata* (Egyptian bollworm), *Earias vitella* (rough northern bollworm), *Ecdytopopha aurantianum, Elasmopalpus lignosellus* (lesser cornstalk borer), *Epiphysias postruttana* (light brown apple moth), *Ephestia* spp. (flour moths), *Ephestia cautella* (almond moth), *Ephestia elutella* (tobbaco moth), *Ephestia kuehniella* (Mediterranean flour moth), *Epimeces* spp., *Epinotia aporema, Erionota thrax* (banana skipper), *Eupoecilia ambiguella* (grape berry moth), *Euxoa auxiliaris* (army cutworm), *Feltia* spp. (cutworms), *Gortyna* spp. (stemborers), *Grapholita molesta* (oriental fruit moth), *Hedylepta indicata* (bean leaf webber), *Helicoverpa* spp. (noctuid moths), *Helicoverpa armigera* (cotton bollworm), *Helicoverpa zea* (bollworm/corn earworm), *Heliothis* spp. (noctuid moths), *Heliothis virescens* (tobacco budworm), *Hellula undalis* (cabbage webworm), *Indarbela* spp. (root borers), *Keiferia lycopersicella* (tomato pinworm), *Leucinodes orbonalis* (eggplant fruit borer), *Leucoptera malifoliella, Lithocollectis* spp., *Lobesia botrana* (grape fruit moth), *Loxagrotis* spp. (noctuid moths), *Loxagrotis albicosta* (western bean cutworm), *Lymantria dispar* (gypsy moth), *Lyonetia clerkella* (apple leaf miner), *Mahasena corbetti* (oil palm bagworm), *Malacosoma* spp. (tent caterpillars), *Mamestra brassicae* (cabbage armyworm), *Maruca testulalis* (bean pod borer), *Metisa plana* (bagworm), *Mythimna unipuncta* (true armyworm), *Neoleucinodes elegantalis* (small tomato borer), *Nymphula depunctalis* (rice caseworm), *Operophthera brumata* (winter moth), *Ostrinia nubilalis* (European corn borer), *Oxydia vesulia, Pandemis cerasana* (common currant tortrix), *Pandemis heparana* (brown apple tortrix), *Papilio demodocus, Pectinophora gossypiella* (pink bollworm), *Peridroma* spp. (cutworms), *Peridroma saucia* (variegated cutworm), *Perileucoptera coffeella* (white coffee leafminer), *Phthorimaea operculella* (potato tuber moth), *Phyllocnisitis citrella, Phyllonorycter* spp. (leafminers), *Pieris rapae* (imported cabbageworm), *Plathypena scabra, Plodia interpunctella* (Indian meal moth), *Plutella xylostella* (diamondback moth), *Polychrosis viteana* (grape berry moth), *Prays endocarpa, Prays oleae* (olive moth), *Pseudaletia* spp. (noctuid moths), *Pseudaletia unipunctata* (armyworm), *Pseudoplusia includens* (soybean looper), *Rachiplusia nu, Scirpophaga incertulas, Sesamia* spp. (stemborers), *Sesamia inferens* (pink rice stem borer), *Sesamia nonagrioides, Setora nitens, Sitotroga cerealella* (Angoumois grain moth), *Sparganothis pilleriana, Spodoptera* spp. (armyworms), *Spodoptera exigua* (beet armyworm), *Spodoptera fugiperda* (fall armyworm), *Spodoptera oridania* (southern armyworm), *Synanthedon* spp. (root borers), *Thecla basilides, Thermisia gemmatalis, Tineola bisselliella* (webbing clothes moth), *Trichoplusia ni* (cabbage looper), *Tuta absoluta*, *Yponomeuta* spp., *Zeuzera coffeae* (red branch borer), and *Zeuzera pyrina* (leopard moth).

In another embodiment, the invention disclosed in this document can be used to control *Mallophaga* (chewing lice). A non-exhaustive list of these pests includes, but is not limited to, *Bovicola ovis* (sheep biting louse), *Menacanthus stramineus* (chicken body louse), and *Menopon gallinea* (common hen house).

In another embodiment, the invention disclosed in this document can be used to control *Orthoptera* (grasshoppers, locusts, and crickets). A non-exhaustive list of these pests includes, but is not limited to, *Anabrus simplex* (Mormon cricket), *Gryllotalpidae* (mole crickets), *Locusta migratoria*, *Melanoplus* spp. (grasshoppers), *Microcentrum retinerve* (angularwinged katydid), *Pterophylla* spp. (kaydids), *chistocerca gregaria, Scudderia furcata* (forktailed bush katydid), and *Valanga nigricorni*.

In another embodiment, the invention disclosed in this document can be used to control *Phthiraptera* (sucking lice). A non-exhaustive list of these pests includes, but is not limited to, *Haematopinus* spp. (cattle and hog lice), *Linognathus ovillus* (sheep louse), *Pediculus humanus capitis* (human body louse), *Pediculus humanus humanus* (human body lice), and *Pthirus pubis* (crab louse), In another embodiment, the invention disclosed in this document can be used to control *Siphonaptera*(fleas). A non-exhaustive list of these pests includes, but is not limited to, *Ctenocephalides canis* (dog flea), *Ctenocephalides felis* (cat flea), and *Pulex irritans* (human flea).

In another embodiment, the invention disclosed in this document can be used to control *Thysanoptera* (thrips). A non-exhaustive list of these pests includes, but is not limited to, *Frankliniella fusca* (tobacco thrips), *Frankliniella occidentalis* (western flower thrips), *Frankliniella shultzei Frankliniella williamsi* (corn thrips), *Heliothrips haemorrhaidalis* (greenhouse thrips), *Riphiphorothrips cruentatus, Scirtothrips* spp., *Scirtothrips citri* (citrus thrips), *Scirtothrips dorsalis* (yellow tea thrips), *Taeniothrips rhopalantennalis*, and *Thrips* spp.

In another embodiment, the invention disclosed in this document can be used to control *Thysanura* (bristletails). A non-exhaustive list of these pests includes, but is not limited to, *Lepisma* spp. (silverfish) and *Thermobia* spp. (firebrats).

In another embodiment, the invention disclosed in this document can be used to control *Acarina* (mites and ticks). A non-exhaustive list of these pests includes, but is not limited to, *Acarapsis woodi* (tracheal mite of honeybees), *Acarus* spp. (food mites), *Acarus siro* (grain mite), *Aceria mangiferae* (mango bud mite), *Aculops* spp., *Aculops lycopersici* (tomato russet mite), *Aculops pelekasi, Aculus pelekassi, Aculus schlechtendali* (apple rust mite), *Amblyomma americanum* (lone star tick), *Boophilus* spp. (ticks), *Brevipalpus obovatus* (privet mite), *Brevipalpus phoenicis* (red and black flat mite), *Demodex* spp. (mange mites), *Dermacentor* spp. (hard ticks), *Dermacentor variabilis* (american dog tick), *Dermatophagoides pteronyssinus* (house dust mite), *Eotetranycus* spp., *Eotetranychus carpini* (yellow spider mite), *Epitimerus* spp., *Eriophyes* spp., *Ixodes* spp. (ticks), *Metatetranycus* spp., *Notoedres cati, Oligonychus* spp., *Oligonychus coffee, Oligonychus ilicus* (southern red mite), *Panonychus* spp., *Panonychus citri* (citrus red mite), *Panonychus ulmi* (European red mite), *Phyllocoptruta oleivora* (citrus rust mite), *Polyphagotarsonemun latus* (broad mite), *Rhipicephalus sanguineus* (brown dog tick), *Rhizoglyphus* spp. (bulb mites), *Sarcoptes scabiei* (itch mite), *Tegolophus perseaflorae, Tetranychus* spp., *Tetranychus urticae* (twospotted spider mite), and *Varroa destructor* (honey bee mite).

In another embodiment, the invention disclosed in this document can be used to control *Nematoda* (nematodes). A non-exhaustive list of these pests includes, but is not limited to, *Aphelenchoides* spp. (bud and leaf & pine wood nematodes), *Belonolaimus* spp. (sting nematodes), *Criconemella* spp. (ring nematodes), *Dirofilaria immitis* (dog heartworm), *Ditylenchus* spp. (stem and bulb nematodes), *Heterodera* spp. (cyst nematodes), *Heterodera zeae* (corn cyst nematode), *Hirschmanniella* spp. (root nematodes), *Hoplolaimus* spp. (lance nematodes), *Meloidogyne* spp. (root knot nematodes), *Meloidogyne incognita* (root knot nematode), *Onchocerca volvulus* (hook-tail worm), *Pratylenchus* spp. (lesion nematodes), *Radopholus* spp. (burrowing nematodes), and *Rotylenchus reniformis* (kidney-shaped nematode).

In another embodiment, the invention disclosed in this document can be used to control *Symphyla* (symphylans). A non-exhaustive list of these pests includes, but is not limited to, *Scutigerella immaculata*.

For more detailed information consult "Handbook of Pest Control—The Behavior, Life History, and Control of Household Pests" by Arnold Mallis, 9$^{th}$ Edition, copyright 2004 by GIE Media Inc.

Mixtures

Some of the pesticides that can be employed beneficially in combination with the invention disclosed in this document include, but are not limited to the following:

1,2 dichloropropane, 1,3 dichloropropene, abamectin, acephate, acequinocyl, acetamiprid, acethion, acetoprole, acrinathrin, acrylonitrile, alanycarb, aldicarb, aldoxycarb, aldrin, allethrin, allosamidin, allyxycarb, alpha-cypermethrin, alpha-ecdysone, alpha-endosulfan, AKD-1022, amidithion, amidoflumet, aminocarb, amiton, amitraz, anabasine, arsenous oxide, athidathion, azadirachtin, azamethiphos, azinphos ethyl, azinphos methyl, azobenzene, azocyclotin, azothoate,

*Bacillus thuringiensis*, barium hexafluorosilicate, barthrin, benclothiaz, bendiocarb, benfuracarb, benomyl, benoxafos, bensultap, benzoximate, benzyl benzoate, beta-cyfluthrin, beta-cypermethrin, bifenazate, bifenthrin, binapacryl, bioallethrin, bioethanomethrin, biopermethrin, bistrifluoron, borax, boric acid, bromfenvinfos, bromo DDT, bromocyclen, bromophos, bromophos ethyl, bromopropylate, bufencarb, buprofezin, butacarb, butathiofos, butocarboxim, butonate, butoxycarboxim, cadusafos, calcium arsenate, calcium polysulfide, camphechlor, carbanolate, carbaryl, carbofuran, carbon disulfide, carbon tetrachloride, carbophenothion, carbosulfan, cartap, chinomethionat, chlorantraniliprole, chlorbenside, chlorbicyclen, chlordane, chlordecone, chlordimeform, chlorethoxyfos, chlorfenapyr, chlorfenethol, chlorfenson, chlorfensulphide, chlorfenvinphos, chlorfluazuron, chlormephos, chlorobenzilate, 3-(4-chloro-2,6-diemthylphenyl)-4-hydroxy-8-oxa-1-azaspiro[4,5]dec-3-en-2-one, 3-(4'-chloro-2,4-dimethyl[1,1'-biphenyl]-3-yl)-4-hydroxy-8-oxa-1-azaspiro[4,5]dec-3-en-2-one, 4-[[(6-chloro-3-pyridinyl)methyl]methylamino]-2(5H)-furanone, 4-[[(6-chloro-3-pyridinyl)methyl]cyclopropylamino]-2(5H)-furanone, 3-chloro-N2-[(1S)-1-methyl-2-(methylsulfonyl)ethyl]-N1-[2-methyl-4-[1,2,2,2-tetrafluoro-1-(trifluoromethyl)ethyl]phenyl]-1,2-benzenedicarboxamide, chloroform, chloromebuform, chloromethiuron, chloropicrin, chloropropylate, chlorphoxim, chlorprazophos, chlorpyrifos, chlorpyrifos-methyl, chlorthiophos, chromafenozide, cinerin I, cinerin II, cismethrin, cloethocarb, clofentezine, closantel, clothianidin, copper acetoarsenite, copper arsenate, copper naphthenate, copper oleate, coumaphos, coumithoate, crotamiton, crotoxyphos, cruentaren A & B, crufomate, cryolite, cyanofenphos, cyanophos, cyanthoate, cyanthraniliprole, cyclethrin, cycloprothrin, cyenopyrafen, cyflumetofen, cyfluthrin, cyhalothrin, cyhexatin, cypermethrin, cyphenothrin, cyromazine, cythioate, 2-cyano-N-ethyl-4-fluoro-3-methoxy-benenesulfonamide, 2-cyano-N-ethyl-3-methoxy-benzenesulfonamide, 2-cyano-3-difluoromethoxy-N-ethyl-4-fluoro-benzenesulfonamide, 2-cyano-3-fluoromethoxy-N-ethyl-benzenesulfonamide, 2-cyano-6-fluoro-3-methoxy-N,N-dimethyl-benzenesulfonamide, 2-cyano-N-ethyl-6-fluoro-3-methoxy-N-methyl-benzenesulfonamide, 2-cyano-3-difluoromethoxy-N,N-diemthyl-benzenesulfonamide.

d-limonene, dazomet, DBCP, DCIP, DDT, decarbofuran, deltamethrin, demephion, demephion O, demephion S, demeton, demeton methyl, demeton O, demeton O methyl, demeton S, demeton S methyl, demeton S methylsulphon, diafenthiuron, dialifos, diamidafos, diazinon, dicapthon, dichlofenthion, dichlofluanid, dichlorvos, dicofol, dicresyl, dicrotophos, dicyclanil, dieldrin, dienochlor, diflovidazin, diflubenzuron, 3-(difluoromethyl)-N-[2-(3,3-dimethylbutyl) phenyl]-1-methyl-1H-pyrazole-4-carboxamide, dilor, dimefluthrin, dimefox, dimetan, dimethoate, dimethrin, dimethylvinphos, dimetilan, dinex, dinobuton, dinocap, dinocap 4, dinocap 6, dinocton, dinopenton, dinoprop, dinosam, dinosulfon, dinotefuran, dinoterbon, diofenolan, dioxabenzofos, dioxacarb, dioxathion, diphenyl sulfone, disulfuram, disulfoton, dithicrofos, DNOC, dofenapyn, doramectin, ecdysterone, emamectin, EMPC, empenthrin, endosulfan, endothion, endrin, EPN, epofenonane, eprinomectin, esfenvalerate, etaphos, ethiofencarb, ethion, ethiprole, ethoate methyl, ethoprophos, ethyl DDD, ethyl formate, ethylene dibromide, ethylene dichloride, ethylene oxide, etofenprox, etoxazole, etrimfos, EXD, F1050, famphur, fenamiphos, fenazaflor, fenazaquin, fenbutatin oxide, fenchlorphos, fenethacarb, fenfluthrin, fenitrothion, fenobucarb, fenothiocarb, fenoxacrim, fenoxycarb, fenpirithrin, fenpropathrin, fenpyroximate, fenson, fensulfothion, fenthion, fenthion ethyl, fentrifanil, fenvalerate, fipronil, FKI-1033, flonicamid, fluacrypyrim, fluazuron, flubendiamide, flubenzimine, flucofuron, flucycloxuron, flucythrinate, fluenetil, flufenerim, flufenoxuron, flufenprox, flumethrin, fluorbenside, fluvalinate, fonofos, formetanate, formothion, formparanate, fosmethilan, fospirate, fosthiazate, fosthietan, fosthietan, furathiocarb, furethrin, furfural, gamma-cyhalothrin, gamma-HCH, halfenprox, halofenozide, HCH, HEOD, heptachlor, heptenophos, heterophos, hexaflumuron, hexythiazox, HHDN, hydramethylnon, hydrogen cyanide, hydroprene, hyquincarb, imicyafos, imidacloprid, imidaclothiz, imiprothrin, indoxacarb, iodomethane, IPSP, isamidofos, isazofos, isobenzan, isocarbophos, isodrin, isofenphos, isoprocarb, isoprothiolane, isothioate, isoxathion, ivermectin jasmolin I, jasmolin II, jodfenphos, juvenile hormone I, juvenile hormone II, juvenile hormone III, JS118, kelevan, kinoprene, lambda cyhalothrin, lead arsenate, lepimectin, leptophos, lindane, lirimfos, lufenuron, lythidathion, malathion, malonoben, mazidox, mecarbam, mecarphon, menazon, mephosfolan, mercurous chloride, mesulfen, mesulfenfos, metaflumizone, metam, methacrifos, methamidophos, methidathion, methiocarb, methocrotophos, methomyl, methoprene, methoxychlor, methoxyfenozide, methyl bromide, methyl isothiocyanate, methylchloroform, methylene chloride, metofluthrin, metolcarb, metoxadiazone, mevinphos, mexacarbate, milbemectin, milbemycin oxime, mipafox, mirex, MNAF, monocrotophos, morphothion, moxidectin, naftalofos, naled, naphthalene, nereistoxin, N-ethyl-2,2-dimethylpropionamide-2-(2,6-dichloro-α,α,α-thrifluoro-p-tolyl) hydrazone, N-ethyl-2,2-dichloro-1-methylcyclopropane-carboxamide-2-(2,6-dichloro-α,α,α-thrifluoro-p-tolyl) hydrazone nicotine, nifluridide, nikkomycins, nitenpyram, nithiazine, nitrilacarb, novaluron, noviflumuron, omethoate, oxamyl, oxydemeton methyl, oxydeprofos, oxydisulfoton, paradichlorobenzene, parathion, parathion methyl, penfluoron, pentachlorophenol, pentmethrin, permethrin, phenkapton, phenothrin, phenthoate, phorate, phosalone, phosfolan, phosmet, phosnichlor, phosphamidon, phosphine, phosphocarb, phoxim, phoxim methyl, piperonyl butoxide, pirimetaphos, pirimicarb, pirimiphos ethyl, pirimiphos methyl, potassium arsenite, potassium thiocyanate, pp' DDT, prallethrin, precocene I, precocene II, precocene III, primidophos, proclonol, profenofos, profluthrin, promacyl, promecarb, propaphos, propargite, propetamphos, propoxur, prothidathion, prothiofos, prothoate, protrifenbute, pyraclofos, pyrafluprole, pyrazophos, pyresmethrin, pyrethrin I, pyrethrin II, pyridaben, pyridalyl, pyridaphenthion, pyrifluquinazon, pyrimidifen, pyrimitate, pyriprole, pyriproxyfen, Qcide, quassia, quinalphos, quinalphos, quinalphos methyl, quinothion, quantifies, rafoxanide, resmethrin, rotenone, ryania, sabadilla, schradan, selamectin, silafluofen, sodium arsenite, sodium fluoride, sodium hexafluorosilicate, sodium thiocyanate, sophamide, spinetoram, spinosad, spirodiclofen, spiromesifen, spirotetramat, sulcofuron, sulfuram, sulfluramid, sulfotep, sulfoxaflor, sulfur, sulfuryl fluoride, sulprofos, tau-fluvalinate, tazimcarb, TDE, tebufenozide, tebufenpyrad, tebupirimfos, teflubenzuron, tefluthrin, temephos, TEPP, terallethrin, terbufos, tetrachloroethane, tetrachlorvinphos, tetradifon, tetramethrin, tetranactin, tetrasul, thetacypermethrin, thiacloprid, thiamethoxam, thicrofos, thiocarboxime, thiocyclam, thiodicarb, thiofanox, thiometon, thionazin, thioquinox, thiosultap, thuringiensin, tolfenpyrad, tralomethrin, transfluthrin, transpermethrin, triarathene, triazamate, triazophos, trichlorfon, trichlormetaphos 3, trichloronat, trifenofos, triflumuron, trimethacarb, triprene, vamidothion, vaniliprole, verticilide XDE-208, XMC, xylylcarb, Zeta-cypermethrin and zolaprofos.

Additionally, any combination of the above pesticides can be used.

The invention disclosed in this document can also be used with herbicides and fungicides, both for reasons of economy and synergy.

The invention disclosed in this document can be used with antimicrobials, bactericides, defoliants, safeners, synergists, algaecides, attractants, desiccants, pheromones, repellants, animal dips, avicides, disinfectants, semiochemicals, and molluscicides (these categories not necessarily mutually exclusive) for reasons of economy, and synergy.

For more information consult "Compendium of Pesticide Common Names" located at http://www.alanwood.net/pesticides/index.html as of the filing date of this document. Also consult "The Pesticide Manual" 14th Edition, edited by C D S Tomlin, copyright 2006 by British Crop Production Council.

Synergistic Mixtures

The invention disclosed in this document can be used with other compounds such as the ones mentioned under the heading "Mixtures" to form synergistic mixtures where the mode of action of the compounds in the mixtures are the same, similar, or different.

Examples of mode of actions include, but are not limited to: acetyl choline esterase inhibitor; sodium channel modulator; chitin biosynthesis inhibitor; GABA-gated chloride channel antagonist; GABA and glutamate-gated chloride channel agonist; acetyl choline receptor agonist; MET I inhibitor; Mg-stimulated ATPase inhibitor; nicotinic acetylcholine receptor; Midgut membrane disrupter; and oxidative phosphorylation disrupter.

Additionally, the following compounds are known as synergists and can be used with the invention disclosed in this document: piperonyl butoxide, piprotal, propyl isome, sesamex, sesamolin, and sulfoxide.

Formulations

A pesticide is rarely suitable for application in its pure form. It is usually necessary to add other substances so that the pesticide can be used at the required concentration and in an appropriate form, permitting ease of application, handling, transportation, storage, and maximum pesticide activity. Thus, pesticides are formulated into, for example, baits, concentrated emulsions, dusts, emulsifiable concentrates, fumigants, gels, granules, microencapsulations, seed treatments, suspension concentrates, suspoemulsions, tablets, water soluble liquids, water dispersible granules or dry flowables, wettable powders, and ultra low volume solutions.

For further information on formulation types see "Catalogue of pesticide formulation types and international coding system" Technical Monograph n°2, $5^{th}$ Edition by CropLife International (2002).

Pesticides are applied most often as aqueous suspensions or emulsions prepared from concentrated formulations of such pesticides. Such water-soluble, water-suspendable, or emulsifiable formulations, are either solids, usually known as wettable powders, or water dispersible granules, or liquids usually known as emulsifiable concentrates, or aqueous suspensions. Wettable powders, which may be compacted to form water dispersible granules, comprise an intimate mixture of the pesticide, a carrier, and surfactants. The concentration of the pesticide is usually from about 10% to about 90% by weight. The carrier is usually chosen from among the attapulgite clays, the montmorillonite clays, the diatomaceous earths, or the purified silicates. Effective surfactants, comprising from about 0.5% to about 10% of the wettable powder, are found among sulfonated lignins, condensed naphthalenesulfonates, naphthalenesulfonates, alkylbenzenesulfonates, alkyl sulfates, and nonionic surfactants such as ethylene oxide adducts of alkyl phenols.

Emulsifiable concentrates of pesticides comprise a convenient concentration of a pesticide, such as from about 50 to about 500 grams per liter of liquid dissolved in a carrier that is either a water miscible solvent or a mixture of water-immiscible organic solvent and emulsifiers. Useful organic solvents include aromatics, especially xylenes and petroleum fractions, especially the high-boiling naphthalenic and olefinic portions of petroleum such as heavy aromatic naphtha. Other organic solvents may also be used, such as the terpenic solvents including rosin derivatives, aliphatic ketones such as cyclohexanone, and complex alcohols such as 2-ethoxyethanol. Suitable emulsifiers for emulsifiable concentrates are chosen from conventional anionic and nonionic surfactants.

Aqueous suspensions comprise suspensions of water-insoluble pesticides dispersed in an aqueous carrier at a concentration in the range from about 5% to about 50% by weight. Suspensions are prepared by finely grinding the pesticide and vigorously mixing it into a carrier comprised of water and surfactants. Ingredients, such as inorganic salts and synthetic or natural gums, may also be added, to increase the density and viscosity of the aqueous carrier. It is often most effective to grind and mix the pesticide at the same time by preparing the aqueous mixture and homogenizing it in an implement such as a sand mill, ball mill, or piston-type homogenizer.

Pesticides may also be applied as granular compositions that are particularly useful for applications to the soil. Granular compositions usually contain from about 0.5% to about 10% by weight of the pesticide, dispersed in a carrier that comprises clay or a similar substance. Such compositions are usually prepared by dissolving the pesticide in a suitable solvent and applying it to a granular carrier which has been pre-formed to the appropriate particle size, in the range of from about 0.5 to 3 mm. Such compositions may also be formulated by making a dough or paste of the carrier and compound and crushing and drying to obtain the desired granular particle size.

Dusts containing a pesticide are prepared by intimately mixing the pesticide in powdered form with a suitable dusty agricultural carrier, such as kaolin clay, ground volcanic rock, and the like. Dusts can suitably contain from about 1% to about 10% of the pesticide. They can be applied as a seed dressing, or as a foliage application with a dust blower machine.

It is equally practical to apply a pesticide in the form of a solution in an appropriate organic solvent, usually petroleum oil, such as the spray oils, which are widely used in agricultural chemistry.

Pesticides can also be applied in the form of an aerosol composition. In such compositions the pesticide is dissolved or dispersed in a carrier, which is a pressure-generating propellant mixture. The aerosol composition is packaged in a container from which the mixture is dispensed through an atomizing valve.

Pesticide baits are formed when the pesticide is mixed with food or an attractant or both. When the pests eat the bait they also consume the pesticide. Baits may take the form of granules, gels, flowable powders, liquids, or solids. They are used in pest harborages.

Fumigants are pesticides that have a relatively high vapor pressure and hence can exist as a gas in sufficient concentrations to kill pests in soil or enclosed spaces. The toxicity of the fumigant is proportional to its concentration and the exposure time. They are characterized by a good capacity for diffusion and act by penetrating the pest's respiratory system or being absorbed through the pest's cuticle. Fumigants are applied to control stored product pests under gas proof sheets, in gas sealed rooms or buildings or in special chambers.

Pesticides can be microencapsulated by suspending the pesticide particles or droplets in plastic polymers of various types. By altering the chemistry of the polymer or by changing factors in the processing, microcapsules can be formed of various sizes, solubility, wall thicknesses, and degrees of penetrability. These factors govern the speed with which the active ingredient within is released, which, in turn, affects the residual performance, speed of action, and odor of the product.

Oil solution concentrates are made by dissolving pesticide in a solvent that will hold the pesticide in solution. Oil solutions of a pesticide usually provide faster knockdown and kill of pests than other formulations due to the solvents themselves having pesticidal action and the dissolution of the waxy covering of the integument increasing the speed of uptake of the pesticide. Other advantages of oil solutions include better storage stability, better penetration of crevices, and better adhesion to greasy surfaces.

Another embodiment is an oil-in-water emulsion, wherein the emulsion comprises oily globules which are each provided with a lamellar liquid crystal coating and are dispersed in an aqueous phase, wherein each oily globule comprises at least one compound which is agriculturally active, and is individually coated with a monolamellar or oligolamellar layer comprising: (1) at least one non-ionic lipophilic surface-active agent, (2) at least one non-ionic hydrophilic surface-active agent and (3) at least one ionic surface-active agent, wherein the globules having a mean particle diameter of less than 800 nanometers. Further information on the embodiment is disclosed in U.S. patent publication 20070027034 published Feb. 1, 2007, having patent application Ser. No. 11/495,228. For ease of use this embodiment will be referred to as "OIWE".

For further information consult "Insect Pest Management" $2^{nd}$ Edition by D. Dent, copyright CAB International (2000). Additionally, for more detailed information consult "Handbook of Pest Control—The Behavior, Life History, and Control of Household Pests" by Arnold Mallis, $9^{th}$ Edition, copyright 2004 by GIE Media Inc.

Other Formulation Components

Generally, the invention disclosed in this document when used in a formulation, such formulation can also contain other components. These components include, but are not limited to, (this is a non-exhaustive and non-mutually exclusive list) wetters, spreaders, stickers, penetrants, buffers, sequestering agents, drift reduction agents, compatibility agents, antifoam agents, cleaning agents, and emulsifiers. A few components are described forthwith.

A wetting agent is a substance that when added to a liquid increases the spreading or penetration power of the liquid by reducing the interfacial tension between the liquid and the surface on which it is spreading. Wetting agents are used for two main functions in agrochemical formulations: during processing and manufacture to increase the rate of wetting of powders in water to make concentrates for soluble liquids or suspension concentrates; and during mixing of a product with water in a spray tank to reduce the wetting time of wettable powders and to improve the penetration of water into water-dispersible granules. Examples of wetting agents used in wettable powder, suspension concentrate, and water-dispersible granule formulations are: sodium lauryl sulphate; sodium dioctyl sulphosuccinate; alkyl phenol ethoxylates; and aliphatic alcohol ethoxylates.

A dispersing agent is a substance which adsorbs onto the surface of a particles and helps to preserve the state of dispersion of the particles and prevents them from reaggregating. Dispersing agents are added to agrochemical formulations to facilitate dispersion and suspension during manufacture, and to ensure the particles redisperse into water in a spray tank. They are widely used in wettable powders, suspension concentrates and water-dispersible granules. Surfactants that are used as dispersing agents have the ability to adsorb strongly onto a particle surface and provide a charged or steric barrier to reaggregation of particles. The most commonly used surfactants are anionic, non-ionic, or mixtures of the two types. For wettable powder formulations, the most common dispersing agents are sodium lignosulphonates. For suspension concentrates, very good adsorption and stabilization are obtained using polyelectrolytes, such as sodium naphthalene sulphonate formaldehyde condensates. Tristyrylphenol ethoxylate phosphate esters are also used. Non-ionics such as alkylarylethylene oxide condensates and EO-PO block copolymers are sometimes combined with anionics as dispersing agents for suspension concentrates, In recent years, new types of very high molecular weight polymeric surfactants have been developed as dispersing agents. These have very long hydrophobic 'backbones' and a large number of ethylene oxide chains forming the 'teeth' of a 'comb' surfactant. These high molecular weight polymers can give very good long-term stability to suspension concentrates because the hydrophobic backbones have many anchoring points onto the particle surfaces. Examples of dispersing agents used in agrochemical formulations are: sodium lignosulphonates; sodium naphthalene sulphonate formaldehyde condensates; tristyrylphenol ethoxylate phosphate esters; aliphatic alcohol ethoxylates; alky ethoxylates; EO-PO block copolymers; and graft copolymers.

An emulsifying agent is a substance which stabilizes a suspension of droplets of one liquid phase in another liquid phase. Without the emulsifying agent the two liquids would separate into two immiscible liquid phases. The most commonly used emulsifier blends contain alkylphenol or aliphatic alcohol with 12 or more ethylene oxide units and the oil-soluble calcium salt of dodecylbenzene sulphonic acid. A range of hydrophile-lipophile balance ("HLB") values from 8 to 18 will normally provide good stable emulsions. Emulsion stability can sometimes be improved by the addition of a small amount of an EO-PO block copolymer surfactant.

A solubilizing agent is a surfactant which will form micelles in water at concentrations above the critical micelle concentration. The micelles are then able to dissolve or solubilized water-insoluble materials inside the hydrophobic part of the micelle. The type of surfactants usually used for solubilization are non-ionics: sorbitan monooleates; sorbitan monooleate ethoxylates; and methyl oleate esters.

Surfactants are sometimes used, either alone or with other additives such as mineral or vegetable oils as adjuvants to spray-tank mixes to improve the biological performance of the pesticide on the target. The types of surfactants used for bioenhancement depend generally on the nature and mode of action of the pesticide. However, they are often non-ionics such as: alky ethoxylates; linear aliphatic alcohol ethoxylates; aliphatic amine ethoxylates.

A carrier or diluent in an agricultural formulation is a material added to the pesticide to give a product of the required strength. Carriers are usually materials with high absorptive capacities, while diluents are usually materials with low absorptive capacities. Carriers and diluents are used in the formulation of dusts, wettable powders, granules and water-dispersible granules.

Organic solvents are used mainly in the formulation of emulsifiable concentrates, ULV formulations, and to a lesser extent granular formulations. Sometimes mixtures of solvents are used. The first main groups of solvents are aliphatic paraffinic oils such as kerosene or refined paraffins. The second main group and the most common comprises the aromatic solvents such as xylene and higher molecular weight fractions of $C_9$ and $C_{10}$ aromatic solvents. Chlorinated hydrocarbons are useful as cosolvents to prevent crystallization of pesticides when the formulation is emulsified into water. Alcohols are sometimes used as cosolvents to increase solvent power.

Thickeners or gelling agents are used mainly in the formulation of suspension concentrates, emulsions and suspoemulsions to modify the rheology or flow properties of the liquid and to prevent separation and settling of the dispersed particles or droplets. Thickening, gelling, and anti-settling agents generally fall into two categories, namely water-insoluble particulates and water-soluble polymers. It is possible to produce suspension concentrate formulations using clays and silicas. Examples of these types of materials, include, but are not limited to, montmorillonite, e.g. bentonite; magnesium aluminum silicate; and attapulgite. Water-soluble polysaccharides have been used as thickening-gelling agents for many years. The types of polysaccharides most commonly used are natural extracts of seeds and seaweeds or are synthetic derivatives of cellulose. Examples of these types of materials include, but are not limited to, guar gum; locust bean gum; carrageenam; alginates; methyl cellulose; sodium carboxymethyl cellulose (SCMC); hydroxyethyl cellulose (HEC). Other types of anti-settling agents are based on modified starches, polyacrylates, polyvinyl alcohol and polyethylene oxide. Another good anti-settling agent is xanthan gum.

Microorganisms cause spoilage of formulated products. Therefore preservation agents are used to eliminate or reduce their effect. Examples of such agents include, but are limited to: propionic acid and its sodium salt; sorbic acid and its sodium or potassium salts; benzoic acid and its sodium salt; p-hydroxy benzoic acid sodium salt; methyl p-hydroxy benzoate; and 1,2-benzisothiazalin-3-one (BIT).

The presence of surfactants, which lower interfacial tension, often causes water-based formulations to foam during mixing operations in production and in application through a spray tank. In order to reduce the tendency to foam, anti-foam agents are often added either during the production stage or before filling into bottles. Generally, there are two types of anti-foam agents, namely silicones and non-silicones. Silicones are usually aqueous emulsions of dimethyl polysiloxane while the non-silicone anti-foam agents are water-insoluble oils, such as octanol and nonanol, or silica. In both cases, the function of the anti-foam agent is to displace the surfactant from the air-water interface.

For further information see "Chemistry and Technology of Agrochemical Formulations" edited by D. A. Knowles, copyright 1998 by Kluwer Academic Publishers. Also see "Insecticides in Agriculture and Environment—Retrospects and Prospects" by A. S. Perry, I. Yamamoto, I. Ishaaya, and R. Perry, copyright 1998 by Springer-Verlag.

Applications

The actual amount of pesticide to be applied to loci of pests is not critical and can readily be determined by those skilled in the art. In general, concentrations from about 0.01 grams of pesticide per hectare to about 5000 grams of pesticide per hectare are expected to provide good control.

The locus to which a pesticide is applied can be any locus inhabited by an pest, for example, vegetable crops, fruit and nut trees, grape vines, ornamental plants, domesticated animals, the interior or exterior surfaces of buildings, and the soil around buildings.

Generally, with baits, the baits are placed in the ground where, for example, termites can come into contact with the bait. Baits can also be applied to a surface of a building, (horizontal, vertical, or slant, surface) where, for example, ants, termites, cockroaches, and flies, can come into contact with the bait.

Because of the unique ability of the eggs of some pests to resist pesticides repeated applications may be desirable to control newly emerged larvae.

Systemic movement of pesticides in plants may be utilized to control pests on one portion of the plant by applying the pesticides to a different portion of the plant. For example, control of foliar-feeding insects can be controlled by drip irrigation or furrow application, or by treating the seed before planting. Seed treatment can be applied to all types of seeds, including those from which plants genetically transformed to express specialized traits will germinate. Representative examples include seeds or plants expressing proteins and/or double stranded RNA toxic to invertebrate pests, such as *Bacillus thuringiensis*, Bt Cry toxins, Bt Vip toxins, RNAi, or other insecticidal toxins, those expressing herbicide resistance, such as "Roundup Ready" seed, or those with "stacked" foreign genes expressing insecticidal toxins, herbicide resistance, nutrition-enhancement or any other beneficial traits. Furthermore, such seed treatments with the invention disclosed in this document can further enhance the ability of a plant to better withstand stressful growing conditions. This results in a healthier, more vigorous plant, which can lead to higher yields at harvest time.

It should be readily apparent that the invention can be used with plants genetically transformed to express specialized traits, such as *Bacillus thuringiensis*, RNAi, or other insecticidal toxins, or those expressing herbicide resistance, or those with "stacked" foreign genes expressing insecticidal toxins, herbicide resistance, nutrition-enhancement or any other beneficial traits.

The invention disclosed in this document is suitable for controlling endoparasites and ectoparasites in the veterinary medicine sector or in the field of animal keeping (which for the avoidance of doubt includes pets, for example, cats, dogs, and birds). Compounds according to the invention are applied here in a known manner, such as by oral administration in the form of, for example, tablets, capsules, drinks, granules, by dermal application in the form of, for example, dipping, spraying, pouring on, spotting on, and dusting, and by parenteral administration in the form of, for example, an injection.

The invention disclosed in this document can also be employed advantageously in livestock keeping, for example, cattle, sheep, pigs, chickens, and geese. Suitable formulations are administered orally to the animals with the drinking water or feed. The dosages and formulations that are suitable depend on the species.

Before a pesticide can be used or sold commercially, such pesticide undergoes lengthy evaluation processes by various governmental authorities (local, regional, state, national, international). Voluminous data requirements are specified by regulatory authorities and must be addressed through data generation and submission by the product registrant or by another on the product registrant's behalf. These governmental authorities then review such data and if a determination of safety is concluded, provide the potential user or seller with product registration approval. Thereafter, in that locality where the product registration is granted and supported, such user or seller may use or sell such pesticide.

The headings in this document are for convenience only and must not be used to interpret any portion thereof.

For the avoidance of doubt Ar1 is sometimes referred to as Ar1 for typographic and formatting reasons. Additionally, Ar2 is sometimes referred to as Ar2 for typographic and formatting reasons. For the purposes of this invention the saturation of a double or triple bond with other atoms is considered a substitution.

What is claimed is:

1. A compound having the following formula:

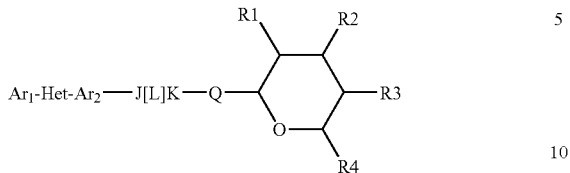

wherein:
(a) $Ar_1$ is substituted phenyl wherein said substituted phenyl has one or more substituents independently selected from F, Cl, Br, I, $C_1$-$C_6$ alkyl, $C_1$-$C_6$ haloalkyl, and $C_1$-$C_6$ haloalkoxy,
(b) Het is a 5 or 6 membered, saturated or unsaturated, heterocyclic ring, containing one or more heteroatoms independently selected from nitrogen, sulfur, or oxygen, and where $Ar_1$ and $Ar_2$ are not ortho to each other but may be meta or para and where said heterocyclic ring may also be substituted with one or more substituents independently selected from H, OH, F, Cl, Br, I, CN, $NO_2$, oxo, $C_1$-$C_6$ alkyl, $C_1$-$C_6$ haloalkyl, $C_1$-$C_6$ hydroxyalkyl, $C_3$-$C_6$ cycloalkyl, $C_3$-$C_6$ halocycloalkyl, $C_3$-$C_6$ hydroxycycloalkyl, $C_3$-$C_6$ cycloalkoxy, $C_3$-$C_6$ halocycloalkoxy, $C_3$-$C_6$ hydroxycycloalkoxy, $C_1$-$C_6$ alkoxy, $C_1$-$C_6$ haloalkoxy, $C_2$-$C_6$ alkenyl, $C_2$-$C_6$ alkynyl, $S(=O)_n(C_1$-$C_6$ alkyl), $S(=O)_n(C_1$-$C_6$ haloalkyl), $OSO_2(C_1$-$C_6$ alkyl), $OSO_2(C_1$-$C_6$ haloalkyl), $C(=O)H$, $C(=O)OH$, $C(=O)NR_xR_y$, $(C_1$-$C_6$ alkyl)$NR_xR_y$, $C(=O)(C_1$-$C_6$ alkyl), $C(=O)O(C_1$-$C_6$ alkyl), $C(=O)(C_1$-$C_6$ haloalkyl), $C(=O)O(C_1$-$C_6$ haloalkyl), $C(=O)(C_3$-$C_6$ cycloalkyl), $C(=O)O(C_3$-$C_6$ cycloalkyl), $C(=O)(C_2$-$C_6$ alkenyl), $C(=O)O(C_2$-$C_6$ alkenyl), $(C_1$-$C_6$ alkyl)$O(C_1$-$C_6$ alkyl), $(C_1$-$C_6$ alkyl)$S(C_1$-$C_6$ alkyl), $C(=O)(C_1$-$C_6$ alkyl)$C(=O)O(C_1$-$C_6$ alkyl), phenyl, phenoxy, substituted phenyl and substituted phenoxy (wherein such substituted phenyl and substituted phenoxy have one or more substituents independently selected from H, OH, F, Cl, Br, I, CN, $NO_2$, $C_1$-$C_6$ alkyl, $C_1$-$C_6$ haloalkyl, $C_1$-$C_6$ hydroxyalkyl, $C_3$-$C_6$ cycloalkyl, $C_3$-$C_6$ halocycloalkyl, $C_3$-$C_6$ hydroxycycloalkyl, $C_3$-$C_6$ cycloalkoxy, $C_3$-$C_6$ halocycloalkoxy, $C_3$-$C_6$ hydroxycycloalkoxy, $C_1$-$C_6$ alkoxy, $C_1$-$C_6$ haloalkoxy, $C_2$-$C_6$ alkenyl, $C_2$-$C_6$ alkynyl, $S(=O)_n(C_1$-$C_6$ alkyl), $S(=O)_n(C_1$-$C_6$ haloalkyl), $OSO_2(C_1$-$C_6$ alkyl), $OSO_2(C_1$-$C_6$ haloalkyl), $C(=O)H$, $C(=O)OH$, $C(=O)NR_xR_y$, $(C_1$-$C_6$ alkyl)$NR_xR_y$, $C(=O)(C_1$-$C_6$ alkyl), $C(=O)O(C_1$-$C_6$ alkyl), $C(=O)(C_1$-$C_6$ haloalkyl), $C(=O)O(C_1$-$C_6$ haloalkyl), $C(=O)(C_3$-$C_6$ cycloalkyl), $C(=O)O(C_3$-$C_6$ cycloalkyl), $C(=O)(C_1$-$C_6$ haloalkyl), $C(=O)(C_2$-$C_6$ alkenyl), $C(=O)O(C_2$-$C_6$ alkenyl), $(C_1$-$C_6$ alkyl)$O(C_1$-$C_6$ alkyl), $(C_1$-$C_6$ alkyl)$S(C_1$-$C_6$ alkyl), $C(=O)(C_1$-$C_6$ alkyl)$C(=O)O(C_1$-$C_6$ alkyl), phenyl, and phenoxy);
(c) $Ar_2$ is
(1) furanyl, phenyl, pyridazinyl, pyridyl, pyrimidinyl, thienyl, or
(2) substituted furanyl, substituted phenyl, substituted pyridazinyl, substituted pyridyl, substituted pyrimidinyl, or substituted thienyl,
wherein said substituted furanyl, substituted phenyl, substituted pyridazinyl, substituted pyridyl, substituted pyrimidinyl, and substituted thienyl, have one or more substituents independently selected from H, OH, F, Cl, Br, I, CN, $NO_2$, $C_1$-$C_6$ alkyl, $C_1$-$C_6$ haloalkyl, $C_1$-$C_6$ hydroxyalkyl, $C_3$-$C_6$ cycloalkyl, $C_3$-$C_6$ halocycloalkyl, $C_3$-$C_6$ hydroxycycloalkyl, $C_3$-$C_6$ cycloalkoxy, $C_3$-$C_6$ halocycloalkoxy, $C_3$-$C_6$ hydroxycycloalkoxy, $C_1$-$C_6$ alkoxy, $C_1$-$C_6$ haloalkoxy, $C_2$-$C_6$ alkenyl, $C_2$-$C_6$ alkynyl, $S(=O)_n(C_1$-$C_6$ alkyl), $S(=O)_n(C_1$-$C_6$ haloalkyl), $OSO_2(C_1$-$C_6$ alkyl), $OSO_2(C_1$-$C_6$ haloalkyl), $C(=O)H$, $C(=O)OH$, $C(=O)NR_xR_y$, $(C_1$-$C_6$ alkyl)$NR_xR_y$, $C(=O)(C_1$-$C_6$ alkyl), $C(=O)O(C_1$-$C_6$ alkyl), $C(=O)(C_1$-$C_6$ haloalkyl), $C(=O)O(C_1$-$C_6$ haloalkyl), $C(=O)(C_3$-$C_6$ cycloalkyl), $C(=O)O(C_3$-$C_6$ cycloalkyl), $C(=O)(C_2$-$C_6$ alkenyl), $C(=O)O(C_2$-$C_6$ alkenyl), $(C_1$-$C_6$ alkyl)$O(C_1$-$C_6$ alkyl), $(C_1$-$C_6$ alkyl)$S(C_1$-$C_6$ alkyl), $C(=O)(C_1$-$C_6$ alkyl)$C(=O)O(C_1$-$C_6$ alkyl), phenyl, phenoxy, substituted phenyl and substituted phenoxy (wherein such substituted phenyl and substituted phenoxy have one or more substituents independently selected from H, OH, F, Cl, Br, I, CN, $NO_2$, $C_1$-$C_6$ alkyl, $C_1$-$C_6$ haloalkyl, $C_1$-$C_6$ hydroxyalkyl, $C_3$-$C_6$ cycloalkyl, $C_3$-$C_6$ halocycloalkyl, $C_3$-$C_6$ hydroxycycloalkyl, $C_3$-$C_6$ cycloalkoxy, $C_3$-$C_6$ halocycloalkoxy, $C_3$-$C_6$ hydroxycycloalkoxy, $C_1$-$C_6$ alkoxy, $C_1$-$C_6$ haloalkoxy, $C_2$-$C_6$ alkenyl, $C_2$-$C_6$ alkynyl, $S(=O)_n(C_1$-$C_6$ alkyl), $S(=O)_n(C_1$-$C_6$ haloalkyl), $OSO_2(C_1$-$C_6$ alkyl), $OSO_2(C_1$-$C_6$ haloalkyl), $C(=O)H$, $C(=O)OH$, $C(=O)NR_xR_y$, $(C_1$-$C_6$ alkyl)$NR_xR_y$, $C(=O)(C_1$-$C_6$ alkyl), $C(=O)O(C_1$-$C_6$ alkyl), $C(=O)(C_1$-$C_6$ haloalkyl), $C(=O)O(C_1$-$C_6$ haloalkyl), $C(=O)(C_3$-$C_6$ cycloalkyl), $C(=O)O(C_3$-$C_6$ cycloalkyl), $C(=O)(C_1$-$C_6$ haloalkyl), $C(=O)(C_2$-$C_6$ alkenyl), $C(=O)O(C_2$-$C_6$ alkenyl), $(C_1$-$C_6$ alkyl)$O(C_1$-$C_6$ alkyl), $(C_1$-$C_6$ alkyl)$S(C_1$-$C_6$ alkyl), $C(=O)(C_1$-$C_6$ alkyl)$C(=O)O(C_1$-$C_6$ alkyl), phenyl, and phenoxy);
(d) J is O, N, NR5, CR5, C=O, or J and $Ar_2$ form a 3, 4, 5, or 6 membered ring;
(e) L is a single or double bond;
(f) K is CR5, C=O, N, NR5, or C=S;
(g) Q is O or S;
(h) R1 is H, OH, F, Cl, Br, I, oxo, $C_1$-$C_6$ alkyl, $C_1$-$C_6$ haloalkyl, $C_1$-$C_6$ alkoxy, $C_3$-$C_6$ cycloalkoxy, $C_1$-$C_6$ haloalkoxy, $C_2$-$C_6$ alkenyloxy, $(C_1$-$C_6$ alkyl)$O(C_1$-$C_6$ alkyl), $(C_1$-$C_6$ alkyl)$O(C_1$-$C_6$ alkoxy), $OC(=O)(C_1$-$C_6$ alkyl), $OC(=O)(C_3$-$C_6$ cycloalkyl), $OC(=O)(C_1$-$C_6$ haloalkyl), $OC(=O)(C_2$-$C_6$ alkenyl), or $NR_xR_y$;
(i) R2 is H, OH, F, Cl, Br, I, oxo, $C_1$-$C_6$ alkyl, $C_1$-$C_6$ haloalkyl, $C_1$-$C_6$ alkoxy, $C_3$-$C_6$ cycloalkoxy, $C_1$-$C_6$ haloalkoxy, $C_2$-$C_6$ alkenyloxy, $(C_1$-$C_6$ alkyl)$O(C_1$-$C_6$ alkyl), $(C_1$-$C_6$ alkyl)$O(C_1$-$C_6$ alkoxy), $OC(=O)(C_1$-$C_6$ alkyl), $OC(=O)(C_3$-$C_6$ cycloalkyl), $OC(=O)(C_1$-$C_6$ haloalkyl), $OC(=O)(C_2$-$C_6$ alkenyl), or $NR_xR_y$;
j) R3 is H, OH, F, Cl, Br, I, oxo, $C_1$-$C_6$ alkyl, $C_1$-$C_6$ haloalkyl, $C_1$-$C_6$ alkoxy, $C_3$-$C_6$ cycloalkoxy, $C_1$-$C_6$ haloalkoxy, $C_2$-$C_6$ alkenyloxy, $(C_1$-$C_6$ alkyl)$O(C_1$-$C_6$ alkyl), $(C_1$-$C_6$ alkyl)$O(C_1$-$C_6$ alkoxy), $OC(=O)(C_1$-$C_6$ alkyl), $OC(=O)(C_3$-$C_6$ cycloalkyl), $OC(=O)(C_1$-$C_6$ haloalkyl), $OC(=O)(C_2$-$C_6$ alkenyl), or $NR_xR_y$;
(k) R4 is H, $C_1$-$C_6$ alkyl, $C_1$-$C_6$ haloalkyl, $C_1$-$C_6$ alkoxy, $C_1$-$C_6$ haloalkoxy, $C_2$-$C_6$ alkenyloxy, $(C_1$-$C_6$ alkyl)$O(C_1$-$C_6$ alkyl); and
(l) R5 is H, OH, F, Cl, Br, I, CN, $NO_2$, $C_1$-$C_6$ alkyl, $C_1$-$C_6$ haloalkyl, $C_1$-$C_6$ hydroxyalkyl, $C_3$-$C_6$ cycloalkyl, $C_3$-$C_6$ halocycloalkyl, $C_3$-$C_6$ hydroxycycloalkyl, $C_3$-$C_6$ cycloalkoxy, $C_3$-$C_6$ halocycloalkoxy, $C_3$-$C_6$ hydroxycycloalkoxy, $C_1$-$C_6$ alkoxy, $C_1$-$C_6$ haloalkoxy, $C_2$-$C_6$ alkenyl, $C_2$-$C_6$ alkynyl, $S(=O)_n(C_1$-$C_6$ alkyl), $S(=O)_n$ ($C_1$-$C_6$ haloalkyl), $OSO_2$($C_1$-$C_6$ alkyl), $OSO_2$($C_1$-$C_6$ haloalkyl), C(=O)H, C(=O)OH, C(=O)$NR_xR_y$, ($C_1$-$C_6$ alkyl)$NR_xR_y$, C(=O)($C_1$-$C_6$ alkyl), C(=O)O($C_1$-$C_6$ alkyl), C(=O)($C_1$-$C_6$ haloalkyl), C(=O)O($C_1$-$C_6$ haloalkyl), C(=O)($C_3$-$C_6$ cycloalkyl), C(=O)O($C_3$-$C_6$ cycloalkyl), C(=O)($C_2$-$C_6$ alkenyl), C(=O)O($C_2$-$C_6$ alkenyl), ($C_1$-$C_6$ alkyl)O($C_1$-$C_6$ alkyl), ($C_1$-$C_6$ alkyl)S($C_1$-$C_6$ alkyl), C(=O)($C_1$-$C_6$ alkyl)C(=O)O($C_1$-$C_6$ alkyl), phenyl, phenoxy, wherein each alkyl, haloalkyl, hydroxyalkyl, cycloalkyl, halocycloalkyl, hydroxycycloalkyl, cycloalkoxy, halocycloalkoxy, hydroxycycloalkoxy, alkoxy, haloalkoxy, alkenyl, alkynyl, phenyl, and phenoxy are optionally substituted with one or more substituents independently selected from OH, F, Cl, Br, I, CN, $NO_2$, oxo, $C_1$-$C_6$ alkyl, $C_1$-$C_6$ haloalkyl, $C_1$-$C_6$ hydroxyalkyl, $C_3$-$C_6$ cycloalkyl, $C_3$-$C_6$ halocycloalkyl, $C_3$-$C_6$ hydroxycycloalkyl, $C_3$-$C_6$ cycloalkoxy, $C_3$-$C_6$ halocycloalkoxy, $C_3$-$C_6$ hydroxycycloalkoxy, $C_1$-$C_6$ alkoxy, $C_1$-$C_6$ haloalkoxy, $C_2$-$C_6$ alkenyl, $C_2$-$C_6$ alkynyl, S(=O)$_n$($C_1$-$C_6$ alkyl), S(=O)$_n$($C_1$-$C_6$ haloalkyl), $OSO_2$($C_1$-$C_6$ alkyl), $OSO_2$($C_1$-$C_6$ haloalkyl), C(=O)H, C(=O)OH, C(=O)$NR_xR_y$, ($C_1$-$C_6$ alkyl)$NR_xR_y$, C(=O)($C_1$-$C_6$ alkyl), C(=O)O($C_1$-$C_6$ alkyl), C(=O)($C_1$-$C_6$ haloalkyl), C(=O)O($C_1$-$C_6$ haloalkyl), C(=O)($C_3$-$C_6$ cycloalkyl), C(=O)O($C_3$-$C_6$ cycloalkyl), C(=O)($C_2$-$C_6$ alkenyl), C(=O)O($C_2$-$C_6$ alkenyl), ($C_1$-$C_6$ alkyl)O($C_1$-$C_6$ alkyl), ($C_1$-$C_6$ alkyl)S($C_1$-$C_6$ alkyl), C(=O)($C_1$-$C_6$ alkyl)C(=O)O($C_1$-$C_6$ alkyl), phenyl, and phenoxy;

(m) n=0, 1, or 2;

(n) $R_x$ and $R_y$ are independently selected from H, $C_1$-$C_6$ alkyl, $C_1$-$C_6$ haloalkyl, $C_1$-$C_6$ hydroxyalkyl, $C_3$-$C_6$ cycloalkyl, $C_3$-$C_6$ halocycloalkyl, $C_3$-$C_6$ hydroxycycloalkyl, $C_3$-$C_6$ cycloalkoxy, $C_3$-$C_6$ halocycloalkoxy, $C_3$-$C_6$ hydroxycycloalkoxy, $C_1$-$C_6$ alkoxy, $C_1$-$C_6$ haloalkoxy, $C_2$-$C_6$ alkenyl, $C_2$-$C_6$ alkynyl, S(=O)$_n$($C_1$-$C_6$ alkyl), S(=O)$_n$($C_1$-$C_6$ haloalkyl), $OSO_2$($C_1$-$C_6$ alkyl), $OSO_2$($C_1$-$C_6$ haloalkyl), C(=O)H, C(=O)OH, C(=O)($C_1$-$C_6$ alkyl), C(=O)O($C_1$-$C_6$ alkyl), C(=O)($C_1$-$C_6$ haloalkyl), C(=O)O($C_1$-$C_6$ haloalkyl), C(=O)($C_3$-$C_6$ cycloalkyl), C(=O)O($C_3$-$C_6$ cycloalkyl), C(=O)($C_2$-$C_6$ alkenyl), C(=O)O($C_2$-$C_6$ alkenyl), ($C_1$-$C_6$ alkyl)O($C_1$-$C_6$ alkyl), ($C_1$-$C_6$ alkyl)S($C_1$-$C_6$ alkyl), C(=O)($C_1$-$C_6$ alkyl)C(=O)O($C_1$-$C_6$ alkyl), phenyl, and phenoxy.

2. A compound having the following formula:

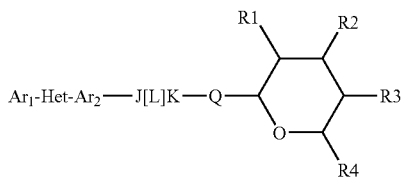

wherein:
(a) $Ar_1$ is
(1) furanyl, phenyl, pyridazinyl, pyridyl, pyrimidinyl, thienyl, or
(2) substituted furanyl, substituted phenyl, substituted pyridazinyl, substituted pyridyl, substituted pyrimidinyl, or substituted thienyl,
wherein said substituted furanyl, substituted phenyl, substituted pyridazinyl, substituted pyridyl, substituted pyrimidinyl, and substituted thienyl, have one or more substituents independently selected from H, OH, F, Cl, Br, I, CN, $NO_2$, $C_1$-$C_6$ alkyl, $C_1$-$C_6$ haloalkyl, $C_1$-$C_6$ hydroxyalkyl, $C_3$-$C_6$ cycloalkyl, $C_3$-$C_6$ halocycloalkyl, $C_3$-$C_6$ hydroxycycloalkyl, $C_3$-$C_6$ cycloalkoxy, $C_3$-$C_6$ halocycloalkoxy, $C_3$-$C_6$ hydroxycycloalkoxy, $C_1$-$C_6$ alkoxy, $C_1$-$C_6$ haloalkoxy, $C_2$-$C_6$ alkenyl, $C_2$-$C_6$ alkynyl, S(=O)$_2$($C_1$-$C_6$ alkyl), S(=O)$_n$($C_1$-$C_6$ haloalkyl), $OSO_2$($C_1$-$C_6$ alkyl), $OSO_2$($C_1$-$C_6$ haloalkyl), C(=O)H, C(=O)OH, C(=O)$NR_xR_y$, ($C_1$-$C_6$ alkyl)$NR_xR_y$, C(=O)($C_1$-$C_6$ alkyl), C(=O)O($C_1$-$C_6$ alkyl), C(=O)($C_1$-$C_6$ haloalkyl), C(=O)O($C_1$-$C_6$ haloalkyl), C(=O)($C_3$-$C_6$ cycloalkyl), C(=O)O($C_3$-$C_6$ cycloalkyl), C(=O)($C_2$-$C_6$ alkenyl), C(=O)O($C_2$-$C_6$ alkenyl), ($C_1$-$C_6$ alkyl)O($C_1$-$C_6$ alkyl), ($C_1$-$C_6$ alkyl)S($C_1$-$C_6$ alkyl), C(=O)($C_1$-$C_6$ alkyl)C(=O)O($C_1$-$C_6$ alkyl), phenyl, phenoxy, substituted phenyl and substituted phenoxy (wherein such substituted phenyl and substituted phenoxy have one or more substituents independently selected from H, OH, F, Cl, Br, I, CN, $NO_2$, $C_1$-$C_6$ alkyl, $C_1$-$C_6$ haloalkyl, $C_1$-$C_6$ hydroxyalkyl, $C_3$-$C_6$ cycloalkyl, $C_3$-$C_6$ halocycloalkyl, $C_3$-$C_6$ hydroxycycloalkyl, $C_3$-$C_6$ cycloalkoxy, $C_3$-$C_6$ halocycloalkoxy, $C_3$-$C_6$ hydroxycycloalkoxy, $C_1$-$C_6$ alkoxy, $C_1$-$C_6$ haloalkoxy, $C_2$-$C_6$ alkenyl, $C_2$-$C_6$ alkynyl, S(=O)$_n$($C_1$-$C_6$ alkyl), S(=O)$_n$($C_1$-$C_6$ haloalkyl), $OSO_2$($C_1$-$C_6$ alkyl), $OSO_2$($C_1$-$C_6$ haloalkyl), C(=O)H, C(=O)OH, C(=O)$NR_xR_y$, ($C_1$-$C_6$ alkyl)$NR_xR_y$, C(=O)($C_1$-$C_6$ alkyl), C(=O)O($C_1$-$C_6$ alkyl), C(=O)($C_1$-$C_6$ haloalkyl), C(=O)O($C_1$-$C_6$ haloalkyl), C(=O)($C_3$-$C_6$ cycloalkyl), C(=O)O($C_3$-$C_6$ cycloalkyl), C(=O)($C_2$-$C_6$ alkenyl), C(=O)O($C_2$-$C_6$ alkenyl), ($C_1$-$C_6$ alkyl)O($C_1$-$C_6$ alkyl), ($C_1$-$C_6$ alkyl)S($C_1$-$C_6$ alkyl), C(=O)($C_1$-$C_6$ alkyl)C(=O)O($C_1$-$C_6$ alkyl)phenyl, and phenoxy);

(b) Het is selected from the group consisting of imidazolyl, isothiazolyl, isoxazolyl, 1,2,4-oxadiazolyl, 1,3,4-oxadiazolyl, oxazolinyl, oxazolyl, piperazinyl, piperidinyl, pyrazinyl, pyrazolinyl, pyrazolyl, pyridazinyl, pyridyl, pyrimidinyl, pyrrolyl, 1,2,3,4-tetrazolyl, thiadiazolyl, thiazolinyl, thiazolyl, 1,2,3-triazinyl, 1,2,4-triazinyl, 1,3,5-triazinyl, 1,2,3-triazolyl, 1,2,4-triazolyl, substituted imidazolyl, substituted isothiazolyl, substituted isoxazolyl, substituted 1,2,4-oxadiazolyl, substituted 1,3,4 oxadiazolyl, substituted oxazolinyl, substituted oxazolyl, substituted piperazinyl, substituted piperidinyl, substituted pyrazinyl, substituted pyrazolinyl, substituted pyrazolyl, substituted pyridazinyl, substituted pyridyl, substituted pyrimidinyl, substituted pyrrolyl, substituted tetrazolyl, substituted thiadiazolyl, substituted thiazolinyl, substituted thiazolyl, substituted 1,2,3-triazinyl, substituted 1,2,4-triazinyl, substituted 1,3,5-triazinyl, substituted 1,2,3-triazolyl, and substituted 1,2,4-triazolyl, where said substituted groups have one or more substituents independently selected from H, OH, F, Cl, Br, I, CN, $NO_2$, oxo, $C_1$-$C_6$ alkyl, $C_1$-$C_6$ haloalkyl, $C_1$-$C_6$ hydroxyalkyl, $C_3$-$C_6$ cycloalkyl, $C_3$-$C_6$ halocycloalkyl, $C_3$-$C_6$ hydroxycycloalkyl, $C_3$-$C_6$ cycloalkoxy, $C_3$-$C_6$ halocycloalkoxy, $C_3$-$C_6$ hydroxycycloalkoxy, $C_1$-$C_6$ alkoxy, $C_1$-$C_6$ haloalkoxy, $C_2$-$C_6$ alkenyl, $C_2$-$C_6$ alkynyl, S(=O)$_n$($C_1$-$C_6$ alkyl), S(=O)$_n$($C_1$-$C_6$ haloalkyl), $OSO_2$($C_1$-$C_6$ alkyl), $OSO_2$($C_1$-$C_6$ haloalkyl), C(=O)H, C(=O)OH, C(=O)$NR_xR_y$, ($C_1$-$C_6$ alkyl)$NR_xR_y$, C(=O)($C_1$-$C_6$ alkyl), C(=O)O($C_1$-$C_6$ alkyl), C(=O)(C$_1$-C$_6$ haloalkyl), C(=O)(C$_3$-C$_6$ cycloalkyl), C(=O)O(C$_3$-C$_6$ cycloalkyl), C(=O)(C$_1$-C$_6$ haloalkyl), C(=O)(C$_2$-C$_6$ alkenyl), C(=O)O(C$_2$-C$_6$ alkenyl), (C$_1$-C$_6$ alkyl)O(C$_1$-C$_6$ alkyl), (C$_1$-C$_6$ alkyl)S(C$_1$-C$_6$ alkyl), C(=O)(C$_1$-C$_6$ alkyl)C(=O)O(C$_1$-C$_6$ alkyl)phenyl, phenoxy, substituted phenyl and substituted phenoxy (wherein such substituted phenyl and substituted phenoxy have one or more substituents independently selected from H, OH, F, Cl, Br, I, CN, NO$_2$, oxo, C$_1$-C$_6$ alkyl, C$_1$-C$_6$ haloalkyl, C$_1$-C$_6$ hydroxyalkyl, C$_3$-C$_6$ cycloalkyl, C$_3$-C$_6$ halocycloalkyl, C$_3$-C$_6$ hydroxycycloalkyl, C$_3$-C$_6$ cycloalkoxy, C$_3$-C$_6$ halocycloalkoxy, C$_3$-C$_6$ hydroxycycloalkoxy, C$_1$-C$_6$ alkoxy, C$_1$-C$_6$ haloalkoxy, C$_2$-C$_6$ alkenyl, C$_2$-C$_6$ alkynyl, S(=O)$_n$(C$_1$-C$_6$ alkyl), S(=O)$_n$(C$_1$-C$_6$ haloalkyl), OSO$_2$(C$_1$-C$_6$ alkyl), OSO$_2$(C$_1$-C$_6$ haloalkyl), C(=O)H, C(=O)OH, C(=O)NR$_x$R$_y$, (C$_1$-C$_6$ alkyl)NR$_x$R$_y$, C(=O)(C$_1$-C$_6$ alkyl), C(=O)O(C$_1$-C$_6$ alkyl), C(=O)(C$_1$-C$_6$ haloalkyl), C(=O)(C$_3$-C$_6$ cycloalkyl), C(=O)O(C$_3$-C$_6$ cycloalkyl), C(=O)(C$_1$-C$_6$ haloalkyl), C(=O)(C$_2$-C$_6$ alkenyl), C(=O)O(C$_2$-C$_6$ alkenyl), (C$_1$-C$_6$ alkyl)O(C$_1$-C$_6$ alkyl), (C$_1$-C$_6$ alkyl)S(C$_1$-C$_6$ alkyl), C(=O)(C$_1$-C$_6$ alkyl)C(=O)O(C$_1$-C$_6$ alkyl)phenyl, and phenoxy);

(c) Ar$_2$ is
(1) furanyl, phenyl, pyridazinyl, pyridyl, pyrimidinyl, thienyl, or
(2) substituted furanyl, substituted phenyl, substituted pyridazinyl, substituted pyridyl, substituted pyrimidinyl, or substituted thienyl, wherein said substituted furanyl, substituted phenyl, substituted pyridazinyl, substituted pyridyl, substituted pyrimidinyl, and substituted thienyl, have one or more substituents independently selected from H, OH, F, Cl, Br, I, CN, NO$_2$, C$_1$-C$_6$ alkyl, C$_1$-C$_6$ haloalkyl, C$_1$-C$_6$ hydroxyalkyl, C$_3$-C$_6$ cycloalkyl, C$_3$-C$_6$ halocycloalkyl, C$_3$-C$_6$ hydroxycycloalkyl, C$_3$-C$_6$ cycloalkoxy, C$_3$-C$_6$ halocycloalkoxy, C$_3$-C$_6$ hydroxycycloalkoxy, C$_1$-C$_6$ alkoxy, C$_1$-C$_6$ haloalkoxy, C$_2$-C$_6$ alkenyl, C$_2$-C$_6$ alkynyl, S(=O)$_n$(C$_1$-C$_6$ alkyl), S(=O)$_n$(C$_1$-C$_6$ haloalkyl), OSO$_2$(C$_1$-C$_6$ alkyl), OSO$_2$(C$_1$-C$_6$ haloalkyl), C(=O)H, C(=O)OH, C(=O)NR$_x$R$_y$, (C$_1$-C$_6$ alkyl)NR$_x$R$_y$, C(=O)(C$_1$-C$_6$ alkyl), C(=O)O(C$_1$-C$_6$ alkyl), C(=O)(C$_1$-C$_6$ haloalkyl), C(=O)(C$_3$-C$_6$ cycloalkyl), C(=O)O(C$_3$-C$_6$ cycloalkyl), C(=O)(C$_2$-C$_6$ alkenyl), C(=O)O(C$_2$-C$_6$ alkenyl), (C$_1$-C$_6$ alkyl)O(C$_1$-C$_6$ alkyl), (C$_1$-C$_6$ alkyl)S(C$_1$-C$_6$ alkyl), C(=O)(C$_1$-C$_6$ alkyl)C(=O)O(C$_1$-C$_6$ alkyl), phenyl, phenoxy, substituted phenyl and substituted phenoxy (wherein such substituted phenyl and substituted phenoxy have one or more substituents independently selected from H, OH, F, Cl, Br, I, CN, NO$_2$, C$_1$-C$_6$ alkyl, C$_1$-C$_6$ haloalkyl, C$_1$-C$_6$ hydroxyalkyl, C$_3$-C$_6$ cycloalkyl, C$_3$-C$_6$ halocycloalkyl, C$_3$-C$_6$ hydroxycycloalkyl, C$_3$-C$_6$ cycloalkoxy, C$_3$-C$_6$ halocycloalkoxy, C$_3$-C$_6$ hydroxycycloalkoxy, C$_1$-C$_6$ alkoxy, C$_1$-C$_6$ haloalkoxy, C$_2$-C$_6$ alkenyl, C$_2$-C$_6$ alkynyl, S(=O)$_n$(C$_1$-C$_6$ alkyl), S(=O)$_n$(C$_1$-C$_6$ haloalkyl), OSO$_2$(C$_1$-C$_6$ alkyl), OSO$_2$(C$_1$-C$_6$ haloalkyl), C(=O)H, C(=O)OH, C(=O)NR$_x$R$_y$, (C$_1$-C$_6$ alkyl)NR$_x$R$_y$, C(=O)(C$_1$-C$_6$ alkyl), C(=O)O(C$_1$-C$_6$ alkyl), C(=O)(C$_1$-C$_6$ haloalkyl), C(=O)O(C$_1$-C$_6$ haloalkyl), C(=O)(C$_3$-C$_6$ cycloalkyl), C(=O)O(C$_3$-C$_6$ cycloalkyl), C(=O)(C$_2$-C$_6$ alkenyl), C(=O)O(C$_2$-C$_6$ alkenyl), (C$_1$-C$_6$ alkyl)O(C$_1$-C$_6$ alkyl), (C$_1$-C$_6$ alkyl)S(C$_1$-C$_6$ alkyl), C(=O)(C$_1$-C$_6$ alkyl)C(=O)O(C$_1$-C$_6$ alkyl), phenyl, and phenoxy);

(d) J is O, N, NR5, CR5, C=O, or J and Ar$_2$ form a 3, 4, 5, or 6 membered ring;
(e) L is a single or double bond;
(f) K is CR5, C=O, N, NR5, or C=S;
(g) Q is O or S;
(h) R1 is H, OH, F, Cl, Br, I, oxo, C$_1$-C$_6$ alkyl, C$_1$-C$_6$ haloalkyl, C$_1$-C$_6$ alkoxy, C$_3$-C$_6$ cycloalkoxy, C$_1$-C$_6$ haloalkoxy, C$_2$-C$_6$ alkenyloxy, (C$_1$-C$_6$ alkyl)O(C$_1$-C$_6$ alkyl), (C$_1$-C$_6$ alkyl)O(C$_1$-C$_6$ alkoxy), OC(=O)(C$_1$-C$_6$ alkyl), OC(=O)(C$_3$-C$_6$ cycloalkyl), OC(=O)(C$_1$-C$_6$ haloalkyl), OC(=O)(C$_2$-C$_6$ alkenyl), or NR$_x$R$_y$;
(i) R2 is H, OH, F, Cl, Br, I, oxo, C$_1$-C$_6$ alkyl, C$_1$-C$_6$ haloalkyl, C$_1$-C$_6$ alkoxy, C$_3$-C$_6$ cycloalkoxy, C$_1$-C$_6$ haloalkoxy, C$_2$-C$_6$ alkenyloxy, (C$_1$-C$_6$ alkyl)O(C$_1$-C$_6$ alkyl), (C$_1$-C$_6$ alkyl)O(C$_1$-C$_6$ alkoxy), OC(=O)(C$_1$-C$_6$ alkyl), OC(=O)(C$_3$-C$_6$ cycloalkyl), OC(=O)(C$_1$-C$_6$ haloalkyl), OC(=O)(C$_2$-C$_6$ alkenyl), or NR$_x$R$_y$;
j) R3 is H, OH, F, Cl, Br, I, oxo, C$_1$-C$_6$ alkyl, C$_1$-C$_6$ haloalkyl, C$_1$-C$_6$ alkoxy, C$_3$-C$_6$ cycloalkoxy, C$_1$-C$_6$ haloalkoxy, C$_2$-C$_6$ alkenyloxy, (C$_1$-C$_6$ alkyl)O(C$_1$-C$_6$ alkyl), (C$_1$-C$_6$ alkyl)O(C$_1$-C$_6$ alkoxy), OC(=O)(C$_1$-C$_6$ alkyl), OC(=O)(C$_3$-C$_6$ cycloalkyl), OC(=O)(C$_1$-C$_6$ haloalkyl), OC(=O)(C$_2$-C$_6$ alkenyl), or NR$_x$R$_y$;
(k) R4 is H, C$_1$-C$_6$ alkyl, C$_1$-C$_6$ haloalkyl, C$_1$-C$_6$ alkoxy, C$_1$-C$_6$ haloalkoxy, C$_2$-C$_6$ alkenyloxy, (C$_1$-C$_6$ alkyl)O(C$_1$-C$_6$ alkyl); and
(l) R5 is H, OH, F, Cl, Br, I, CN, NO$_2$, C$_1$-C$_6$ alkyl, C$_1$-C$_6$ haloalkyl, C$_1$-C$_6$ hydroxyalkyl, C$_3$-C$_6$ cycloalkyl, C$_3$-C$_6$ halocycloalkyl, C$_3$-C$_6$ hydroxycycloalkyl, C$_3$-C$_6$ cycloalkoxy, C$_3$-C$_6$ halocycloalkoxy, C$_3$-C$_6$ hydroxycycloalkoxy, C$_1$-C$_6$ alkoxy, C$_1$-C$_6$ haloalkoxy, C$_2$-C$_6$ alkenyl, C$_2$-C$_6$ alkynyl, S(=O)$_n$(C$_1$-C$_6$ alkyl), S(=O)$_n$(C$_1$-C$_6$ haloalkyl), OSO$_2$(C$_1$-C$_6$ alkyl), OSO$_2$(C$_1$-C$_6$ haloalkyl), C(=O)H, C(=O)OH, C(=O)NR$_x$R$_y$, (C$_1$-C$_6$ alkyl)NR$_x$R$_y$, C(=O)(C$_1$-C$_6$ alkyl), C(=O)O(C$_1$-C$_6$ alkyl), C(=O)(C$_1$-C$_6$ haloalkyl), C(=O)O(C$_1$-C$_6$ haloalkyl), C(=O)(C$_3$-C$_6$ cycloalkyl), C(=O)O(C$_3$-C$_6$ cycloalkyl), C(=O)(C$_2$-C$_6$ alkenyl), C(=O)O(C$_2$-C$_6$ alkenyl), (C$_1$-C$_6$ alkyl)O(C$_1$-C$_6$ alkyl), (C$_1$-C$_6$ alkyl)S(C$_1$-C$_6$ alkyl), C(=O)(C$_1$-C$_6$ alkyl)C(=O)O(C$_1$-C$_6$ alkyl), phenyl, phenoxy, wherein each alkyl, haloalkyl, hydroxyalkyl, cycloalkyl, halocycloalkyl, hydroxycycloalkyl, cycloalkoxy, halocycloalkoxy, hydroxycycloalkoxy, alkoxy, haloalkoxy, alkenyl, alkynyl, phenyl, and phenoxy are optionally substituted with one or more substituents independently selected from OH, F, Cl, Br, I, CN, NO$_2$, oxo, C$_1$-C$_6$ alkyl, C$_1$-C$_6$ haloalkyl, C$_1$-C$_6$ hydroxyalkyl, C$_3$-C$_6$ cycloalkyl, C$_3$-C$_6$ halocycloalkyl, C$_3$-C$_6$ hydroxycycloalkyl, C$_3$-C$_6$ cycloalkoxy, C$_3$-C$_6$ halocycloalkoxy, C$_3$-C$_6$ hydroxycycloalkoxy, C$_1$-C$_6$ alkoxy, C$_1$-C$_6$ haloalkoxy, C$_2$-C$_6$ alkenyl, C$_2$-C$_6$ alkynyl, S(=O)$_n$(C$_1$-C$_6$ alkyl), S(=O)$_n$(C$_1$-C$_6$ haloalkyl), OSO$_2$(C$_1$-C$_6$ alkyl), OSO$_2$(C$_1$-C$_6$ haloalkyl), C(=O)H, C(=O)OH, C(=O)NR$_x$R$_y$, (C$_1$-C$_6$ alkyl)NR$_x$R$_y$, C(=O)(C$_1$-C$_6$ alkyl), C(=O)O(C$_1$-C$_6$ alkyl), C(=O)(C$_1$-C$_6$ haloalkyl), C(=O)O(C$_1$-C$_6$ haloalkyl), C(=O)(C$_3$-C$_6$ cycloalkyl), C(=O)O(C$_3$-C$_6$ cycloalkyl), C(=O)(C$_2$-C$_6$ alkenyl), C(=O)O(C$_2$-C$_6$ alkenyl), (C$_1$-C$_6$ alkyl)O(C$_1$-C$_6$ alkyl), (C$_1$-C$_6$ alkyl)S(C$_1$-C$_6$ alkyl), C(=O)(C$_1$-C$_6$ alkyl)C(=O)O(C$_1$-C$_6$ alkyl), phenyl, and phenoxy;

(m) n=0, 1, or 2;
(n) $R_x$ and $R_y$ are independently selected from H, $C_1$-$C_6$ alkyl, $C_1$-$C_6$ haloalkyl, $C_1$-$C_6$ hydroxyalkyl, $C_3$-$C_6$ cycloalkyl, $C_3$-$C_6$ halocycloalkyl, $C_3$-$C_6$ hydroxycycloalkyl, $C_3$-$C_6$ cycloalkoxy, $C_3$-$C_6$ halocycloalkoxy, $C_3$-$C_6$ hydroxycycloalkoxy, $C_1$-$C_6$ alkoxy, $C_1$-$C_6$ haloalkoxy, $C_2$-$C_6$ alkenyl, $C_2$-$C_6$ alkynyl, $S(=O)_n(C_1$-$C_6$ alkyl), $S(=O)_n(C_1$-$C_6$ haloalkyl), $OSO_2(C_1$-$C_6$ alkyl), $OSO_2(C_1$-$C_6$ haloalkyl), $C(=O)H$, $C(=O)OH$, $C(=O)(C_1$-$C_6$ alkyl), $C(=O)O(C_1$-$C_6$ alkyl), $C(=O)(C_1$-$C_6$ haloalkyl), $C(=O)O(C_1$-$C_6$ haloalkyl), $C(=O)(C_3$-$C_6$ cycloalkyl), $C(=O)O(C_3$-$C_6$ cycloalkyl), $C(=O)(C_2$-$C_6$ alkenyl), $C(=O)O(C_2$-$C_6$ alkenyl), $(C_1$-$C_6$ alkyl)$O(C_1$-$C_6$ alkyl), $(C_1$-$C_6$ alkyl)$S(C_1$-$C_6$ alkyl), $C(=O)(C_1$-$C_6$ alkyl)$C(=O)O(C_1$-$C_6$ alkyl), phenyl, and phenoxy.

3. A compound having the following formula:

Ar₁-Het-Ar₂—J[L]K—Q—[pyranyl ring with substituents R1, R2, R3, R4 and O]

wherein:
(a) $Ar_1$ is
  (1) furanyl, phenyl, pyridazinyl, pyridyl, pyrimidinyl, thienyl, or
  (2) substituted furanyl, substituted phenyl, substituted pyridazinyl, substituted pyridyl, substituted pyrimidinyl, or substituted thienyl,
    wherein said substituted furanyl, substituted phenyl, substituted pyridazinyl, substituted pyridyl, substituted pyrimidinyl, and substituted thienyl, have one or more substituents independently selected from H, OH, F, Cl, Br, I, CN, $NO_2$, $C_1$-$C_6$ alkyl, $C_1$-$C_6$ haloalkyl, $C_1$-$C_6$ hydroxyalkyl, $C_3$-$C_6$ cycloalkyl, $C_3$-$C_6$ halocycloalkyl, $C_3$-$C_6$ hydroxycycloalkyl, $C_3$-$C_6$ cycloalkoxy, $C_3$-$C_6$ halocycloalkoxy, $C_3$-$C_6$ hydroxycycloalkoxy, $C_1$-$C_6$ alkoxy, $C_1$-$C_6$ haloalkoxy, $C_2$-$C_6$ alkenyl, $C_2$-$C_6$ alkynyl, $S(=O)_n(C_1$-$C_6$ alkyl), $S(=O)_n(C_1$-$C_6$ haloalkyl), $OSO_2(C_1$-$C_6$ alkyl), $OSO_2(C_1$-$C_6$ haloalkyl), $C(=O)H$, $C(=O)OH$, $C(=O)NR_xR_y$, $(C_1$-$C_6$ alkyl)$NR_xR_y$, $C(=O)(C_1$-$C_6$ alkyl), $C(=O)O(C_1$-$C_6$ alkyl), $C(=O)(C_1$-$C_6$ haloalkyl), $C(=O)O(C_1$-$C_6$ haloalkyl), $C(=O)(C_3$-$C_6$ cycloalkyl), $C(=O)O(C_3$-$C_6$ cycloalkyl), $C(=O)(C_2$-$C_6$ alkenyl), $C(=O)O(C_2$-$C_6$ alkenyl), $(C_1$-$C_6$ alkyl)$O(C_1$-$C_6$ alkyl), $(C_1$-$C_6$ alkyl)$S(C_1$-$C_6$ alkyl), $C(=O)(C_1$-$C_6$ alkyl)$C(=O)O(C_1$-$C_6$ alkyl), phenyl, phenoxy, substituted phenyl and substituted phenoxy (wherein such substituted phenyl and substituted phenoxy have one or more substituents independently selected from H, OH, F, Cl, Br, I, CN, $NO_2$, $C_1$-$C_6$ alkyl, $C_1$-$C_6$ haloalkyl, $C_1$-$C_6$ hydroxyalkyl, $C_3$-$C_6$ cycloalkyl, $C_3$-$C_6$ halocycloalkyl, $C_3$-$C_6$ hydroxycycloalkyl, $C_3$-$C_6$ cycloalkoxy, $C_3$-$C_6$ halocycloalkoxy, $C_3$-$C_6$ hydroxycycloalkoxy, $C_1$-$C_6$ alkoxy, $C_1$-$C_6$ haloalkoxy, $C_2$-$C_6$ alkenyl, $C_2$-$C_6$ alkynyl, $S(=O)_n(C_1$-$C_6$ alkyl), $S(=O)_n(C_1$-$C_6$ haloalkyl), $OSO_2(C_1$-$C_6$ alkyl), $OSO_2(C_1$-$C_6$ haloalkyl), $C(=O)H$, $C(=O)OH$, $C(=O)NR_xR_y$, $(C_1$-$C_6$ alkyl)$NR_xR_y$, $C(=O)(C_1$-$C_6$ alkyl), $C(=O)O(C_1$-$C_6$ alkyl), $C(=O)(C_1$-$C_6$ haloalkyl), $C(=O)O(C_1$-$C_6$ haloalkyl), $C(=O)(C_3$-$C_6$ cycloalkyl), $C(=O)O(C_3$-$C_6$ cycloalkyl), $C(=O)(C_1$-$C_6$ haloalkyl), $C(=O)(C_2$-$C_6$ alkenyl), $C(=O)O(C_2$-$C_6$ alkenyl), $(C_1$-$C_6$ alkyl)$O(C_1$-$C_6$ alkyl), $(C_1$-$C_6$ alkyl)$S(C_1$-$C_6$ alkyl), $C(=O)(C_1$-$C_6$ alkyl)$C(=O)O(C_1$-$C_6$ alkyl)phenyl, and phenoxy);

(b) A compound according to claim 1 wherein: Het is selected from the group consisting of imidazolyl, isoxazolyl, 1,2,4-oxadiazolyl, pyrazinyl, pyrimidinyl, thiazolyl, 1,3,5-triazinyl, 1,2,4-triazolyl, substituted imidazolyl, substituted pyrazolyl, and substituted 1,2,4-triazolyl, where said substituted groups have one or more substituents independently selected from oxo, $C_1$-$C_6$ alkyl, $C_1$-$C_6$ haloalkyl, $C_2$-$C_6$ alkenyl, and $C(=O)O(C_1$-$C_6$ alkyl);

(c) $Ar_2$ is
  (1) furanyl, phenyl, pyridazinyl, pyridyl, pyrimidinyl, thienyl, or
  (2) substituted furanyl, substituted phenyl, substituted pyridazinyl, substituted pyridyl, substituted pyrimidinyl, or substituted thienyl,
    wherein said substituted furanyl, substituted phenyl, substituted pyridazinyl, substituted pyridyl, substituted pyrimidinyl, and substituted thienyl, have one or more substituents independently selected from H, OH, F, Cl, Br, I, CN, $NO_2$, $C_1$-$C_6$ alkyl, $C_1$-$C_6$ haloalkyl, $C_1$-$C_6$ hydroxyalkyl, $C_3$-$C_6$ cycloalkyl, $C_3$-$C_6$ halocycloalkyl, $C_3$-$C_6$ hydroxycycloalkyl, $C_3$-$C_6$ cycloalkoxy, $C_3$-$C_6$ halocycloalkoxy, $C_3$-$C_6$ hydroxycycloalkoxy, $C_1$-$C_6$ alkoxy, $C_1$-$C_6$ haloalkoxy, $C_2$-$C_6$ alkenyl, $C_2$-$C_6$ alkynyl, $S(=O)_n(C_1$-$C_6$ alkyl), $S(=O)_n(C_1$-$C_6$ haloalkyl), $OSO_2(C_1$-$C_6$ alkyl), $OSO_2(C_1$-$C_6$ haloalkyl), $C(=O)H$, $C(=O)OH$, $C(=O)NR_xR_y$, $(C_1$-$C_6$ alkyl)$NR_xR_y$, $C(=O)(C_1$-$C_6$ alkyl), $C(=O)O(C_1$-$C_6$ alkyl), $C(=O)(C_1$-$C_6$ haloalkyl), $C(=O)O(C_1$-$C_6$ haloalkyl), $C(=O)(C_3$-$C_6$ cycloalkyl), $C(=O)O(C_3$-$C_6$ cycloalkyl), $C(=O)(C_1$-$C_6$ haloalkyl), $C(=O)(C_2$-$C_6$ alkenyl), $C(=O)O(C_2$-$C_6$ alkenyl), $(C_1$-$C_6$ alkyl)$O(C_1$-$C_6$ alkyl), $(C_1$-$C_6$ alkyl)$S(C_1$-$C_6$ alkyl), $C(=O)(C_1$-$C_6$ alkyl)$C(=O)O(C_1$-$C_6$ alkyl), phenyl, and phenoxy);

(d) J is O, N, NR5, CR5, C=O, or J and $Ar_2$ form a 3, 4, 5, or 6 membered ring;
(e) L is a single or double bond;
(f) K is CR5, C=O, N, NR5, or C=S;
(g) Q is O or S;

(h) R1 is H, OH, F, Cl, Br, I, oxo, $C_1$-$C_6$ alkyl, $C_1$-$C_6$ haloalkyl, $C_1$-$C_6$ alkoxy, $C_3$-$C_6$ cycloalkoxy, $C_1$-$C_6$ haloalkoxy, $C_2$-$C_6$ alkenyloxy, ($C_1$-$C_6$ alkyl)O($C_1$-$C_6$ alkyl), ($C_1$-$C_6$ alkyl)O($C_1$-$C_6$ alkoxy), OC(=O)($C_1$-$C_6$ alkyl), OC(=O)($C_3$-$C_6$ cycloalkyl), OC(=O)($C_1$-$C_6$ haloalkyl), OC(=O)($C_2$-$C_6$ alkenyl), or $NR_xR_y$;

(i) R2 is H, OH, F, Cl, Br, I, oxo, $C_1$-$C_6$ alkyl, $C_1$-$C_6$ haloalkyl, $C_1$-$C_6$ alkoxy, $C_3$-$C_6$ cycloalkoxy, $C_1$-$C_6$ haloalkoxy, $C_2$-$C_6$ alkenyloxy, ($C_1$-$C_6$ alkyl)O($C_1$-$C_6$ alkyl), ($C_1$-$C_6$ alkyl)O($C_1$-$C_6$ alkoxy), OC(=O)($C_1$-$C_6$ alkyl), OC(=O)($C_3$-$C_6$ cycloalkyl), OC(=O)($C_1$-$C_6$ haloalkyl), OC(=O)($C_2$-$C_6$ alkenyl), or $NR_xR_y$;

(j) R3 is H, OH, F, Cl, Br, I, oxo, $C_1$-$C_6$ alkyl, $C_1$-$C_6$ haloalkyl, $C_1$-$C_6$ alkoxy, $C_3$-$C_6$ cycloalkoxy, $C_1$-$C_6$ haloalkoxy, $C_2$-$C_6$ alkenyloxy, ($C_1$-$C_6$ alkyl)O($C_1$-$C_6$ alkyl), ($C_1$-$C_6$ alkyl)O($C_1$-$C_6$ alkoxy), OC(=O)($C_1$-$C_6$ alkyl), OC(=O)($C_3$-$C_6$ cycloalkyl), OC(=O)($C_1$-$C_6$ haloalkyl), OC(=O)($C_2$-$C_6$ alkenyl), or $NR_xR_y$;

(k) R4 is H, $C_1$-$C_6$ alkyl, $C_1$-$C_6$ haloalkyl, $C_1$-$C_6$ alkoxy, $C_1$-$C_6$ haloalkoxy, $C_2$-$C_6$ alkenyloxy, ($C_1$-$C_6$ alkyl)O ($C_1$-$C_6$ alkyl); and (l) R5 is H, OH, F, Cl, Br, I, CN, $NO_2$, $C_1$-$C_6$ alkyl, $C_1$-$C_6$ haloalkyl, $C_1$-$C_6$ hydroxyalkyl, $C_3$-$C_6$ cycloalkyl, $C_3$-$C_6$ halocycloalkyl, $C_3$-$C_6$ hydroxycycloalkyl, $C_3$-$C_6$ cycloalkoxy, $C_3$-$C_6$ halocycloalkoxy, $C_3$-$C_6$ hydroxycycloalkoxy, $C_1$-$C_6$ alkoxy, $C_1$-$C_6$ haloalkoxy, $C_2$-$C_6$ alkenyl, $C_2$-$C_6$ alkynyl, S(=O)$_n$($C_1$-$C_6$ alkyl), S(=O)$_n$($C_1$-$C_6$ haloalkyl), $OSO_2$($C_1$-$C_6$ alkyl), $OSO_2$($C_1$-$C_6$ haloalkyl), C(=O)H, C(=O)OH, C(=O)$NR_xR_y$, ($C_1$-$C_6$ alkyl)$NR_xR_y$, C(=O)($C_1$-$C_6$ alkyl), C(=O)O($C_1$-$C_6$ alkyl), C(=O)($C_1$-$C_6$ haloalkyl), C(=O)O($C_1$-$C_6$ haloalkyl), C(=O)($C_3$-$C_6$ cycloalkyl), C(=O)O($C_3$-$C_6$ cycloalkyl), C(=O)($C_2$-$C_6$ alkenyl), C(=O)O($C_2$-$C_6$ alkenyl), ($C_1$-$C_6$ alkyl)O($C_1$-$C_6$ alkyl), ($C_1$-$C_6$ alkyl)S($C_1$-$C_6$ alkyl), C(=O)($C_1$-$C_6$ alkyl)C(=O)O($C_1$-$C_6$ alkyl), phenyl, phenoxy, wherein each alkyl, haloalkyl, hydroxyalkyl, cycloalkyl, halocycloalkyl, hydroxycycloalkyl, cycloalkoxy, halocycloalkoxy, hydroxycycloalkoxy, alkoxy, haloalkoxy, alkenyl, alkynyl, phenyl, and phenoxy are optionally substituted with one or more substituents independently selected from OH, F, Cl, Br, I, CN, $NO_2$, oxo, $C_1$-$C_6$ alkyl, $C_1$-$C_6$ haloalkyl, $C_1$-$C_6$ hydroxyalkyl, $C_3$-$C_6$ cycloalkyl, $C_3$-$C_6$ halocycloalkyl, $C_3$-$C_6$ hydroxycycloalkyl, $C_3$-$C_6$ cycloalkoxy, $C_3$-$C_6$ halocycloalkoxy, $C_3$-$C_6$ hydroxycycloalkoxy, $C_1$-$C_6$ alkoxy, $C_1$-$C_6$ haloalkoxy, $C_2$-$C_6$ alkenyl, $C_2$-$C_6$ alkynyl, S(=O)$_n$($C_1$-$C_6$ alkyl), S(=O)$_n$($C_1$-$C_6$ haloalkyl), $OSO_2$($C_1$-$C_6$ alkyl), $OSO_2$($C_1$-$C_6$ haloalkyl), C(=O)H, C(=O)OH, C(=O)$NR_xR_y$, ($C_1$-$C_6$ alkyl)$NR_xR_y$, C(=O)($C_1$-$C_6$ alkyl), C(=O)O($C_1$-$C_6$ alkyl), C(=O)($C_1$-$C_6$ haloalkyl), C(=O)O($C_1$-$C_6$ haloalkyl), C(=O)($C_3$-$C_6$ cycloalkyl), C(=O)O($C_3$-$C_6$ cycloalkyl), C(=O) ($C_2$-$C_6$ alkenyl), C(=O)O($C_2$-$C_6$ alkenyl), ($C_1$-$C_6$ alkyl)O($C_1$-$C_6$ alkyl), ($C_1$-$C_6$ alkyl)S($C_1$-$C_6$ alkyl), C(=O)($C_1$-$C_6$ alkyl)C(=O)O($C_1$-$C_6$ alkyl), phenyl, and phenoxy;

(m) n=0, 1, or 2;

(n) $R_x$ and $R_y$ are independently selected from H, $C_1$-$C_6$ alkyl, $C_1$-$C_6$ haloalkyl, $C_1$-$C_6$ hydroxyalkyl, $C_3$-$C_6$ cycloalkyl, $C_3$-$C_6$ halocycloalkyl, $C_3$-$C_6$ hydroxycycloalkyl, $C_3$-$C_6$ cycloalkoxy, $C_3$-$C_6$ halocycloalkoxy, $C_3$-$C_6$ hydroxycycloalkoxy, $C_1$-$C_6$ alkoxy, $C_1$-$C_6$ haloalkoxy, $C_2$-$C_6$ alkenyl, $C_2$-$C_6$ alkynyl, S(=O)$_n$($C_1$-$C_6$ alkyl), S(=O)$_n$($C_1$-$C_6$ haloalkyl), $OSO_2$($C_1$-$C_6$ alkyl), $OSO_2$($C_1$-$C_6$ haloalkyl), C(=O)H, C(=O)OH, C(=O)($C_1$-$C_6$ alkyl), C(=O)O($C_1$-$C_6$ alkyl), C(=O) ($C_1$-$C_6$ haloalkyl), C(=O)O($C_1$-$C_6$ haloalkyl), C(=O) ($C_3$-$C_6$ cycloalkyl), C(=O)O($C_3$-$C_6$ cycloalkyl), C(=O)($C_2$-$C_6$ alkenyl), C(=O)O($C_2$-$C_6$ alkenyl), ($C_1$-$C_6$ alkyl)O($C_1$-$C_6$ alkyl), ($C_1$-$C_6$ alkyl)S($C_1$-$C_6$ alkyl), C(=O)($C_1$-$C_6$ alkyl)C(=O)O($C_1$-$C_6$ alkyl), phenyl, and phenoxy.

4. A compound having the following formula:

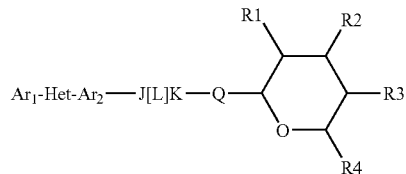

wherein:

(a) $Ar_1$ is (1) furanyl, phenyl, pyridazinyl, pyridyl, pyrimidinyl, thienyl, or (2) substituted furanyl, substituted phenyl, substituted pyridazinyl, substituted pyridyl, substituted pyrimidinyl, or substituted thienyl, wherein said substituted furanyl, substituted phenyl, substituted pyridazinyl, substituted pyridyl, substituted pyrimidinyl, and substituted thienyl, have one or more substituents independently selected from H, OH, F, Cl, Br, I, CN, $NO_2$, $C_1$-$C_6$ alkyl, $C_1$-$C_6$ haloalkyl, $C_1$-$C_6$ hydroxyalkyl, $C_3$-$C_6$ cycloalkyl, $C_3$-$C_6$ halocycloalkyl, $C_3$-$C_6$ hydroxycycloalkyl, $C_3$-$C_6$ cycloalkoxy, $C_3$-$C_6$ halocycloalkoxy, $C_3$-$C_6$ hydroxycycloalkoxy, $C_1$-$C_6$ alkoxy, $C_1$-$C_6$ haloalkoxy, $C_2$-$C_6$ alkenyl, $C_2$-$C_6$ alkynyl, S(=O)$_n$($C_1$-$C_6$ alkyl), S(=O)$_n$($C_1$-$C_6$ haloalkyl), $OSO_2$($C_1$-$C_6$ alkyl), $OSO_2$($C_1$-$C_6$ haloalkyl), C(=O)H, C(=O)OH, C(=O)$NR_xR_y$, ($C_1$-$C_6$ alkyl)$NR_xR_y$, C(=O)($C_1$-$C_6$ alkyl), C(=O)O($C_1$-$C_6$ alkyl), C(=O)($C_1$-$C_6$ haloalkyl), C(=O)O($C_1$-$C_6$ haloalkyl), C(=O)($C_3$-$C_6$ cycloalkyl), C(=O)O ($C_3$-$C_6$ cycloalkyl), C(=O)($C_2$-$C_6$ alkenyl), C(=O)O($C_2$-$C_6$ alkenyl), ($C_1$-$C_6$ alkyl)O($C_1$-$C_6$ alkyl), ($C_1$-$C_6$ alkyl)S($C_1$-$C_6$ alkyl), C(=O)($C_1$-$C_6$ alkyl)C(=O)O($C_1$-$C_6$ alkyl), phenyl, phenoxy, substituted phenyl and substituted phenoxy (wherein such substituted phenyl and substituted phenoxy have one or more substituents independently selected from H, OH, F, Cl, Br, I, CN, $NO_2$, $C_1$-$C_6$ alkyl, $C_1$-$C_6$ haloalkyl, $C_1$-$C_6$ hydroxyalkyl, $C_3$-$C_6$ cycloalkyl, $C_3$-$C_6$ halocycloalkyl, $C_3$-$C_6$ hydroxycycloalkyl, $C_3$-$C_6$ cycloalkoxy, $C_3$-$C_6$ halocycloalkoxy, $C_3$-$C_6$ hydroxycycloalkoxy, $C_1$-$C_6$ alkoxy, $C_1$-$C_6$ haloalkoxy, $C_2$-$C_6$ alkenyl, $C_2$-$C_6$ alkynyl, S(=O)$_n$($C_1$-$C_6$ alkyl), S(=O)$_n$($C_1$-$C_6$ haloalkyl), $OSO_2$($C_1$-$C_6$ alkyl), $OSO_2$($C_1$-$C_6$ haloalkyl), C(=O)H, C(=O)OH, C(=O)$NR_xR_y$, ($C_1$-$C_6$ alkyl)$NR_xR_y$, C(=O)($C_1$-$C_6$ alkyl), C(=O)O($C_1$-$C_6$ alkyl), C(=O)($C_1$-$C_6$ haloalkyl), C(=O)O($C_1$-$C_6$ haloalkyl), C(=O)($C_3$-$C_6$ cycloalkyl), C(=O)O($C_3$-$C_6$ cycloalkyl), C(=O) ($C_2$-$C_6$ alkenyl), C(=O)O($C_2$-$C_6$ alkenyl), ($C_1$-$C_6$ alkyl)O($C_1$-$C_6$ alkyl), ($C_1$-$C_6$ alkyl)S($C_1$-$C_6$ alkyl), C(=O)($C_1$-$C_6$ alkyl)C(=O)O($C_1$-$C_6$ alkyl)phenyl, and phenoxy);

(b) Het is a 5 or 6 membered, saturated or unsaturated, heterocyclic ring, containing one or more heteroatoms independently selected from nitrogen, sulfur, or oxygen, and where $Ar_1$ and $Ar_2$ are not ortho to each other but may be meta or para, such as, for a and where said heterocyclic ring may also be substituted with one or more substituents independently selected from H, OH, F, Cl, Br, I, CN, $NO_2$, oxo, $C_1$-$C_6$ alkyl, $C_1$-$C_6$ haloalkyl, $C_1$-$C_6$ hydroxyalkyl, $C_3$-$C_6$ cycloalkyl, $C_3$-$C_6$ halocycloalkyl, $C_3$-$C_6$ hydroxycycloalkyl, $C_3$-$C_6$ cycloalkoxy, $C_3$-$C_6$ halocycloalkoxy, $C_3$-$C_6$ hydroxycycloalkoxy, $C_1$-$C_6$ alkoxy, $C_1$-$C_6$ haloalkoxy, $C_2$-$C_6$ alkenyl, $C_2$-$C_6$ alkynyl, $S(=O)_n(C_1$-$C_6$ alkyl), $S(=O)_n(C_1$-$C_6$ haloalkyl), $OSO_2(C_1$-$C_6$ alkyl), $OSO_2(C_1$-$C_6$ haloalkyl), $C(=O)H$, $C(=O)OH$, $C(=O)NR_xR_y$, ($C_1$-$C_6$ alkyl)$NR_xR_y$, $C(=O)(C_1$-$C_6$ alkyl), $C(=O)O(C_1$-$C_6$ alkyl), $C(=O)(C_1$-$C_6$ haloalkyl), $C(=O)O(C_1$-$C_6$ haloalkyl), $C(=O)(C_3$-$C_6$ cycloalkyl), $C(=O)O(C_3$-$C_6$ cycloalkyl), $C(=O)(C_2$-$C_6$ alkenyl), $C(=O)O(C_2$-$C_6$ alkenyl), ($C_1$-$C_6$ alkyl)$O(C_1$-$C_6$ alkyl), ($C_1$-$C_6$ alkyl)$S(C_1$-$C_6$ alkyl), $C(=O)(C_1$-$C_6$ alkyl)$C(=O)O(C_1$-$C_6$ alkyl), phenyl, and phenoxy, substituted phenyl and substituted phenoxy (wherein such substituted phenyl and substituted phenoxy have one or more substituents independently selected from H, OH, F, Cl, Br, I, CN, $NO_2$, $C_1$-$C_6$ alkyl, $C_1$-$C_6$ haloalkyl, $C_1$-$C_6$ hydroxyalkyl, $C_3$-$C_6$ cycloalkyl, $C_3$-$C_6$ halocycloalkyl, $C_3$-$C_6$ hydroxycycloalkyl, $C_3$-$C_6$ cycloalkoxy, $C_3$-$C_6$ halocycloalkoxy, $C_3$-$C_6$ hydroxycycloalkoxy, $C_1$-$C_6$ alkoxy, $C_1$-$C_6$ haloalkoxy, $C_2$-$C_6$ alkenyl, $C_2$-$C_6$ alkynyl, $S(=O)_n(C_1$-$C_6$ alkyl), $S(=O)_n(C_1$-$C_6$ haloalkyl), $OSO_2(C_1$-$C_6$ alkyl), $OSO_2(C_1$-$C_6$ haloalkyl), $C(=O)H$, $C(=O)OH$, $C(=O)NR_xR_y$, $C(=O)(C_1$-$C_6$ alkyl)$NR_xR_y$, $C(=O)(C_1$-$C_6$ alkyl), $C(=O)O(C_1$-$C_6$ alkyl), $C(=O)(C_1$-$C_6$ haloalkyl), $C(=O)O(C_1$-$C_6$ haloalkyl), $C(=O)(C_3$-$C_6$ cycloalkyl), $C(=O)O(C_3$-$C_6$ cycloalkyl), $C(=O)(C_2$-$C_6$ alkenyl), $C(=O)O(C_2$-$C_6$ alkenyl), ($C_1$-$C_6$ alkyl)$O(C_1$-$C_6$ alkyl), ($C_1$-$C_6$ alkyl)$S(C_1$-$C_6$ alkyl), $C(=O)(C_1$-$C_6$ alkyl)$C(=O)O(C_1$-$C_6$ alkyl), phenyl, and phenoxy);

(c) $Ar_2$ is substituted phenyl wherein said substituted phenyl has one or more substituents independently selected from F, Cl, Br, I, $C_1$-$C_6$ alkyl, $C_1$-$C_6$ haloalkyl, and $C_1$-$C_6$ alkoxy, (d) J is O, N, NR5, CR5, C=O, or J and $Ar_2$ form a 3, 4, 5, or 6 membered ring;

(e) L is a single or double bond;

(f) K is CR5, C=O, N, NR5, or C=S;

(g) Q is O or S;

(h) R1 is H, OH, F, Cl, Br, I, oxo, $C_1$-$C_6$ alkyl, $C_1$-$C_6$ haloalkyl, $C_1$-$C_6$ alkoxy, $C_3$-$C_6$ cycloalkoxy, $C_1$-$C_6$ haloalkoxy, $C_2$-$C_6$ alkenyloxy, ($C_1$-$C_6$ alkyl)$O(C_1$-$C_6$ alkyl), ($C_1$-$C_6$ alkyl)$O(C_1$-$C_6$ alkoxy), $OC(=O)(C_1$-$C_6$ alkyl), $OC(=O)(C_3$-$C_6$ cycloalkyl), $OC(=O)(C_1$-$C_6$ haloalkyl), $OC(=O)(C_2$-$C_6$ alkenyl), or $NR_xR_y$;

(i) R2 is H, OH, F, Cl, Br, I, oxo, $C_1$-$C_6$ alkyl, $C_1$-$C_6$ haloalkyl, $C_1$-$C_6$ alkoxy, $C_3$-$C_6$ cycloalkoxy, $C_1$-$C_6$ haloalkoxy, $C_2$-$C_6$ alkenyloxy, ($C_1$-$C_6$ alkyl)$O(C_1$-$C_6$ alkyl), ($C_1$-$C_6$ alkyl)$O(C_1$-$C_6$ alkoxy), $OC(=O)(C_1$-$C_6$ alkyl), $OC(=O)(C_3$-$C_6$ cycloalkyl), $OC(=O)(C_1$-$C_6$ haloalkyl), $OC(=O)(C_2$-$C_6$ alkenyl), or $NR_xR_y$;

j) R3 is H, OH, F, Cl, Br, I, oxo, $C_1$-$C_6$ alkyl, $C_1$-$C_6$ haloalkyl, $C_1$-$C_6$ alkoxy, $C_3$-$C_6$ cycloalkoxy, $C_1$-$C_6$ haloalkoxy, $C_2$-$C_6$ alkenyloxy, ($C_1$-$C_6$ alkyl)$O(C_1$-$C_6$ alkyl), ($C_1$-$C_6$ alkyl)$O(C_1$-$C_6$ alkoxy), $OC(=O)(C_1$-$C_6$ alkyl), $OC(=O)(C_3$-$C_6$ cycloalkyl), $OC(=O)(C_1$-$C_6$ haloalkyl), $OC(=O)(C_2$-$C_6$ alkenyl), or $NR_xR_y$;

(k) R4 is H, $C_1$-$C_6$ alkyl, $C_1$-$C_6$ haloalkyl, $C_1$-$C_6$ alkoxy, $C_1$-$C_6$ haloalkoxy, $C_2$-$C_6$ alkenyloxy, ($C_1$-$C_6$ alkyl)$O(C_1$-$C_6$ alkyl); and (l) R5 is H, OH, F, Cl, Br, I, CN, $NO_2$, $C_1$-$C_6$ alkyl, $C_1$-$C_6$ haloalkyl, $C_1$-$C_6$ hydroxyalkyl, $C_3$-$C_6$ cycloalkyl, $C_3$-$C_6$ halocycloalkyl, $C_3$-$C_6$ hydroxycycloalkyl, $C_3$-$C_6$ cycloalkoxy, $C_3$-$C_6$ halocycloalkoxy, $C_3$-$C_6$ hydroxycycloalkoxy, $C_1$-$C_6$ alkoxy, $C_1$-$C_6$ haloalkoxy, $C_2$-$C_6$ alkenyl, $C_2$-$C_6$ alkynyl, $S(=O)_n(C_1$-$C_6$ alkyl), $S(=O)_n(C_1$-$C_6$ haloalkyl), $OSO_2(C_1$-$C_6$ alkyl), $OSO_2(C_1$-$C_6$ haloalkyl), $C(=O)H$, $C(=O)OH$, $C(=O)NR_xR_y$, ($C_1$-$C_6$ alkyl)$NR_xR_y$, $C(=O)(C_1$-$C_6$ alkyl), $C(=O)O(C_1$-$C_6$ alkyl), $C(=O)(C_1$-$C_6$ haloalkyl), $C(=O)O(C_1$-$C_6$ haloalkyl), $C(=O)(C_3$-$C_6$ cycloalkyl), $C(=O)O(C_3$-$C_6$ cycloalkyl), $C(=O)(C_2$-$C_6$ alkenyl), $C(=O)O(C_2$-$C_6$ alkenyl), ($C_1$-$C_6$ alkyl)$O(C_1$-$C_6$ alkyl), ($C_1$-$C_6$ alkyl)$S(C_1$-$C_6$ alkyl), $C(=O)(C_1$-$C_6$ alkyl)$C(=O)O(C_1$-$C_6$ alkyl), phenyl, phenoxy, wherein each alkyl, haloalkyl, hydroxyalkyl, cycloalkyl, halocycloalkyl, hydroxycycloalkyl, cycloalkoxy, halocycloalkoxy, hydroxycycloalkoxy, alkoxy, haloalkoxy, alkenyl, alkynyl, phenyl, and phenoxy are optionally substituted with one or more substituents independently selected from OH, F, Cl, Br, I, CN, $NO_2$, oxo, $C_1$-$C_6$ alkyl, $C_1$-$C_6$ haloalkyl, $C_1$-$C_6$ hydroxyalkyl, $C_3$-$C_6$ cycloalkyl, $C_3$-$C_6$ halocycloalkyl, $C_3$-$C_6$ hydroxycycloalkyl, $C_3$-$C_6$ cycloalkoxy, $C_3$-$C_6$ halocycloalkoxy, $C_3$-$C_6$ hydroxycycloalkoxy, $C_1$-$C_6$ alkoxy, $C_1$-$C_6$ haloalkoxy, $C_2$-$C_6$ alkenyl, $C_2$-$C_6$ alkynyl, $S(=O)_n(C_1$-$C_6$ alkyl), $S(=O)_n(C_1$-$C_6$ haloalkyl), $OSO_2(C_1$-$C_6$ alkyl), $OSO_2(C_1$-$C_6$ haloalkyl), $C(=O)H$, $C(=O)OH$, $C(=O)NR_xR_y$, ($C_1$-$C_6$ alkyl)$NR_xR_y$, $C(=O)(C_1$-$C_6$ alkyl), $C(=O)O(C_1$-$C_6$ alkyl), $C(=O)(C_1$-$C_6$ haloalkyl), $C(=O)O(C_1$-$C_6$ haloalkyl), $C(=O)(C_3$-$C_6$ cycloalkyl), $C(=O)O(C_3$-$C_6$ cycloalkyl), $C(=O)(C_2$-$C_6$ alkenyl), $C(=O)O(C_2$-$C_6$ alkenyl), ($C_1$-$C_6$ alkyl)$O(C_1$-$C_6$ alkyl), ($C_1$-$C_6$ alkyl)$S(C_1$-$C_6$ alkyl), $C(=O)(C_1$-$C_6$ alkyl)$C(=O)O(C_1$-$C_6$ alkyl), phenyl, and phenoxy;

(m) n=0, 1, or 2;

(n) $R_x$ and $R_y$ are independently selected from H, $C_1$-$C_6$ alkyl, $C_1$-$C_6$ haloalkyl, $C_1$-$C_6$ hydroxyalkyl, $C_3$-$C_6$ cycloalkyl, $C_3$-$C_6$ halocycloalkyl, $C_3$-$C_6$ hydroxycycloalkyl, $C_3$-$C_6$ cycloalkoxy, $C_3$-$C_6$ halocycloalkoxy, $C_3$-$C_6$ hydroxycycloalkoxy, $C_1$-$C_6$ alkoxy, $C_1$-$C_6$ haloalkoxy, $C_2$-$C_6$ alkenyl, $C_2$-$C_6$ alkynyl, $S(=O)_n(C_1$-$C_6$ alkyl), $S(=O)_n(C_1$-$C_6$ haloalkyl), $OSO_2(C_1$-$C_6$ alkyl), $OSO_2(C_1$-$C_6$ haloalkyl), $C(=O)H$, $C(=O)OH$, $C(=O)(C_1$-$C_6$ alkyl), $C(=O)O(C_1$-$C_6$ alkyl), $C(=O)(C_1$-$C_6$ haloalkyl), $C(=O)O(C_1$-$C_6$ haloalkyl), $C(=O)(C_3$-$C_6$ cycloalkyl), $C(=O)O(C_3$-$C_6$ cycloalkyl), $C(=O)(C_2$-$C_6$ alkenyl), $C(=O)O(C_2$-$C_6$ alkenyl), ($C_1$-$C_6$ alkyl)$O(C_1$-$C_6$ alkyl), ($C_1$-$C_6$ alkyl)$S(C_1$-$C_6$ alkyl), $C(=O)(C_1$-$C_6$ alkyl)$C(=O)O(C_1$-$C_6$ alkyl), phenyl, and phenoxy.

5. A compound having the following formula:

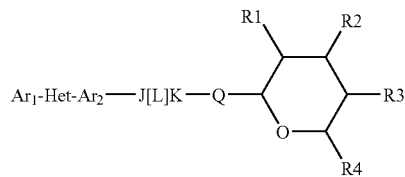

wherein:
(a) $Ar_1$ is
(1) furanyl, phenyl, pyridazinyl, pyridyl, pyrimidinyl, thienyl, or (2) substituted furanyl, substituted phenyl, substituted pyridazinyl, substituted pyridyl, substituted pyrimidinyl, or substituted thienyl, wherein said substituted furanyl, substituted phenyl, substituted pyridazinyl, substituted pyridyl, substituted pyrimidinyl, and substituted thienyl, have one or more substituents independently selected from H, OH, F, Cl, Br, I, CN, $NO_2$, $C_1$-$C_6$ alkyl, $C_1$-$C_6$ haloalkyl, $C_1$-$C_6$ hydroxyalkyl, $C_3$-$C_6$ cycloalkyl, $C_3$-$C_6$ halocycloalkyl, $C_3$-$C_6$ hydroxycycloalkyl, $C_3$-$C_6$ cycloalkoxy, $C_3$-$C_6$ halocycloalkoxy, $C_3$-$C_6$ hydroxycycloalkoxy, $C_1$-$C_6$ alkoxy, $C_1$-$C_6$ haloalkoxy, $C_2$-$C_6$ alkenyl, $C_2$-$C_6$ alkynyl, $S(=O)_n$($C_1$-$C_6$ alkyl), $S(=O)_n$($C_1$-$C_6$ haloalkyl), $OSO_2$($C_1$-$C_6$ alkyl), $OSO_2$($C_1$-$C_6$ haloalkyl), $C(=O)H$, $C(=O)OH$, $C(=O)NR_xR_y$, ($C_1$-$C_6$ alkyl)$NR_xR_y$, $C(=O)(C_1$-$C_6$ alkyl), $C(=O)O(C_1$-$C_6$ alkyl), $C(=O)(C_1$-$C_6$ haloalkyl), $C(=O)O(C_1$-$C_6$ haloalkyl), $C(=O)(C_3$-$C_6$ cycloalkyl), $C(=O)O(C_3$-$C_6$ cycloalkyl), $C(=O)(C_2$-$C_6$ alkenyl), $C(=O)O(C_2$-$C_6$ alkenyl), ($C_1$-$C_6$ alkyl)$O(C_1$-$C_6$ alkyl), ($C_1$-$C_6$ alkyl)$S(C_1$-$C_6$ alkyl), $C(=O)(C_1$-$C_6$ alkyl)$C(=O)O(C_1$-$C_6$ alkyl), phenyl, phenoxy, substituted phenyl and substituted phenoxy (wherein such substituted phenyl and substituted phenoxy have one or more substituents independently selected from H, OH, F, Cl, Br, I, CN, $NO_2$, $C_1$-$C_6$ alkyl, $C_1$-$C_6$ haloalkyl, $C_1$-$C_6$ hydroxyalkyl, $C_3$-$C_6$ cycloalkyl, $C_3$-$C_6$ halocycloalkyl, $C_3$-$C_6$ hydroxycycloalkyl, $C_3$-$C_6$ cycloalkoxy, $C_3$-$C_6$ halocycloalkoxy, $C_3$-$C_6$ hydroxycycloalkoxy, $C_1$-$C_6$ alkoxy, $C_1$-$C_6$ haloalkoxy, $C_2$-$C_6$ alkenyl, $C_2$-$C_6$ alkynyl, $S(=O)_n$($C_1$-$C_6$ alkyl), $S(=O)_n$($C_1$-$C_6$ haloalkyl), $OSO_2$($C_1$-$C_6$ alkyl), $OSO_2$($C_1$-$C_6$ haloalkyl), $C(=O)H$, $C(=O)OH$, $C(=O)NR_xR_y$, ($C_1$-$C_6$ alkyl)$NR_xR_y$, $C(=O)(C_1$-$C_6$ alkyl), $C(=O)O(C_1$-$C_6$ alkyl), $C(=O)(C_1$-$C_6$ haloalkyl), $C(=O)O(C_1$-$C_6$ haloalkyl), $C(=O)(C_3$-$C_6$ cycloalkyl), $C(=O)O(C_3$-$C_6$ cycloalkyl), $C(=O)(C_2$-$C_6$ alkenyl), $C(=O)O(C_2$-$C_6$ alkenyl), ($C_1$-$C_6$ alkyl)$O(C_1$-$C_6$ alkyl), ($C_1$-$C_6$ alkyl)$S(C_1$-$C_6$ alkyl), $C(=O)(C_1$-$C_6$ alkyl)$C(=O)O(C_1$-$C_6$ alkyl)phenyl, and phenoxy);

(b) Het is a 5 or 6 membered, saturated or unsaturated, heterocyclic ring, containing one or more heteroatoms independently selected from nitrogen, sulfur, or oxygen, and where $Ar_1$ and $Ar_2$ are not ortho to each other but may be meta or para, such as, for a and where said heterocyclic ring may also be substituted with one or more substituents independently selected from H, OH, F, Cl, Br, I, CN, $NO_2$, oxo, $C_1$-$C_6$ alkyl, $C_1$-$C_6$ haloalkyl, $C_1$-$C_6$ hydroxyalkyl, $C_3$-$C_6$ cycloalkyl, $C_3$-$C_6$ halocycloalkyl, $C_3$-$C_6$ hydroxycycloalkyl, $C_3$-$C_6$ cycloalkoxy, $C_3$-$C_6$ halocycloalkoxy, $C_3$-$C_6$ hydroxycycloalkoxy, $C_1$-$C_6$ alkoxy, $C_1$-$C_6$ haloalkoxy, $C_2$-$C_6$ alkenyl, $C_2$-$C_6$ alkynyl, $S(=O)_n$($C_1$-$C_6$ alkyl), $S(=O)_n$($C_1$-$C_6$ haloalkyl), $OSO_2$($C_1$-$C_6$ alkyl), $OSO_2$($C_1$-$C_6$ haloalkyl), $C(=O)H$, $C(=O)OH$, $C(=O)NR_xR_y$, ($C_1$-$C_6$ alkyl)$NR_xR_y$, $C(=O)(C_1$-$C_6$ alkyl), $C(=O)O(C_1$-$C_6$ alkyl), $C(=O)(C_1$-$C_6$ haloalkyl), $C(=O)O(C_1$-$C_6$ haloalkyl), $C(=O)(C_3$-$C_6$ cycloalkyl), $C(=O)O(C_3$-$C_6$ cycloalkyl), $C(=O)(C_2$-$C_6$ alkenyl), $C(=O)O(C_2$-$C_6$ alkenyl), ($C_1$-$C_6$ alkyl)$O(C_1$-$C_6$ alkyl), ($C_1$-$C_6$ alkyl)$S(C_1$-$C_6$ alkyl), $C(=O)(C_1$-$C_6$ alkyl)$C(=O)O(C_1$-$C_6$ alkyl), phenyl, phenoxy, substituted phenyl and substituted phenoxy (wherein such substituted phenyl and substituted phenoxy have one or more substituents independently selected from H, OH, F, Cl, Br, I, CN, $NO_2$, $C_1$-$C_6$ alkyl, $C_1$-$C_6$ haloalkyl, $C_1$-$C_6$ hydroxyalkyl, $C_3$-$C_6$ cycloalkyl, $C_3$-$C_6$ halocycloalkyl, $C_3$-$C_6$ hydroxycycloalkyl, $C_3$-$C_6$ cycloalkoxy, $C_3$-$C_6$ halocycloalkoxy, $C_3$-$C_6$ hydroxycycloalkoxy, $C_1$-$C_6$ alkoxy, $C_1$-$C_6$ haloalkoxy, $C_2$-$C_6$ alkenyl, $C_2$-$C_6$ alkynyl, $S(=O)_n$($C_1$-$C_6$ alkyl), $S(=O)_n$($C_1$-$C_6$ haloalkyl), $OSO_2$($C_1$-$C_6$ alkyl), $OSO_2$($C_1$-$C_6$ haloalkyl), $C(=O)H$, $C(=O)OH$, $C(=O)NR_xR_y$, $C(=O)(C_1$-$C_6$ alkyl) $NR_xR_y$, $C(=O)(C_1$-$C_6$ alkyl), $C(=O)O(C_1$-$C_6$ alkyl), $C(=O)(C_1$-$C_6$ haloalkyl), $C(=O)O(C_1$-$C_6$ haloalkyl), $C(=O)(C_3$-$C_6$ cycloalkyl), $C(=O)O(C_3$-$C_6$ cycloalkyl), $C(=O)(C_2$-$C_6$ alkenyl), $C(=O)O(C_2$-$C_6$ alkenyl), ($C_1$-$C_6$ alkyl)$O(C_1$-$C_6$ alkyl), ($C_1$-$C_6$ alkyl)$S(C_1$-$C_6$ alkyl), $C(=O)(C_1$-$C_6$ alkyl)$C(=O)O(C_1$-$C_6$ alkyl), phenyl, and phenoxy);

(c) $Ar_2$ is
(1) furanyl, phenyl, pyridazinyl, pyridyl, pyrimidinyl, thienyl, or
(2) substituted furanyl, substituted phenyl, substituted pyridazinyl, substituted pyridyl, substituted pyrimidinyl, or substituted thienyl, wherein said substituted furanyl, substituted phenyl, substituted pyridazinyl, substituted pyridyl, substituted pyrimidinyl, and substituted thienyl, have one or more substituents independently selected from H, OH, F, Cl, Br, I, CN, $NO_2$, $C_1$-$C_6$ alkyl, $C_1$-$C_6$ haloalkyl, $C_1$-$C_6$ hydroxyalkyl, $C_3$-$C_6$ cycloalkyl, $C_3$-$C_6$ halocycloalkyl, $C_3$-$C_6$ hydroxycycloalkyl, $C_3$-$C_6$ cycloalkoxy, $C_3$-$C_6$ halocycloalkoxy, $C_3$-$C_6$ hydroxycycloalkoxy, $C_1$-$C_6$ alkoxy, $C_1$-$C_6$ haloalkoxy, $C_2$-$C_6$ alkenyl, $C_2$-$C_6$ alkynyl, $S(=O)_n$($C_1$-$C_6$ alkyl), $S(=O)_n$($C_1$-$C_6$ haloalkyl), $OSO_2$($C_1$-$C_6$ alkyl), $OSO_2$($C_1$-$C_6$ haloalkyl), $C(=O)H$, $C(=O)OH$, $C(=O)NR_xR_y$, ($C_1$-$C_6$ alkyl) $NR_xR_y$, $C(=O)(C_1$-$C_6$ alkyl), $C(=O)O(C_1$-$C_6$ alkyl), $C(=O)(C_1$-$C_6$ haloalkyl), $C(=O)O(C_1$-$C_6$ haloalkyl), $C(=O)(C_3$-$C_6$ cycloalkyl), $C(=O)O(C_3$-$C_6$ cycloalkyl), $C(=O)(C_2$-$C_6$ alkenyl), $C(=O)O(C_2$-$C_6$ alkenyl), ($C_1$-$C_6$ alkyl)$O(C_1$-$C_6$ alkyl), ($C_1$-$C_6$ alkyl)$S(C_1$-$C_6$ alkyl), $C(=O)(C_1$-$C_6$ alkyl)$C(=O)O(C_1$-$C_6$ alkyl), phenyl, phenoxy, substituted phenyl and substituted phenoxy (wherein such substituted phenyl and substituted phenoxy have one or more substituents independently selected from H, OH, F, Cl, Br, I, CN, $NO_2$, $C_1$-$C_6$ alkyl, $C_1$-$C_6$ haloalkyl, $C_1$-$C_6$ hydroxyalkyl, $C_3$-$C_6$ cycloalkyl, $C_3$-$C_6$ halocycloalkyl, $C_3$-$C_6$ hydroxycycloalkyl, $C_3$-$C_6$ cycloalkoxy, $C_3$-$C_6$ halocycloalkoxy, $C_3$-$C_6$ hydroxycycloalkoxy, $C_1$-$C_6$ alkoxy, $C_1$-$C_6$ haloalkoxy, $C_2$-$C_6$ alkenyl, $C_2$-$C_6$ alkynyl, $S(=O)_n$($C_1$-$C_6$ alkyl), $S(=O)_n$($C_1$-$C_6$ haloalkyl), $OSO_2$($C_1$-$C_6$ alkyl), $OSO_2$($C_1$-$C_6$ haloalkyl), $C(=O)H$, $C(=O)OH$, $C(=O)NR_xR_y$, ($C_1$-$C_6$ alkyl)$NR_xR_y$, $C(=O)(C_1$-$C_6$ alkyl), $C(=O)O(C_1$-$C_6$ alkyl), $C(=O)(C_1$-$C_6$ haloalkyl), $C(=O)O(C_1$-$C_6$ haloalkyl), $C(=O)(C_3$-$C_6$ cycloalkyl), $C(=O)O(C_3$-$C_6$ cycloalkyl), $C(=O)(C_1$-$C_6$ haloalkyl), $C(=O)(C_2$-$C_6$ alkenyl), $C(=O)O(C_2$-$C_6$ alkenyl), ($C_1$-$C_6$ alkyl)$O(C_1$-$C_6$ alkyl), ($C_1$-$C_6$ alkyl)$S(C_1$-$C_6$ alkyl), $C(=O)(C_1$-$C_6$ alkyl) $C(=O)O(C_1$-$C_6$ alkyl), phenyl, and phenoxy);

(d) J is O, N, NR5, CR5, C=O, or J and $Ar_2$ form a 3, 4, 5, or 6 membered ring;

(e) L is a single or double bond;

(f) K is CR5, C=O, N, NR5, or C=S;

(g) Q is O or S;

(h) R1 is H, OH, F, Cl, Br, I, oxo, $C_1$-$C_6$ alkyl, $C_1$-$C_6$ haloalkyl, $C_1$-$C_6$ alkoxy, $C_3$-$C_6$ cycloalkoxy, $C_1$-$C_6$ haloalkoxy, $C_2$-$C_6$ alkenyloxy, ($C_1$-$C_6$ alkyl)O($C_1$-$C_6$ alkyl), ($C_1$-$C_6$ alkyl)O($C_1$-$C_6$ alkoxy), OC(=O)($C_1$-$C_6$ alkyl), OC(=O)($C_3$-$C_6$ cycloalkyl), OC(=O)($C_1$-$C_6$ haloalkyl), OC(=O)($C_2$-$C_6$ alkenyl), or $NR_xR_y$;

(i) R2 is H, OH, F, Cl, Br, I, oxo, $C_1$-$C_6$ alkyl, $C_1$-$C_6$ haloalkyl, $C_1$-$C_6$ alkoxy, $C_3$-$C_6$ cycloalkoxy, $C_1$-$C_6$ haloalkoxy, $C_2$-$C_6$ alkenyloxy, ($C_1$-$C_6$ alkyl)O($C_1$-$C_6$ alkyl), ($C_1$-$C_6$ alkyl)O($C_1$-$C_6$ alkoxy), OC(=O)($C_1$-$C_6$ alkyl), OC(=O)($C_3$-$C_6$ cycloalkyl), OC(=O)($C_1$-$C_6$ haloalkyl), OC(=O)($C_2$-$C_6$ alkenyl), or $NR_xR_y$;

j) R3 is H, OH, F, Cl, Br, I, oxo, $C_1$-$C_6$ alkyl, $C_1$-$C_6$ haloalkyl, $C_1$-$C_6$ alkoxy, $C_3$-$C_6$ cycloalkoxy, $C_1$-$C_6$ haloalkoxy, $C_2$-$C_6$ alkenyloxy, ($C_1$-$C_6$ alkyl)O($C_1$-$C_6$ alkyl), ($C_1$-$C_6$ alkyl)O($C_1$-$C_6$ alkoxy), OC(=O)($C_1$-$C_6$ alkyl), OC(=O)($C_3$-$C_6$ cycloalkyl), OC(=O)($C_1$-$C_6$ haloalkyl), OC(=O)($C_2$-$C_6$ alkenyl), or $NR_xR_y$;

(k) R4 is H, $C_1$-$C_6$ alkyl, $C_1$-$C_6$ haloalkyl, $C_1$-$C_6$ alkoxy, $C_1$-$C_6$ haloalkoxy, $C_2$-$C_6$ alkenyloxy, ($C_1$-$C_6$ alkyl)O($C_1$-$C_6$ alkyl); and (l) $R_5$ is $C_1$-$C_6$ alkyl, $C_1$-$C_6$ haloalkyl, $C_1$-$C_6$ hydroxyalkyl, $C_2$-$C_6$ alkenyl, C(=O)($C_1$-$C_6$ alkyl), ($C_1$-$C_6$ alkyl)O($C_1$-$C_6$ alkyl), and C(=O)($C_1$-$C_6$ alkyl)C(=O)O($C_1$-$C_6$ alkyl);

(m) n=0, 1, or 2;

(n) $R_x$ and $R_y$ are independently selected from H, $C_1$-$C_6$ alkyl, $C_1$-$C_6$ haloalkyl, $C_1$-$C_6$ hydroxyalkyl, $C_3$-$C_6$ cycloalkyl, $C_3$-$C_6$ halocycloalkyl, $C_3$-$C_6$ hydroxycycloalkyl, $C_3$-$C_6$ cycloalkoxy, $C_3$-$C_6$ halocycloalkoxy, $C_3$-$C_6$ hydroxycycloalkoxy, $C_1$-$C_6$ alkoxy, $C_1$-$C_6$ haloalkoxy, $C_2$-$C_6$ alkenyl, $C_2$-$C_6$ alkynyl, S(=O)$_n$($C_1$-$C_6$ alkyl), S(=O)$_n$($C_1$-$C_6$ haloalkyl), OSO$_2$($C_1$-$C_6$ alkyl), OSO$_2$($C_1$-$C_6$ haloalkyl), C(=O)H, C(=O)OH, C(=O)($C_1$-$C_6$ alkyl), C(=O)O($C_1$-$C_6$ alkyl), C(=O)($C_1$-$C_6$ haloalkyl), C(=O)O($C_1$-$C_6$ haloalkyl), C(=O)($C_3$-$C_6$ cycloalkyl), C(=O)O($C_3$-$C_6$ cycloalkyl), C(=O)($C_2$-$C_6$ alkenyl), C(=O)O($C_2$-$C_6$ alkenyl), ($C_1$-$C_6$ alkyl)O($C_1$-$C_6$ alkyl), ($C_1$-$C_6$ alkyl)S($C_1$-$C_6$ alkyl), C(=O)($C_1$-$C_6$ alkyl)C(=O)O($C_1$-$C_6$ alkyl), phenyl, and phenoxy.

6. A compound that is a pesticidally acceptable acid addition salt of a compound according to claims 1, 2, 3, 4, or 5.

7. A composition comprising a mixture of a compound according to claims 1, 2, 3, 4, 5 or a pesticidally acceptable acid addition salt thereof with at least one other compound selected from antibiotic insecticides, macrocyclic lactone insecticides, avermectin insecticides, milbemycin insecticides, spinosyn insecticides, arsenical insecticides, botanical insecticides, carbamate insecticides, benzofuranyl methylcarbamate insecticides, dimethylcarbamate insecticides, oxime carbamate insecticides, phenyl methylcarbamate insecticides, diamide insecticides, desiccant insecticides, dinitrophenol insecticides, fluorine insecticides, formamidine insecticides, fumigant insecticides, inorganic insecticides, insect growth regulators, chitin synthesis inhibitors, juvenile hormone mimics, juvenile hormones, moulting hormone agonists, moulting hormones, moulting inhibitors, precocenes, nereistoxin analogue insecticides, nicotinoid insecticides, nitroguanidine insecticides, nitromethylene insecticides, pyridylmethylamine insecticides, organochlorine insecticides, organophosphorus insecticides, oxadiazine insecticides, oxadiazolone insecticides, phthalimide insecticides, pyrazole insecticides, pyrethroid insecticides, pyrimidinamine insecticides, pyrrole insecticides, tetramic acid insecticides, tetronic acid insecticides, thiazole insecticides, thiazolidine insecticides, thiourea insecticides, sulfoximine insecticides, and urea insecticides.

8. A compound having the following formula:

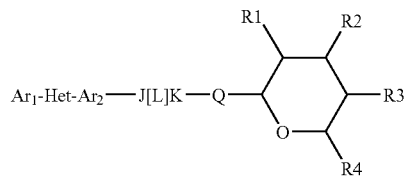

wherein:

(a) $Ar_1$ is phenyl, pyridyl, thienyl, substituted phenyl, substituted pyridazinyl, or substituted pyridyl,
  wherein said substituted phenyl has one or more substituents independently selected from F, Cl, Br, I, CN, $CH_3$, $C_3H_7$, $C_4H_9$, $OCH_3$, $OC_4H_9$, $CF_3$, $C_2F_5$, $C_3F_7$, $OCF_3$, $OC_2F_5$, $OCH_2CF_3$, $OCF_2CHF_2$, $SCF_3$, $SCH_3$, S(=O)$CF_3$, S(=O)$_2CF_3$, OPhCl, and C(OH)$C_2H_5$,
  wherein said substituted pyridazinyl has one or more Cl,
  wherein said substituted pyridyl has one or more substituents independently selected from F, Cl, I, $CF_3$, $OCF_3$, $OCF_2CHFCF_3$, and $OCH_2CF_3$;

(b) Het is imidazolyl, isoxazolyl, 1,3,4 oxadiazolyl, pyrazinyl, pyrazolinyl, pyrazolyl, pyridyl, pyrimidinyl, pyrrolyl, 1,2,3,4-tetrazolyl, thiazolyl, 1,3,5-triazinyl, 1,2,3-triazolyl, 1,2,4-triazolyl, substituted pyrazolinyl, substituted pyrimidinyl, or substituted 1,2,4-triazolyl,
  wherein said substituted pyrazolyl has one or more substituents independently selected from H, $CH_3$, $C_3H_7$, C(=O)$OCH_3$, C(=O)$OC_2H_5$, and C(=O)$OC_4H_9$,
  wherein said substituted pyrimidinyl has one or more substituents independently selected from $CF_3$ and $C_3F_7$,
  wherein said substituted 1,2,4-triazolyl has one or more substituents selected from $CH_3$ and oxo;

(c) $Ar_2$ is phenyl, thienyl, or substituted phenyl,
  wherein said substituted phenyl has one or more substituents independently selected from F, Cl, $OCH_3$, and $CF_3$;

(d) J is NH, CH, CCH$_3$, or C=O;

(e) L is a single or double bond;

(f) K is C=O, N, NH, or C=S;

(g) Q is O, or S;

(h) R1 is $OCH_3$ or $OC_2H_5$;

(i) R2 is $OCH_2CH=CH_2$, $OCH_3$, $OC_2H_5$, $OC_3H_7$, or $OC_4H_9$;

(j) R3 is OH, $OCH_3$, $OC_2H_5$, or $OC_3H_7$; and (k) R4 is $CH_3$ or $CH_2OCH_3$.

* * * * *